(12) United States Patent
Glick et al.

(10) Patent No.: US 11,447,460 B2
(45) Date of Patent: Sep. 20, 2022

(54) COMPOUNDS AND COMPOSITIONS FOR TREATING CONDITIONS ASSOCIATED WITH NLRP ACTIVITY

(71) Applicant: Novartis AG, Basel (CH)

(72) Inventors: Gary Glick, Ann Arbor, MI (US); Shomir Ghosh, Brookline, MA (US); William R. Roush, Jupiter, FL (US); Dong-Ming Shen, Boston, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/094,487

(22) PCT Filed: Apr. 18, 2017

(86) PCT No.: PCT/US2017/028139
§ 371 (c)(1),
(2) Date: Oct. 18, 2018

(87) PCT Pub. No.: WO2017/184604
PCT Pub. Date: Oct. 26, 2017

(65) Prior Publication Data
US 2019/0119241 A1 Apr. 25, 2019

Related U.S. Application Data

(60) Provisional application No. 62/324,081, filed on Apr. 18, 2016, provisional application No. 62/324,071, filed on Apr. 18, 2016, provisional application No. 62/411,358, filed on Oct. 21, 2016.

(51) Int. Cl.

| | | |
|---|---|---|
| C07D 333/34 | (2006.01) |
| C07D 215/36 | (2006.01) |
| C07D 265/30 | (2006.01) |
| C07D 213/28 | (2006.01) |
| C07D 307/64 | (2006.01) |
| C07D 231/44 | (2006.01) |
| C07D 277/34 | (2006.01) |
| C07D 307/82 | (2006.01) |
| C07C 381/00 | (2006.01) |
| C07C 311/29 | (2006.01) |
| C07C 317/14 | (2006.01) |
| C07C 311/37 | (2006.01) |
| C07C 311/51 | (2006.01) |
| C07D 231/18 | (2006.01) |
| C07D 277/36 | (2006.01) |

(52) U.S. Cl.
CPC .......... *C07D 333/34* (2013.01); *C07C 311/29* (2013.01); *C07C 311/37* (2013.01); *C07C 311/51* (2013.01); *C07C 317/14* (2013.01); *C07C 381/00* (2013.01); *C07D 213/28* (2013.01); *C07D 215/36* (2013.01); *C07D 231/18* (2013.01); *C07D 231/44* (2013.01); *C07D 265/30* (2013.01); *C07D 277/34* (2013.01); *C07D 277/36* (2013.01); *C07D 307/64* (2013.01); *C07D 307/82* (2013.01)

(58) Field of Classification Search
CPC .. C07D 333/34; C07D 231/44; C07D 231/18; C07D 277/34; C07D 277/36; C07D 307/82; C07D 307/64; C07D 215/36; C07D 265/30; C07D 213/28; C07C 381/00; C07C 311/29; C07C 311/37; C07C 311/51; C07C 317/14; A61P 9/14; A61P 9/10; A61P 43/00
USPC .......................................................... 549/65
See application file for complete search history.

(56) References Cited

U.S. PATENT DOCUMENTS

| | | |
|---|---|---|
| 5,053,072 A | 10/1991 | Ort et al. |
| 6,166,064 A | 12/2000 | Dombroski et al. |
| 2002/0091272 A1* | 7/2002 | Wu ...................... C07D 409/12 548/557 |

FOREIGN PATENT DOCUMENTS

| | | |
|---|---|---|
| CN | 103159649 A | 6/2013 |
| CN | 103159674 A | 6/2013 |
| CN | 103172547 A | 6/2013 |
| JP | H02282371 A | 11/1990 |
| JP | H0454168 A | 2/1992 |
| JP | H06234729 A | 8/1994 |
| JP | 2001097946 A | 4/2001 |
| WO | 98/32733 A1 | 7/1998 |
| WO | 00/39077 A2 | 7/2000 |
| WO | 2007/032028 A1 | 3/2007 |
| WO | 2009/080835 A1 | 7/2009 |

OTHER PUBLICATIONS

Ammazzalorso et al., "Titanium-Promoted Acylation of Sulfonamides to N-Acylsulfonamide PPARα Antagonists," Synthetic Comm. 45(22):2546-54 (2015).
Luo et al., "Metronidazole acid acyl sulfonamide: A novel class of anticancer agents and potential EGFR tyrosine kinase inhibitors," Bioorganic & Medicinal Chemistry. 19(2):6069-76 (2011).

(Continued)

*Primary Examiner* — Taylor V Oh
(74) *Attorney, Agent, or Firm* — Asha K. Nadipuram

(57) ABSTRACT

In one aspect, compounds of Formula A, or a pharmaceutically acceptable salt thereof, are featured, or a pharmaceutically acceptable salt thereof, wherein the variables shown in Formula A can be as defined anywhere herein.

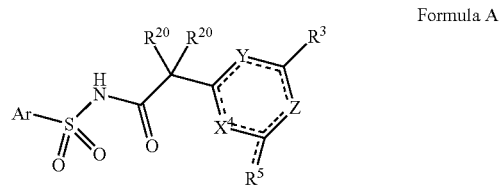

Formula A

6 Claims, No Drawings

(56) References Cited

OTHER PUBLICATIONS

Raushel et al., "Efficient Synthesis of 1-Sulfonyl-1,2,3-triazoles," Org Lett. 12(21):4952-5 (2010).
Shen et al., "Benzyl anion transfer in the fragmentation of N-(phenylsulfonyl)-benzeneacetamides: a gas-phase intramolecular SNAr reaction," Org Biomol Chem. 13(40):10205-11 (2015).
Smith et al., "Structure-Based Identification of Novel Ligands Targeting Multiple Sites within a Chemokine-G-Protein-Coupled-Receptor Interface," J Med Chem. 59(9):4342-51 (2016).
Yavari et al., "Sulfonoketenimides as Key Intermediates for the Synthesis of N-Tosyl-acetoyloxy Alkanimines," Synlett. 2(7):959-60 (2014).
Cano et al., "Copper(I) complexes as catalysts for the synthesis of N-sulfonyl-1,2,3-triazoles from N-sulfonylazides and alkynes," Org Biomol Chem. 8(3):536-8 (2010).
Jhan et al., "Efficient copper-catalyzed intramolecular N-arylation for the synthesis of oxindoles," Tetrahedron Letters 54(9):1155-9 (2013).
Soltani Rad et al. "Highly efficient one-pot synthesis of N-Acylsulfonamides using cyanuric chloride at room temperature," Synthesis 2010(15):2599-603 (2010).
Wakeham et al., "Iodide as an activating agent for acid chlorides in acylation reactions," Org Lett. 15(3):702-5 (2013).
Akagi, "A New Binding Model for Structurally Diverse ALS Inhibitors," Pestic Sci. 47:309-18 (1996).
Cloudsdale et al., "Herbicidal Sulfonylamides," ACS Symposium Series. 584:37-45 (1995).
Miura et al., "Synthesis of Oxindoles by Palladium-catalyzed C—H Bond Amidation." Chem Lett. 38(4):328-9 (2009).
Rozenstveig et al., "A novel regiospecific cascade synthesis of sulfonamide derivatives from N-(2-polychloroethyl) sulfonamides via chloroaziridine intermediates in the presence of mercaptoethanol," Mol Divers. 14(3):533-41 (2010).
Reddy et al., "A new and efficient method for the facile synthesis of N-acyl sulfonamides under Lewis acid catalysis," Tetrahedron Letters. 48:7528-32 (2007).
Coll et al., "A small-molecule inhibitor of the NLRP3 inflammasome for the treatment of inflammatory diseases," Nat Med. 21(3):248-55 (2015).
CAS RN 1825712-63-7, STN Entry Date Dec. 9, 2015, Benzeneacetamide, 2,4,5-trifluoro-N-(2-thiazolylsulfonyl) (1 page).
CAS RN 1825669-10-0, STN Entry Date Dec. 9, 2015, Benzeneacetamide, 2,4,5-trifluoro-N-[(1-methyl-1H-1,2,3-triazol-5-yl)sulfonyl]—(1 page).
CAS RN 1825668-90-3, STN Entry Date Dec. 9, 2015, Benzeneacetamide, 2,4,5-trifluoro-N-[(1-methyl-1H-pyrazol-4-yl)sulfonyl]—(1 page).
CAS RN 1808570-83-3, STN Entry Date Sep. 29, 2015, Benzeneacetamide, 2-chloro-N-[(2,5-dimethyl-3-furanyl)sulfonyl]— (1 page).
CAS RN 1797869-17-0, STN Entry Date Jul. 9, 2015, Benzeneacetamide, N-[(2,5-dimethyl-3-furanyl)sulfonyl]-2,3-difluoro— (1 page).
CAS RN 1797843-95-8, STN Entry Date Jul. 9, 2015, Benzeneacetamide, N-[(2,5-dimethyl-3-furanyl)sulfonyl]-3,4-difluoro— (1 page).
CAS RN 1797636-55-5, STN Entry Date Jul. 9, 2015, Benzeneacetamide, 2-fluoro-N-[[1-(2-methylpropyl)-1H-imidazol-4-yl]sulfonyl]—(1 page).
CAS RN 1797635-79-0, STN Entry Date Jul. 9, 2015, Benzeneacetamide, N-[(2,4-dimethyl-5-thiazolyl)sulfonyl]-2,6-dimethyl—(1 page).
CAS RN 1797388-91-0, STN Entry Date Jul. 8, 2015, Benzeneacetamide, 2,6-dimethyl-N-[[1-(1-methylethyl)-1H-imidazol-4-yl]sulfonyl]—(1 page).
CAS RN 1797042-65-9, STN Entry Date Jul. 8, 2015, Benzeneacetamide, N-[(3,5-dimethyl-4-isoxazolyl)sulfonyl]-2-methoxy—(1 page).
CAS RN 1796967-52-6, STN Entry Date Jul. 8, 2015, Benzeneacetamide, N-[(1-ethyl-2-methyl-1H-imidazol-4-yl)sulfonyl]-2,6-dimethyl—(1 page).
CAS RN 1645539-23-6, STN Entry Date Feb. 8, 2015, Benzeneacetamide, N-[(2,5-dimethyl-3-furanyl)sulfonyl]-2,6-difluoro— (1 page).
CAS RN 1645528-79-5, STN Entry Date Feb. 8, 2015, Benzeneacetamide, N-[(3,5-dimethyl-4-isoxazolyl)sulfonyl]-2-ethyl— (1 page).
CAS RN 1645415-63-9, STN Entry Date Feb. 8, 2015, Benzeneacetamide, N-[(1-ethyl-1H-pyrazol-4-yl)sulfonyl]-2,4,6-trimethyl—(1 page).
CAS RN 1645382-23-5, STN Entry Date Feb. 8, 2015, Benzeneacetamide, N-[(2,5-dimethyl-3-furanyl)sulfonyl]-2-methyl— (1 page).
CAS RN 1645371-18-1, STN Entry Date Feb. 8, 2015, Benzeneacetamide, N-[(2,5-dimethyl-3-furanyl)sulfonyl]-2,6-dimethyl—(1 page).
CAS RN 1626504-75-3, STN Entry Date Sep. 26, 2014, Benzeneacetamide, N-[(3,5-dimethyl-4-isoxazolyl)sulfonyl]-2-methyl—(1 page).
CAS RN 1465407-34-4, STN Entry Date Oct. 29, 2013, Benzeneacetamide, 2,3-difluoro-N-(3-thienylsulfonyl)—(1 page).
CAS RN 1465353-38-1, STN Entry Date Oct. 29, 2013, Benzeneacetamide, 2,3-difluoro-N-(2-thienylsulfonyl)—(1 page).
CAS RN 1436064-76-4, STN Entry Date Jun. 9, 2013, Benzeneacetamide, N-[(3,5-dimethyl-4-isoxazolyl)sulfonyl]-2,5-dimethyl—(1 page).
CAS RN 1428045-22-0, STN Entry Date Apr. 11, 2013, Benzeneacetamide, N-[(3,5-dimethyl-4-isoxazolyl)sulfonyl]-3-methoxy-4-methyl—(1 page).
CAS RN 1427992-48-0, STN Entry Date Apr. 11, 2013, Benzeneacetamide, N-[(3,5-dimethyl-4-isoxazolyl)sulfonyl]-3,4-dimethoxy—(1 page).
CAS RN 1376340-40-7, STN Entry Date Jun. 7, 2012, Benzeneacetamide, 5-bromo-N-[(3,5-dimethyl-4-isoxazolyl)sulfonyl]-2-methoxy—(1 page).
CAS RN 1375912-62-1, STN Entry Date Jun. 7, 2012, Benzeneacetamide, 5-bromo-2-methoxy-N-[(1,3,5-trimethyl-1H-pyrazol-4-yl)sulfonyl]—(1 page).
CAS RN 1285942-13-3, STN Entry Date Apr. 26, 2011, Benzeneacetamide, N-[(5-chloro-2-thienyl)sulfonyl]-3,4,5-trimethoxy— (1 page).
CAS RN 1259068-27-3, STN Entry Date Jan. 12, 2011, 2-Thiophenecarboxylic acid, 3-[[[2-(2-methoxyphenyl)acetyl]amino]sulfonyl]-, methyl ester (1 page).
CAS RN 1211223-40-3, STN Entry Date Mar. 18, 2010,1 H-Pyrrole-2-carboxamide, 4-[[[2-(3-fluoro-4-methoxyphenyl) acetyl]amino]sulfonyl]-1-methyl—(1 page).

* cited by examiner

COMPOUNDS AND COMPOSITIONS FOR TREATING CONDITIONS ASSOCIATED WITH NLRP ACTIVITY

This application is a National Stage application under 35 U.S.C. § 371 of International Patent Application No. PCT/US2017/028139, filed Apr. 18, 2017, which claims priority to U.S. Provisional Patent Application Ser. No. 62/411,358, filed Oct. 21, 2016, 62/324,071, filed Apr. 18, 2016 and 62/324,081, filed Apr. 18, 2016; the entire contents of which are herein incorporated by reference.

TECHNICAL FIELD

This disclosure features chemical entities (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination of the compound) that are useful, e.g., for treating a condition, disease or disorder in which a decrease or increase in NLRP1/3 activity (e.g., an increase, e.g., a condition, disease or disorder associated with NLRP1/3 signaling) contributes to the pathology and/or symptoms and/or progression of the condition, disease or disorder in a subject (e.g., a human). This disclosure also features compositions as well as other methods of using and making the same.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

The NLRP1 inflammasome is a component of the inflammatory process and its aberrant activation is pathogenic in inherited disorders such as generalized vitiligo associated with autoimmune disease (autoimmune thyroid disease, latent autoimmune diabetes in adults, rheumatoid arthritis, psoriasis, pernicious anemia, systemic lupus erythematosus, and Addison's disease).

NLRP1 and NLRP3 can form a complex and they have been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NLRP1/3, wherein the compounds inhibit NLRP1 or NLRP3 or both NLRP3 and NLRP1.

SUMMARY

This disclosure features chemical entities (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination of the compound) that are useful, e.g., for treating a condition, disease or disorder in which a decrease or increase in NLRP1 or NLRP3 or both NLRP1 and NLRP3 activity, also referred to herein "NLRP1/3" activity (e.g., an increase, e.g., a condition, disease or disorder associated with NLRP1/3 signaling).

In some embodiments, provided herein is a compound of Formula A

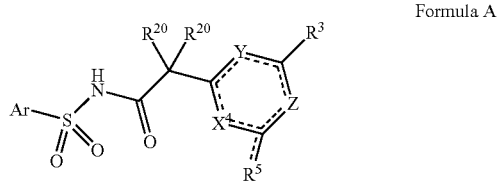

Formula A or a pharmaceutically acceptable salt thereof, wherein the variables in Formula A can be as defined anywhere herein.

In some embodiments, provided herein is a compound of Formula I

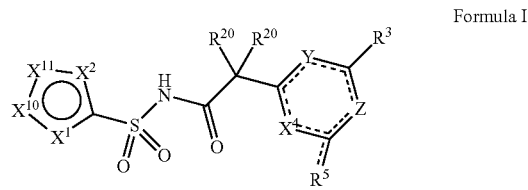

Formula I or a pharmaceutically acceptable salt thereof, wherein the variables in Formula I can be as defined anywhere herein.

In some embodiments, provided herein is a compound of Formula II

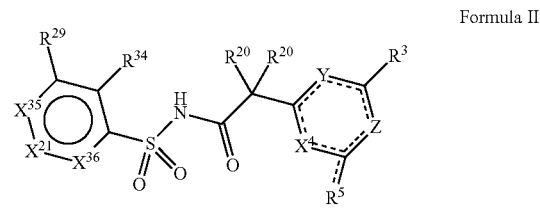

Formula II or a pharmaceutically acceptable salt thereof, wherein the variables in Formula II can be as defined anywhere herein.

This disclosure also features compositions as well as other methods of using and making the same.

An "antagonist" of NLRP1/3 includes compounds that inhibit the ability of NLRP1/3 to induce the production of IL-1β and/or IL-18 by directly binding to NLRP1/3, or by inactivating, destabilizing, altering distribution, of NLRP1/3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP1 or NLRP3 or both NLRP1 and NLRP3 activity are featured that include contacting NLRP1 or NLRP3 or both NLRP1 and NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP1 or NLRP3 or both NLRP1 and NLRP3 (also referred to herein as "NLRP1/3"), as well as in vivo methods.

In a further aspect, methods of treatment of a disease in which NLRP1/3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP1/3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP1/3" is meant to include, without limitation, nucleic acids, polynucleotides, oligonucleotides, sense and antisense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP1/3, or a pharmaceutically acceptable salt and/or hydrate and/or cocrystal thereof;) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclic rings include five-membered, six-membered, and seven-membered heterocyclic rings.

The term "cycloalkyl" as used herein includes an aromatic or nonaromatic cyclic hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to an aromatic or nonaromatic 5-8 membered monocyclic, 8-12 membered bicyclic, or 11-14 membered tricyclic ring system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "hydroxy" refers to an OH group.

The term "amino" refers to an NH$_2$ group.

The term "oxo" refers to O. By way of example, substitution of a CH$_2$ a group with oxo gives a C=O group.

As used herein, a curved line connecting two atoms indicates a chain of length as specified by the recited number or number range. For example, a chain connecting an atom "Atom 1" to an atom "Atom 2" may be depicted as

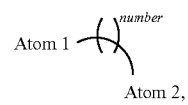

where the number outside the parenthetical indicates the number or range of numbers in the chain.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The details of one or more embodiments of the invention are set forth in the accompanying drawings and the description below. Other features and advantages of the invention will be apparent from the description and drawings, and from the claims.

DETAILED DESCRIPTION

In some embodiments, provided herein is a compound of Formula A

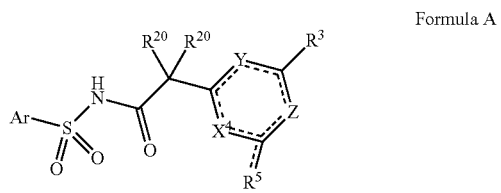

Formula A or a pharmaceutically acceptable salt thereof, wherein:

Ar is a heteroaryl group

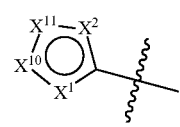

or an aryl or heteroaryl group

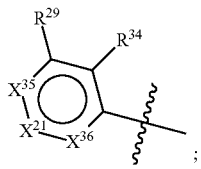

$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;
$X^{35}$ is N or $CR^{35}$;
$X^{21}$ is N or $CR^{21}$;
$X^{36}$ is N or $CR^{36}$;
$X^4$ is $CR^4$, N or $NR^{24}$;
each $R^{20}$ is the same or different and is independently selected from hydrogen and $C_1$-$C_6$ alkyl;
Y is N or $CR^2$;
Z is N or $CR^8$;
$R^8$ is selected from H, CN, halo $CO_2C_1$-$C_6$ alkyl, $CO_2C_3$-$C_8$ cycloalkyl, $CONR^{11}R^{12}$, $C_1$-$C_6$ alkyl, $C_1$-$C_6$ alkoxy, $C_1$-$C_6$ haloalkoxy, and $C_1$-$C_6$ haloalkyl;
$R^2$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^3$ is hydrogen, $C_1$-$C_6$ alkoxy, halo, $C_1$-$C_6$ haloalkyl, CN, $C_1$-$C_6$ haloalkoxy, $C_3$-$C_7$ cycloalkyl or $C_1$-$C_6$ alkyl optionally substituted with hydroxy;
$R^4$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^{24}$ is absent and $R^5$ is hydrogen, $C_1$-$C_6$ alkoxy, halo, $C_1$-$C_6$ haloalkyl, CN, $C_1$-$C_6$ haloalkoxy, $C_3$-$C_7$ cycloalkyl or $C_1$-$C_6$ alkyl optionally substituted with hydroxy;
or $R^{24}$ is $C_1$-$C_6$ alkyl or $C_3$-$C_8$ cycloalkyl and $R^5$ is =O; provided that at least one of $R^2$, $R^3$, $R^4$ and $R^5$ is not hydrogen;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

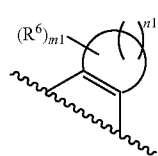

Ring A and ring B is

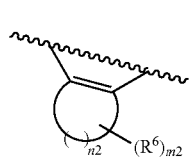

Ring B wherein
ring A is a carbocyclic ring or a heterocyclic ring containing 1 or 2 heteroatoms independently selected from O, N, and S;

n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, F, $C_1$-$C_6$ alkyl, $C_1$-$C_6$ alkoxy, $NR^{11}R^{12}$, oxo, and =$NR^{13}$;
or two $R^6$ taken together with the atom or atoms connecting them form a 3-to-8-membered carbocyclic or saturated heterocyclic ring containing 1 or 2 heteroatoms independently selected from O, N, and S;
each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkyl, $C_1$-$C_6$ alkoxy, $NR^{11}NR^{12}$, =$NR^{13}$, $COOC_1$-$C_6$ alkyl, $C_6$-$C_{10}$ aryl, and $CONR^{11}R^{12}$;
and each of $R^1$, $R^{10}$, $R^{41}$ and $R^{42}$ when bonded to nitrogen is independently selected from H, $C_1$-$C_6$ alkyl, $C_1$-$C_6$ haloalkyl, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl, $S(O_2)C_1$-$C_6$ alkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkyl, $C_1$-$C_6$ alkoxy, $NR^{11}R^{12}$, =$NR^{13}$, $COOC_1$-$C_6$ alkyl, $C_6$-$C_{10}$ aryl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;
each of $R^{34}$, $R^{29}$, $R^{35}$, $R^{21}$ and $R^{36}$ is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $CONR^{11}R^{12}$, $C_3$-$C_7$ cycloalkyl, 3- to 7-membered heterocycloalkyl, $C_6$-$C_{10}$ aryl, $OC_1$-$C_6$ alkyl, $NH_2$, $NHC_1$-$C_6$ alkyl, $N(C_1$-$C_6$ alkyl$)_2$, $NO_2$, $COC_1$-$C_6$ alkyl, $SF_5$ and $S(O_2)C_1$-$C_6$ akyl;
wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $C_1$-$C_6$ alkyl, $NR^{11}R^{12}$, =$NR^{13}$, $COOC_1$-$C_6$ alkyl, $CONR^{11}R^{12}$, $C_3$-$C_7$ cycloalkyl, 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl), NHCO (3- to 7-membered heterocycloalkyl), and $NHCOC_2$-$C_6$ alkynyl,
wherein the $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl,
or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring, a five-to-eight-membered carbocyclic non-aromatic ring, a five- or six-membered heteroaromatic ring or a five-to-eight-membered heterocyclic non-aromatic ring, wherein the ring formed by the two groups together with the adjacent ring carbons is optionally substituted with one or more $OC_1-C_6$ alkyl, $NH_2$, $NHC_1-C_6$ alkyl, $N(C_1-C_6$ alkyl$)_2$;

$R^{13}$ is $C_1-C_6$ alkyl;

each of $R^{11}$ and $R^{12}$ at each occurrence is independently selected from hydrogen, $C_1-C_6$ alkyl, $CO_2R^{15}$ and $CONR^{17}R^{18}$; or $R^{11}$ and $R^{12}$ taken together with the nitrogen they are attached to form a 3- to 7-membered ring optionally containing one or more heteroatoms in addition to the nitrogen they are attached to;

$R^{15}$ is $C_1-C_6$ alkyl;

each of $R^{17}$ and $R^{18}$ at each occurrence is independently selected from hydrogen and $C_1-C_6$ alkyl.

In some embodiments, provided herein is a compound of Formula I

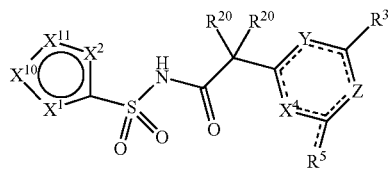

Formula I or a pharmaceutically acceptable salt thereof, wherein:
$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;
$X^4$ is $CR^4$, N or $NR^{24}$;

each $R^{20}$ is the same or different and is independently selected from hydrogen and $C_1-C_6$ alkyl;

Y is N or $CR^2$;
Z is N or $CR^8$;

$R^8$ is selected from H, CN, halo, $CO_2C_1-C_6$ alkyl, $CO_2C_3-C_8$ cycloalkyl, $CONR^{11}R^{12}$, $C_1-C_6$ alkyl, $C_1-C_6$ alkoxy, $C_1-C_6$ haloalkoxy, and $C_1-C_6$ haloalkyl;

$R^2$ is hydrogen, $C_1-C_6$ alkoxy, halo, $C_1-C_6$ haloalkyl, $C_3-C_7$ cycloalkyl or $C_1-C_6$ alkyl optionally substituted with hydroxy;

$R^3$ is hydrogen, $C_1-C_6$ alkoxy, halo, $C_1-C_6$ haloalkyl, CN, $C_1-C_6$ haloalkoxy, $C_3-C_7$ cycloalkyl or $C_1-C_6$ alkyl optionally substituted with hydroxy;

$R^4$ is hydrogen, $C_1-C_6$ alkoxy, halo, $C_1-C_6$ haloalkyl, $C_3-C_7$ cycloalkyl or $C_1-C_6$ alkyl optionally substituted with hydroxy;

$R^{24}$ is absent and $R^5$ is hydrogen, $C_1-C_6$ alkoxy, halo, $C_1-C_6$ haloalkyl, CN, $C_1-C_6$ haloalkoxy, $C_3-C_7$ cycloalkyl or $C_1-C_6$ alkyl optionally substituted with hydroxy;

or $R^{24}$ is $C_1-C_6$ alkyl or $C_3-C_8$ cycloalkyl and $R^5$ is =O; provided that at least one of $R^2$, $R^3$, $R^4$ and $R^5$ is not hydrogen;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

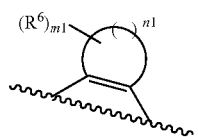

Ring A and ring B is

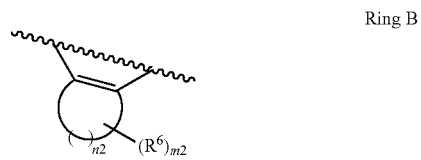

Ring B wherein ring A is a carbocyclic ring or a heterocyclic ring containing 1 or 2 heteroatoms independently selected from O, N, and S;

n1 is from 2 to 5;

m1 is from 1 to 10;

wherein ring B is a carbocyclic ring or a heterocyclic ring containing 1 or 2 heteroatoms independently selected from O, N, and S;

n2 is from 2 to 5;

m2 is from 1 to 10;

wherein each $R^6$ in each ring is the same or different and is selected from H, F, $C_1-C_6$ alkyl, $C_1-C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

each of $R^1$, $R^{10}$, $R^{41}$ and $R^{42}$ when bonded to carbon is independently selected from H, $C_1-C_6$ alkyl, $C_1-C_6$ haloalkyl, CN, halo, $CO_2C_1-C_6$ alkyl, $CO_2C_3-C_8$ cycloalkyl, $C_6-C_{10}$ aryl, $CONR^{11}R^{12}$, $C_3-C_7$ cycloalkyl, $S(O_2)C_1-C_6$ akyl and 3- to 7-membered heterocycloalkyl, wherein the $C_1-C_6$ alkyl, $C_3-C_7$ cycloalkyl and 3- to 7-membered heterocycloalkyl is optionally substituted with one or more substituents each independently selected from hydroxy, oxo, $C_1-C_6$ alkyl, $C_1-C_6$ alkoxy, $NR^{11}R^{12}$, $=NR^{13}$, $COOC_1-C_6$ alkyl, $C_6-C_{10}$ aryl, and $CONR^{11}R^{12}$;

and each of $R^1$, $R^{10}$, $R^{41}$ and $R^{42}$ when bonded to nitrogen is independently selected from H, $C_1-C_6$ alkyl, $C_1-C_6$ haloalkyl, $CO_2C_1-C_6$ alkyl, $CO_2C_3-C_8$ cycloalkyl, $C_6-C_{10}$ aryl, $CONR^{11}R^{12}$, $C_3-C_7$ cycloalkyl, $S(O_2)C_1-C_6$ akyl and 3- to 7-membered heterocycloalkyl, wherein the $C_1-C_6$ alkyl, $C_3-C_7$ cycloalkyl and 3- to 7-membered heterocycloalkyl is optionally substituted with one or more substituents each independently selected from hydroxy, $C_1-C_6$ alkyl, oxo, $C_1-C_6$ alkoxy, $NR^{11}R^{12}$, $=NR^{13}$, $COOC_1-C_6$ alkyl, $C_6-C_{10}$ aryl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1-C_6$ alkoxy, $NR^{11}R^{12}$, $=NR^{13}$, $COOC_1-C_6$ alkyl, and $CONR^{11}R^{12}$;

$R^{13}$ is $C_1-C_6$ alkyl;

each of $R^{11}$ and $R^{12}$ at each occurrence is independently selected from hydrogen, $C_1-C_6$ alkyl, $CO_2R^{15}$ and $CONR^{17}R^{18}$; or $R^{11}$ and $R^{12}$ taken together with the nitrogen they are attached to form a 3- to 7-membered ring optionally containing one or more heteroatoms in addition to the nitrogen they are attached to;

$R^{15}$ is $C_1-C_6$ alkyl;

each of $R^{17}$ and $R^{18}$ at each occurrence is independently selected from hydrogen and $C_1-C_6$ alkyl.

In some embodiments, provided herein is a compound of Formula II

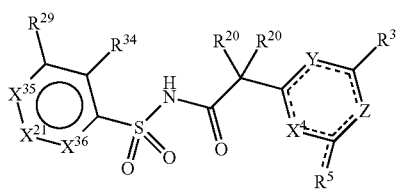

Formula II or a pharmaceutically acceptable salt thereof, wherein:
$X^{35}$ is N or $CR^{35}$;
$X^{21}$ is N or $CR^{21}$;
$X^{36}$ is N or $CR^{36}$;
$X^4$ is $CR^4$, N or $NR^{24}$;
each $R^{20}$ is the same or different and is independently selected from hydrogen and $C_1$-$C_6$ alkyl;
Y is N or $CR^2$;
Z is N or $CR^8$;
$R^8$ is selected from H, CN, halo, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ alkoxy, $C_1$-$C_6$ haloalkoxy, and $C_1$-$C_6$ haloalkyl;
$R^2$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^3$ is hydrogen, $C_1$-$C_6$ alkoxy, halo, $C_1$-$C_6$ haloalkyl, CN, $C_1$-$C_6$ haloalkoxy, $C_3$-$C_7$ cycloalkyl or $C_1$-$C_6$ alkyl optionally substituted with hydroxy;
$R^4$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^{24}$ is absent and $R^5$ is hydrogen, $C_1$-$C_6$ alkoxy, halo, $C_1$-$C_6$ haloalkyl, CN, $C_1$-$C_6$ haloalkoxy, $C_3$-$C_7$ cycloalkyl or $C_1$-$C_6$ alkyl optionally substituted with hydroxy;
or $R^{24}$ is $C_1$-$C_6$ alkyl or $C_3$-$C_8$ cycloalkyl and $R^5$ is =O; provided that at least one of $R^2$, $R^3$, $R^4$ and $R^5$ is not hydrogen;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

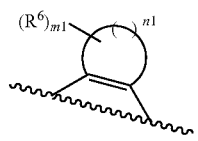

Ring A and ring B is

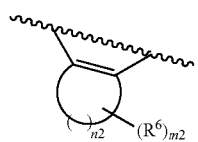

Ring B wherein
ring A is a carbocyclic ring or a heterocyclic ring containing 1 or 2 heteroatoms independently selected from O, N, and S;
n1 is from 2 to 5;
m1 is from 1 to 10;

wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, F, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
each of $R^{34}$, $R^{29}$, $R^{35}$, $R^{21}$ and $R^{36}$ is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $CONR^{11}R^{12}$, $C_3$-$C_7$ cycloalkyl, 3- to 7-membered heterocycloalkyl, $C_6$-$C_{10}$ aryl, $OC_1$-$C_6$ alkyl, $NH_2$, $NHC_1$-$C_6$ alkyl, $N(C_1$-$C_6$ alkyl$)_2$, $NO_2$, $COC_1$-$C_6$ alkyl, $SF_5$ and $S(O_2)C_1$-$C_6$ akyl;
wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $C_1$-$C_6$ alkyl, $NR^{11}R^{12}$, $=NR^{13}$, $COOC_1$-$C_6$ alkyl, $CONR^{11}R^{12}$, $C_3$-$C_7$ cycloalkyl, 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl), NHCO (3- to 7-membered heterocycloalkyl), and $NHCOC_2$-$C_6$ alkynyl,
wherein the $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl,
or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring, a five-to-eight-membered carbocyclic non-aromatic ring, a five- or six-membered heteroaromatic ring or a five-to-eight-membered heterocyclic non-aromatic ring, wherein the ring formed by the two groups together with the adjacent ring carbons is optionally substituted with one or more $OC_1$-$C_6$ alkyl, $NH_2$, $NHC_1$-$C_6$ alkyl, $N(C_1$-$C_6$ alkyl$)_2$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$; or $R^{11}$ and $R^{12}$ taken together with the nitrogen they are attached to form a 3- to 7-membered ring optionally containing one or more heteroatoms in addition to the nitrogen they are attached to;
$R^{15}$ is $C_1$-$C_6$ alkyl;
each of $R^{17}$ and $R^{18}$ at each occurrence is independently selected from hydrogen and $C_1$-$C_6$ alkyl.

In some embodiments, provided herein is a compound of Formula A

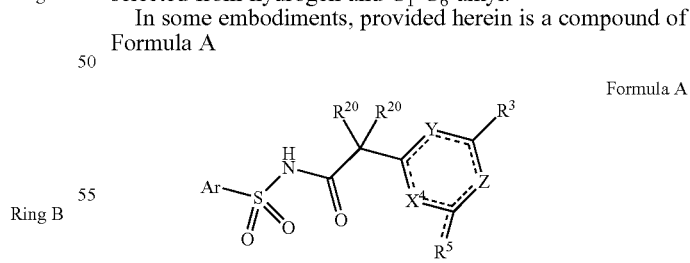

Formula A or a pharmaceutically acceptable salt thereof, wherein:
Ar is a heteroaryl group

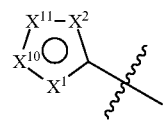

or an aryl or heteroaryl group

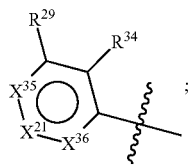

$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;
$X^{35}$ is N or $CR^{35}$;
$X^{21}$ is N or $CR^{21}$;
$X^{36}$ is N or $CR^{36}$;
$X^4$ is $CR^4$, N or $NR^{24}$;
each $R^{20}$ is the same or different and is independently selected from hydrogen and $C_1$-$C_6$ alkyl;
Y is N or $CR^2$;
Z is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^3$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^4$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^{24}$ is absent and $R^5$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
or $R^{24}$ is $C_1$-$C_6$ alkyl or $C_3$-$C_8$ cycloalkyl and $R^5$ is =O;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

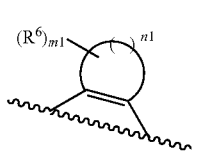

Ring A and ring B is

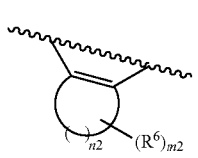

Ring B wherein
ring A is a carbocyclic ring or a heterocyclic ring containing 1 or 2 heteroatoms independently selected from O, N, and S;

n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and =$NR^{13}$;
or two $R^6$ taken together with the atom or atoms connecting them form a 3-to-8-membered carbocyclic or saturated heterocyclic ring containing 1 or 2 heteroatoms independently selected from O, N, and S;
each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $C_6$-$C_{10}$ aryl, and $CONR^{11}R^{12}$;
and each of $R^1$, $R^{10}$, $R^{41}$ and $R^{42}$ when bonded to nitrogen is independently selected from H, $C_1$-$C_6$ alkyl, $C_1$-$C_6$ haloalkyl, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $C_6$-$C_{10}$ aryl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;
each of $R^{34}$, $R^{29}$, $R^{35}$, $R^{21}$ and $R^{36}$ is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $CONR^{11}R^{12}$, $C_3$-$C_7$ cycloalkyl, 3- to 7-membered heterocycloalkyl, $C_6$-$C_{10}$ aryl, $OC_1$-$C_6$ alkyl, $NH_2$, $NHC_1$-$C_6$ alkyl, $N(C_1$-$C_6$ alkyl$)_2$, $NO_2$, $COC_1$-$C_6$ alkyl,
wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $CONR^{11}R^{12}$, $C_3$-$C_7$ cycloalkyl, 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl), NHCO (3- to 7-membered heterocycloalkyl), and $NHCOC_2$-$C_6$ alkynyl,
wherein the $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl,
or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring, a five-to-eight-membered carbocyclic non-aromatic ring, a five- or six-membered heteroaromatic ring or a five-to-eight-membered heterocyclic non-aromatic ring, wherein the ring formed by the two groups together with the adjacent ring carbons is optionally substituted with one or more $OC_1$-$C_6$ alkyl, $NH_2$, $NHC_1$-$C_6$ alkyl, $N(C_1$-$C_6$ alkyl)$_2$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl.

In some embodiments, provided herein is a compound of Formula I

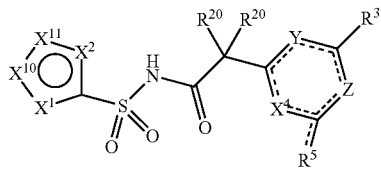

Formula I or a pharmaceutically acceptable salt thereof, wherein:

$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;
$X^4$ is $CR^4$, N or $NR^{24}$;

each $R^{20}$ is the same or different and is independently selected from hydrogen and $C_1$-$C_6$ alkyl;

Y is N or $CR^2$;

Z is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;

$R^2$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;

$R^3$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;

$R^4$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;

$R^{24}$ is absent and $R^5$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;

or $R^{24}$ is $C_1$-$C_6$ alkyl or $C_3$-$C_8$ cycloalkyl and $R^5$ is =O;

provided that at least one of $R^2$, $R^3$, $R^4$ and $R^5$ is not hydrogen, and that $R^2$ and $R^4$ are not both hydroxymethyl;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

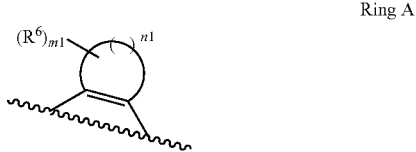

Ring A and ring B is

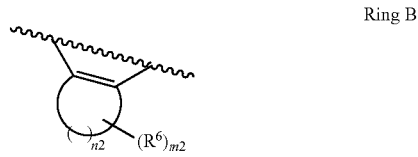

Ring B wherein ring A is a carbocyclic ring or a heterocyclic ring containing 1 or 2 heteroatoms independently selected from O, N, and S;

n1 is from 2 to 5;

m1 is from 1 to 10;

wherein ring B is a carbocyclic ring or a heterocyclic ring containing 1 or 2 heteroatoms independently selected from O, N, and S;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and =$NR^{13}$;

or two $R^6$ taken together with the atom or atoms connecting them form a 3-to-8-membered carbocyclic or saturated heterocyclic ring containing 1 or 2 heteroatoms independently selected from O, N, and S;

each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $C_6$-$C_{10}$ aryl, and $CONR^{11}R^{12}$;

and each of $R^1$, $R^{10}$, $R^{41}$ and $R^{42}$, when bonded to nitrogen is independently selected from H, $C_1$-$C_6$ alkyl, $C_1$-$C_6$ haloalkyl, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $C_6$-$C_{10}$ aryl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl.

In some embodiments, provided herein is a compound of Formula II

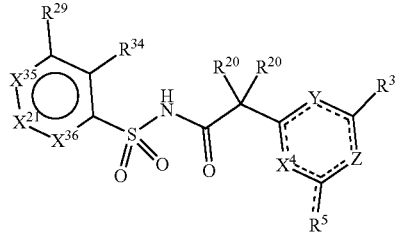

Formula II or a pharmaceutically acceptable salt thereof, wherein:
$X^{35}$ is N or $CR^{35}$;
$X^{21}$ is N or $CR^{21}$;
$X^{36}$ is N or $CR^{36}$;
$X^4$ is $CR^4$, N or $NR^{24}$;
each $R^{20}$ is the same or different and is independently selected from hydrogen and $C_1$-$C_6$ alkyl;
Y is N or $CR^2$;
Z is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^3$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^4$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^{24}$ is absent and $R^5$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
or $R^{24}$ is $C_1$-$C_6$ alkyl or $C_3$-$C_8$ cycloalkyl and $R^5$ is =O;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is Ring A

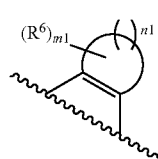

and ring B is

Ring B

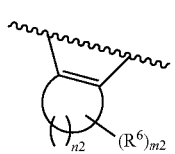

wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and =$NR^{13}$;
or two $R^6$ taken together with the atom or atoms connecting them form a 3-to-8-membered carbocyclic or saturated heterocyclic ring containing 1 or 2 heteroatoms independently selected from O, N, and S;
each of $R^{34}$, $R^{29}$, $R^{35}$, $R^{21}$ and $R^{36}$ is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $CONR^{11}R^{12}$, $C_3$-$C_7$ cycloalkyl, 3- to 7-membered heterocycloalkyl, $C_6$-$C_{10}$ aryl, $OC_1$-$C_6$ alkyl, $NH_2$, $NHC_1$-$C_6$ alkyl, $N(C_1$-$C_6$ alkyl$)_2$, $NO_2$, $COC_1$-$C_6$ alkyl,
wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $CONR^{11}R^{12}$, $C_3$-$C_7$ cycloalkyl, 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl), NHCO (3- to 7-membered heterocycloalkyl), and $NHCOC_2$-$C_6$ alkynyl,
wherein the $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl,
or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring, a five-to-eight-membered carbocyclic non-aromatic ring, a five- or six-membered heteroaromatic ring or a five-to-eight-membered heterocyclic non-aromatic ring, wherein the ring formed by the two groups together with the adjacent ring carbons is optionally substituted with one or more $OC_1$-$C_6$ alkyl, $NH_2$, $NHC_1$-$C_6$ alkyl, $N(C_1$-$C_6$ alkyl$)_2$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl.

In some embodiments the variables shown in the formulae herein are as follows:
The Groups $X^1$, $X^{10}$, $X^{11}$ and $X^2$
In some embodiments of one or more formulae herein, $X^1$ is O.
In some embodiments of one or more formulae herein, $X^1$ is S.
In some embodiments of one or more formulae herein, $X^1$ is N.
In some embodiments of one or more formulae herein, $X^1$ is $CR^{41}$.
In some embodiments of one or more formulae herein, $X^1$ is $NR^{41}$.

In some embodiments of one or more formulae herein, $X^{10}$ is O.

In some embodiments of one or more formulae herein, $X^{10}$ is S.

In some embodiments of one or more formulae herein, $X^{10}$ is N.

In some embodiments of one or more formulae herein, $X^{10}$ is $CR^{10}$.

In some embodiments of one or more formulae herein, $X^{10}$ is $NR^{10}$.

In some embodiments of one or more formulae herein, $X^{11}$ is O.

In some embodiments of one or more formulae herein, $X^{11}$ is S.

In some embodiments of one or more formulae herein, $X^{11}$ is N.

In some embodiments of one or more formulae herein, $X^{11}$ is $CR^{1}$.

In some embodiments of one or more formulae herein, $X^{11}$ is $NR^{1}$.

In some embodiments of one or more formulae herein, $X^{2}$ is O.

In some embodiments of one or more formulae herein, $X^{2}$ is S.

In some embodiments of one or more formulae herein, $X^{2}$ is N.

In some embodiments of one or more formulae herein, $X^{2}$ is $CR^{42}$.

In some embodiments of one or more formulae herein, $X^{2}$ is $NR^{42}$.

The Groups $X^{35}$, $X^{21}$, and $X^{36}$

In some embodiments of one or more formulae herein, $X^{35}$ is N.

In some embodiments of one or more formulae herein, $X^{35}$ is $CR^{35}$.

In some embodiments of one or more formulae herein, $X^{21}$ is N.

In some embodiments of one or more formulae herein, $X^{21}$ is $CR^{21}$.

In some embodiments of one or more formulae herein, $X^{36}$ is N.

In some embodiments of one or more formulae herein, $X^{36}$ is $CR^{36}$.

The Group $X^{4}$

In some embodiments of one or more formulae herein, $X^{4}$ is $CR^{4}$.

In some embodiments of one or more formulae herein, $X^{4}$ is N.

In some embodiments of one or more formulae herein, $X^{4}$ is $NR^{24}$.

The Group $R^{20}$

In some embodiments of one or more formulae herein, each $R^{20}$ is hydrogen.

In some embodiments of one or more formulae herein, each one $R^{20}$ is $C_1$-$C_6$ alkyl, In some embodiments of one or more formulae herein, one $R^{20}$ is hydrogen and the other $R^{20}$ is $C_1$-$C_6$ alkyl.

In some embodiments of one or more formulae herein, one $R^{20}$ is hydrogen, the other $R^{20}$ is $C_1$-$C_6$ alkyl, and the carbon bonded to each $R^{20}$ has (S) stereochemistry.

In some embodiments of one or more formulae herein, one $R^{20}$ is hydrogen, the other $R^{20}$ is $C_1$-$C_6$ alkyl, and the carbon bonded to each $R^{20}$ has (R) stereochemistry.

The Group Y

In some embodiments of one or more formulae herein, Y is $CR^{2}$.

In some embodiments of one or more formulae herein, Y is N.

The Groups $R^{2}$, $R^{4}$, $R^{3}$, $R^{5}$ and $R^{24}$

In some embodiments of one or more formulae herein, $R^{2}$ is hydrogen.

In some embodiments of one or more formulae herein, $R^{2}$ is $C_1$-$C_6$ alkoxy.

In some embodiments of one or more formulae herein, $R^{2}$ is methoxy.

In some embodiments of one or more formulae herein, $R^{2}$ is halo.

In some embodiments of one or more formulae herein, $R^{2}$ is $C_1$-$C_6$ haloalkyl.

In some embodiments of one or more formulae herein, $R^{2}$ is $CF_3$.

In some embodiments of one or more formulae herein, $R^{2}$ is $C_3$-$C_7$ cycloalkyl.

In some embodiments of one or more formulae herein, $R^{2}$ is $C_1$-$C_6$ alkyl optionally substituted with hydroxy.

In some embodiments of one or more formulae herein, $R^{2}$ is isopropyl.

In some embodiments of one or more formulae herein, $R^{2}$ is methyl.

In some embodiments of one or more formulae herein, $R^{3}$ is hydrogen.

In some embodiments of one or more formulae herein, $R^{3}$ is $C_1$-$C_6$ alkoxy.

In some embodiments of one or more formulae herein, $R^{3}$ is methoxy.

In some embodiments of one or more formulae herein, $R^{3}$ is $C_1$-$C_6$ haloalkoxy.

In some embodiments of one or more formulae herein, $R^{3}$ is CN.

In some embodiments of one or more formulae herein, $R^{3}$ is halo.

In some embodiments of one or more formulae herein, $R^{3}$ is $C_1$-$C_6$ haloalkyl.

In some embodiments of one or more formulae herein, $R^{3}$ is $CF_3$.

In some embodiments of one or more formulae herein, $R^{3}$ is $C_3$-$C_7$ cycloalkyl.

In some embodiments of one or more formulae herein, $R^{3}$ is $C_1$-$C_6$ alkyl optionally substituted with hydroxy.

In some embodiments of one or more formulae herein, $R^{3}$ is isopropyl.

In some embodiments of one or more formulae herein, $R^{3}$ is methyl.

In some embodiments of one or more formulae herein, $R^{4}$ is hydrogen.

In some embodiments of one or more formulae herein, $R^{4}$ is $C_1$-$C_6$ alkoxy.

In some embodiments of one or more formulae herein, $R^{4}$ is methoxy.

In some embodiments of one or more formulae herein, $R^{4}$ is halo.

In some embodiments of one or more formulae herein, $R^{4}$ is $C_1$-$C_6$ haloalkyl.

In some embodiments of one or more formulae herein, $R^{4}$ is $CF_3$.

In some embodiments of one or more formulae herein, $R^{4}$ is $C_3$-$C_7$ cycloalkyl.

In some embodiments of one or more formulae herein, $R^{4}$ is $C_1$-$C_6$ alkyl optionally substituted with hydroxy.

In some embodiments of one or more formulae herein, $R^{4}$ is isopropyl.

In some embodiments of one or more formulae herein, $R^{4}$ is methyl.

In some embodiments of one or more formulae herein, $R^5$ is hydrogen.

In some embodiments of one or more formulae herein, $R^5$ is $C_1$-$C_6$ alkoxy.

In some embodiments of one or more formulae herein, $R^5$ is methoxy.

In some embodiments of one or more formulae herein, $R^5$ is $C_1$-$C_6$ haloalkoxy.

In some embodiments of one or more formulae herein, $R^5$ is CN.

In some embodiments of one or more formulae herein, $R^5$ is halo.

In some embodiments of one or more formulae herein, $R^5$ is $C_1$-$C_6$ haloalkyl.

In some embodiments of one or more formulae herein, $R^5$ is $CF_3$.

In some embodiments of one or more formulae herein, $R^5$ is $C_3$-$C_7$ cycloalkyl.

In some embodiments of one or more formulae herein, $R^5$ is $C_1$-$C_6$ alkyl optionally substituted with hydroxy.

In some embodiments of one or more formulae herein, each of $R^2$ and $R^4$ is hydrogen.

In some embodiments of one or more formulae herein, each of $R^2$ and $R^4$ is $C_1$-$C_6$ alkyl optionally substituted with hydroxy.

In some embodiments of one or more formulae herein, $R^5$ is isopropyl.

In some embodiments of one or more formulae herein, $R^5$ is methyl.

In some embodiments of one or more formulae herein, each of $R^2$ and $R^4$ is isopropyl.

In some embodiments of one or more formulae herein, each of $R^2$ and $R^4$ is t-butyl.

In some embodiments of one or more formulae herein, each of $R^2$ and $R^4$ is methyl.

In some embodiments of one or more formulae herein, each of $R^2$ and $R^4$ is hydroxymethyl.

In some embodiments of one or more formulae herein, each of $R^3$ and $R^5$ is hydrogen.

In some embodiments of one or more formulae herein, each of $R^3$ and $R^5$ is $C_1$-$C_6$ alkyl optionally substituted with hydroxy.

In some embodiments of one or more formulae herein, each of $R^3$ and $R^5$ is isopropyl.

In some embodiments of one or more formulae herein, each of $R^3$ and $R^5$ is t-butyl.

In some embodiments of one or more formulae herein, each of $R^3$ and $R^5$ is methyl.

In some embodiments of one or more formulae herein, each of $R^3$ and $R^5$ is hydroxymethyl.

In some embodiments of one or more formulae herein, each of $R^3$ and $R^5$ is hydrogen and each of $R^2$ and $R^4$ is $C_1$-$C_6$ alkyl optionally substituted with hydroxy.

In some embodiments of one or more formulae herein, each of $R^3$ and $R^5$ is hydrogen and each of $R^2$ and $R^4$ is isopropyl.

In some embodiments of one or more formulae herein, each of $R^3$ and $R^5$ is hydrogen and each of $R^2$ and $R^4$ is t-butyl.

In some embodiments of one or more formulae herein, each of $R^3$ and $R^5$ is hydrogen and each of $R^2$ and $R^4$ is methyl.

In some embodiments of one or more formulae herein, each of $R^3$ and $R^5$ is hydrogen and each of $R^2$ and $R^4$ is hydroxymethyl.

In some embodiments of one or more formulae herein, each of $R^2$ and $R^4$ is hydrogen and each of $R^3$ and $R^5$ is $C_1$-$C_6$ alkyl optionally substituted with hydroxy.

In some embodiments of one or more formulae herein, each of $R^2$ and $R^4$ is hydrogen and each of $R^3$ and $R^5$ is isopropyl.

In some embodiments of one or more formulae herein, each of $R^2$ and $R^4$ is hydrogen and each of $R^3$ and $R^5$ is t-butyl.

In some embodiments of one or more formulae herein, each of $R^2$ and $R^4$ is hydrogen and each of $R^3$ and $R^5$ is methyl.

In some embodiments of one or more formulae herein, each of $R^2$ and $R^4$ is hydrogen and each of $R^3$ and $R^5$ is hydroxymethyl.

In some embodiments of one or more formulae herein, $R^2$ and $R^3$ taken together with the carbons connecting them form ring A.

In some embodiments of one or more formulae herein, $R^4$ and $R^5$ taken together with the carbons connecting them form ring B.

In some embodiments of one or more formulae herein, $R^2$ and $R^3$ taken together with the carbons connecting them form ring A and $R^4$ and $R^5$ taken together with the carbons connecting them form ring B.

In some embodiments of one or more formulae herein, at least one of $R^2$, $R^3$, $R^4$ and $R^5$ is not hydrogen.

In some embodiments of one or more formulae herein, $R^2$ and $R^4$ are not both hydroxymethyl.

In some embodiments of one or more formulae herein, at least one of $R^2$, $R^3$, $R^4$ and $R^5$ is not hydrogen and $R^2$ and $R^4$ are not both hydroxymethyl.

In some embodiments of one or more formulae herein, $R^{24}$ is absent and $R^5$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxyl.

In some embodiments of one or more formulae herein, $R^{24}$ is $C_1$-$C_6$ alkyl and $R^5$ is =O.

In some embodiments of one or more formulae herein, $R^{24}$ is $C_3$-$C_8$ cycloalkyl and $R^5$ is =O.

Rings A and B

In some embodiments of one or more formulae herein, ring A is a carbocyclic ring.

In some embodiments of one or more formulae herein, ring A is a heterocyclic ring containing 1 or 2 heteroatoms independently selected from O, N, and S.

In some embodiments of one or more formulae herein, ring B is a carbocyclic ring.

In some embodiments of one or more formulae herein, ring B is a heterocyclic ring containing 1 or 2 heteroatoms independently selected from O, N, and S.

In some embodiments, ring A is a carbocyclic ring and n1 is 3.

In some embodiments, ring A is a carbocyclic ring and n1 is 4.

In some embodiments, ring A is a heterocyclic ring containing 1 or 2 heteroatoms independently selected from O, N, and S and n1 is 3.

In some embodiments, ring A is a heterocyclic ring containing 1 or 2 heteroatoms independently selected from O, N, and S and n1 is 4.

In some embodiments, ring B is a carbocyclic ring and n2 is 3.

In some embodiments, ring B is a carbocyclic ring and n2 is 4.

In some embodiments, ring B is a heterocyclic ring containing 1 or 2 heteroatoms independently selected from O, N, and S and n2 is 3.

In some embodiments, ring B is a heterocyclic ring containing 1 or 2 heteroatoms independently selected from O, N, and S and n2 is 4.

In some embodiments, ring A is the same as ring B.

In some embodiments, ring A is

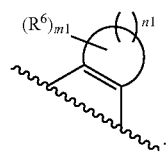

In some embodiments, ring B is

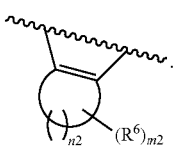

In some embodiments, ring B is

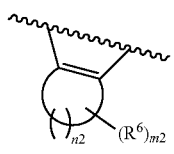

and is the same as ring A.

In some embodiments, ring A is

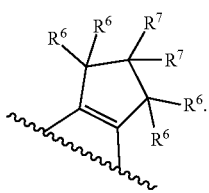

In some embodiments, ring B is

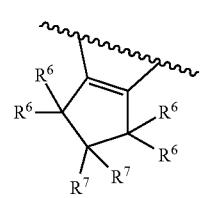

and is the same as ring A.

In some embodiments, ring A is a heterocyclic ring of the formula

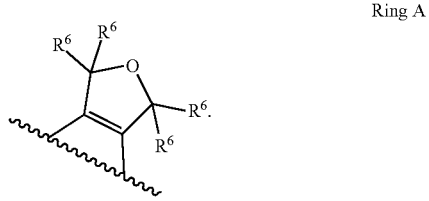

In some embodiments, ring A is a heterocyclic ring of the formula

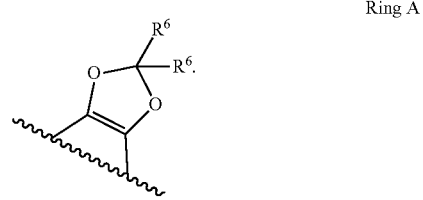

The Groups $R^6$ and $R^7$ and the Variables n1, n2, m1 and m2 in Ring A and Ring B In some embodiments of one or more formulae herein, $R^6$ is H.

In some embodiments of one or more formulae herein, $R^6$ is F.

In some embodiments of one or more formulae herein, $R^6$ is $C_1$-$C_6$ alkyl.

In some embodiments of one or more formulae herein, $R^6$ is $C_1$-$C_6$ alkoxy.

In some embodiments of one or more formulae herein, $R^6$ is methoxy.

In some embodiments of one or more formulae herein, $R^6$ is $NR^{11}R^{12}$.

In some embodiments of one or more formulae herein, $R^6$ is oxo.

In some embodiments of one or more formulae herein, $R^6$ is =$NR^{13}$.

In some embodiments of one or more formulae herein, n1 is 2.

In some embodiments of one or more formulae herein, n1 is 3.

In some embodiments of one or more formulae herein, n1 is 4.

In some embodiments of one or more formulae herein, n1 is 5.

In some embodiments of one or more formulae herein, n2 is 2.

In some embodiments of one or more formulae herein, n2 is 3.

In some embodiments of one or more formulae herein, n2 is 4.

In some embodiments of one or more formulae herein, n2 is 5.

In some embodiments of one or more formulae herein, m1 is 1.

In some embodiments of one or more formulae herein, m1 is 2.

In some embodiments of one or more formulae herein, m1 is 3.

In some embodiments of one or more formulae herein, m1 is 4.

In some embodiments of one or more formulae herein, m2 is 1.

In some embodiments of one or more formulae herein, m2 is 2.

In some embodiments of one or more formulae herein, m2 is 3.

In some embodiments of one or more formulae herein, m2 is 4.

In some embodiments of one or more formulae herein, two $R^6$ taken together with the atom or atoms connecting them form a 3-to-8-membered carbocyclic or saturated heterocyclic ring containing 1 or 2 heteroatoms independently selected from O, N, and S.

In some embodiments of one or more formulae herein, each $R^6$ in each ring is H.

In some embodiments of one or more formulae herein, each $R^6$ in each ring is F.

In some embodiments of one or more formulae herein, each $R^6$ in each ring is $C_1$-$C_6$ alkyl.

In some embodiments of one or more formulae herein, each $R^7$ in each ring is H.

In some embodiments of one or more formulae herein, each $R^7$ in each ring is $C_1$-$C_6$ alkyl.

In some embodiments of one or more formulae herein, each $R^6$ in each ring is H and each $R^7$ in each ring is H.

In some embodiments of one or more formulae herein, each $R^6$ in each ring is H and each $R^7$ in each ring is $C_1$-$C_6$ alkyl.

In some embodiments of one or more formulae herein, each $R^6$ in each ring is $C_1$-$C_6$ alkyl and each $R^7$ in each ring is H.

In some embodiments of one or more formulae herein, each $R^6$ in each ring is $C_1$-$C_6$ alkyl and each $R^7$ in each ring is $C_1$-$C_6$ alkyl.

The Group Z

In some embodiments of one or more formulae herein, Z is N and $X^4$ is $CR^4$.

In some embodiments of one or more formulae herein, Z is N and $X^4$ is $NR^{24}$.

In some embodiments of one or more formulae herein, Z is $CR^8$.

The Group $R^8$

In some embodiments of one or more formulae herein, $R^8$ is selected from H, CN, halo, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ alkoxy, $C_1$-$C_6$ haloalkoxy, and $C_1$-$C_6$ haloalkyl.

In some embodiments of one or more formulae herein, $R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl.

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl.

In some embodiments of one or more formulae herein, $R^8$ is selected from H, CN, Cl, F, $CO_2C_1$-$C_6$ alkyl and $CONH_2$.

In some embodiments of one or more formulae herein, $R^8$ is H.

In some embodiments of one or more formulae herein, $R^8$ is CN.

In some embodiments of one or more formulae herein, $R^8$ is halo.

In some embodiments of one or more formulae herein, $R^8$ is Cl.

In some embodiments of one or more formulae herein, $R^8$ is F.

In some embodiments of one or more formulae herein, $R^8$ is $CO_2C_1$-$C_6$ alkyl.

In some embodiments of one or more formulae herein, $R^8$ is $CO_2C_3$-$C_8$ cycloalkyl.

In some embodiments of one or more formulae herein, $R^8$ is $CONH_2$.

In some embodiments of one or more formulae herein, $R^8$ is $CONR^{11}R^{12}$.

In some embodiments of one or more formulae herein, $R^8$ is $C_1$-$C_6$ alkyl.

In some embodiments of one or more formulae herein, $R^8$ is $C_1$-$C_6$ alkoxy.

In some embodiments of one or more formulae herein, $R^8$ is $C_1$-$C_6$ haloalkoxy.

In some embodiments of one or more formulae herein, $R^8$ is $OCF_3$.

In some embodiments of one or more formulae herein, $R^8$ is $C_1$-$C_6$ haloalkyl.

In some embodiments of one or more formulae herein, $R^8$ is $CF_3$.

The Groups $R^1$, $R^{10}$, $R^{41}$ and $R^{42}$

In some embodiments of one or more formulae herein, each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl, $S(O_2)C_1$-$C_6$ akyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkyl, $C_1$-$C_6$ alkoxy, $N^{11}R^{12}$, $=NR^{13}$, $COOC_1$-$C_6$ alkyl, $C_6$-$C_{10}$ aryl, and $CONR^{11}R^{12}$.

In some embodiments of one or more formulae herein, each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, $C_6$-$C_{10}$ aryl, and $CONR^{11}R^{12}$.

In some embodiments of one or more formulae herein, each of $R^1$, $R^{10}$, $R^{41}$ and $R^{42}$ when bonded to nitrogen is independently selected from H, $C_1$-$C_6$ alkyl, $C_1$-$C_6$ haloalkyl, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, $C_6$-$C_{10}$ aryl, and $CONR^{11}R^{12}$.

In some embodiments of one or more formulae herein, $R^1$ is H.

In some embodiments of one or more formulae herein, $R^1$ is $C_1$-$C_6$ alkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is $C_3$-$C_7$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is $C_1$-$C_6$ alkyl optionally substituted with one or more substituents each independently selected from hydroxy, amino and oxo.

In some embodiments of one or more formulae herein, $R^1$ is $C_1$-$C_6$ alkyl substituted with hydroxy.

In some embodiments of one or more formulae herein, $R^1$ is 2-hydroxy-2-propyl.

In some embodiments of one or more formulae herein, $R^1$ is $C_1$-$C_6$ alkyl optionally substituted with $C_6$-$C_{10}$ aryl.

In some embodiments of one or more formulae herein, $R^1$ is methyl.

In some embodiments of one or more formulae herein, $R^1$ is isopropyl.

In some embodiments of one or more formulae herein, $R^1$ is benzyl.

In some embodiments of one or more formulae herein, $R^1$ is $C_1$-$C_6$ alkyl substituted with $NR^{11}R^{12}$.

In some embodiments of one or more formulae herein, $R^1$ is $C_1$-$C_6$ alkyl substituted with $NH_2$.

In some embodiments of one or more formulae herein, $R^1$ is $C_1$-$C_6$ alkyl substituted with $NH(C_1$-$C_6$ alkyl).

In some embodiments of one or more formulae herein, $R^1$ is $C_1$-$C_6$ alkyl substituted with $N(C_1$-$C_6$ alkyl$)_2$.

In some embodiments of one or more formulae herein, $R^1$ is dimethylaminomethyl.

In some embodiments of one or more formulae herein, $R^1$ is $C_1$-$C_6$ alkyl substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of one or more formulae herein, $R^1$ is $S(O_2)C_1$-$C_6$ akyl.

In some embodiments of one or more formulae herein, $R^1$ is $S(O_2)CH_3$.

In some embodiments of one or more formulae herein, $R^1$ is $C_6$-$C_{10}$ aryl.

In some embodiments of one or more formulae herein, $R^1$ is phenyl.

In some embodiments of one or more formulae herein, $R^1$ is $C_3$-$C_7$ cycloalkyl optionally substituted with one or more substituents each independently selected from hydroxy, amino and oxo.

In some embodiments of one or more formulae herein, $R^1$ is $C_3$-$C_7$ cycloalkyl.

In some embodiments of one or more formulae herein, $R^1$ is $C_3$-$C_7$ cycloalkyl substituted with hydroxy.

In some embodiments of one or more formulae herein, $R^1$ is 1-hydroxy-1-cyclopropyl.

In some embodiments of one or more formulae herein, $R^1$ is 1-hydroxy-1-cyclobutyl.

In some embodiments of one or more formulae herein, $R^1$ is 1-hydroxy-1-cyclopentyl.

In some embodiments of one or more formulae herein, $R^1$ is 3- to 7-membered heterocycloalkyl optionally substituted with one or more substituents each independently selected from hydroxy, amino and oxo.

In some embodiments of one or more formulae herein, $R^1$ 3- to 7-membered heterocycloalkyl.

In some embodiments of one or more formulae herein, $R^1$ is 3- to 7-membered heterocycloalkyl substituted with hydroxy.

In some embodiments of one or more formulae herein, $R^1$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$. In some embodiments of one or more formulae herein, $R^1$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, amino and oxo. In some embodiments, $R^1$ is pyridyl optionally substituted with one or more substituents each independently selected from hydroxy, amino and oxo. In some embodiments, $R^1$ is pyrimidinyl optionally substituted with one or more substituents each independently selected from hydroxy, amino and oxo. In some embodiments, $R^1$ is pyrrolyl optionally substituted with one or more substituents each independently selected from hydroxy, amino and oxo. In some embodiments, $R^1$ is pyrazolyl optionally substituted with one or more substituents each independently selected from hydroxy, amino and oxo. In some embodiments, $R^1$ is imidazolyl optionally substituted with one or more substituents each independently selected from hydroxy, amino and oxo. In some embodiments, $R^1$ is oxazolyl optionally substituted with one or more substituents each independently selected from hydroxy, amino and oxo. In some embodiments, $R^1$ is thiazolyl optionally substituted with one or more substituents each independently selected from hydroxy, amino and oxo.

In some embodiments of one or more formulae herein, $R^{10}$ is selected from H, $C_1$-$C_6$ alkyl, $C_3$-$C_7$ cycloalkyl and 3- to 7-membered heterocycloalkyl, wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is H.

In some embodiments of one or more formulae herein, $R^{10}$ is $C_1$-$C_6$ alkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is $C_3$-$C_7$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is $C_1$-$C_6$ alkyl optionally substituted with one or more substituents each independently selected from hydroxy, amino and oxo.

In some embodiments of one or more formulae herein, $R^{10}$ is $C_1$-$C_6$ alkyl substituted with hydroxy.

In some embodiments of one or more formulae herein, $R^{10}$ is 2-hydroxy-2-propyl.

In some embodiments of one or more formulae herein, $R^{10}$ is $C_1$-$C_6$ alkyl optionally substituted with $C_6$-$C_{10}$ aryl.

In some embodiments of one or more formulae herein, $R^{10}$ is methyl.

In some embodiments of one or more formulae herein, $R^{10}$ is isopropyl.

In some embodiments of one or more formulae herein, $R^{10}$ is benzyl.

In some embodiments of one or more formulae herein, $R^{10}$ is $C_1$-$C_6$ alkyl substituted with $NR^{11}R^{12}$.

In some embodiments of one or more formulae herein, $R^{10}$ is $C_1$-$C_6$ alkyl substituted with $NH_2$.

In some embodiments of one or more formulae herein, $R^{10}$ is $C_1$-$C_6$ alkyl substituted with $NH(C_1$-$C_6$ alkyl).

In some embodiments of one or more formulae herein, $R^{10}$ is $C_1$-$C_6$ alkyl substituted with $N(C_1$-$C_6$ alkyl$)_2$.

In some embodiments of one or more formulae herein, $R^{10}$ is dimethylaminomethyl.

In some embodiments of one or more formulae herein, $R^{10}$ is $C_1$-$C_6$ alkyl substituted with $NR^{11}R^{12}$, wherein and $R^{12}$ taken together with the nitrogen they are attached to form a 3- to 7-membered ring optionally containing one or more heteroatoms in addition to the nitrogen they are attached to.

In some embodiments of one or more formulae herein, $R^{10}$ is $S(O_2)C_1$-$C_6$ akyl.

In some embodiments of one or more formulae herein, $R^{10}$ is $S(O_2)CH_3$.

In some embodiments of one or more formulae herein, $R^{10}$ is $C_6$-$C_{10}$ aryl.

In some embodiments of one or more formulae herein, $R^{10}$ is phenyl.

In some embodiments of one or more formulae herein, $R^{10}$ is $C_3$-$C_7$ cycloalkyl optionally substituted with one or more substituents each independently selected from hydroxy, amino and oxo.

In some embodiments of one or more formulae herein, $R^{10}$ is $C_3$-$C_7$ cycloalkyl.

In some embodiments of one or more formulae herein, $R^{10}$ is $C_3$-$C_7$ cycloalkyl substituted with hydroxy.

In some embodiments of one or more formulae herein, $R^{10}$ is 1-hydroxy-1-cyclopropyl.

In some embodiments of one or more formulae herein, $R^{10}$ is 1-hydroxy-1-cyclobutyl.

In some embodiments of one or more formulae herein, $R^{10}$ is 1-hydroxy-1-cyclopentyl.

In some embodiments of one or more formulae herein, $R^{10}$ is 3- to 7-membered heterocycloalkyl optionally substituted with one or more substituents each independently selected from hydroxy, amino and oxo.

In some embodiments of one or more formulae herein, $R^{10}$ is 3- to 7-membered heterocycloalkyl.

In some embodiments of one or more formulae herein, $R^{10}$ is 3- to 7-membered heterocycloalkyl substituted with hydroxy.

In some embodiments of one or more formulae herein, $R^{10}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$. In some embodiments of one or more formulae herein, $R^{10}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, amino and oxo. In some embodiments, $R^{10}$ is pyridyl optionally substituted with one or more substituents each independently selected from hydroxy, amino and oxo. In some embodiments, $R^{10}$ is pyrimidinyl optionally substituted with one or more substituents each independently selected from hydroxy, amino and oxo. In some embodiments, $R^{10}$ is pyrrolyl optionally substituted with one or more substituents each independently selected from hydroxy, amino and oxo. In some embodiments, $R^{10}$ is pyrazolyl optionally substituted with one or more substituents each independently selected from hydroxy, amino and oxo. In some embodiments, $R^{10}$ is imidazolyl optionally substituted with one or more substituents each independently selected from hydroxy, amino and oxo. In some embodiments, $R^{10}$ is oxazolyl optionally substituted with one or more substituents each independently selected from hydroxy, amino and oxo. In some embodiments, $R^{10}$ is thiazolyl optionally substituted with one or more substituents each independently selected from hydroxy, amino and oxo.

In some embodiments of one or more formulae herein, $R^{41}$ is H.

In some embodiments of one or more formulae herein, $R^{41}$ is $C_1$-$C_6$ alkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{41}$ is $C_3$-$C_7$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{41}$ is $C_1$-$C_6$ alkyl optionally substituted with one or more substituents each independently selected from hydroxy, amino and oxo.

In some embodiments of one or more formulae herein, $R^{41}$ is $C_1$-$C_6$ alkyl substituted with hydroxy.

In some embodiments of one or more formulae herein, $R^{41}$ is 2-hydroxy-2-propyl.

In some embodiments of one or more formulae herein, $R^{41}$ is $C_1$-$C_6$ alkyl optionally substituted with $C_6$-$C_{10}$ aryl.

In some embodiments of one or more formulae herein, $R^{41}$ is methyl.

In some embodiments of one or more formulae herein, $R^{41}$ is isopropyl.

In some embodiments of one or more formulae herein, $R^{41}$ is benzyl.

In some embodiments of one or more formulae herein, $R^{41}$ is $C_6$-$C_{10}$ aryl.

In some embodiments of one or more formulae herein, $R^{41}$ is phenyl.

In some embodiments of one or more formulae herein, $R^{41}$ is $C_1$-$C_6$ alkyl substituted with $NR^{11}R^{12}$.

In some embodiments of one or more formulae herein, $R^{41}$ is $C_1$-$C_6$ alkyl substituted with $NH_2$.

In some embodiments of one or more formulae herein, $R^{41}$ is $C_1$-$C_6$ alkyl substituted with $NH(C_1$-$C_6$ alkyl).

In some embodiments of one or more formulae herein, $R^{41}$ is $C_1$-$C_6$ alkyl substituted with $N(C_1$-$C_6$ alkyl$)_2$.

In some embodiments of one or more formulae herein, $R^{41}$ is dimethylaminomethyl.

In some embodiments of one or more formulae herein, $R^{41}$ is $C_1$-$C_6$ alkyl substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of one or more formulae herein, $R^{41}$ is $S(O_2)C_1$-$C_6$ akyl.

In some embodiments of one or more formulae herein, $R^{41}$ is $S(O_2)CH_3$.

In some embodiments of one or more formulae herein, $R^{41}$ is $C_3$-$C_7$ cycloalkyl optionally substituted with one or more substituents each independently selected from hydroxy, amino and oxo.

In some embodiments of one or more formulae herein, $R^{41}$ is $C_3$-$C_7$ cycloalkyl.

In some embodiments of one or more formulae herein, $R^{41}$ is $C_3$-$C_7$ cycloalkyl substituted with hydroxy.

In some embodiments of one or more formulae herein, $R^{41}$ is 1-hydroxy-1-cyclopropyl.

In some embodiments of one or more formulae herein, $R^{41}$ is 1-hydroxy-1-cyclobutyl.

In some embodiments of one or more formulae herein, $R^{41}$ is 1-hydroxy-1-cyclopentyl.

In some embodiments of one or more formulae herein, $R^{41}$ is 3- to 7-membered heterocycloalkyl optionally substituted with one or more substituents each independently selected from hydroxy, amino and oxo.

In some embodiments of one or more formulae herein, $R^{41}$ is 3- to 7-membered heterocycloalkyl.

In some embodiments of one or more formulae herein, $R^{41}$ is 3- to 7-membered heterocycloalkyl substituted with hydroxy.

In some embodiments of one or more formulae herein, $R^{41}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$. In some embodiments of one or more formulae herein, $R^{41}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, amino and oxo. In some embodiments, $R^{41}$ is pyridyl optionally substituted with one or more substituents each independently selected from hydroxy, amino and oxo. In some embodiments, $R^{41}$ is pyrimidinyl optionally substituted with one or more substituents each independently selected from hydroxy, amino and oxo. In some embodiments, $R^{41}$ is pyrrolyl optionally substituted with one or more substituents each independently selected from hydroxy, amino and oxo. In some embodiments, $R^{41}$ is pyrazolyl optionally substituted with one or more substituents each independently selected from hydroxy, amino and oxo. In some embodiments, $R^{41}$ is imidazolyl optionally substituted with one or more substituents each independently selected from hydroxy, amino and oxo. In some embodiments, $R^{41}$ is oxazolyl optionally substituted with one or more substituents each independently selected from hydroxy, amino and oxo. In some embodiments, $R^{41}$ is thiazolyl optionally substituted with one or more substituents each independently selected from hydroxy, amino and oxo.

In some embodiments of one or more formulae herein, $R^{42}$ is selected from H, $C_1$-$C_6$ alkyl, $C_3$-$C_7$ cycloalkyl and 3- to 7-membered heterocycloalkyl, wherein $R^{42}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{42}$ is H.

In some embodiments of one or more formulae herein, $R^{42}$ is $C_1$-$C_6$ alkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{42}$ is $C_3$-$C_7$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{42}$ is $C_1$-$C_6$ alkyl optionally substituted with one or more substituents each independently selected from hydroxy, amino and oxo.

In some embodiments of one or more formulae herein, $R^{42}$ is $C_1$-$C_6$ alkyl substituted with hydroxy.

In some embodiments of one or more formulae herein, $R^{42}$ is 2-hydroxy-2-propyl.

In some embodiments of one or more formulae herein, $R^{42}$ is $C_1$-$C_6$ alkyl optionally substituted with $C_6$-$C_{10}$ aryl.

In some embodiments of one or more formulae herein, $R^{42}$ is methyl.

In some embodiments of one or more formulae herein, $R^{42}$ is isopropyl.

In some embodiments of one or more formulae herein, $R^{42}$ is benzyl.

In some embodiments of one or more formulae herein, $R^{42}$ is $C_1$-$C_6$ alkyl substituted with $NR^{11}R^{12}$.

In some embodiments of one or more formulae herein, $R^{42}$ is $C_1$-$C_6$ alkyl substituted with $NH_2$.

In some embodiments of one or more formulae herein, $R^{42}$ is $C_1$-$C_6$ alkyl substituted with $NH(C_1$-$C_6$ alkyl).

In some embodiments of one or more formulae herein, $R^{42}$ is $C_1$-$C_6$ alkyl substituted with $N(C_1$-$C_6$ alkyl$)_2$.

In some embodiments of one or more formulae herein, $R^{42}$ is dimethylaminomethyl.

In some embodiments of one or more formulae herein, $R^{42}$ is $C_1$-$C_6$ alkyl substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of one or more formulae herein, $R^{42}$ is $S(O_2)C_1$-$C_6$ akyl.

In some embodiments of one or more formulae herein, $R^{42}$ is $S(O_2)CH_3$.

In some embodiments of one or more formulae herein, $R^{42}$ is $C_6$-$C_{10}$ aryl.

In some embodiments of one or more formulae herein, $R^{42}$ is phenyl.

In some embodiments of one or more formulae herein, $R^{42}$ is $C_3$-$C_7$ cycloalkyl optionally substituted with one or more substituents each independently selected from hydroxy, amino and oxo.

In some embodiments of one or more formulae herein, $R^{42}$ is $C_3$-$C_7$ cycloalkyl.

In some embodiments of one or more formulae herein, $R^{42}$ is $C_3$-$C_7$ cycloalkyl substituted with hydroxy.

In some embodiments of one or more formulae herein, $R^{42}$ is 1-hydroxy-1-cyclopropyl.

In some embodiments of one or more formulae herein, $R^{42}$ is 1-hydroxy-1-cyclobutyl.

In some embodiments of one or more formulae herein, $R^{42}$ is 1-hydroxy-1-cyclopentyl.

In some embodiments of one or more formulae herein, $R^{42}$ is 3- to 7-membered heterocycloalkyl optionally substituted with one or more substituents each independently selected from hydroxy, amino and oxo.

In some embodiments of one or more formulae herein, $R^{42}$ is 3- to 7-membered heterocycloalkyl.

In some embodiments of one or more formulae herein, $R^{42}$ is 3- to 7-membered heterocycloalkyl substituted with hydroxy.

In some embodiments of one or more formulae herein, $R^{42}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$. In some embodiments of one or more formulae herein, $R^{42}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, amino and oxo. In some embodiments, $R^{42}$ is pyridyl optionally substituted with one or more substituents each independently selected from hydroxy, amino and oxo. In some embodiments, $R^{42}$ is pyrimidinyl optionally substituted with one or more substituents each independently selected from hydroxy, amino and oxo. In some embodiments, $R^{42}$ is pyrrolyl optionally substituted with one or more substituents each independently selected from hydroxy, amino and oxo. In some embodiments, $R^{42}$ is pyrazolyl optionally substituted with one or more substituents each independently selected from hydroxy, amino and oxo. In some embodiments, $R^{42}$ is imidazolyl optionally substituted with one or more substituents each independently selected from hydroxy, amino and oxo. In some embodiments, $R^{42}$ is oxazolyl optionally substituted with one or more substituents each independently selected from hydroxy, amino and oxo. In some embodiments, $R^{42}$ is thiazolyl optionally substituted with one or more substituents each independently selected from hydroxy, amino and oxo.

In some embodiments of one or more formulae herein, one of $R^1$ and $R^{10}$ is $C_1$-$C_6$ alkyl optionally substituted with one or more substituents each independently selected from hydroxy, amino and oxo, and the other of $R^1$ and $R^{10}$ is $C_3$-$C_7$ cycloalkyl optionally substituted with one or more substituents each independently selected from hydroxy, amino and oxo.

In some embodiments of one or more formulae herein, one of $R^1$ and $R^{10}$ is 2-hydroxy-2-propyl and the other of $R^1$ and $R^{10}$ is 1-hydroxy-1-cyclobutyl.

In some embodiments of one or more formulae herein, one of $R^1$ and $R^{10}$ is 2-hydroxy-2-propyl and the other of $R^1$ and $R^{10}$ is 1-hydroxy-1-cyclopentyl.

In some embodiments of one or more formulae herein, $R^1$ is optionally substituted with one or more substituents each independently selected from hydroxy, amino and oxo, and the hydroxy, amino or oxo substituent is at the carbon of $R^1$ directly bonded to the five-membered heteroaryl ring of the formulae herein.

In some embodiments of one or more formulae herein, $R^{10}$ is optionally substituted with one or more substituents each independently selected from hydroxy, amino and oxo, and the hydroxy, amino or oxo substituent is at the carbon of $R^{10}$ directly bonded to the five-membered heteroaryl ring of the formulae herein.

In some embodiments of one or more formulae herein, $R^1$ and $R^{10}$ taken together with the atoms connecting them form a three-membered carbocyclic ring.

In some embodiments of one or more formulae herein, $R^1$ and $R^{10}$ taken together with the atoms connecting them form a four-membered carbocyclic ring.

In some embodiments of one or more formulae herein, $R^1$ and $R^{10}$ taken together with the atoms connecting them form a five-membered carbocyclic ring.

In some embodiments of one or more formulae herein, $R^1$ and $R^{10}$ taken together with the atoms connecting them form a six-membered carbocyclic ring.

In some embodiments of one or more formulae herein, $R^1$ and $R^{10}$ taken together with the atoms connecting them form a seven-membered carbocyclic ring.

In some embodiments of one or more formulae herein, $R^1$ and $R^{10}$ taken together with the atoms connecting them form an eight-membered carbocyclic ring.

In some embodiments of one or more formulae herein, $R^1$ and $R^{10}$ taken together with the atoms connecting them form a three-membered heterocyclic ring containing 1 or 2 heteroatoms independently selected from O, N, and S.

In some embodiments of one or more formulae herein, $R^1$ and $R^{10}$ taken together with the atoms connecting them form a four-membered heterocyclic ring containing 1 or 2 heteroatoms independently selected from O, N, and S.

In some embodiments of one or more formulae herein, $R^1$ and $R^{10}$ taken together with the atoms connecting them form a five-membered heterocyclic ring containing 1 or 2 heteroatoms independently selected from O, N, and S.

In some embodiments of one or more formulae herein, $R^1$ and $R^{10}$ taken together with the atoms connecting them form a six-membered heterocyclic ring containing 1 or 2 heteroatoms independently selected from O, N, and S.

In some embodiments of one or more formulae herein, $R^1$ and $R^{10}$ taken together with the atoms connecting them form a seven-membered heterocyclic ring containing 1 or 2 heteroatoms independently selected from O, N, and S.

In some embodiments of one or more formulae herein, $R^1$ and $R^{10}$ taken together with the atoms connecting them form an eight-membered heterocyclic ring containing 1 or 2 heteroatoms independently selected from O, N, and S.

In some embodiments of one or more formulae herein, $R^1$ and $R^{10}$ taken together with the atoms connecting them form a carbocyclic ring substituted with hydroxy.

In some embodiments of one or more formulae herein, $R^1$ and $R^{10}$ taken together with the atoms connecting them form a carbocyclic ring substituted with oxo.

In some embodiments of one or more formulae herein, $R^1$ and $R^{10}$ taken together with the atoms connecting them form a carbocyclic ring substituted with $C_1$-$C_6$ alkoxy.

In some embodiments of one or more formulae herein, $R^1$ and $R^{10}$ taken together with the atoms connecting them form a carbocyclic ring substituted with $NR^{11}R^{12}$.

In some embodiments of one or more formulae herein, $R^1$ and $R^{10}$ taken together with the atoms connecting them form a carbocyclic ring substituted with $=NR^{13}$.

In some embodiments of one or more formulae herein, $R^1$ and $R^{10}$ taken together with the atoms connecting them form a carbocyclic ring substituted with $COOC_1$-$C_6$ alkyl.

In some embodiments of one or more formulae herein, $R^1$ and $R^{10}$ taken together with the atoms connecting them form a carbocyclic ring substituted with $CONR^{11}R^{12}$.

The Groups $R^{11}$ and $R^{12}$

In some embodiments of one or more formulae herein, $R^{11}$ is hydrogen.

In some embodiments of one or more formulae herein, $R^{11}$ is $C_1$-$C_6$ alkyl.

In some embodiments of one or more formulae herein, $R^{11}$ is $CO_2R^{15}$.

In some embodiments of one or more formulae herein, $R^{11}$ is $CONR^{17}R^{18}$.

In some embodiments of one or more formulae herein, $R^{12}$ is hydrogen.

In some embodiments of one or more formulae herein, $R^{12}$ is $C_1$-$C_6$ alkyl.

In some embodiments of one or more formulae herein, $R^{12}$ is $CO_2R^{15}$.

In some embodiments of one or more formulae herein, $R^{12}$ is $CONR^{17}R^{18}$.

In some embodiments of one or more formulae herein, the group $NR^{11}R^{12}$ is amino.

In some embodiments of one or more formulae herein, the group $NR^{11}R^{12}$ is methylamino.

In some embodiments of one or more formulae herein, the group $NR^{11}R^{12}$ is dimethylamino.

In some embodiments of one or more formulae herein, $R^{11}$ and $R^{12}$ taken together with the nitrogen they are attached to in the $NR^{11}R^{12}$ group form a 3- to 7-membered ring optionally containing one or more heteroatoms in addition to the nitrogen they are attached to.

The Groups $R^{13}$, $R^{15}$, $R^{17}$ and $R^{18}$

In some embodiments of one or more formulae herein, $R^{13}$ is $C_1$-$C_6$ alkyl.

In some embodiments of one or more formulae herein, $R^{15}$ is $C_1$-$C_6$ alkyl.

In some embodiments of one or more formulae herein, $R^{17}$ is hydrogen.

In some embodiments of one or more formulae herein, $R^{17}$ is $C_1$-$C_6$ alkyl.

In some embodiments of one or more formulae herein, $R^{18}$ is hydrogen.

In some embodiments of one or more formulae herein, $R^{18}$ is $C_1$-$C_6$ alkyl.

The Groups $R^{34}$, $R^{29}$, $R^{35}$, $R^{21}$ and $R^{36}$

In some embodiments of one or more formulae herein, each of $R^{34}$, $R^{29}$, $R^{35}$, $R^{21}$ and $R^{36}$ is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $CONR^{11}R^{12}$, $C_3$-$C_7$ cycloalkyl, 3- to 7-membered heterocycloalkyl, $C_6$-$C_{10}$ aryl, $OC_1$-$C_6$ alkyl, $NH_2$, $NHC_1$-$C_6$ alkyl, $N(C_1$-$C_6$ alkyl$)_2$, $NO_2$, $COC_1$-$C_6$ alkyl, $SF_5$ and $S(O_2)C_1$-$C_6$ alkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $C_1$-$C_6$ alkyl, $NR^{11}R^{12}$, =$NR^{13}$, $COOC_1$-$C_6$ alkyl, $CONR^{11}R^{12}$, $C_3$-$C_7$ cycloalkyl, 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl), NHCO (3- to 7-membered heterocycloalkyl), and $NHCOC_2$-$C_6$ alkynyl, wherein the $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl, or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring, a five-to-eight-membered carbocyclic non-aromatic ring, a five- or six-membered heteroaromatic ring or a five-to-eight-membered heterocyclic non-aromatic ring, wherein the ring formed by the two groups together with the adjacent ring carbons is optionally substituted with one or more $OC_1$-$C_6$ alkyl, $NH_2$, $NHC_1$-$C_6$ alkyl, $N(C_1$-$C_6$ alkyl$)_2$.

In some embodiments of one or more formulae herein, each of $R^{34}$, $R^{29}$, $R^{35}$, $R^{21}$ and $R^{36}$ is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $CONR^{11}R^{12}$, $C_3$-$C_7$ cycloalkyl, 3- to 7-membered heterocycloalkyl, $C_6$-$C_{10}$ aryl, $OC_1$-$C_6$ alkyl, $NH_2$, $NHC_1$-$C_6$ alkyl, $N(C_1$-$C_6$ alkyl$)_2$, $NO_2$, $COC_1$-$C_6$ alkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, $CONR^{11}R^{12}$, $C_3$-$C_7$ cycloalkyl, 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl), NHCO (3- to 7-membered heterocycloalkyl), and $NHCOC_2$-$C_6$ alkynyl, wherein the $C_6$-$C_{10}$ aryl, 5- to 10-membered heteroaryl, $NHCOC_6$-$C_{10}$ aryl, NHCO (5- to 10-membered heteroaryl) and NHCO (3- to 7-membered heterocycloalkyl) are optionally substituted with one or more substituents independently selected from halo, $C_1$-$C_6$ alkyl, and $OC_1$-$C_6$ alkyl, or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring, a five-to-eight-membered carbocyclic non-aromatic ring, a five- or six-membered heteroaromatic ring or a five-to-eight-membered heterocyclic non-aromatic ring, wherein the ring formed by the two groups together with the adjacent ring carbons is optionally substituted with one or more $OC_1$-$C_6$ alkyl, $NH_2$, $NHC_1$-$C_6$ alkyl, $N(C_1$-$C_6$ alkyl$)_2$.

In some embodiments of one or more formulae herein, $R^{34}$ is H.

In some embodiments of one or more formulae herein, $R^{34}$ is CN.

In some embodiments of one or more formulae herein, $R^{34}$ is $C_1$-$C_6$ alkyl.

In some embodiments of one or more formulae herein, $R^{34}$ is $CH_3$.

In some embodiments of one or more formulae herein, $R^{34}$ is halo.

In some embodiments of one or more formulae herein, $R^{34}$ is Cl.

In some embodiments of one or more formulae herein, $R^{34}$ is F.

In some embodiments of one or more formulae herein, $R^{29}$ is H.

In some embodiments of one or more formulae herein, $R^{29}$ is CN.

In some embodiments of one or more formulae herein, $R^{29}$ is Cl.

In some embodiments of one or more formulae herein, $R^{29}$ is F.

In some embodiments of one or more formulae herein, $R^{29}$ is $C_1$-$C_6$ alkyl.

In some embodiments of one or more formulae herein, $R^{29}$ is $CH_3$.

In some embodiments of one or more formulae herein, $R^{29}$ is $C_1$-$C_6$ alkyl substituted with hydroxy.

In some embodiments of one or more formulae herein, $R^{29}$ is 2-hydroxy-2-propyl.

In some embodiments of one or more formulae herein, $R^{29}$ is 1-hydroxy-1-cyclopropyl.

In some embodiments of one or more formulae herein, $R^{29}$ is $C_1$-$C_6$ alkyl substituted with oxo.

In some embodiments of one or more formulae herein, $R^{29}$ is $C_1$-$C_6$ alkyl substituted with $C_1$-$C_6$ alkoxy.

In some embodiments of one or more formulae herein, $R^{29}$ is $C_1$-$C_6$ alkyl substituted with $NR^{11}R^{12}$.

In some embodiments of one or more formulae herein, $R^{29}$ is $C_1$-$C_6$ alkyl substituted with $COOC_1$-$C_6$ alkyl.

In some embodiments of one or more formulae herein, $R^{29}$ is $C_1$-$C_6$ alkyl substituted with $CONR^{11}R^{12}$.

In some embodiments of one or more formulae herein, $R^{29}$ is $C_1$-$C_6$ alkyl substituted with $C_3$-$C_7$ cycloalkyl.

In some embodiments of one or more formulae herein, $R^{29}$ is $C_1$-$C_6$ alkyl substituted with 3- to 7-membered heterocycloalkyl.

In some embodiments of one or more formulae herein, $R^{29}$ is $C_1$-$C_6$ alkyl substituted with $C_6$-$C_{10}$ aryl.

In some embodiments of one or more formulae herein, $R^{29}$ is $C_1$-$C_6$ alkyl substituted with 5- to 10-membered heteroaryl.

In some embodiments of one or more formulae herein, $R^{29}$ is $C_1$-$C_6$ alkyl substituted with $NR^{11}R^{12}$.

In some embodiments of one or more formulae herein, $R^{29}$ is $C_1$-$C_6$ alkyl substituted with $NH_2$.

In some embodiments of one or more formulae herein, $R^{29}$ is $C_1$-$C_6$ alkyl substituted with $NH(C_1$-$C_6$ alkyl).

In some embodiments of one or more formulae herein, $R^{29}$ is $C_1$-$C_6$ alkyl substituted with $N(C_1$-$C_6$ alkyl)$_2$.

In some embodiments of one or more formulae herein, $R^{29}$ is dimethylaminomethyl.

In some embodiments of one or more formulae herein, $R^{29}$ is $C_1$-$C_6$ alkyl substituted with $NR^{11}R^{12}$ wherein $R^{11}$ and $R^{12}$ taken together with the nitrogen they are attached to form a 3- to 7-membered ring optionally containing one or more heteroatoms in addition to the nitrogen they are attached to.

In some embodiments of one or more formulae herein, $R^{29}$ is $S(O_2)C_1$-$C_6$ alkyl.

In some embodiments of one or more formulae herein, $R^{29}$ is $S(O_2)CH_3$.

In some embodiments of one or more formulae herein, $R^{29}$ is $C_1$-$C_6$ alkyl substituted with $NHCOC_6$-$C_{10}$ aryl.

In some embodiments of one or more formulae herein, $R^{29}$ is $C_1$-$C_6$ alkyl substituted with NHCO (5- to 10-membered heteroaryl).

In some embodiments of one or more formulae herein, $R^{29}$ is $C_1$-$C_6$ alkyl substituted with NHCO (3- to 7-membered heterocycloalkyl).

In some embodiments of one or more formulae herein, $R^{29}$ is $C_1$-$C_6$ alkyl substituted with NHCO (3- to 7-membered heterocycloalkyl) optionally substituted with oxo.

In some embodiments of one or more formulae herein, $R^{29}$ is $C_1$-$C_6$ alkyl substituted with $NHCOC_2$-$C_6$ alkynyl.

In some embodiments of one or more formulae herein, $R^{29}$ is $C_1$-$C_6$ haloalkyl.

In some embodiments of one or more formulae herein, $R^{29}$ is halo.

In some embodiments of one or more formulae herein, $R^{29}$ is $C_3$-$C_7$ cycloalkyl.

In some embodiments of one or more formulae herein, $R^{29}$ is $C_3$-$C_7$ cycloalkyl substituted with hydroxy.

In some embodiments of one or more formulae herein, $R^{29}$ is $C_3$-$C_7$ cycloalkyl substituted with $C_1$-$C_6$ alkoxy.

In some embodiments of one or more formulae herein, $R^{29}$ is $C_3$-$C_7$ cycloalkyl substituted with $NR^{11}R^{12}$.

In some embodiments of one or more formulae herein, $R^{29}$ is $C_3$-$C_7$ cycloalkyl substituted with $COOC_1$-$C_6$ alkyl.

In some embodiments of one or more formulae herein, $R^{29}$ is $C_3$-$C_7$ cycloalkyl substituted with $CONR^{11}R^{12}$.

In some embodiments of one or more formulae herein, $R^{29}$ is $C_3$-$C_7$ cycloalkyl substituted substituted with $C_1$-$C_6$ alkyl.

In some embodiments of one or more formulae herein, $R^{29}$ is 3- to 7-membered heterocycloalkyl.

In some embodiments of one or more formulae herein, $R^{29}$ is 3- to 7-membered nonaromatic monocyclic heterocycloalkyl.

In some embodiments of one or more formulae herein, $R^{29}$ is 1,3-dioxolan-2-yl.

In some embodiments of one or more formulae herein, $R^{29}$ is 3- to 7-membered nonaromatic monocyclic heterocycloalkyl substituted with hydroxy.

In some embodiments of one or more formulae herein, $R^{29}$ is 3- to 7-membered nonaromatic monocyclic heterocycloalkyl substituted with oxo.

In some embodiments of one or more formulae herein, $R^{29}$ is 3- to 7-membered nonaromatic monocyclic heterocycloalkyl substituted with $C_1$-$C_6$ alkoxy.

In some embodiments of one or more formulae herein, $R^{29}$ is 3- to 7-membered heterocycloalkyl substituted with $C_1$-$C_6$ alkyl.

In some embodiments of one or more formulae herein, $R^{29}$ is 3- to 7-membered nonaromatic monocyclic heterocycloalkyl substituted with $C_1$-$C_6$ alkyl.

In some embodiments of one or more formulae herein, $R^{29}$ is 2-methyl-1,3-dioxolan-2-yl.

In some embodiments of one or more formulae herein, $R^{29}$ is 3- to 7-membered heterocycloalkyl substituted with hydroxy.

In some embodiments of one or more formulae herein, $R^{29}$ is 3- to 7-membered heterocycloalkyl substituted with $C_1$-$C_6$ alkoxy.

In some embodiments of one or more formulae herein, $R^{29}$ is 3- to 7-membered heterocycloalkyl substituted with $NR^{11}R^{12}$.

In some embodiments of one or more formulae herein, $R^{29}$ is 3- to 7-membered heterocycloalkyl substituted with $COOC_1$-$C_6$ alkyl.

In some embodiments of one or more formulae herein, $R^{29}$ is 3- to 7-membered heterocycloalkyl substituted with $CONR^{11}R^{12}$.

In some embodiments of one or more formulae herein, $R^{29}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is pyridyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is pyrimidinyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is pyrrolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is pyrazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is imidazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is oxazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{29}$ is thiazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$.

In some embodiments of one or more formulae herein, $R^{29}$ is $S(O_2)C_1$-$C_6$ alkyl.

In some embodiments of one or more formulae herein, $R^{29}$ is $S(O_2)CH_3$.

In some embodiments of one or more formulae herein, $R^{35}$ is H.

In some embodiments of one or more formulae herein, $R^{35}$ is CN.

In some embodiments of one or more formulae herein, $R^{35}$ is Cl.

In some embodiments of one or more formulae herein, $R^{35}$ is F.

In some embodiments of one or more formulae herein, $R^{35}$ is $C_1$-$C_6$ alkyl.

In some embodiments of one or more formulae herein, $R^{35}$ is $CH_3$.

In some embodiments of one or more formulae herein, $R^{35}$ is $C_1$-$C_6$ alkyl substituted with hydroxy.

In some embodiments of one or more formulae herein, $R^{35}$ is 2-hydroxy-2-propyl.

In some embodiments of one or more formulae herein, $R^{35}$ is 1-hydroxy-1-cyclopropyl.

In some embodiments of one or more formulae herein, $R^{35}$ is $C_1$-$C_6$ alkyl substituted with oxo.

In some embodiments of one or more formulae herein, $R^{35}$ is $C_1$-$C_6$ alkyl substituted with $C_1$-$C_6$ alkoxy.

In some embodiments of one or more formulae herein, $R^{35}$ is $C_1$-$C_6$ alkyl substituted with $NR^{11}R^{12}$.

In some embodiments of one or more formulae herein, $R^{35}$ is $C_1$-$C_6$ alkyl substituted with $COOC_1$-$C_6$ alkyl.

In some embodiments of one or more formulae herein, $R^{35}$ is $C_1$-$C_6$ alkyl substituted with $CONR^{11}R^{12}$.

In some embodiments of one or more formulae herein, $R^{35}$ is $C_1$-$C_6$ alkyl substituted with $C_3$-$C_7$ cycloalkyl.

In some embodiments of one or more formulae herein, $R^{35}$ is $C_1$-$C_6$ alkyl substituted with 3- to 7-membered heterocycloalkyl.

In some embodiments of one or more formulae herein, $R^{35}$ is $C_1$-$C_6$ alkyl substituted with $C_6$-$C_{10}$ aryl.

In some embodiments of one or more formulae herein, $R^{35}$ is $C_1$-$C_6$ alkyl substituted with 5- to 10-membered heteroaryl.

In some embodiments of one or more formulae herein, $R^{35}$ is $C_1$-$C_6$ alkyl substituted with $NR^{11}R^{12}$.

In some embodiments of one or more formulae herein, $R^{35}$ is $C_1$-$C_6$ alkyl substituted with $NH_2$.

In some embodiments of one or more formulae herein, $R^{35}$ is $C_1$-$C_6$ alkyl substituted with $NH(C_1$-$C_6$ alkyl).

In some embodiments of one or more formulae herein, $R^{35}$ is $C_1$-$C_6$ alkyl substituted with $N(C_1$-$C_6$ alkyl)$_2$.

In some embodiments of one or more formulae herein, $R^{35}$ is dimethylaminomethyl.

In some embodiments of one or more formulae herein, $R^{35}$ is $C_1$-$C_6$ alkyl substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of one or more formulae herein, $R^{35}$ is $S(O_2)C_1$-$C_6$ akyl.

In some embodiments of one or more formulae herein, $R^{35}$ is $S(O_2)CH_3$.

In some embodiments of one or more formulae herein, $R^{35}$ is $C_1$-$C_6$ alkyl substituted with $NHCOC_6$-$C_{10}$ aryl.

In some embodiments of one or more formulae herein, $R^{35}$ is $C_1$-$C_6$ alkyl substituted with NHCO (5- to 10-membered heteroaryl).

In some embodiments of one or more formulae herein, $R^{35}$ is $C_1$-$C_6$ alkyl substituted with NHCO (3- to 7-membered heterocycloalkyl).

In some embodiments of one or more formulae herein, $R^{35}$ is $C_1$-$C_6$ alkyl substituted with NHCO (3- to 7-membered heterocycloalkyl) optionally substituted with oxo.

In some embodiments of one or more formulae herein, $R^{35}$ is $C_1$-$C_6$ alkyl substituted with $NHCOC_2$-$C_6$ alkynyl.

In some embodiments of one or more formulae herein, $R^{35}$ is $C_1$-$C_6$ haloalkyl.

In some embodiments of one or more formulae herein, $R^{35}$ is halo.

In some embodiments of one or more formulae herein, $R^{35}$ is $C_3$-$C_7$ cycloalkyl.

In some embodiments of one or more formulae herein, $R^{35}$ is $C_3$-$C_7$ cycloalkyl substituted with hydroxy.

In some embodiments of one or more formulae herein, $R^{35}$ is $C_3$-$C_7$ cycloalkyl substituted with $C_1$-$C_6$ alkoxy.

In some embodiments of one or more formulae herein, $R^{35}$ is $C_3$-$C_7$ cycloalkyl substituted with $NR^{11}R^{12}$.

In some embodiments of one or more formulae herein, $R^{35}$ is $C_3$-$C_7$ cycloalkyl substituted with $COOC_1$-$C_6$ alkyl.

In some embodiments of one or more formulae herein, $R^{35}$ is $C_3$-$C_7$ cycloalkyl substituted with $CONR^{11}R^{12}$.

In some embodiments of one or more formulae herein, $R^{35}$ is $C_3$-$C_7$ cycloalkyl substituted substituted with $C_1$-$C_6$ alkyl.

In some embodiments of one or more formulae herein, $R^{35}$ is 3- to 7-membered heterocycloalkyl.

In some embodiments of one or more formulae herein, $R^{35}$ is 3- to 7-membered nonaromatic monocyclic heterocycloalkyl.

In some embodiments of one or more formulae herein, $R^{35}$ is 1,3-dioxolan-2-yl.

In some embodiments of one or more formulae herein, $R^{35}$ is 3- to 7-membered nonaromatic monocyclic heterocycloalkyl substituted with hydroxy.

In some embodiments of one or more formulae herein, $R^{35}$ is 3- to 7-membered nonaromatic monocyclic heterocycloalkyl substituted with oxo.

In some embodiments of one or more formulae herein, $R^{35}$ is 3- to 7-membered nonaromatic monocyclic heterocycloalkyl substituted with $C_1$-$C_6$ alkoxy.

In some embodiments of one or more formulae herein, $R^{35}$ is 3- to 7-membered heterocycloalkyl substituted with $C_1$-$C_6$ alkyl.

In some embodiments of one or more formulae herein, $R^{35}$ is 3- to 7-membered nonaromatic monocyclic heterocycloalkyl substituted with $C_1$-$C_6$ alkyl.

In some embodiments of one or more formulae herein, $R^{35}$ is 2-methyl-1,3-dioxolan-2-yl.

In some embodiments of one or more formulae herein, $R^{35}$ is 3- to 7-membered heterocycloalkyl substituted with hydroxy.

In some embodiments of one or more formulae herein, $R^{35}$ is 3- to 7-membered heterocycloalkyl substituted with $C_1$-$C_6$ alkoxy.

In some embodiments of one or more formulae herein, $R^{35}$ is 3- to 7-membered heterocycloalkyl substituted with $NR^{11}R^{12}$.

In some embodiments of one or more formulae herein, $R^{35}$ is 3- to 7-membered heterocycloalkyl substituted with $COOC_1$-$C_6$ alkyl.

In some embodiments of one or more formulae herein, $R^{35}$ is 3- to 7-membered heterocycloalkyl substituted with $CONR^{11}R^{12}$.

In some embodiments of one or more formulae herein, $R^{35}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is pyridyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is pyrimidinyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is pyrrolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is pyrazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is imidazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is oxazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{35}$ is thiazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$.

In some embodiments of one or more formulae herein, $R^{35}$ is $S(O_2)C_1$-$C_6$ alkyl.

In some embodiments of one or more formulae herein, $R^{35}$ is $S(O_2)CH_3$.

In some embodiments of one or more formulae herein, $R^{21}$ is H.

In some embodiments of one or more formulae herein, $R^{21}$ is CN.

In some embodiments of one or more formulae herein, $R^{21}$ is Cl.

In some embodiments of one or more formulae herein, $R^{21}$ is F.

In some embodiments of one or more formulae herein, $R^{21}$ is $C_1$-$C_6$ alkyl.

In some embodiments of one or more formulae herein, $R^{21}$ is $CH_3$.

In some embodiments of one or more formulae herein, $R^{21}$ is $C_1$-$C_6$ alkyl substituted with hydroxy.

In some embodiments of one or more formulae herein, $R^{21}$ is 2-hydroxy-2-propyl.

In some embodiments of one or more formulae herein, $R^{21}$ is 1-hydroxy-1-cyclopropyl.

In some embodiments of one or more formulae herein, $R^{21}$ is $C_1$-$C_6$ alkyl substituted with oxo.

In some embodiments of one or more formulae herein, $R^{21}$ is $C_1$-$C_6$ alkyl substituted with $C_1$-$C_6$ alkoxy.

In some embodiments of one or more formulae herein, $R^{21}$ is $C_1$-$C_6$ alkyl substituted with $NR^{11}R^{12}$.

In some embodiments of one or more formulae herein, $R^{21}$ is $C_1$-$C_6$ alkyl substituted with $COOC_1$-$C_6$ alkyl.

In some embodiments of one or more formulae herein, $R^{21}$ is $C_1$-$C_6$ alkyl substituted with $CONR^{11}R^{12}$.

In some embodiments of one or more formulae herein, $R^{21}$ is $C_1$-$C_6$ alkyl substituted with $C_3$-$C_7$ cycloalkyl.

In some embodiments of one or more formulae herein, $R^{21}$ is $C_1$-$C_6$ alkyl substituted with 3- to 7-membered heterocycloalkyl.

In some embodiments of one or more formulae herein, $R^{21}$ is $C_1$-$C_6$ alkyl substituted with $C_6$-$C_{10}$ aryl.

In some embodiments of one or more formulae herein, $R^{21}$ is $C_1$-$C_6$ alkyl substituted with 5- to 10-membered heteroaryl.

In some embodiments of one or more formulae herein, $R^{21}$ is $C_1$-$C_6$ alkyl substituted with $NR^{11}R^{12}$.

In some embodiments of one or more formulae herein, $R^{21}$ is $C_1$-$C_6$ alkyl substituted with $NH_2$.

In some embodiments of one or more formulae herein, $R^{21}$ is $C_1$-$C_6$ alkyl substituted with $NH(C_1$-$C_6$ alkyl).

In some embodiments of one or more formulae herein, $R^{21}$ is $C_1$-$C_6$ alkyl substituted with $N(C_1$-$C_6$ alkyl)$_2$.

In some embodiments of one or more formulae herein, $R^{21}$ is dimethylaminomethyl.

In some embodiments of one or more formulae herein, $R^{21}$ is $C_1$-$C_6$ alkyl substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of one or more formulae herein, $R^{21}$ is $S(O_2)C_1$-$C_6$ akyl.

In some embodiments of one or more formulae herein, $R^{21}$ is $S(O_2)CH_3$.

In some embodiments of one or more formulae herein, $R^{21}$ is $C_1$-$C_6$ alkyl substituted with $NHCOC_6$-$C_{10}$ aryl.

In some embodiments of one or more formulae herein, $R^{21}$ is $C_1$-$C_6$ alkyl substituted with NHCO (5- to 10-membered heteroaryl).

In some embodiments of one or more formulae herein, $R^{21}$ is $C_1$-$C_6$ alkyl substituted with NHCO (3- to 7-membered heterocycloalkyl).

In some embodiments of one or more formulae herein, $R^{21}$ is $C_1$-$C_6$ alkyl substituted with NHCO (3- to 7-membered heterocycloalkyl) optionally substituted with oxo.

In some embodiments of one or more formulae herein, $R^{21}$ is $C_1$-$C_6$ alkyl substituted with $NHCOC_2$-$C_6$ alkynyl.

In some embodiments of one or more formulae herein, $R^{21}$ is $C_1$-$C_6$ haloalkyl.

In some embodiments of one or more formulae herein, $R^{21}$ is halo.

In some embodiments of one or more formulae herein, $R^{21}$ is $C_3$-$C_7$ cycloalkyl.

In some embodiments of one or more formulae herein, $R^{21}$ is $C_3$-$C_7$ cycloalkyl substituted with hydroxy.

In some embodiments of one or more formulae herein, $R^{21}$ is $C_3$-$C_7$ cycloalkyl substituted with $C_1$-$C_6$ alkoxy.

In some embodiments of one or more formulae herein, $R^{21}$ is $C_3$-$C_7$ cycloalkyl substituted with $NR^{11}R^{12}$.

In some embodiments of one or more formulae herein, $R^{21}$ is $C_3$-$C_7$ cycloalkyl substituted with $COOC_1$-$C_6$ alkyl.

In some embodiments of one or more formulae herein, $R^{21}$ is $C_3$-$C_7$ cycloalkyl substituted with $CONR^{11}R^{12}$.

In some embodiments of one or more formulae herein, $R^{21}$ is $C_3$-$C_7$ cycloalkyl substituted with $C_1$-$C_6$ alkyl.

In some embodiments of one or more formulae herein, $R^{29}$ is 3- to 7-membered heterocycloalkyl.

In some embodiments of one or more formulae herein, $R^{21}$ is 3- to 7-membered nonaromatic monocyclic heterocycloalkyl.

In some embodiments of one or more formulae herein, $R^{21}$ is 1,3-dioxolan-2-yl.

In some embodiments of one or more formulae herein, $R^{21}$ is 3- to 7-membered nonaromatic monocyclic heterocycloalkyl substituted with hydroxy.

In some embodiments of one or more formulae herein, $R^{21}$ is 3- to 7-membered nonaromatic monocyclic heterocycloalkyl substituted with oxo.

In some embodiments of one or more formulae herein, $R^{21}$ is 3- to 7-membered nonaromatic monocyclic heterocycloalkyl substituted with $C_1$-$C_6$ alkoxy.

In some embodiments of one or more formulae herein, $R^{21}$ is 3- to 7-membered heterocycloalkyl substituted with $C_1$-$C_6$ alkyl.

In some embodiments of one or more formulae herein, $R^{21}$ is 3- to 7-membered nonaromatic monocyclic heterocycloalkyl substituted with $C_1$-$C_6$ alkyl.

In some embodiments of one or more formulae herein, $R^{21}$ is 2-methyl-1,3-dioxolan-2-yl.

In some embodiments of one or more formulae herein, $R^{21}$ is 3- to 7-membered heterocycloalkyl substituted with hydroxy.

In some embodiments of one or more formulae herein, $R^{21}$ is 3- to 7-membered heterocycloalkyl substituted with $C_1$-$C_6$ alkoxy.

In some embodiments of one or more formulae herein, $R^{21}$ is 3- to 7-membered heterocycloalkyl substituted with $NR^{11}R^{12}$.

In some embodiments of one or more formulae herein, $R^{21}$ is 3- to 7-membered heterocycloalkyl substituted with $COOC_1$-$C_6$ alkyl.

In some embodiments of one or more formulae herein, $R^{21}$ is 3- to 7-membered heterocycloalkyl substituted with $CONR^{11}R^{12}$.

In some embodiments of one or more formulae herein, $R^{21}$ is 5- to 7-membered aromatic monocyclic radical having 1-3 heteroatoms selected from O, N, or S, wherein 0, 1, 2 or 3 atoms of each ring are optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is pyridyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is pyrimidinyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is pyrrolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is pyrazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is imidazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is oxazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$. In some embodiments, $R^{21}$ is thiazolyl optionally substituted with one or more substituents each independently selected from hydroxy, $C_1$-$C_6$ alkoxy, $NR^{11}R^{12}$, $COOC_1$-$C_6$ alkyl, and $CONR^{11}R^{12}$.

In some embodiments of one or more formulae herein, $R^{21}$ is $S(O_2)C_1$-$C_6$ alkyl.

In some embodiments of one or more formulae herein, $R^{21}$ is $S(O_2)CH_3$.

In some embodiments of one or more formulae herein, $R^{36}$ is H.

In some embodiments of one or more formulae herein, $R^{36}$ is CN.

In some embodiments of one or more formulae herein, $R^{36}$ is $C_1$-$C_6$ alkyl.

In some embodiments of one or more formulae herein, $R^{36}$ is $CH_3$.

In some embodiments of one or more formulae herein, $R^{36}$ is halo.

In some embodiments of one or more formulae herein, $R^{36}$ is Cl.

In some embodiments of one or more formulae herein, $R^{36}$ is F.

The Moieties

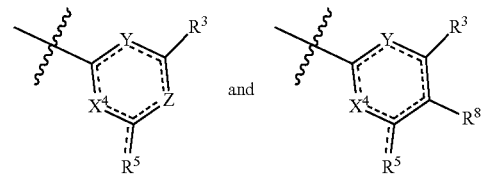

and

In some embodiments of one or more formulae herein, the moiety

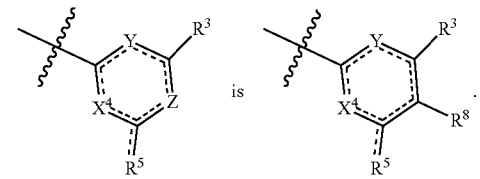

is

In some embodiments of one or more formulae herein,

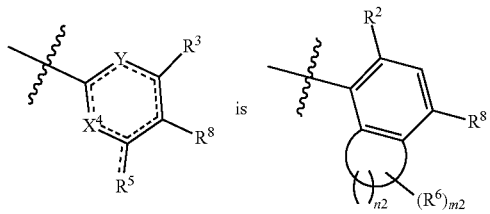

is (RHS1).

In some embodiments of one or more formulae herein, RHS1 is

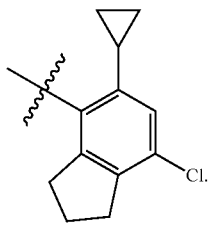 [SMILES: *c1c(C2CC2)cc(Cl)c2c1CCC2]

In some embodiments of one or more formulae herein, RHS1 is

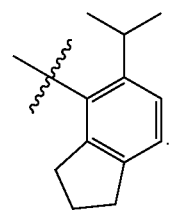 [SMILES: *c1c(C(C)C)ccc2c1CCC2]

In some embodiments of one or more formulae herein, RHS1 is

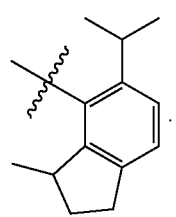 [SMILES: *c1c(C(C)C)ccc2c1C(C)CC2]

In some embodiments of one or more formulae herein, RHS1 is

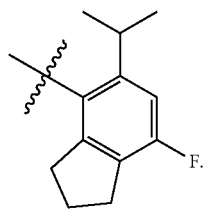 [SMILES: *c1c(C(C)C)cc(F)c2c1CCC2]

In some embodiments of one or more formulae herein, RHS1 is

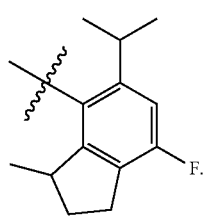 [SMILES: *c1c(C(C)C)cc(F)c2c1C(C)CC2]

In some embodiments of one or more formulae herein, RHS1 is

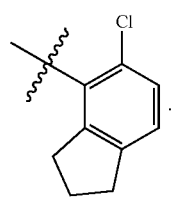 [SMILES: *c1c(Cl)ccc2c1CCC2]

In some embodiments of one or more formulae herein, RHS1 is

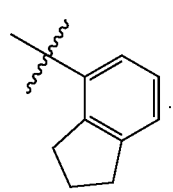 [SMILES: *c1cccc2c1CCC2]

In some embodiments of one or more formulae herein, RHS1 is

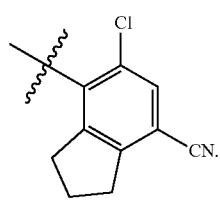 [SMILES: *c1c(Cl)cc(C#N)c2c1CCC2]

In some embodiments of one or more formulae herein, RHS1 is

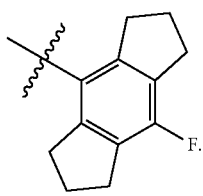 [SMILES: *c1c2c(c(F)c3c1CCC3)CCC2]

In some embodiments of one or more formulae herein,

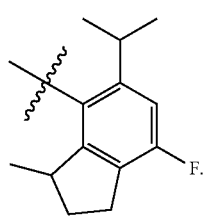 [SMILES: *c1c(C(C)C)cc(F)c2c1C(C)CC2]

(RHS2).

In some embodiments of one or more formulae herein, RHS2 is

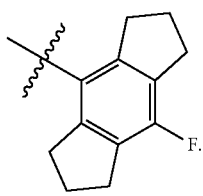 [SMILES: *c1c2c(c(F)c3c1CCC3)CCC2]

In some embodiments of one or more formulae herein, RHS2 is

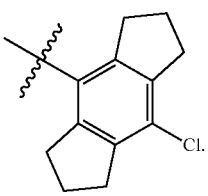 [SMILES: *c1c2c(c(Cl)c3c1CCC3)CCC2]

In some embodiments of one or more formulae herein, RHS2 is

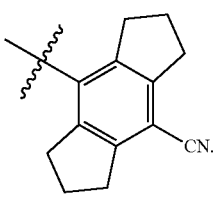 [SMILES: *c1c2c(c(C#N)c3c1CCC3)CCC2]

In some embodiments of one or more formulae herein, RHS2 is

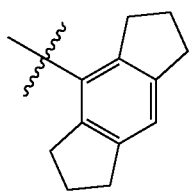

In some embodiments of one or more formulae herein, RHS2 is

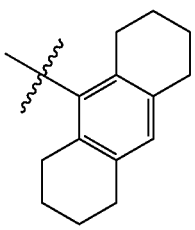

In some embodiments of one or more formulae herein,

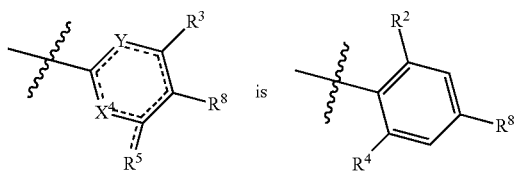 is (RHS3).

In some embodiments of one or more formulae herein, RHS3 is

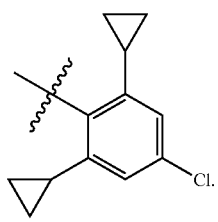 [SMILES: *c1c(C2CC2)cc(Cl)cc1C1CC1]

In some embodiments of one or more formulae herein, RHS3 is

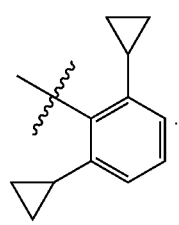 [SMILES: *c1c(C2CC2)cccc1C1CC1]

In some embodiments of one or more formulae herein, RHS3 is

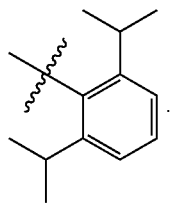 [SMILES: *c1c(C(C)C)cccc1C(C)C]

In some embodiments of one or more formulae herein, RHS3 is

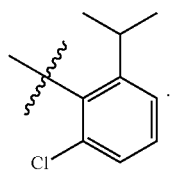 [SMILES: *c1c(Cl)cccc1C(C)C]

In some embodiments of one or more formulae herein, RHS3 is

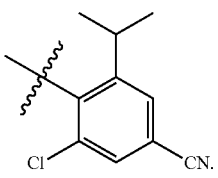 [SMILES: *c1c(Cl)cc(C#N)cc1C(C)C]

In some embodiments of one or more formulae herein, RHS3 is

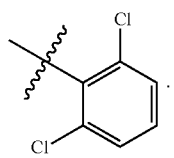 [SMILES: *c1c(Cl)cccc1Cl]

In some embodiments of one or more formulae herein, RHS3 is

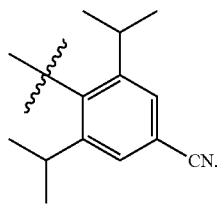 [SMILES: *c1c(C(C)C)cc(C#N)cc1C(C)C]

In some embodiments of one or more formulae herein, RHS3 is

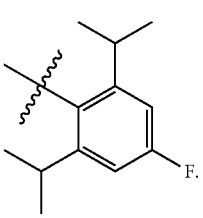 [SMILES: *c1c(C(C)C)cc(F)cc1C(C)C]

In some embodiments of one or more formulae herein, RHS3 is

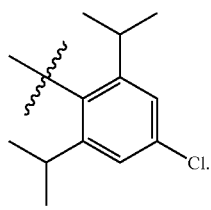 [SMILES: *c1c(C(C)C)cc(Cl)cc1C(C)C]

In some embodiments of one or more formulae herein, RHS3 is

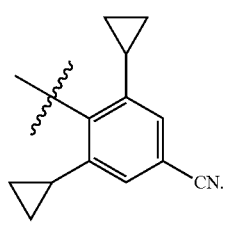 [SMILES: *c1c(C2CC2)cc(C#N)cc1C1CC1]

In some embodiments of one or more formulae herein, RHS3 is

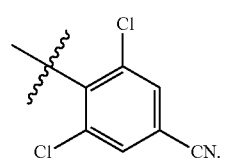 [SMILES: *c1c(Cl)cc(C#N)cc1Cl]

In some embodiments of one or more formulae herein, RHS3 is

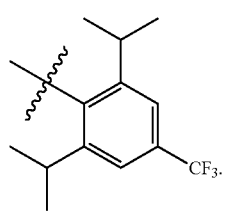 [SMILES: *c1c(C(C)C)cc(C(F)(F)F)cc1C(C)C]

In some embodiments of one or more formulae herein,

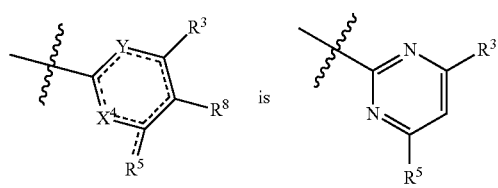

(RHS4).

In some embodiments of one or more formulae herein, RHS4 is

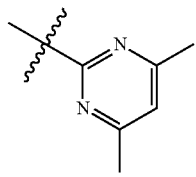

In some embodiments of one or more formulae herein, RHS4 is

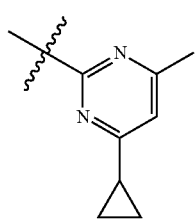

In some embodiments of one or more formulae herein, RHS4 is

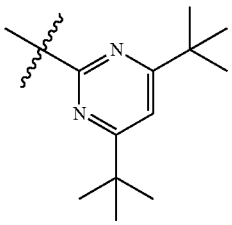

In some embodiments of one or more formulae herein,

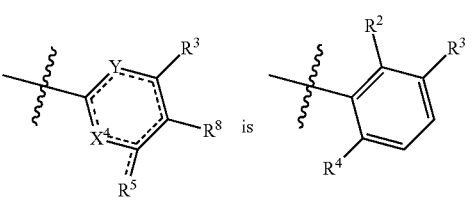

(RHS5).

In some embodiments of one or more formulae herein, RHS5 is

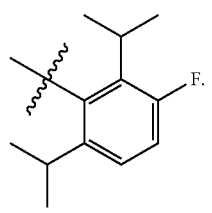 [SMILES: *c1c(C(C)C)ccc(F)c1C(C)C]

In some embodiments of one or more formulae herein, RHS5 is

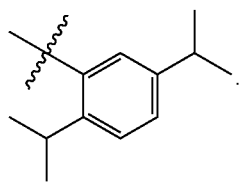 [SMILES: *c1cc(C(C)C)ccc1C(C)C]

In some embodiments of one or more formulae herein,

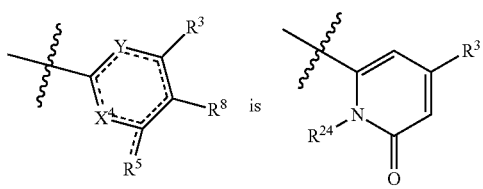

(RHS6).

In some embodiments of one or more formulae herein, RHS6 is

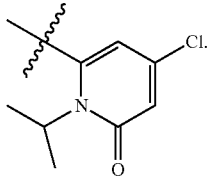 [SMILES: *c1cc(Cl)cc(=O)n1C(C)C]

In some embodiments of one or more formulae herein,

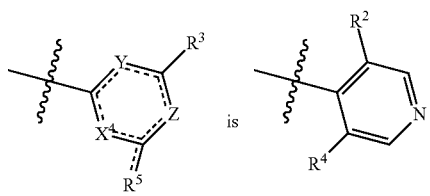

(RHS7).

In some embodiments of one or more formulae herein, RHS7 is

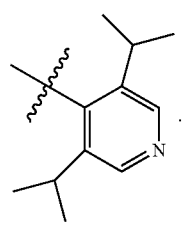 [SMILES: *c1c(C(C)C)cncc1C(C)C]

In some embodiments of one or more formulae herein, RHS7 is

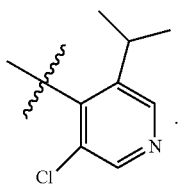 [SMILES: *c1c(Cl)cncc1C(C)C]

In some embodiments of one or more formulae herein, RHS7 is

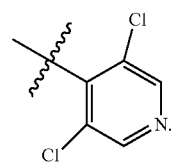 [SMILES: *c1c(Cl)cncc1Cl]

In some embodiments of one or more formulae herein, RHS7 is

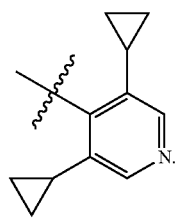

In some embodiments of one or more formulae herein,

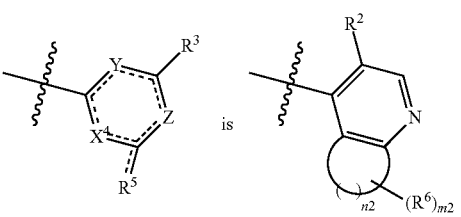

(RHS8).

In some embodiments of one or more formulae herein, RHS8 is

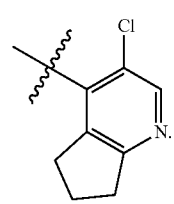 [SMILES: *c1c(Cl)cnc2c1CCC2]

In some embodiments of one or more formulae herein,

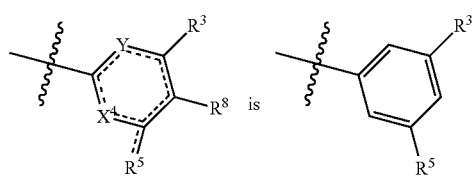

(RHS9).

In some embodiments of one or more formulae herein, RHS9 is

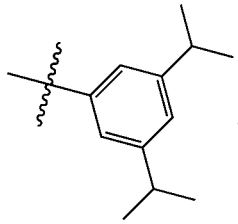

In some embodiments of one or more formulae herein,

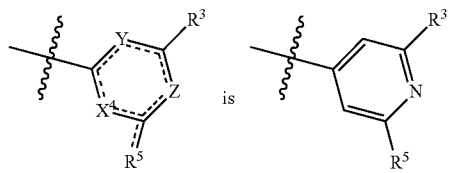

(RHS10).

In some embodiments of one or more formulae herein, RHS10 is

![structure]

In some embodiments of one or more formulae herein,

![structures] is (RHS11).

In some embodiments of one or more formulae herein, RHS11 is

![structure]

In some embodiments of one or more formulae herein,

![structures] is (RHS12).

The Moiety

![structure]

In some embodiments of one or more formulae herein,

![structures] is (LHS1).

In some embodiments of one or more formulae herein, LHS1 is

![structure]

In some embodiments of one or more formulae herein, LHS1 is

![structure]

In some embodiments of one or more formulae herein, LHS1 is

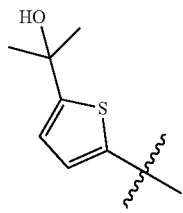

In some embodiments of one or more formulae herein, LHS1 is

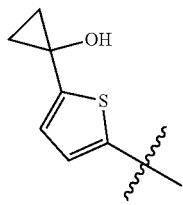

In some embodiments of one or more formulae herein,

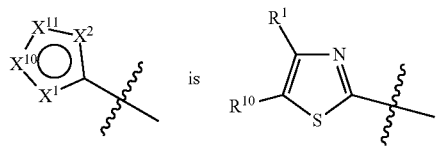 is (LHS2).

In some embodiments of one or more formulae herein, LHS2 is

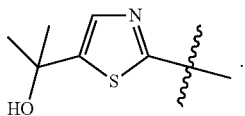 [SMILES: *c1ncc(C(C)(C)O)s1]

In some embodiments of one or more formulae herein, LHS2 is

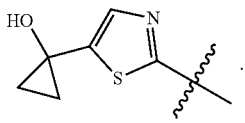

In some embodiments of one or more formulae herein, LHS2 is

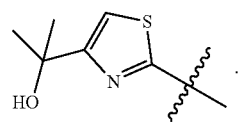 [SMILES: *c1nc(C(C)(C)O)cs1]

In some embodiments of one or more formulae herein, LHS2 is

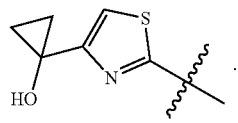 [SMILES: *c1nc(C2(O)CC2)cs1]

In some embodiments of one or more formulae herein, LHS2 is

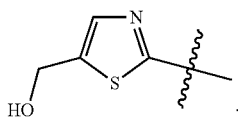 [SMILES: *c1ncc(CO)s1]

In some embodiments of one or more formulae herein, LHS2 is

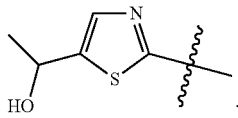 [SMILES: *c1ncc(C(C)O)s1]

In some embodiments of one or more formulae herein, LHS2 is

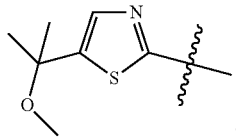

In some embodiments of one or more formulae herein,

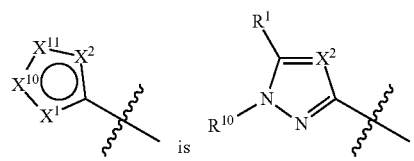 is (LHS3).

In some embodiments of one or more formulae herein, LHS3 is

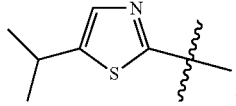

In some embodiments of one or more formulae herein, LHS3 is

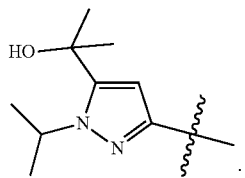

In some embodiments of one or more formulae herein, LHS3 is

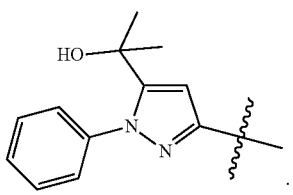 [SMILES: *c1cc(C(C)(C)O)n(-c2ccccc2)n1]

In some embodiments of one or more formulae herein, LHS3 is

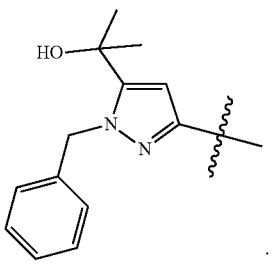 [SMILES: *c1cc(C(C)(C)O)n(Cc2ccccc2)n1]

In some embodiments of one or more formulae herein, LHS3 is

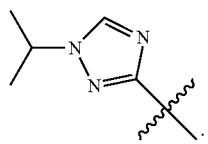 [SMILES: *c1ncn(C(C)C)n1]

In some embodiments of one or more formulae herein, LHS3 is

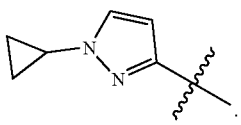 [SMILES: *c1ccn(C2CC2)n1]

In some embodiments of one or more formulae herein, LHS3 is

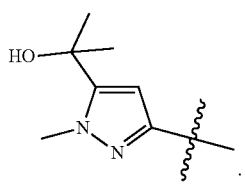 [SMILES: *c1cc(C(C)(C)O)n(C)n1]

In some embodiments of one or more formulae herein, LHS3 is

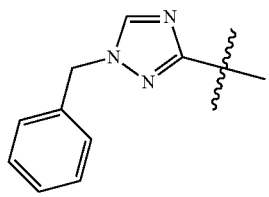

In some embodiments of one or more formulae herein,

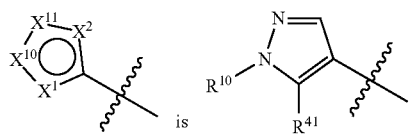

(LHS4).

In some embodiments of one or more formulae herein, LHS4 is

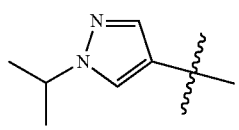

In some embodiments of one or more formulae herein, LHS4 is


In some embodiments of one or more formulae herein,

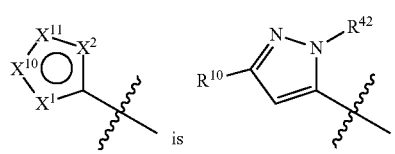

(LHS5).

In some embodiments of one or more formulae herein, LHS5 is

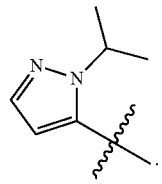

In some embodiments of one or more formulae herein,

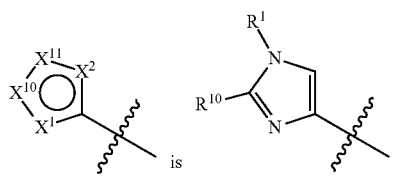 is (LHS6).

In some embodiments of one or more formulae herein, LHS6 is

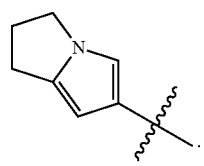 [SMILES: *c1cc2n(c1)CCC2]

In some embodiments of one or more formulae herein,

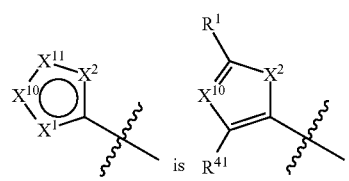 is (LHS7).

In some embodiments of LHS7, $X^{10}$ is N; and $X^2$ is O.
In some embodiments of LHS7, $X^{10}$ is N; and $X^2$ is S.
In some embodiments of one or more formulae herein, LHS7 is

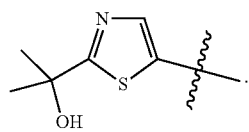 [SMILES: *c1cnc(C(C)(C)O)s1]

In some embodiments of LHS7, $X^{10}$ is $CR^{10}$; and $X^2$ is O.
In some embodiments of LHS7, $X^{10}$ is $CR^{10}$; and $X^2$ is S.
In some embodiments of LHS7, $X^{10}$ is CH; and $X^2$ is O.
In some embodiments of LHS7, $X^{10}$ is CH; and $X^2$ is S.
In some embodiments of one or more formulae herein,

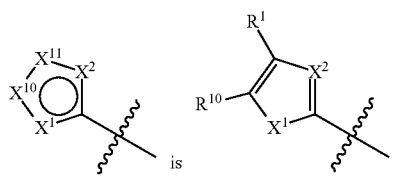 is (LHS8).

In some embodiments of LHS8, $X^1$ is O; and $X^2$ is N.
In some embodiments of LHS8, $X^1$ is S; and $X^2$ is N.
In some embodiments of LHS8, $X^1$ is O; and $X^2$ is $CR^{42}$.
In some embodiments of LHS8, $X^1$ is S; and $X^2$ is $CR^{42}$.
In some embodiments of LHS8, $X^1$ is O; and $X^2$ is CH.
In some embodiments of LHS8, $X^1$ is S; and $X^2$ is CH.
In some embodiments of LHS8, $X^1$ is O; and $X^2$ is $CCH_3$.
In some embodiments of LHS8, $X^1$ is S; and $X^2$ is $CCH_3$.
In some embodiments of one or more formulae herein,

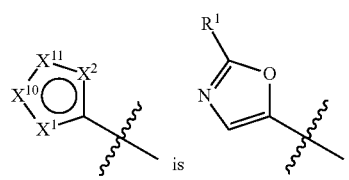 is (LHS11).

In some embodiments of one or more formulae herein, LHS11 is

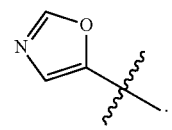 [SMILES: *c1cnco1]

In some embodiments of one or more formulae herein,

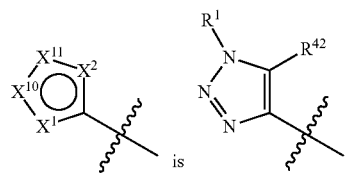 is (LHS15).

In some embodiments of one or more formulae herein, LHS15 is

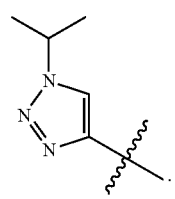 [SMILES: *c1cn(C(C)C)nn1]

In some embodiments of one or more formulae herein,

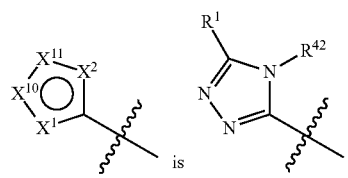 is (LHS16).

In some embodiments of one or more formulae herein, LHS16 is

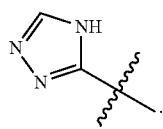 [SMILES: *c1nnc[nH]1]

The Moiety

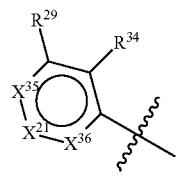

In some embodiments of one or more formulae herein,

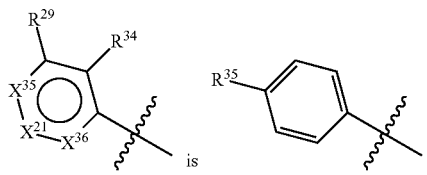

(LHS9).

In some embodiments of one or more formulae herein, LHS9 is

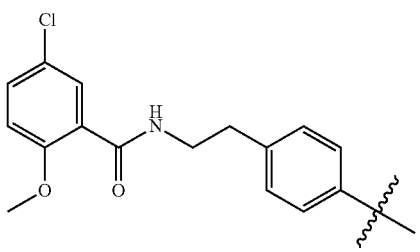

In some embodiments of one or more formulae herein, LHS9 is

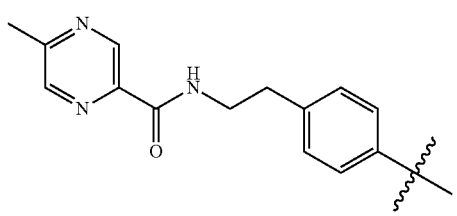

In some embodiments of one or more formulae herein, LHS9 is

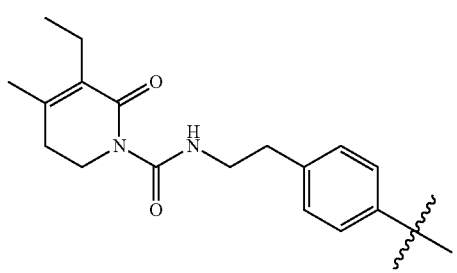

In some embodiments of one or more formulae herein, LHS9 is

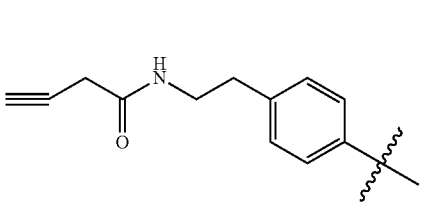

In some embodiments of one or more formulae herein,

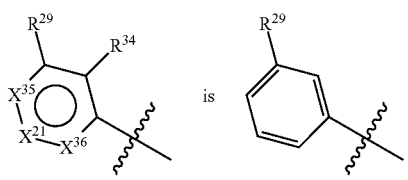

(LHS10).

In some embodiments of one or more formulae herein, LHS10 is

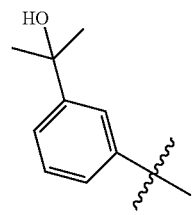

In some embodiments of one or more formulae herein,

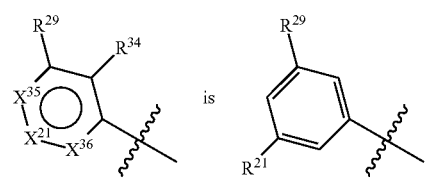

(LHS12).

In some embodiments of one or more formulae herein, LHS12 is

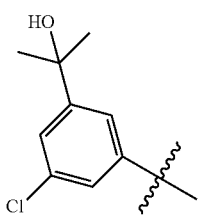

In some embodiments of one or more formulae herein, LHS12 is

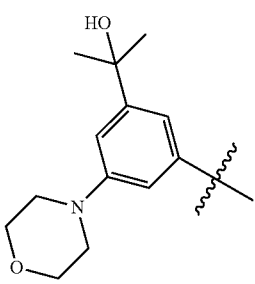

In some embodiments of one or more formulae herein, LHS12 is

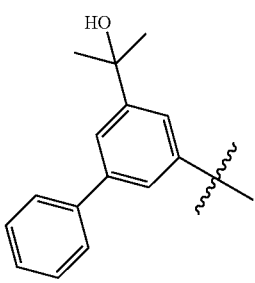

In some embodiments of one or more formulae herein, LHS12 is

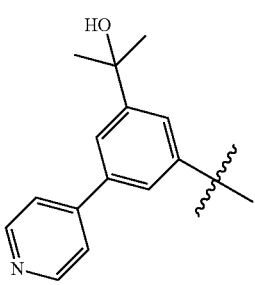

In some embodiments of one or more formulae herein,

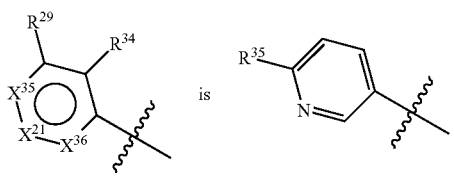

(LHS13).

In some embodiments of one or more formulae herein, LHS13 is

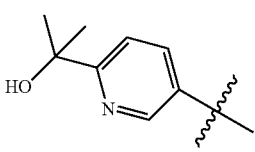

In some embodiments of one or more formulae herein,

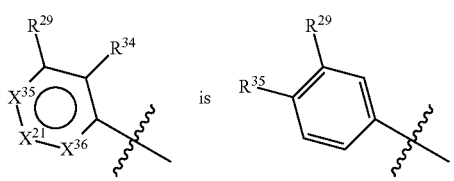

(LHS14).

In some embodiments of one or more formulae herein, LHS14 is

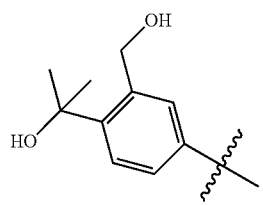

In some embodiments of one or more formulae herein,

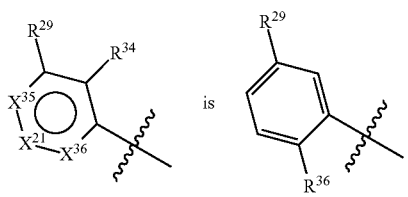

(LHS17).

In some embodiments of one or more formulae herein, LHS17 is

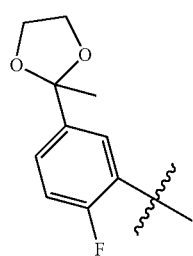

In some embodiments of one or more formulae herein,

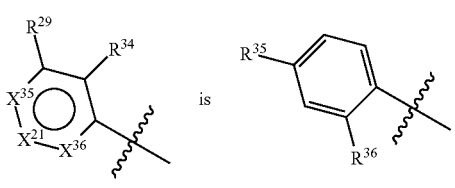

(LHS18).

Additional Embodiments

In some embodiments of one or more formulae herein Ar is LHS1,

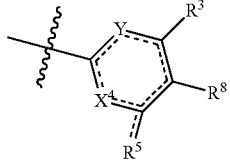

is RHS1, each $R^{20}$ is hydrogen.

In some embodiments of one or more formulae herein Ar is LHS1,

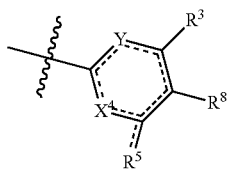

is RHS2, each $R^{20}$ is hydrogen.

In some embodiments of one or more formulae herein Ar is LHS1,

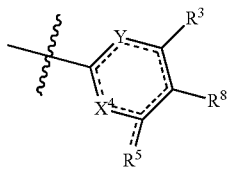

is RHS3, each $R^{20}$ is hydrogen.

In some embodiments of one or more formulae herein Ar is LHS1,

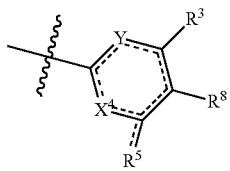

is RHS4, each $R^{20}$ is hydrogen.

In some embodiments of one or more formulae herein Ar is LHS1,

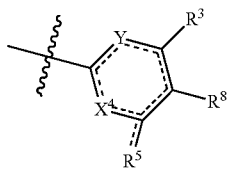

is RHS5, each $R^{20}$ is hydrogen.

In some embodiments of one or more formulae herein Ar is LHS1,

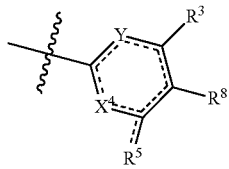

is RHS6, each $R^{20}$ is hydrogen.

In some embodiments of one or more formulae herein Ar is LHS1,

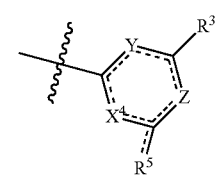

is RHS7, each $R^{20}$ is hydrogen.

In some embodiments of one or more formulae herein Ar is LHS1,

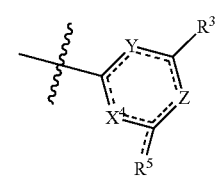

is RHS8, each $R^{20}$ is hydrogen.

In some embodiments of one or more formulae herein Ar is LHS2,

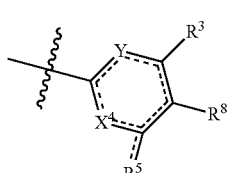

is RHS1, each $R^{20}$ is hydrogen.

In some embodiments of one or more formulae herein Ar is LHS2,

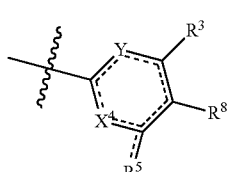

is RHS2, each $R^{20}$ is hydrogen.

In some embodiments of one or more formulae herein Ar is LHS2,

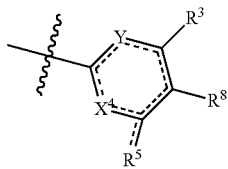

is RHS3, each $R^{20}$ is hydrogen.

In some embodiments of one or more formulae herein Ar is LHS2,

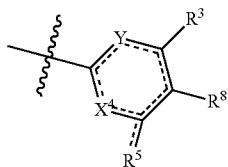

is RHS4, each $R^{20}$ is hydrogen.

In some embodiments of one or more formulae herein Ar is LHS2,

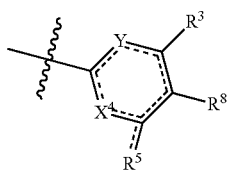

is RHS5, each $R^{20}$ is hydrogen.

In some embodiments of one or more formulae herein Ar is LHS2,

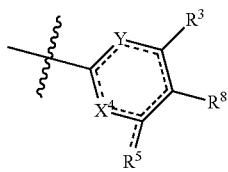

is RHS6, each $R^{20}$ is hydrogen.

In some embodiments of one or more formulae herein Ar is LHS2,

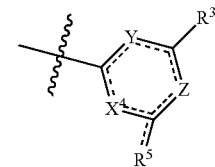

is RHS7, each $R^{20}$ is hydrogen.

In some embodiments of one or more formulae herein Ar is LHS2,

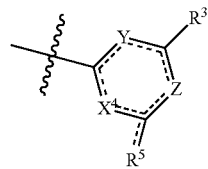

is RHS8, each $R^{20}$ is hydrogen.

In some embodiments of one or more formulae herein Ar is LHS3,

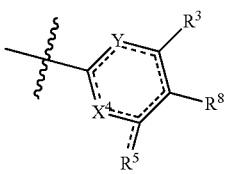

is RHS1, each $R^{20}$ is hydrogen.

In some embodiments of one or more formulae herein Ar is LHS3,

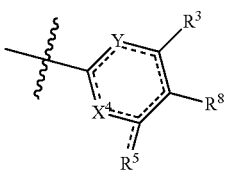

is RHS2, each $R^{20}$ is hydrogen.

In some embodiments of one or more formulae herein Ar is LHS3,

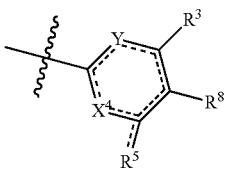

is RHS3, each $R^{20}$ is hydrogen.

In some embodiments of one or more formulae herein Ar is LHS3,

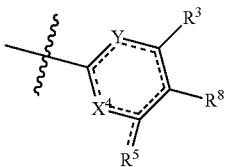

is RHS4, each $R^{20}$ is hydrogen.

In some embodiments of one or more formulae herein Ar is LHS3, is

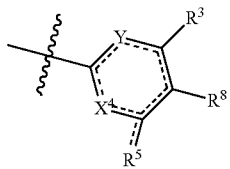

is RHS5, each $R^{20}$ is hydrogen.

In some embodiments of one or more formulae herein Ar is LHS3, is

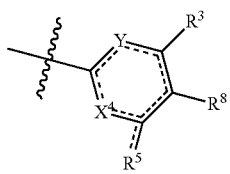

is RHS6, each $R^{20}$ is hydrogen.

In some embodiments of one or more formulae herein Ar is LHS3,

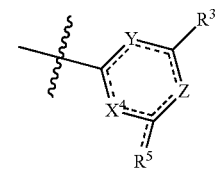

is RHS7, each $R^{20}$ is hydrogen.

In some embodiments of one or more formulae herein Ar is LHS3,

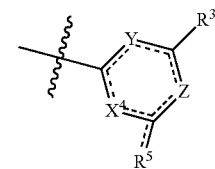

is RHS8, each $R^{20}$ is hydrogen.

In some embodiments of one or more formulae herein Ar is LHS4,

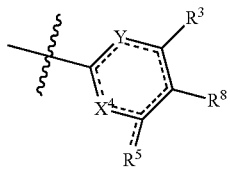

is RHS1, each $R^{20}$ is hydrogen.

In some embodiments of one or more formulae herein Ar is LHS4,

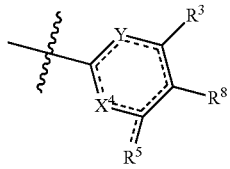

is RHS2, each $R^{20}$ is hydrogen.

In some embodiments of one or more formulae herein Ar is LHS4,

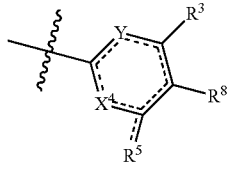

is RHS3, each $R^{20}$ is hydrogen.

In some embodiments of one or more formulae herein Ar is LHS4,

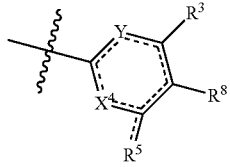

is RHS4, each $R^{20}$ is hydrogen.

In some embodiments of one or more formulae herein Ar is LHS4,

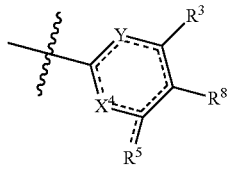

is RHS5, each $R^{20}$ is hydrogen.

In some embodiments of one or more formulae herein Ar is LHS4,

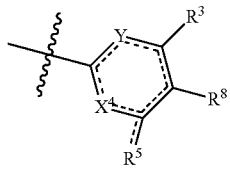

is RHS6, each $R^{20}$ is hydrogen.

In some embodiments of one or more formulae herein Ar is LHS4,

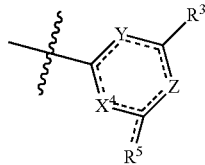

is RHS7, each $R^{20}$ is hydrogen.

In some embodiments of one or more formulae herein Ar is LHS4,

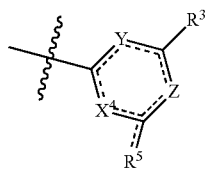

is RHS8, each $R^{20}$ is hydrogen.

In some embodiments of one or more formulae herein Ar is LHS5,

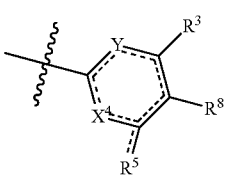

is RHS1, each $R^{20}$ is hydrogen.

In some embodiments of one or more formulae herein Ar is LHS5,

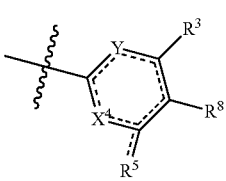

is RHS2, each $R^{20}$ is hydrogen.

In some embodiments of one or more formulae herein Ar is LHS5,

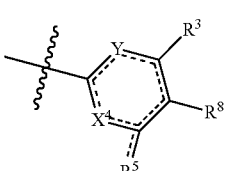

is RHS3, each $R^{20}$ is hydrogen.

In some embodiments of one or more formulae herein Ar is LHS5,

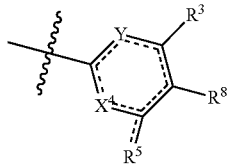

is RHS4, each $R^{20}$ is hydrogen.

In some embodiments of one or more formulae herein Ar is LHS5,

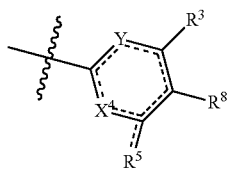

is RHS5, each $R^{20}$ is hydrogen.

In some embodiments of one or more formulae herein Ar is LHS5,

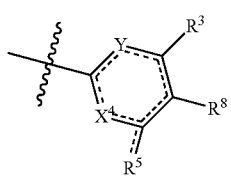

is RHS6, each $R^{20}$ is hydrogen.

In some embodiments of one or more formulae herein Ar is LHS5,

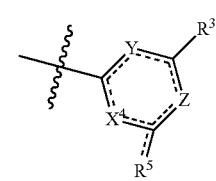

is RHS7, each $R^{20}$ is hydrogen.

In some embodiments of one or more formulae herein Ar is LHS5,

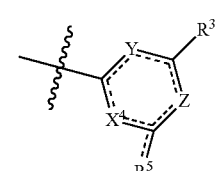

is RHS8, each $R^{20}$ is hydrogen.

In some embodiments of one or more formulae herein Ar is LHS6,

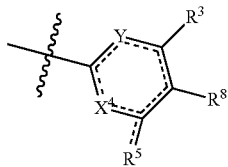

is RHS1, each $R^{20}$ is hydrogen.

In some embodiments of one or more formulae herein Ar is LHS6,

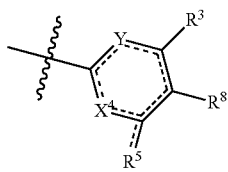

is RHS2, each $R^{20}$ is hydrogen.

In some embodiments of one or more formulae herein Ar is LHS6,

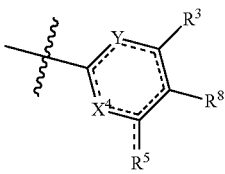

is RHS3, each $R^{20}$ is hydrogen.

In some embodiments of one or more formulae herein Ar is LHS6,

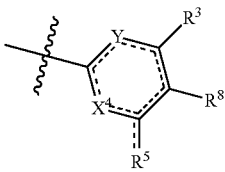

is RHS4, each $R^{20}$ is hydrogen.

In some embodiments of one or more formulae herein Ar is LHS6,

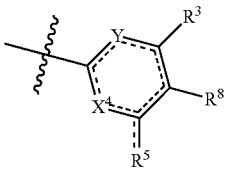

is RHS5, each $R^{20}$ is hydrogen.

In some embodiments of one or more formulae herein Ar is LHS6,

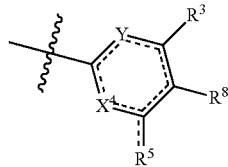

is RHS6, each $R^{20}$ is hydrogen.

In some embodiments of one or more formulae herein Ar is LHS6,

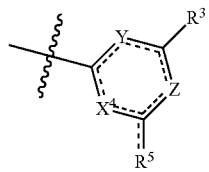

is RHS7, each $R^{20}$ is hydrogen.

In some embodiments of one or more formulae herein Ar is LHS6,

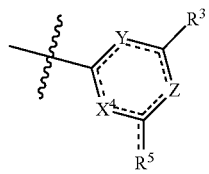

is RHS8, each $R^{20}$ is hydrogen.

In some embodiments of one or more formulae herein Ar is LHS7,

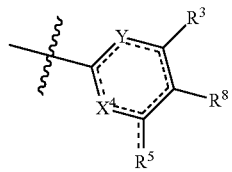

is RHS1, each $R^{20}$ is hydrogen.

In some embodiments of one or more formulae herein Ar is LHS7,

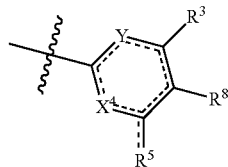

is RHS2, each $R^{20}$ is hydrogen.

In some embodiments of one or more formulae herein Ar is LHS7,

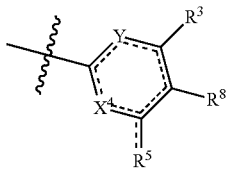

is RHS3, each $R^{20}$ is hydrogen.

In some embodiments of one or more formulae herein Ar is LHS7,

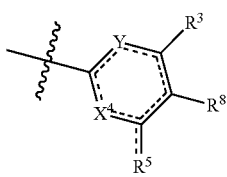

is RHS4, each $R^{20}$ is hydrogen.

In some embodiments of one or more formulae herein Ar is LHS7,

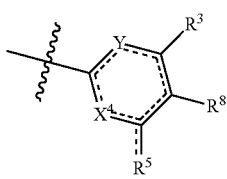

is RHS5, each $R^{20}$ is hydrogen.

In some embodiments of one or more formulae herein Ar is LHS7,

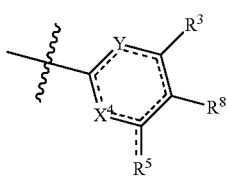

is RHS6, each $R^{20}$ is hydrogen.

In some embodiments of one or more formulae herein Ar is LHS7,

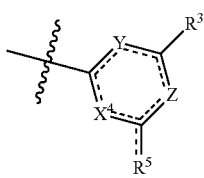

is RHS7, each $R^{20}$ is hydrogen.

In some embodiments of one or more formulae herein Ar is LHS7,

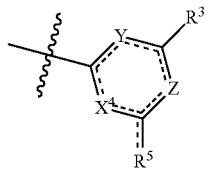

is RHS8, each $R^{20}$ is hydrogen.

In some embodiments of one or more formulae herein Ar is LHS8,

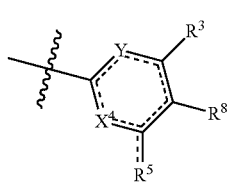

is RHS1, each $R^{20}$ is hydrogen.

In some embodiments of one or more formulae herein Ar is LHS8,

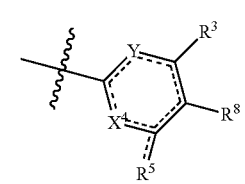

is RHS2, each $R^{20}$ is hydrogen.

In some embodiments of one or more formulae herein Ar is LHS8,

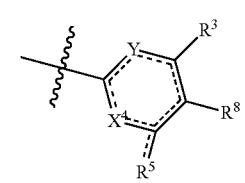

is RHS3, each $R^{20}$ is hydrogen.

In some embodiments of one or more formulae herein Ar is LHS8,

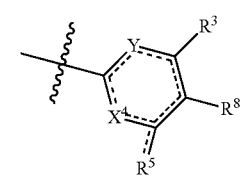

is RHS4, each $R^{20}$ is hydrogen.

In some embodiments of one or more formulae herein Ar is LHS8,

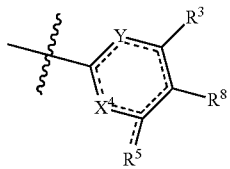

is RHS5, each $R^{20}$ is hydrogen.

In some embodiments of one or more formulae herein Ar is LHS8,

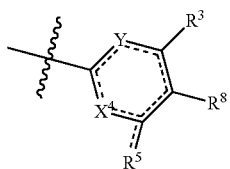

is RHS6, each $R^{20}$ is hydrogen.

In some embodiments of one or more formulae herein Ar is LHS8,

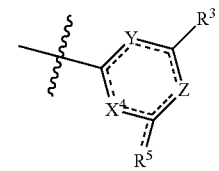

is RHS7, each $R^{20}$ is hydrogen.

In some embodiments of one or more formulae herein Ar is LHS8,

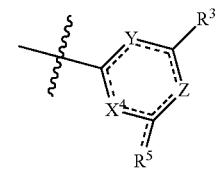

is RHS8, each $R^{20}$ is hydrogen.

In some embodiments of one or more formulae herein Ar is LHS9,

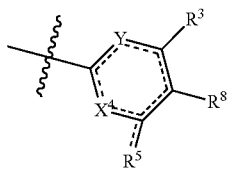

is RHS1, each $R^{20}$ is hydrogen.

In some embodiments of one or more formulae herein Ar is LHS9,

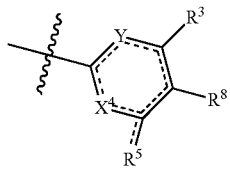

is RHS2, each $R^{20}$ is hydrogen.

In some embodiments of one or more formulae herein Ar is LHS9,

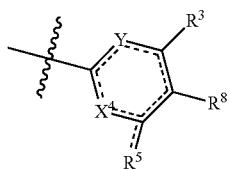

is RHS3, each $R^{20}$ is hydrogen.

In some embodiments of one or more formulae herein Ar is LHS9,

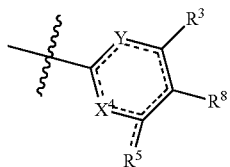

is RHS4, each $R^{20}$ is hydrogen.

In some embodiments of one or more formulae herein Ar is LHS9,

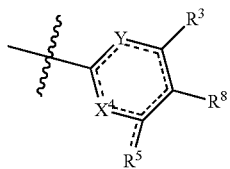

is RHS5, each $R^{20}$ is hydrogen.

In some embodiments of one or more formulae herein Ar is LHS9,

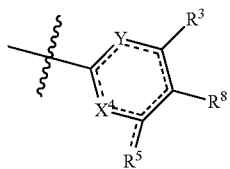

is RHS6, each $R^{20}$ is hydrogen.

In some embodiments of one or more formulae herein Ar is LHS9,

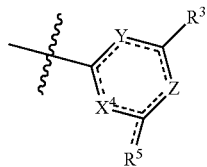

is RHS7, each $R^{20}$ is hydrogen.

In some embodiments of one or more formulae herein Ar is LHS9,

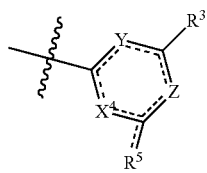

is RHS8, each $R^{20}$ is hydrogen.

In some embodiments of one or more formulae herein Ar is LHS10,

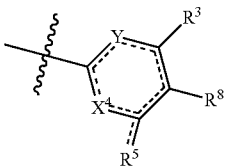

is RHS1, each $R^{20}$ is hydrogen.

In some embodiments of one or more formulae herein Ar is LHS10,

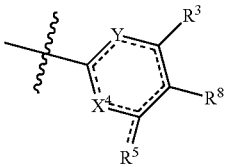

is RHS2, each $R^{20}$ is hydrogen.

In some embodiments of one or more formulae herein Ar is LHS10,

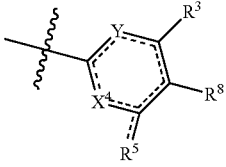

is RHS3, each $R^{20}$ is hydrogen.

In some embodiments of one or more formulae herein Ar is LHS10,

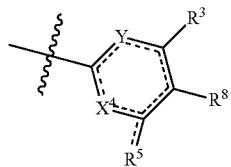

is RHS4, each $R^{20}$ is hydrogen.

In some embodiments of one or more formulae herein Ar is LHS10,

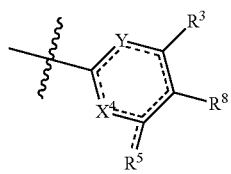

is RHS5, each $R^{20}$ is hydrogen.

In some embodiments of one or more formulae herein Ar is LHS10,

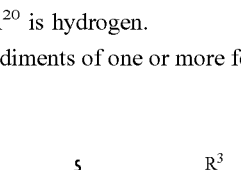

is RHS6, each $R^{20}$ is hydrogen.

In some embodiments of one or more formulae herein Ar is LHS10, is RHS7, each $R^{20}$ is hydrogen.

In some embodiments of one or more formulae herein Ar is LHS10,

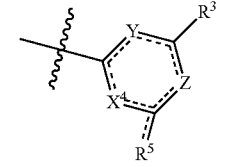

is RHS8, each $R^{20}$ is hydrogen.

In some embodiments of one or more formulae herein Ar is LHS11,

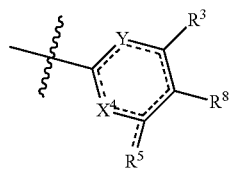

is RHS1, each $R^{20}$ is hydrogen.

In some embodiments of one or more formulae herein Ar is LHS11,

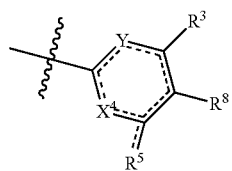

is RHS2, each $R^{20}$ is hydrogen.

In some embodiments of one or more formulae herein Ar is LHS11,

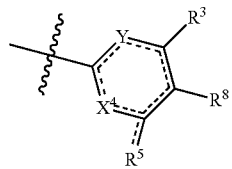

is RHS3, each $R^{20}$ is hydrogen.

In some embodiments of one or more formulae herein Ar is LHS11,

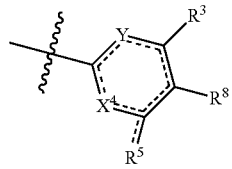

is RHS4, each $R^{20}$ is hydrogen.

In some embodiments of one or more formulae herein Ar is LHS11,

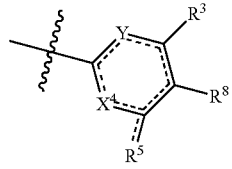

is RHS5, each $R^{20}$ is hydrogen.

In some embodiments of one or more formulae herein Ar is LHS11,

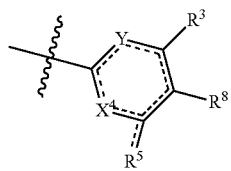

is RHS6, each $R^{20}$ is hydrogen.

In some embodiments of one or more formulae herein Ar is LHS11,

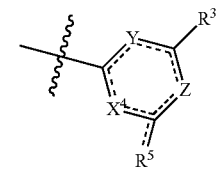

is RHS7, each $R^{20}$ is hydrogen.

In some embodiments of one or more formulae herein Ar is LHS11,

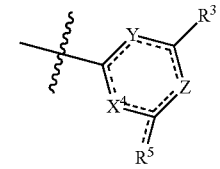

is RHS8, each $R^{20}$ is hydrogen.

In some embodiments of one or more formulae herein Ar is LHS12,

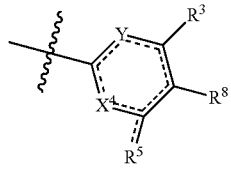

is RHS1, each $R^{20}$ is hydrogen.

In some embodiments of one or more formulae herein Ar is LHS12,

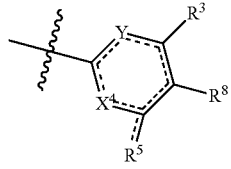

is RHS2, each $R^{20}$ is hydrogen.

In some embodiments of one or more formulae herein Ar is LHS12,

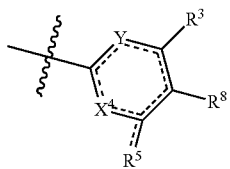

is RHS3, each $R^{20}$ is hydrogen.

In some embodiments of one or more formulae herein Ar is LHS12,

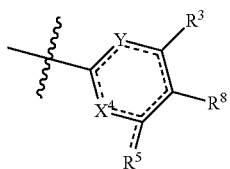

is RHS4, each $R^{20}$ is hydrogen.

In some embodiments of one or more formulae herein Ar is LHS12,

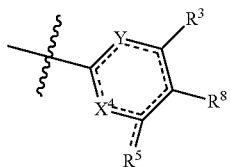

is RHS5, each $R^{20}$ is hydrogen.

In some embodiments of one or more formulae herein Ar is LHS12,

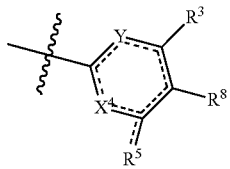

is RHS6, each $R^{20}$ is hydrogen.

In some embodiments of one or more formulae herein Ar is LHS12,

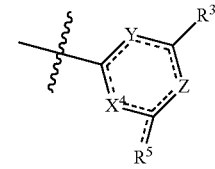

is RHS7, each $R^{20}$ is hydrogen.

In some embodiments of one or more formulae herein Ar is LHS12,

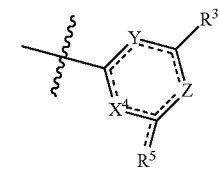

is RHS8, each $R^{20}$ is hydrogen.

In some embodiments of one or more formulae herein Ar is LHS13,

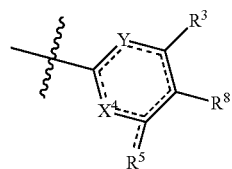

is RHS1, each $R^{20}$ is hydrogen.

In some embodiments of one or more formulae herein Ar is LHS13,

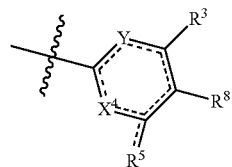

is RHS2, each $R^{20}$ is hydrogen.

In some embodiments of one or more formulae herein Ar is LHS13,

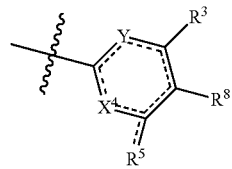

is RHS3, each $R^{20}$ is hydrogen.

In some embodiments of one or more formulae herein Ar is LHS13,

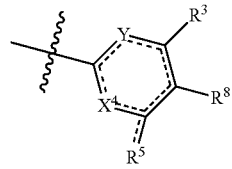

is RHS4, each $R^{20}$ is hydrogen.

In some embodiments of one or more formulae herein Ar is LHS13,

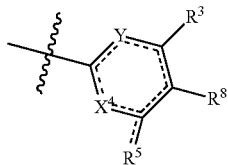

is RHS5, each $R^{20}$ is hydrogen.

In some embodiments of one or more formulae herein Ar is LHS13,

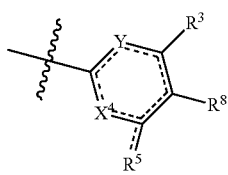

is RHS6, each $R^{20}$ is hydrogen.

In some embodiments of one or more formulae herein Ar is LHS13,

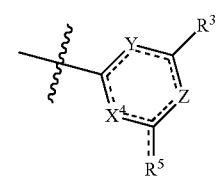

is RHS7, each $R^{20}$ is hydrogen.

In some embodiments of one or more formulae herein Ar is LHS13,

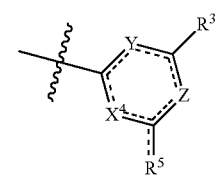

is RHS8, each $R^{20}$ is hydrogen.

In some embodiments of one or more formulae herein Ar is LHS14,

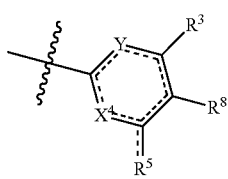

is RHS1, each $R^{20}$ is hydrogen.

In some embodiments of one or more formulae herein Ar is LHS14,

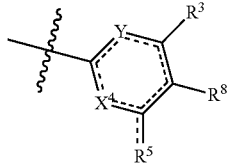

is RHS2, each $R^{20}$ is hydrogen.

In some embodiments of one or more formulae herein Ar is LHS14,

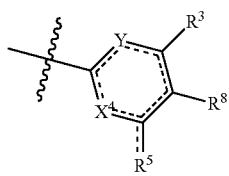

is RHS3, each $R^{20}$ is hydrogen.

In some embodiments of one or more formulae herein Ar is LHS14,

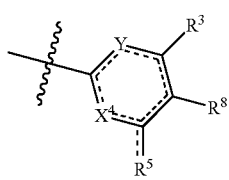

is RHS4, each $R^{20}$ is hydrogen.

In some embodiments of one or more formulae herein Ar is LHS14,

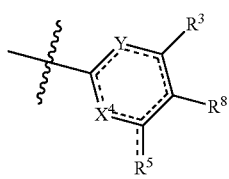

is RHS5, each $R^{20}$ is hydrogen.

In some embodiments of one or more formulae herein Ar is LHS14,

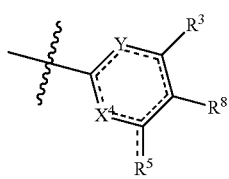

is RHS6, each $R^{20}$ is hydrogen.

In some embodiments of one or more formulae herein Ar is LHS14,

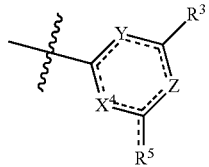

is RHS7, each $R^{20}$ is hydrogen.

In some embodiments of one or more formulae herein Ar is LHS14,

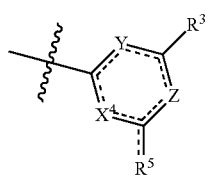

is RHS8, each $R^{20}$ is hydrogen.

In some embodiments of one or more formulae herein Ar is LHS17,

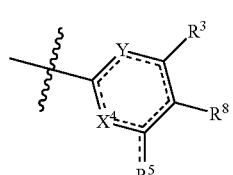

is RHS1, each $R^{20}$ is hydrogen.

In some embodiments of one or more formulae herein Ar is LHS17,

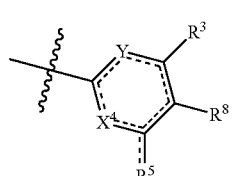

is RHS2, each $R^{20}$ is hydrogen.

In some embodiments of one or more formulae herein Ar is LHS17,

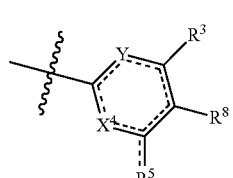

is RHS3, each $R^{20}$ is hydrogen.

In some embodiments of one or more formulae herein Ar is LHS17,

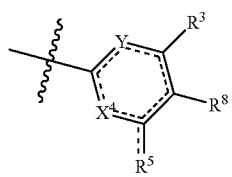

is RHS4, each $R^{20}$ is hydrogen.

In some embodiments of one or more formulae herein Ar is LHS17,

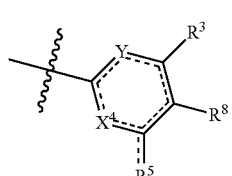

is RHS5, each $R^{20}$ is hydrogen.

In some embodiments of one or more formulae herein Ar is LHS17,

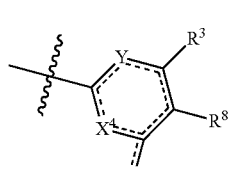

is RHS6, each $R^{20}$ is hydrogen.

In some embodiments of one or more formulae herein Ar is LHS17,

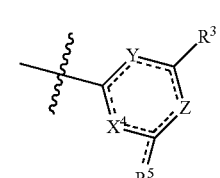

is RHS7, each $R^{20}$ is hydrogen.

In some embodiments of one or more formulae herein Ar is LHS17,

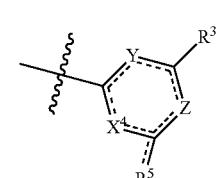

is RHS8, each $R^{20}$ is hydrogen.

In some embodiments of one or more formulae herein Ar is LHS18,

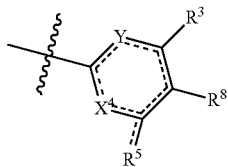

is RHS1, each $R^{20}$ is hydrogen.

In some embodiments of one or more formulae herein Ar is LHS18,

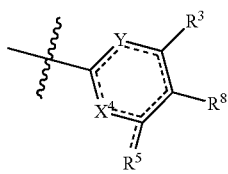

is RHS2, each $R^{20}$ is hydrogen.

In some embodiments of one or more formulae herein Ar is LHS18,

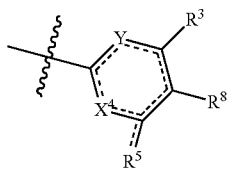

is RHS3, each $R^{20}$ is hydrogen.

In some embodiments of one or more formulae herein Ar is LHS18,

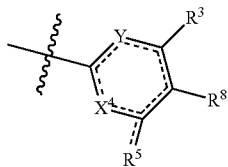

is RHS4, each $R^{20}$ is hydrogen.

In some embodiments of one or more formulae herein Ar is LHS18,

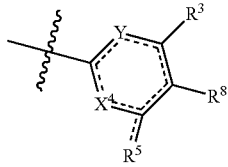

is RHS5, each $R^{20}$ is hydrogen.

In some embodiments of one or more formulae herein Ar is LHS18,

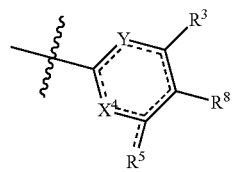

is RHS6, each $R^{20}$ is hydrogen.

In some embodiments of one or more formulae herein Ar is LHS18,

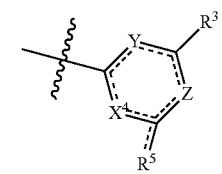

is RHS7, each $R^{20}$ is hydrogen.

In some embodiments of one or more formulae herein Ar is LHS18,

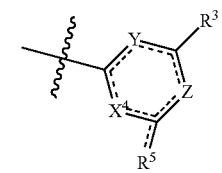

is RHS8, each $R^{20}$ is hydrogen.

In some embodiments of one or more formulae herein Ar is LHS1,

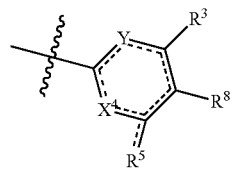

is RHS9, each $R^{20}$ is hydrogen.

In some embodiments of one or more formulae herein Ar is LHS1,

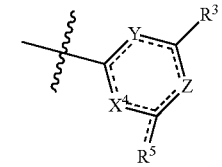

is RHS10, each $R^{20}$ is hydrogen.

In some embodiments of one or more formulae herein Ar is LHS1,

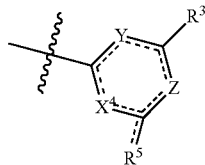

is RHS11, each $R^{20}$ is hydrogen.

In some embodiments of one or more formulae herein Ar is LHS1,

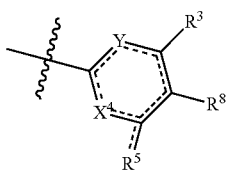

is RHS12, each $R^{20}$ is hydrogen.

In some embodiments of one or more formulae herein Ar is LHS2,

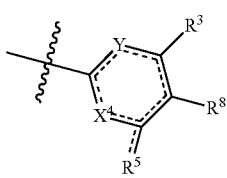

is RHS9, each $R^{20}$ is hydrogen.

In some embodiments of one or more formulae herein Ar is LHS2,

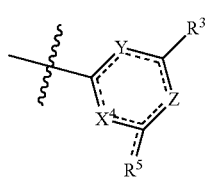

is RHS10, each $R^{20}$ is hydrogen.

In some embodiments of one or more formulae herein Ar is LHS2,

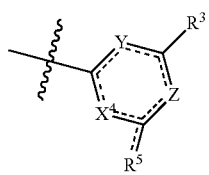

is RHS11, each $R^{20}$ is hydrogen.

In some embodiments of one or more formulae herein Ar is LHS2,

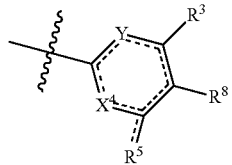

is RHS12, each $R^{20}$ is hydrogen.

In some embodiments of one or more formulae herein Ar is LHS3,

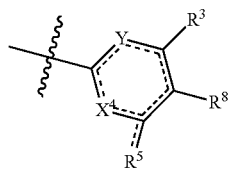

is RHS9, each $R^{20}$ is hydrogen.

In some embodiments of one or more formulae herein Ar is LHS3,

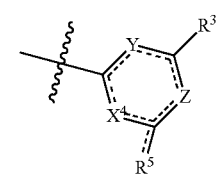

is RHS10, each $R^{20}$ is hydrogen.

In some embodiments of one or more formulae herein Ar is LHS3,

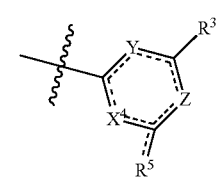

is RHS11, each $R^{20}$ is hydrogen.

In some embodiments of one or more formulae herein Ar is LHS3,

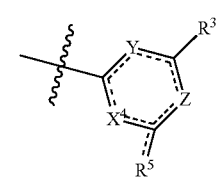

is RHS12, each $R^{20}$ is hydrogen.

In some embodiments of one or more formulae herein Ar is LHS4,

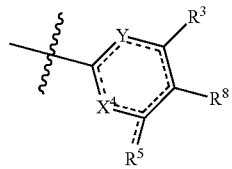

is RHS9, each $R^{20}$ is hydrogen.

In some embodiments of one or more formulae herein Ar is LHS4,

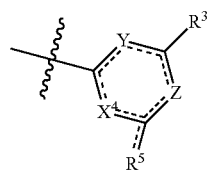

is RHS10, each $R^{20}$ is hydrogen.

In some embodiments of one or more formulae herein Ar is LHS4,

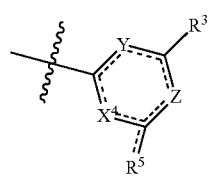

is RHS11, each $R^{20}$ is hydrogen.

In some embodiments of one or more formulae herein Ar is LHS4,

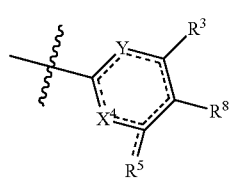

is RHS12, each $R^{20}$ is hydrogen.

In some embodiments of one or more formulae herein Ar is LHS5,

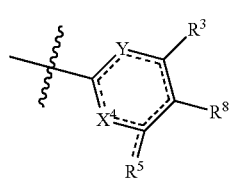

is RHS9, each $R^{20}$ is hydrogen.

In some embodiments of one or more formulae herein Ar is LHS5,

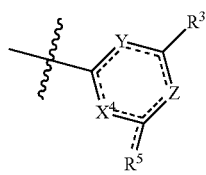

is RHS10, each $R^{20}$ is hydrogen.

In some embodiments of one or more formulae herein Ar is LHS5,

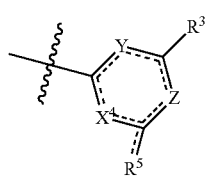

is RHS11, each $R^{20}$ is hydrogen.

In some embodiments of one or more formulae herein Ar is LHS5,

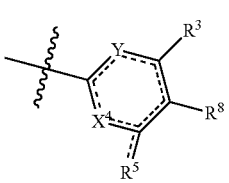

is RHS12, each $R^{20}$ is hydrogen.

In some embodiments of one or more formulae herein Ar is LHS6,

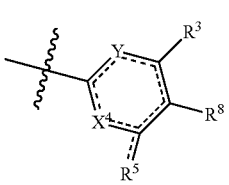

is RHS9, each $R^{20}$ is hydrogen.

In some embodiments of one or more formulae herein Ar is LHS6,

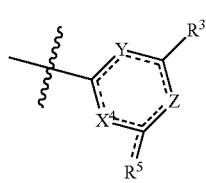

is RHS10, each $R^{20}$ is hydrogen.

In some embodiments of one or more formulae herein Ar is LHS6,

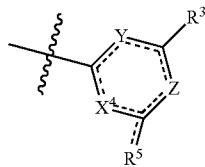

is RHS11, each $R^{20}$ is hydrogen.

In some embodiments of one or more formulae herein Ar is LHS6,

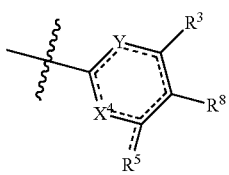

is RHS12, each $R^{20}$ is hydrogen.

In some embodiments of one or more formulae herein Ar is LHS7,

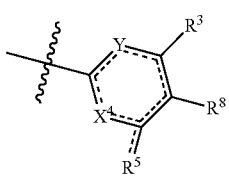

is RHS9, each $R^{20}$ is hydrogen.

In some embodiments of one or more formulae herein Ar is LHS7,

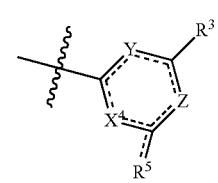

is RHS10, each $R^{20}$ is hydrogen.

In some embodiments of one or more formulae herein Ar is LHS7,

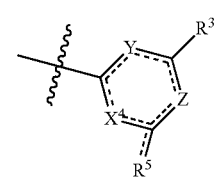

is RHS11, each $R^{20}$ is hydrogen.

In some embodiments of one or more formulae herein Ar is LHS7,

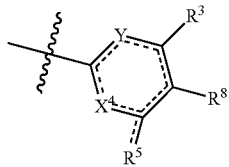

is RHS12, each $R^{20}$ is hydrogen.

In some embodiments of one or more formulae herein Ar is LHS8,

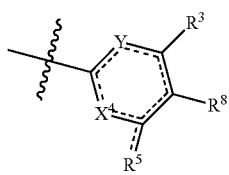

is RHS9, each $R^{20}$ is hydrogen.

In some embodiments of one or more formulae herein Ar is LHS8,

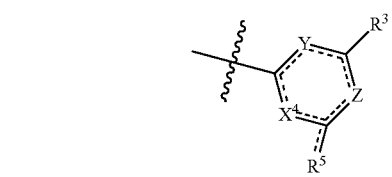

is RHS10, each $R^{20}$ is hydrogen.

In some embodiments of one or more formulae herein Ar is LHS8,

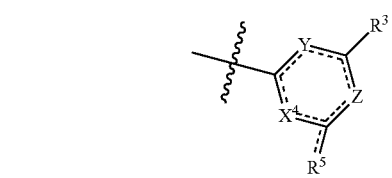

is RHS11, each $R^{20}$ is hydrogen.

In some embodiments of one or more formulae herein Ar is LHS8,

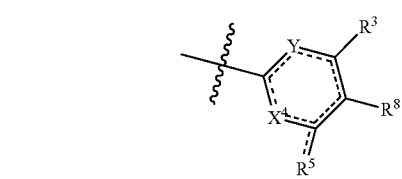

is RHS12, each $R^{20}$ is hydrogen.

In some embodiments of one or more formulae herein Ar is LHS9,

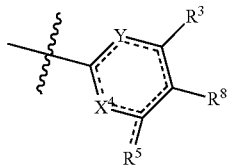

is RHS9, each $R^{20}$ is hydrogen.

In some embodiments of one or more formulae herein Ar is LHS9,

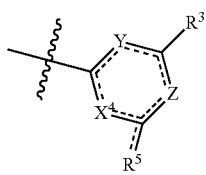

is RHS10, each $R^{20}$ is hydrogen.

In some embodiments of one or more formulae herein Ar is LHS9,

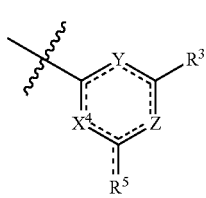

is RHS11, each $R^{20}$ is hydrogen.

In some embodiments of one or more formulae herein Ar is LHS9,

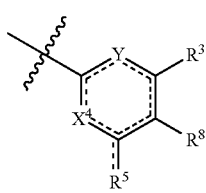

is RHS12, each $R^{20}$ is hydrogen.

In some embodiments of one or more formulae herein Ar is LHS10,

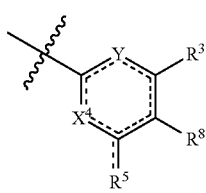

is RHS9, each $R^{20}$ is hydrogen.

In some embodiments of one or more formulae herein Ar is LHS10,

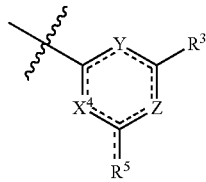

is RHS10, each $R^{20}$ is hydrogen.

In some embodiments of one or more formulae herein Ar is LHS10,

is RHS11, each $R^{20}$ is hydrogen.

In some embodiments of one or more formulae herein Ar is LHS10,

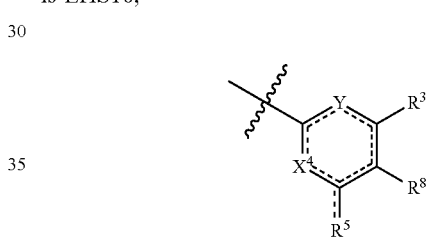

is RHS12, each $R^{20}$ is hydrogen.

In some embodiments of one or more formulae herein Ar is LHS11,

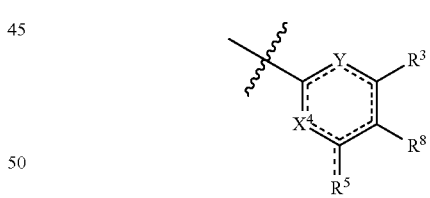

is RHS9, each $R^{20}$ is hydrogen.

In some embodiments of one or more formulae herein Ar is LHS11,

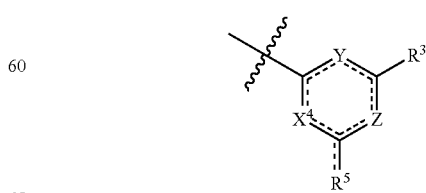

is RHS10, each $R^{20}$ is hydrogen.

In some embodiments of one or more formulae herein Ar is LHS11,

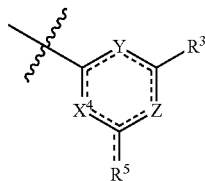

is RHS11, each $R^{20}$ is hydrogen.

In some embodiments of one or more formulae herein Ar is LHS11,

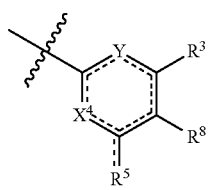

is RHS12, each $R^{20}$ is hydrogen.

In some embodiments of one or more formulae herein Ar is LHS12,

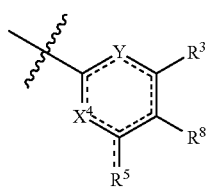

is RHS9, each $R^{20}$ is hydrogen.

In some embodiments of one or more formulae herein Ar is LHS12,

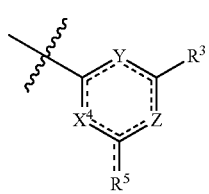

is RHS10, each $R^{20}$ is hydrogen.

In some embodiments of one or more formulae herein Ar is LHS12,

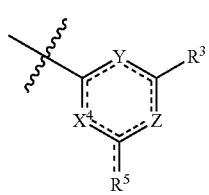

is RHS11, each $R^{20}$ is hydrogen.

In some embodiments of one or more formulae herein Ar is LHS12,

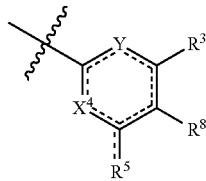

is RHS12, each $R^{20}$ is hydrogen.

In some embodiments of one or more formulae herein Ar is LHS13,

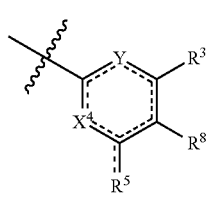

is RHS9, each $R^{20}$ is hydrogen.

In some embodiments of one or more formulae herein Ar is LHS13,

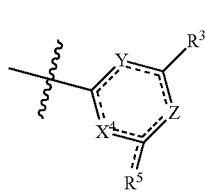

is RHS10, each $R^{20}$ is hydrogen.

In some embodiments of one or more formulae herein Ar is LHS13,

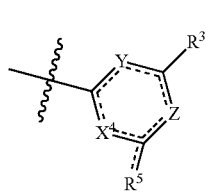

is RHS11, each $R^{20}$ is hydrogen.

In some embodiments of one or more formulae herein Ar is LHS13,

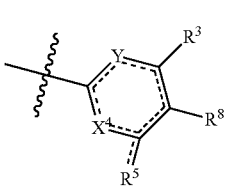

is RHS12, each $R^{20}$ is hydrogen.

In some embodiments of one or more formulae herein Ar is LHS14,

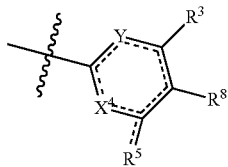

is RHS9, each $R^{20}$ is hydrogen.

In some embodiments of one or more formulae herein Ar is LHS14,

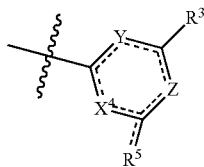

is RHS10, each $R^{20}$ is hydrogen.

In some embodiments of one or more formulae herein Ar is LHS14,

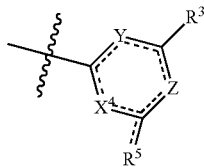

is RHS11, each $R^{20}$ is hydrogen.

In some embodiments of one or more formulae herein Ar is LHS14,

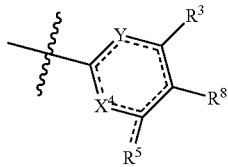

is RHS12, each $R^{20}$ is hydrogen.

In some embodiments of one or more formulae herein Ar is LHS17,

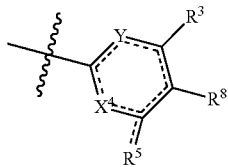

is RHS9, each $R^{20}$ is hydrogen.

In some embodiments of one or more formulae herein Ar is LHS17,

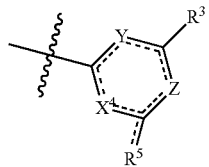

is RHS10, each $R^{20}$ is hydrogen.

In some embodiments of one or more formulae herein Ar is LHS17,

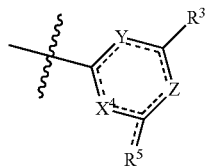

is RHS11, each $R^{20}$ is hydrogen.

In some embodiments of one or more formulae herein Ar is LHS17,

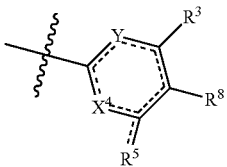

is RHS12, each $R^{20}$ is hydrogen.

In some embodiments of one or more formulae herein Ar is LHS18,

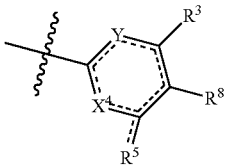

is RHS9, each $R^{20}$ is hydrogen.

In some embodiments of one or more formulae herein Ar is LHS18,

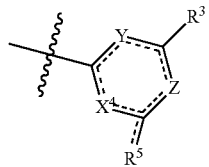

is RHS10, each $R^{20}$ is hydrogen.

In some embodiments of one or more formulae herein Ar is LHS18,

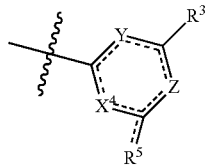

is RHS11, each $R^{20}$ is hydrogen.

In some embodiments of one or more formulae herein Ar is LHS18,

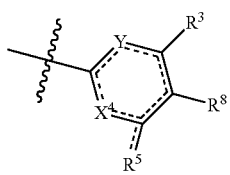

is RHS12, each $R^{20}$ is hydrogen.

In some embodiments of the compound of Formula A, Ar is a heteroaryl group

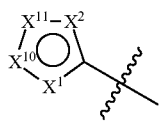

or an aryl or heteroaryl group

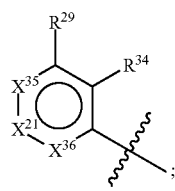

$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;
$X^{35}$ is N or $CR^{35}$;
$X^{21}$ is N or $CR^{21}$;
$X^{36}$ is N or $CR^{36}$;
$X^4$ is $CR^4$, N or $NR^{24}$;
each $R^{20}$ is hydrogen;
Y is $CR^2$;
Z is N or $CR^8$;
$R^8$ is selected from H, CN, Cl, F, $C_1$-$C_6$ alkyl, $C_1$-$C_6$ haloalkoxy, and $C_1$-$C_6$ haloalkyl;
$R^2$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^3$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^4$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;
$R^{24}$ is absent and $R^5$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;

or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

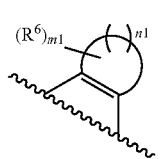

Ring A and ring B is

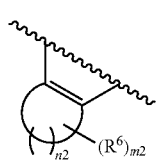

Ring B wherein
each $R^6$ in each ring is H;
each of $R^1$, $R^{10}$, $R^{41}$ and $R^{42}$ when bonded to carbon is independently selected from H, $C_1$-$C_6$ alkyl, $C_1$-$C_6$ haloalkyl, halo, $C_6$-$C_{10}$ aryl, $C_3$-$C_7$ cycloalkyl, $S(O_2)C_1$-$C_6$ akyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, and $NR^{11}R^{12}$;
and each of $R^1$, $R^{10}$, $R^{41}$ and $R^{42}$ when bonded to nitrogen is independently selected from H, $C_1$-$C_6$ alkyl, $C_1$-$C_6$ haloalkyl, $C_6$-$C_{10}$ aryl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, and $NR^{11}R^{12}$;
or $R^1$ and $R^{10}$ taken together with the atoms connecting them form a 3-to-8-membered carbocyclic ring;
each of $R^{34}$, $R^{29}$, $R^{35}$, $R^{11}$ and $R^{36}$ is independently selected from H, $C_1$-$C_6$ alkyl, $C_1$-$C_6$ haloalkyl, halo, $C_3$-$C_7$ cycloalkyl, 3- to 7-membered heterocycloalkyl, $C_6$-$C_{10}$ aryl, and $S(O_2)C_1$-$C_6$ akyl;
wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $C_1$-$C_6$ alkyl, and $NR^{11}R^{12}$,
or two groups selected from $R^{34}$, $R^{29}$, $R^{35}$, $R^{11}$ and $R^{36}$ that are on adjacent ring carbon atoms taken together with the adjacent ring carbons form a 6-membered aromatic ring;
each of $R^{11}$ and $R^{12}$ at each occurrence is hydrogen.

In some embodiments of the compound of Formula A or Formula I,
Ar is a heteroaryl group

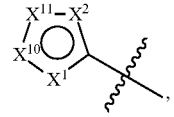

$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;

each of $R^1$, $R^{10}$, $R^{41}$ and $R^{42}$ when bonded to carbon is independently selected from H, $C_1$-$C_6$ alkyl, $C_1$-$C_6$ haloalkyl, halo, $C_6$-$C_{10}$ aryl, $C_3$-$C_7$ cycloalkyl, $S(O_2)C_1$-$C_6$ akyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, and $NR^{11}R^{12}$;

and each of $R^1$, $R^{10}$, $R^{41}$ and $R^{42}$ when bonded to nitrogen is independently selected from H, $C_1$-$C_6$ alkyl, $C_1$-$C_6$ haloalkyl, $C_6$-$C_{10}$ aryl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, and $NR^{11}R^{12}$;

or $R^1$ and $R^{10}$ taken together with the atoms connecting them form a 3-to-8-membered carbocyclic ring.

In some embodiments of the compound of Formula A or Formula II,
Ar is an aryl or heteroaryl group

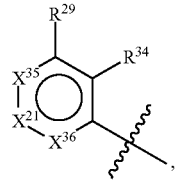, $X^{35}$ is N or $CR^{35}$;
$X^{21}$ is N or $CR^{21}$;
$X^{36}$ is N or $CR^{36}$;

each of $R^{34}$, $R^{29}$, $R^{35}$, $R^{21}$ and $R^{36}$ is independently selected from H, $C_1$-$C_6$ alkyl, $C_1$-$C_6$ haloalkyl, halo, $C_3$-$C_7$ cycloalkyl, 3- to 7-membered heterocycloalkyl, $C_6$-$C_{10}$ aryl, and $S(O_2)C_1$-$C_6$ akyl;

wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $C_1$-$C_6$ alkyl, and $NR^{11}R^{12}$, or two groups selected from $R^{34}$, $R^{29}$, $R^{35}$, $R^{21}$ and $R^{36}$ that are on adjacent ring carbon atoms taken together with the adjacent ring carbons form a 6-membered aromatic ring.

In some embodiments of the compound of Formula A or I,
Ar is a heteroaryl group

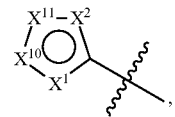, wherein
$X^1$ is O, S, N or CH;
$X^{10}$ is $CR^{10}$ or $NR^{10}$;
$X^{11}$ is N, $CR^1$ or $NR^1$;
$X^2$ is O, S, N or CH;
each of $R^1$ and $R^{10}$ when bonded to carbon is independently selected from H, $C_1$-$C_6$ alkyl, $C_6$-$C_{10}$ aryl, $S(O_2)C_1$-$C_6$ alkyl and $C_3$-$C_7$ cycloalkyl, wherein the $C_1$-$C_6$ alkyl and $C_3$-$C_7$ cycloalkyl is optionally substituted with one or more substituents each independently selected from hydroxy, oxo, $C_1$-$C_6$ alkoxy, and $NR^{11}R^{12}$;

and each of $R^1$, $R^{10}$ when bonded to nitrogen is independently selected from H, $C_1$-$C_6$ alkyl, $C_6$-$C_{10}$ aryl, and $C_3$-$C_7$ cycloalkyl, wherein the $C_1$-$C_6$ alkyl and $C_3$-$C_7$ cycloalkyl is optionally substituted with one or more substituents each independently selected from hydroxy and $C_1$-$C_6$ alkoxy;

$R^8$ is selected from H, CN, Cl, F, $C_1$-$C_6$ alkyl, $C_1$-$C_6$ alkoxy, $C_1$-$C_6$ haloalkoxy, and $C_1$-$C_6$ haloalkyl;

$R^2$ is hydrogen, $C_1$-$C_6$ haloalkyl, $C_3$-$C_7$ cycloalkyl or $C_1$-$C_6$ alkyl;

$R^3$ is hydrogen or halo;

$R^4$ is hydrogen, $C_1$-$C_6$ haloalkyl, $C_3$-$C_7$ cycloalkyl or $C_1$-$C_6$ alkyl;

$R^5$ is hydrogen or halo.

In some embodiments, the compound of formula I is a compound of formula Ia

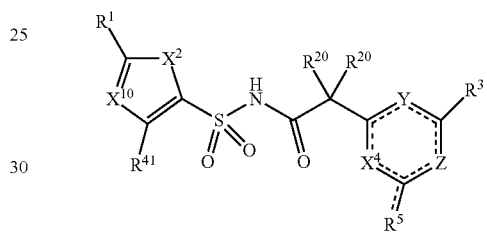

Formula Ia wherein
$X^{10}$ is N or $CR^{10}$;
and
$X^2$ is O, S, or $NR^{42}$.

In some embodiments of the compound of formula Ia
$X^{10}$ is N;
and
$X^2$ is O.

In some embodiments of the compound of formula Ia
$X^{10}$ is N;
and
$X^2$ is S.

In some embodiments of the compound of formula Ia
$X^{10}$ is $CR^{10}$;
and
$X^2$ is O.

In some embodiments of the compound of formula Ia
$X^{10}$ is $CR^{10}$;
and
$X^2$ is S.

In some embodiments of the compound of formula Ia
$X^{10}$ is CH;
and
$X^2$ is O.

In some embodiments of the compound of formula Ia
$X^{10}$ is CH;
and
$X^2$ is S.

In some embodiments, the compound of formula I is a compound of formula Ib

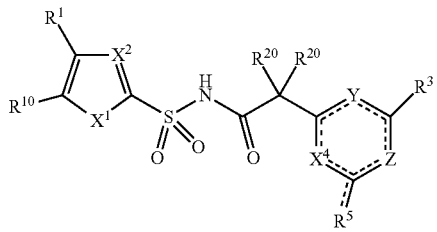

Formula Ib wherein
$X^1$ is O, S, or $NR^{41}$; and
$X^2$ is N or $CR^{42}$.

In some embodiments of the compound of formula Ib
$X^1$ is O; and
$X^2$ is N.

In some embodiments of the compound of formula Ib
$X^1$ is S; and
$X^2$ is N.

In some embodiments of the compound of formula Ib
$X^1$ is O; and
$X^2$ is $CR^{42}$.

In some embodiments of the compound of formula Ib
$X^1$ is S; and
$X^2$ is $CR^{42}$.

In some embodiments of the compound of formula Ib
$X^1$ is O; and
$X^2$ is CH.

In some embodiments of the compound of formula Ib
$X^1$ is S; and
$X^2$ is CH.

In some embodiments of the compound of formula Ib
$X^1$ is S; and
$X^2$ is $CCH_3$.

In some embodiments of the compound of formula A, I, Ia or Ib, $R^1$ is $C_1$-$C_6$ alkyl optionally substituted with hydroxy.

In some embodiments of the compound of formula A, I, Ia or Ib, $R^{10}$ is $C_1$-$C_6$ alkyl optionally substituted with hydroxy.

In some embodiments of the compound of formula A, I, Ia or Ib, $R^1$ is 2-hydroxy-2-propyl.

In some embodiments of the compound of formula A, I, Ia or Ib, $R^{10}$ is 2-hydroxy-2-propyl.

In some embodiments of the compound of formula A, I, Ia or Ib, $R^1$ is $C_3$-$C_7$ cycloalkyl optionally substituted with hydroxy.

In some embodiments of the compound of formula A, I, Ia or Ib, $R^{10}$ is $C_3$-$C_7$ cycloalkyl optionally substituted with hydroxy.

In some embodiments of the compound of formula A, I, Ia or Ib, $R^1$ is 1-hydroxy-1-cyclopropyl.

In some embodiments of the compound of formula A, I, Ia or Ib, $R^{10}$ is 1-hydroxy-1-cyclopropyl.

In some embodiments of the compound of formula A, I, Ia or Ib, $R^{41}$ is $C_1$-$C_6$ alkyl optionally substituted with hydroxy.

In some embodiments of the compound of formula A, I, Ia or Ib, $R^{42}$ is $C_1$-$C_6$ alkyl optionally substituted with hydroxy.

In some embodiments of the compound of formula A, I, Ia or Ib, $R^{41}$ is 2-hydroxy-2-propyl.

In some embodiments of the compound of formula A, I, Ia or Ib, $R^{42}$ is 2-hydroxy-2-propyl.

In some embodiments of the compound of formula A, I, Ia or Ib, $R^{41}$ is $C_3$-$C_7$ cycloalkyl optionally substituted with hydroxy.

In some embodiments of the compound of formula A, I, Ia or Ib, $R^{42}$ is $C_3$-$C_7$ cycloalkyl optionally substituted with hydroxy.

In some embodiments of the compound of formula A, I, Ia or Ib, $R^{41}$ is 1-hydroxy-1-cyclopropyl.

In some embodiments of the compound of formula A, I, Ia or Ib, $R^{42}$ is 1-hydroxy-1-cyclopropyl.

In some embodiments of the compound of formula A, I, Ia or Ib, $R^1$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A, I, Ia or Ib, $R^1$ is aminomethyl. In some embodiments of the compound of formula A, I, Ia or Ib, $R^1$ is methylaminomethyl.

In some embodiments of the compound of formula A, I, Ia or Ib, $R^1$ is dimethylaminomethyl.

In some embodiments of the compound of formula A, I, Ia or Ib, $R^1$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A, I, Ia or Ib, $R^1$ is $S(O_2)C_1$-$C_6$ alkyl.

In some embodiments of the compound of formula A, I, Ia or Ib, $R^1$ is $S(O_2)CH_3$.

In some embodiments of the compound of formula A, I, Ia or Ib, $R^{10}$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A, I, Ia or Ib, $R^{10}$ is aminomethyl. In some embodiments of the compound of formula A, I, Ia or Ib, $R^{10}$ is methylaminomethyl.

In some embodiments of the compound of formula A, I, Ia or Ib, $R^{10}$ is dimethylaminomethyl.

In some embodiments of the compound of formula A, I, Ia or Ib, $R^{10}$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A, I, Ia or Ib, $R^{10}$ is $S(O_2)C_1$-$C_6$ alkyl.

In some embodiments of the compound of formula A, I, Ia or Ib, $R^{10}$ is $S(O_2)CH_3$.

In some embodiments of the compound of formula A, I, Ia or Ib, $R^{41}$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A, I, Ia or Ib, $R^{41}$ is aminomethyl. In some embodiments of the compound of formula A, I, Ia or Ib, $R^{41}$ is methylaminomethyl.

In some embodiments of the compound of formula A, I, Ia or Ib, $R^{41}$ is dimethylaminomethyl.

In some embodiments of the compound of formula A, I, Ia or Ib, $R^{41}$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A, I, Ia or Ib, $R^{41}$ is $S(O_2)C_1$-$C_6$ alkyl.

In some embodiments of the compound of formula A, I, Ia or Ib, $R^{41}$ is $S(O_2)CH_3$.

In some embodiments of the compound of formula A, I, Ia or Ib, $R^{42}$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A, I, Ia or Ib, $R^{42}$ is aminomethyl. In some embodiments of the compound of formula A, I, Ia or Ib, $R^{42}$ is methylaminomethyl.

In some embodiments of the compound of formula A, I, Ia or Ib, $R^{42}$ is dimethylaminomethyl.

In some embodiments of the compound of formula A, I, Ia or Ib, $R^{42}$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A, I, Ia or Ib, $R^{42}$ is $S(O_2)C_1$-$C_6$ alkyl.

In some embodiments of the compound of formula A, I, Ia or Ib, $R^{42}$ is $S(O_2)CH_3$.

In some embodiments of the compound of Formula A or II,

Ar is an aryl or heteroaryl group

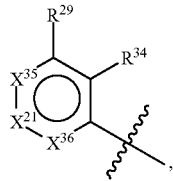

$X^{35}$ is $CR^{35}$;
$X^{21}$ is N or $CR^{21}$; $X^{36}$ is $CR^{36}$;
each of $R^{34}$, $R^{29}$, $R^{35}$, $R^{21}$ and $R^{36}$ is independently selected from H, $C_1$-$C_6$ alkyl, halo, $C_3$-$C_7$ cycloalkyl, 3- to 7-membered nonaromatic monocyclic heterocycloalkyl, $C_6$-$C_{10}$ aryl, and $S(O_2)C_1$-$C_6$ alkyl;
wherein the $C_1$-$C_6$ alkyl, 3- to 7-membered nonaromatic monocyclic heterocycloalkyl, and $C_3$-$C_7$ cycloalkyl is optionally substituted with one or more substituents each independently selected from hydroxyl, $C_1$-$C_6$ alkyl, oxo, $NR^{11}R^{12}$, and 3- to 7-membered heterocycloalkyl, $R^8$ is selected from H, CN, Cl, F, $C_1$-$C_6$ alkyl, $C_1$-$C_6$ alkoxy, $C_1$-$C_6$ haloalkoxy, and $C_1$-$C_6$ haloalkyl;

$R^2$ is hydrogen, $C_1$-$C_6$ haloalkyl, $C_3$-$C_7$ cycloalkyl or $C_1$-$C_6$ alkyl;

$R^3$ is hydrogen or halo;

$R^4$ is hydrogen, $C_1$-$C_6$ haloalkyl, $C_3$-$C_7$ cycloalkyl or $C_1$-$C_6$ alkyl;

$R^5$ is hydrogen or halo.

In some embodiments of the compound of formula A or II, $R^{35}$ is 2-hydroxy-2-propyl.

In some embodiments of the compound of formula A or II, $R^{21}$ is 2-hydroxy-2-propyl.

In some embodiments of the compound of formula A or II, $R^{29}$ is 2-hydroxy-2-propyl.

In some embodiments of the compound of formula A or II, $R^{35}$ is 1-hydroxy-1-cyclopropyl.

In some embodiments of the compound of formula A or II, $R^{21}$ is 1-hydroxy-1-cyclopropyl.

In some embodiments of the compound of formula A or II, $R^{29}$ is 1-hydroxy-1-cyclopropyl.

In some embodiments of the compound of formula A or II, $R^{35}$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A or II, $R^{35}$ is aminomethyl. In some embodiments of the compound of formula A or II, $R^{35}$ is methylaminomethyl. In some embodiments of the compound of formula A or II, $R^{35}$ is dimethylaminomethyl.

In some embodiments of the compound of formula A or II, $R^{35}$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A or II, $R^{35}$ is $S(O_2)C_1$-$C_6$ alkyl.

In some embodiments of the compound of formula A or II, $R^{35}$ is $S(O_2)CH_3$.

In some embodiments of the compound of formula A or II, $R^{21}$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A or II, $R^{21}$ is aminomethyl. In some embodiments of the compound of formula A or II, $R^{21}$ is methylaminomethyl. In some embodiments of the compound of formula A or II, $R^{21}$ is dimethylaminomethyl.

In some embodiments of the compound of formula A or II, $R^{21}$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A or II, $R^{21}$ is $S(O_2)C_1$-$C_6$ alkyl.

In some embodiments of the compound of formula A or II, $R^{21}$ is $S(O_2)CH_3$.

In some embodiments of the compound of formula A or II, $R^{29}$ is $C_1$-$C_6$ alkyl optionally substituted with $NR^{11}R^{12}$, wherein each of $R^{11}$ and $R^{12}$ is independently selected from hydrogen and $C_1$-$C_6$ alkyl.

In some embodiments of the compound of formula A or II, $R^{29}$ is aminomethyl. In some embodiments of the compound of formula A or II, $R^{29}$ is methylaminomethyl. In some embodiments of the compound of formula A or II, $R^{29}$ is dimethylaminomethyl.

In some embodiments of the compound of formula A or II, $R^{29}$ is $C_1$-$C_6$ alkyl optionally substituted with $NR^{11}R^{12}$, wherein $R^{11}$ and $R^{12}$ taken together with the nitrogen they are attached to form a 3- to 7-membered ring optionally containing one or more heteroatoms in addition to the nitrogen they are attached to.

In some embodiments of the compound of formula A or II, $R^{29}$ is $S(O_2)C_1$-$C_6$ alkyl.

In some embodiments of the compound of formula A or II, $R^{29}$ is $S(O_2)CH_3$.

In some embodiments of the compound of formula A or II, $R^{35}$ is 5-membered nonaromatic monocyclic heterocycloalkyl optionally substituted with $C_1$-$C_6$ alkyl.

In some embodiments of the compound of formula A or II, $R^{35}$ is 6-membered nonaromatic monocyclic heterocycloalkyl optionally substituted with $C_1$-$C_6$ alkyl.

In some embodiments of the compound of formula A or II, $R^{35}$ is 7-membered nonaromatic monocyclic heterocycloalkyl optionally substituted with $C_1$-$C_6$ alkyl.

In some embodiments of the compound of formula A or II, $R^{29}$ is 5-membered nonaromatic monocyclic heterocycloalkyl optionally substituted with $C_1$-$C_6$ alkyl.

In some embodiments of the compound of formula A or II, $R^{29}$ is 6-membered nonaromatic monocyclic heterocycloalkyl optionally substituted with $C_1$-$C_6$ alkyl.

In some embodiments of the compound of formula A or II, $R^{29}$ is 7-membered nonaromatic monocyclic heterocycloalkyl optionally substituted with $C_1$-$C_6$ alkyl.

In some embodiments of the compound of formula A or II, $R^{21}$ is 5-membered nonaromatic monocyclic heterocycloalkyl optionally substituted with $C_1$-$C_6$ alkyl.

In some embodiments of the compound of formula A or II, $R^{21}$ is 6-membered nonaromatic monocyclic heterocycloalkyl optionally substituted with $C_1$-$C_6$ alkyl.

In some embodiments of the compound of formula A or II, $R^{21}$ is 7-membered nonaromatic monocyclic heterocycloalkyl optionally substituted with $C_1$-$C_6$ alkyl.

In some embodiments of the compound of formula A or II, $R^{35}$ is 1,3-dioxolan-2-yl.

In some embodiments of the compound of formula A or II, $R^{21}$ is 1,3-dioxolan-2-yl.

In some embodiments of the compound of formula A or II, $R^{29}$ is 1,3-dioxolan-2-yl.

In some embodiments of the compound of formula A or II, $R^{35}$ is 2-methyl-1,3-dioxolan-2-yl.

In some embodiments of the compound of formula A or II, $R^{21}$ is 2-methyl-1,3-dioxolan-2-yl.

In some embodiments of the compound of formula A or II, $R^{29}$ is 2-methyl-1,3-dioxolan-2-yl.

In some embodiments of the compound of formula A or II, $R^{35}$ is $S(O_2)C_1$-$C_6$ alkyl.

In some embodiments of the compound of formula A or II, $R^{21}$ is $S(O_2)C_1$-$C_6$ alkyl.

In some embodiments of the compound of formula A or II, $R^{29}$ is $S(O_2)C_1$-$C_6$ alkyl.

In some embodiments of the compound of formula A or II, $R^{35}$ is $S(O_2)CH_3$.

In some embodiments of the compound of formula A or II, $R^{21}$ is $S(O_2)CH_3$.

In some embodiments of the compound of formula A or II, $R^{29}$ is $S(O_2)CH_3$.

In some embodiments of the compound of formula A or II, $R^{29}$ is $C_1$-$C_6$ alkyl.

In some embodiments of the compound of formula A or II, $R^{35}$ is $C_1$-$C_6$ alkyl.

In some embodiments of the compound of formula A or II, $R^{21}$ is $C_1$-$C_6$ alkyl.

In some embodiments of the compound of formula A or II, $R^{34}$ is $C_1$-$C_6$ alkyl.

In some embodiments of the compound of formula A or II, $R^{36}$ is $C_1$-$C_6$ alkyl.

In some embodiments of the compound of formula A or II, $R^{29}$ is $CH_3$.

In some embodiments of the compound of formula A or II, $R^{35}$ is $CH_3$.

In some embodiments of the compound of formula A or II, $R^{21}$ is $CH_3$.

In some embodiments of the compound of formula A or II, $R^{34}$ is $CH_3$.

In some embodiments of the compound of formula A or II, $R^{36}$ is $CH_3$.

In some embodiments of the compound of formula A or II, $R^{29}$ is halo.

In some embodiments of the compound of formula A or II, $R^{35}$ is halo.

In some embodiments of the compound of formula A or II, $R^{21}$ is halo.

In some embodiments of the compound of formula A or II, $R^{34}$ is halo.

In some embodiments of the compound of formula A or II, $R^{36}$ is halo.

In some embodiments, provided herein is a compound of Formula III

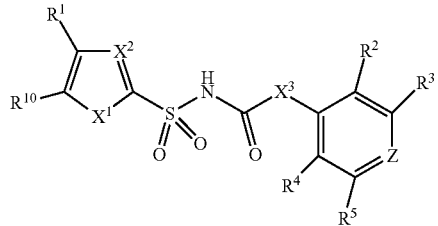

Formula III or a pharmaceutically acceptable salt thereof, wherein:
$X^1$ is O, S, or NH;
$X^2$ is N or $CR^9$;
$X^3$ is $CH_2$;
or $X^3$ and $R^2$ taken together with the atoms connecting them form a four-to-seven-membered carbocyclic ring optionally substituted with one or more $R^{16}$;
or $X^3$ and $R^4$ taken together with the atoms connecting them form a four-to-seven-membered carbocyclic ring optionally substituted with one or more $R^{16}$;
Z is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

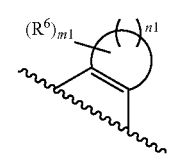

Ring A and ring B is

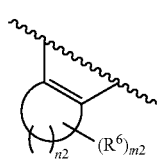

wherein ring A is a carbocyclic ring or a heterocyclic ring containing 1 or 2 heteroatoms independently selected from O, N, and S;

n1 is from 2 to 5;

m1 is from 1 to 10;

wherein ring B is a carbocyclic ring or a heterocyclic ring containing 1 or 2 heteroatoms independently selected from O, N, and S;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and =$NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^1$ is selected from H, $C_1$-$C_6$ alkyl, $C_3$-$C_6$ cycloalkyl and $C_3$-$C_6$ heterocycloalkyl;

wherein $R^1$ is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;

$R^{10}$ is selected from H, $C_1$-$C_6$ alkyl, $C_3$-$C_6$ cycloalkyl and $C_3$-$C_6$ heterocycloalkyl;

wherein $R^{10}$ is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{10}$ is the same or different and is selected from H, $C_1$-$C_6$ alkyl, $C_1$-$C_6$ alkoxy, $NR^{11}R^{12}$, oxo, and =$NR^{13}$.

In some embodiments, provided herein is a compound of Formula III:

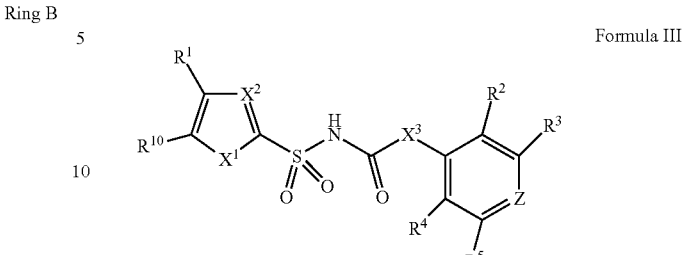

or a pharmaceutically acceptable salt thereof, wherein:

$X^1$ is O, S, or NH;

$X^2$ is N or $CR^9$;

$X^3$ is $CH_2$;

Z is N or $CR^8$;

$R^8$ is selected from H, CN, Cl, F, $CO_2C_1$-$C_6$ alkyl and $CONH_2$;

$R^9$ is selected from H and $C_1$-$C_6$ alkyl;

$R^2$ is hydrogen or $C_1$-$C_6$ alkyl optionally substituted with hydroxy;

$R^3$ is hydrogen or $C_1$-$C_6$ alkyl optionally substituted with hydroxy;

$R^4$ is hydrogen or $C_1$-$C_6$ alkyl optionally substituted with hydroxy and is the same as $R^2$;

$R^5$ is hydrogen or $C_1$-$C_6$ alkyl optionally substituted with hydroxy and is the same as $R^3$;

provided that at least one of $R^2$, $R^3$, $R^4$ and $R^5$ is not hydrogen, and that $R^2$ and $R^4$ are not both hydroxymethyl;

or $R^2$ and $R^3$ taken together with the carbons connecting them form a five-membered ring A and $R^4$ and $R^5$ taken together with the carbons connecting them form a five-membered ring B, wherein ring A is

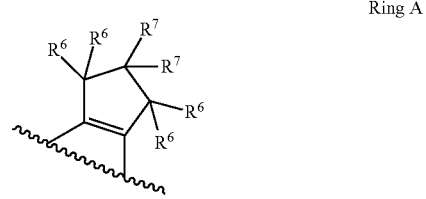

and ring B is

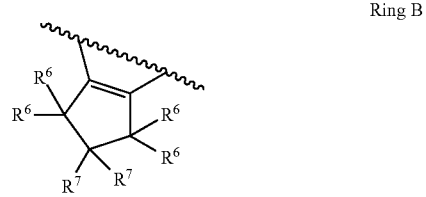

wherein each $R^6$ in each ring is the same and is H or $C_1$-$C_6$ alkyl, and each $R^7$ in each ring is the same and is H or $C_1$-$C_6$ alkyl;

$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo;

$R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo;

or $R^1$ and $R^{10}$ taken together with the atoms connecting them form a five-membered, a six-membered, or a seven-membered carbocyclic or heterocyclic ring.

In some embodiments, provided herein is a compound of Formula III:

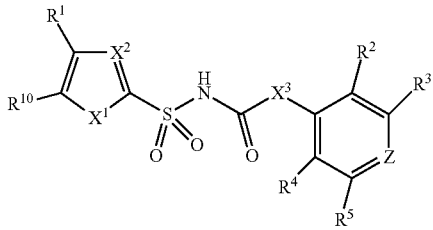

Formula III or a pharmaceutically acceptable salt thereof, wherein:
$X^1$ is O, S, or NH;
$X^2$ is N or $CR^9$;
$X^3$ is $CH_2$;
Z is N or $CR^8$;
$R^8$ is selected from H, CN, Cl, F, $CO_2C_1$-$C_6$ alkyl and $CONH_2$;
$R^9$ is selected from H and $C_1$-$C_6$ alkyl;
$R^2$ is hydrogen or $C_1$-$C_6$ alkyl optionally substituted with hydroxy;
$R^3$ is hydrogen or $C_1$-$C_6$ alkyl optionally substituted with hydroxy;
$R^4$ is hydrogen or $C_1$-$C_6$ alkyl optionally substituted with hydroxy and is the same as $R^2$;
$R^5$ is hydrogen or $C_1$-$C_6$ alkyl optionally substituted with hydroxy and is the same as $R^3$;
or $R^2$ and $R^3$ taken together with the carbons connecting them form a five-membered ring A and $R^4$ and $R^5$ taken together with the carbons connecting them form a five-membered ring B,
wherein ring A is

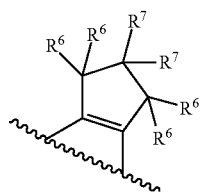

Ring A and ring B is

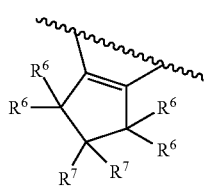

Ring B wherein each $R^6$ in each ring is the same and is H or $C_1$-$C_6$ alkyl, and each IC in each ring is the same and is H or $C_1$-$C_6$ alkyl;

$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo;

$R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo;

or $R^1$ and $R^{10}$ taken together with the atoms connecting them form a five-membered, a six-membered, or a seven-membered carbocyclic or heterocyclic ring.

In some embodiments, the compound of Formula III is a compound of Formula IIIa

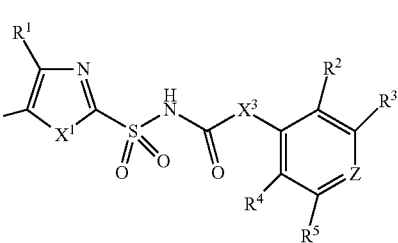

Formula IIIa or a pharmaceutically acceptable salt thereof, wherein:
$X^1$ is O, S, or NH;
$X^3$ is $CH_2$;
or $X^3$ and $R^2$ taken together with the atoms connecting them form a four-to-seven-membered carbocyclic ring optionally substituted with one or more $R^{16}$;
or $X^3$ and $R^4$ taken together with the atoms connecting them form a four-to-seven-membered carbocyclic ring optionally substituted with one or more $R^{16}$;
Z is N or $CR^8$;
$R^8$ is selected from H, CN, Cl, F, $CO_2C_1$-$C_6$ alkyl and $CONH_2$;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

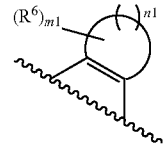

Ring A and ring B is

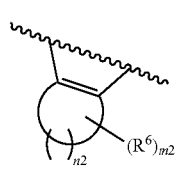

Ring B wherein ring A is a carbocyclic ring or a heterocyclic ring containing 1 or 2 heteroatoms independently selected from O, N, and S;

n1 is from 2 to 5;

m1 is from 1 to 10;

wherein ring B is a carbocyclic ring or a heterocyclic ring containing 1 or 2 heteroatoms independently selected from O, N, and S;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^1$ is selected from H, $C_1$-$C_6$ alkyl and $C_3$-$C_6$ cycloalkyl, wherein $R^1$ is optionally substituted with hydroxy, amino or oxo;

$R^{10}$ is selected from H, $C_1$-$C_6$ alkyl and $C_3$-$C_6$ cycloalkyl, wherein $R^{10}$ is optionally substituted with hydroxy, amino or oxo;

wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$.

In some embodiments, the compound of Formula III is a compound of Formula IIIa

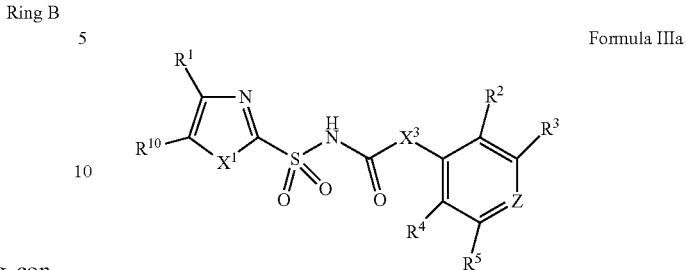

Formula IIIa or a pharmaceutically acceptable salt thereof, wherein $X^1$ is O, S, or NH;

$X^3$ is $CH_2$;

or $X^3$ and $R^2$ taken together with the atoms connecting them form a four-to-seven-membered carbocyclic ring optionally substituted with one or more $R^{16}$;

or $X^3$ and $R^4$ taken together with the atoms connecting them form a four-to-seven-membered carbocyclic ring optionally substituted with one or more $R^{16}$;

Z is N or $CR^8$;

$R^8$ is selected from H, CN, Cl, F, $CO_2C_1$-$C_6$ alkyl and $CONH_2$;

$R^2$ is hydrogen or $C_1$-$C_6$ alkyl optionally substituted with hydroxy;

$R^3$ is hydrogen or $C_1$-$C_6$ alkyl optionally substituted with hydroxy;

$R^4$ is hydrogen or $C_1$-$C_6$ alkyl optionally substituted with hydroxy and is the same as $R^2$;

$R^5$ is hydrogen or $C_1$-$C_6$ alkyl optionally substituted with hydroxy and is the same as $R^3$;

provided that at least one of $R^2$, $R^3$, $R^4$ and $R^5$ is not hydrogen, and that $R^2$ and $R^4$ are not both hydroxymethyl;

or $R^2$ and $R^3$ taken together with the carbons connecting them form a five-membered ring A and $R^4$ and $R^5$ taken together with the carbons connecting them form a five-membered ring B, wherein ring A is

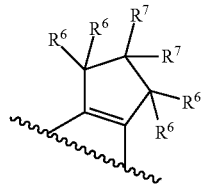

Ring A and ring B is

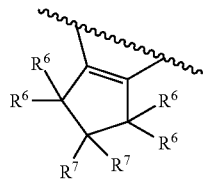

Ring B wherein each $R^6$ in each ring is the same and is H or $C_1$-$C_6$ alkyl, and each $R^7$ in each ring is the same and is H or $C_1$-$C_6$ alkyl;

$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo;

$R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo;

or $R^1$ and $R^{10}$ taken together with the atoms connecting them form a five-membered, a six-membered, or a seven-membered carbocyclic or heterocyclic ring.

In some embodiments, the compound of Formula IIIa is a compound of Formula IIIa-i:

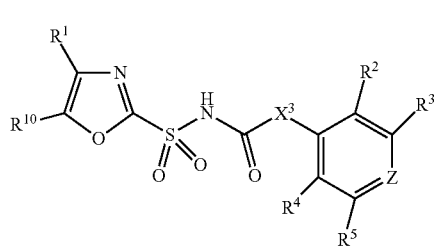

Formula IIIa-i or a pharmaceutically acceptable salt thereof,
wherein:
$X^3$ is NH, O or $CH_2$;
Z is N or $CR^8$;
$R^8$ is selected from H, CN, Cl, F, $CO_2C_1$-$C_6$ alkyl and $CONH_2$;
$R^2$ is $C_1$-$C_6$ alkoxy, halo, $C_1$-$C_6$ haloalkyl, or $C_1$-$C_6$ alkyl optionally substituted with hydroxy;
$R^3$ is hydrogen;
$R^4$ is $C_1$-$C_6$ alkoxy, halo, $C_1$-$C_6$ haloalkyl, or $C_1$-$C_6$ alkyl optionally substituted with hydroxy;
$R^5$ is hydrogen;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

In some embodiments, the compound of Formula IIIa is a compound of Formula IIIa-i:

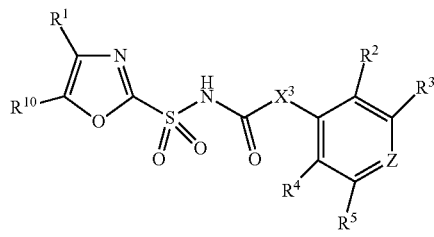

Formula IIIa-i or a pharmaceutically acceptable salt thereof,
wherein:
$X^3$ is NH, O or $CH_2$;
Z is N or $CR^8$;
$R^8$ is selected from H, CN, Cl, F, $CO_2C_1$-$C_6$ alkyl and $CONH_2$;
$R^3$ is $C_1$-$C_6$ alkoxy, halo, $C_1$-$C_6$ haloalkyl, or $C_1$-$C_6$ alkyl optionally substituted with hydroxy;
$R^2$ is hydrogen;
$R^5$ is $C_1$-$C_6$ alkoxy, halo, $C_1$-$C_6$ haloalkyl, or $C_1$-$C_6$ alkyl optionally substituted with hydroxy;
$R^4$ is hydrogen;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

In some embodiments, the compound of Formula IIIa is a compound of Formula IIIa-i:

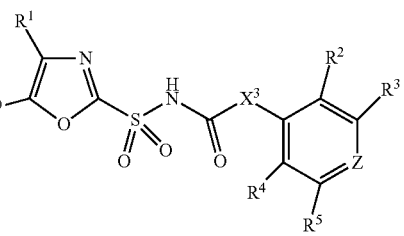

Formula IIIa-i or a pharmaceutically acceptable salt thereof,
wherein:
$X^3$ is NH, O or $CH_2$;
Z is N or $CR^8$;
$R^8$ is selected from H, CN, Cl, F, $CO_2C_1$-$C_6$ alkyl and $CONH_2$;
$R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

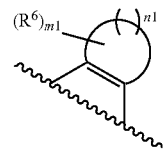

Ring A and ring B is

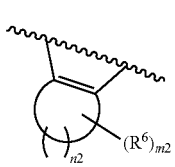

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

In some embodiments, the compound of Formula III is a compound of Formula IIIa-ii Formula IIIa-ii

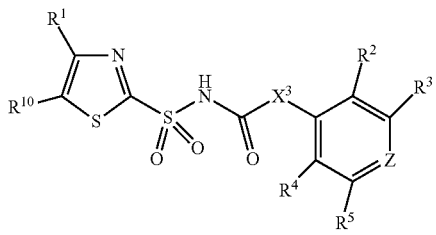

or a pharmaceutically acceptable salt thereof.
In some embodiments, the compound of Formula III is a compound of Formula IIIa-iii Formula IIIa-iii

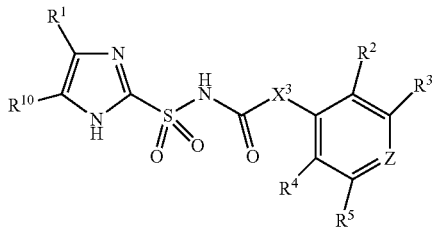

or a pharmaceutically acceptable salt thereof.
In some embodiments of the compound of Formulae IIIa, IIIa-i, IIIa-ii, IIIa-iii, and IIIb, $R^1$ is $C_1$-$C_6$ alkyl or $C_3$-$C_6$ cycloalkyl, wherein $R^1$ is optionally substituted with one or more substituents each independently selected from hydroxy, amino and oxo. In some embodiments of the compound of Formulae IIIa, IIIa-i, IIIa-ii, IIIa-iii, and IIIb, $R^1$ is $C_1$-$C_6$ alkyl optionally substituted with one or more hydroxy. In some embodiments of the compound of Formulae IIIa, IIIa-i, IIIa-ii, IIIa-iii, and IIIb, $R^1$ is $C_1$-$C_6$ alkyl substituted with hydroxy. In some embodiments, the hydroxy is at the carbon of $R^1$ directly bonded to the five-membered heteroaryl ring in Formulae IIIa, IIIa-i, IIIa-ii, IIIa-iii, and IIIb. In some embodiments of the compound of Formulae IIIa, IIIa-i, IIIa-ii, IIIa-iii, and IIIb, $R^1$ is 2-hydroxy-2-propyl.

In some embodiments of the compound of Formulae IIIa, IIIa-i, IIIa-ii, IIIa-iii, and IIIc, $R^{10}$ is $C_1$-$C_6$ alkyl or $C_3$-$C_6$ cycloalkyl, wherein $R^{10}$ is optionally substituted with one or more substituents each independently selected from hydroxy, amino and oxo. In some embodiments of the compound of Formulae IIIa, IIIa-i, IIIa-ii, IIIa-iii, and IIIc, $R^{10}$ is $C_1$-$C_6$ alkyl optionally substituted with one or more hydroxy. In some embodiments of the compound of Formulae IIIa, IIIa-i, IIIa-ii, IIIa-iii, and IIIc, $R^{10}$ is $C_1$-$C_6$ alkyl substituted with hydroxy. In some embodiments, the hydroxy is at the carbon of $R^{10}$ directly bonded to the five-membered heteroaryl ring in Formulae IIIa, IIIa-i, IIIa-ii, IIIa-iii, and IIIc. In some embodiments of the compound of Formulae IIIa, IIIa-i, IIIa-ii, IIIa-iii, and IIIc, $R^{10}$ is 2-hydroxy-2-propyl.

In some embodiments of the compound of Formulae IIIa, IIIa-i, IIIa-ii, and IIIa-iii, $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

In some embodiments of the compound of Formulae IIIa, IIIa-i, IIIa-ii, and IIIa-iii, $R^1$ and $R^{10}$ taken together with the atoms connecting them form a five-membered carbocyclic ring.

In some embodiments of the compound of Formulae IIIa, IIIa-i, IIIa-ii, and IIIa-iii, $R^1$ and $R^{10}$ taken together with the atoms connecting them form a six-membered carbocyclic ring. In some embodiments of the compound of Formulae IIIa, IIIa-i, IIIa-ii, and IIIa-iii, $R^1$ and $R^{10}$ taken together with the atoms connecting them form a five-membered heterocyclic ring containing 1 or 2 heteroatoms independently selected from O, N, and S. In some embodiments of the compound of Formulae IIIa, IIIa-i, IIIa-ii, and IIIa-iii, $R^1$ and $R^{10}$ taken together with the atoms connecting them form a five-membered heterocyclic ring containing 1 or 2 heteroatoms independently selected from O, N, and S.

In some embodiments of the compound of Formulae IIIa, IIIa-i, IIIa-ii, and IIIa-iii, ring A is a carbocyclic ring and n1 is 3.

In some embodiments of the compound of Formulae IIIa, IIIa-i, IIIa-ii, and IIIa-iii, ring A is a carbocyclic ring and n1 is 4.

In some embodiments of the compound of Formulae IIIa, IIIa-i, IIIa-ii, and IIIa-iii, ring A is a heterocyclic ring containing 1 or 2 heteroatoms independently selected from O, N, and S and n1 is 3.

In some embodiments of the compound of Formulae IIIa, IIIa-i, IIIa-ii, and IIIa-iii, ring A is a heterocyclic ring containing 1 or 2 heteroatoms independently selected from O, N, and S and n1 is 4.

In some embodiments of the compound of Formulae IIIa, IIIa-i, IIIa-ii, and IIIa-iii, ring B is a carbocyclic ring and n2 is 3.

In some embodiments of the compound of Formulae IIIa, IIIa-i, IIIa-ii, and IIIa-iii, ring B is a carbocyclic ring and n2 is 4.

In some embodiments of the compound of Formulae IIIa, IIIa-i, IIIa-ii, and IIIa-iii, ring B is a heterocyclic ring containing 1 or 2 heteroatoms independently selected from O, N, and S and n2 is 3.

In some embodiments of the compound of Formulae IIIa, IIIa-i, IIIa-ii, and IIIa-iii, ring B is a heterocyclic ring containing 1 or 2 heteroatoms independently selected from O, N, and S and n2 is 4.

In some embodiments, the compound of Formula III is a compound of Formula IIIb

Formula IIIb

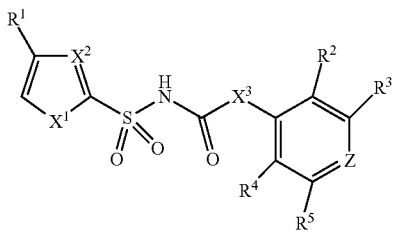

or a pharmaceutically acceptable salt thereof.

In some embodiments, the compound of Formula III is a compound of Formula IIIc

Formula IIIc

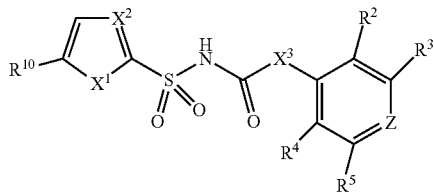

or a pharmaceutically acceptable salt thereof.

In some embodiments, provided herein is a compound of Formula IV

Formula IV

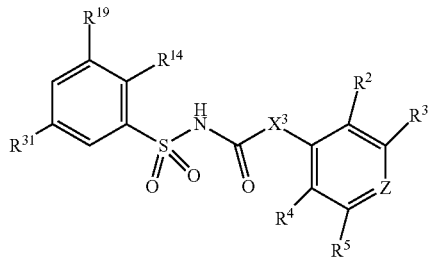

or a pharmaceutically acceptable salt thereof, wherein:
$X^3$ is $CH_2$;
or $X^3$ and $R^2$ taken together with the atoms connecting them form a four-to-seven-membered carbocyclic ring optionally substituted with one or more $R^{16}$;
or $X^3$ and $R^4$ taken together with the atoms connecting them form a four-to-seven-membered carbocyclic ring optionally substituted with one or more $R^{16}$;

Z is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is Ring A

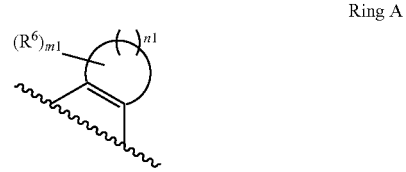

and ring B is

Ring B

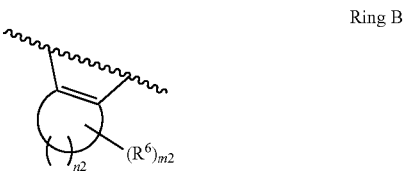

wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{31}$ is selected from H, CN, Cl, or F;
$R^{14}$ is selected from H, CN, Cl, or F;
$R^{19}$ is selected from $C_1$-$C_6$ alkyl, $C(R^{20})_2OH$, $C(R^{20})_2NR^{11}R^{12}$; $C_3$-$C_6$ cycloalkyl and $C_3$-$C_6$ heterocycloalkyl;

wherein, when $R^{19}$ is $C_1$-$C_6$ alkyl, $C_3$-$C_6$ cycloalkyl or $C_3$-$C_6$ heterocycloalkyl, $R^{19}$ is optionally substituted with one or more substituents each independently selected from =$NR^{13}$, $COOC_1$-$C_6$ alkyl, and $CONR^{11}R^{12}$;

each $R^{20}$ is the same and is H or $C_1$-$C_6$ alkyl;

or two $R^{20}$ taken together with the carbon connecting them form a three- to -eight-membered heterocyclic ring containing 1 or 2 heteroatoms independently selected from O, N, and S, or a three-membered, six-membered, seven-membered, or eight-membered carbocyclic ring, wherein the heterocyclic ring or carbocyclic ring is optionally substituted with one or more substituents each independently selected from H, $C_1$-$C_6$ alkyl, $C_1$-$C_6$ alkoxy, $NR^{11}R^{12}$; oxo, and =$NR^{13}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and =$NR^{13}$.

In some embodiments, provided herein is a compound of Formula IV

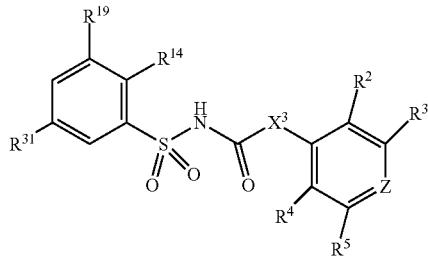

Formula IV or a pharmaceutically acceptable salt thereof, wherein:
$X^3$ is $CH_2$;
or $X^3$ and $R^2$ taken together with the atoms connecting them form a four-to-seven-membered carbocyclic ring optionally substituted with one or more $R^{16}$;
Z is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

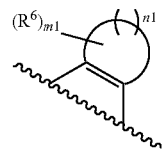

Ring A and ring B is

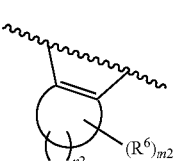

Ring B wherein ring A is a carbocyclic ring or a heterocyclic ring containing 1 or 2 heteroatoms independently selected from O, N, and S;

n1 is from 2 to 5;

m1 is from 1 to 10;

wherein ring B is a carbocyclic ring or a heterocyclic ring containing 1 or 2 heteroatoms independently selected from O, N, and S;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and =$NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^{31}$ is selected from H, CN, Cl, or F;

$R^{14}$ is selected from H, CN, Cl, or F;

$R^{19}$ is selected from $C_1$-$C_6$ alkyl, $C(R^{20})_2OH$, $C(R^{20})_2NR^{11}R^{12}$, $C_3$-$C_6$ cycloalkyl and $C_3$-$C_6$ heterocycloalkyl;

wherein, when $R^{19}$ is $C_1$-$C_6$ alkyl, $C_3$-$C_6$ cycloalkyl or $C_3$-$C_6$ heterocycloalkyl, $R^{19}$ is optionally substituted with one or more substituents each independently selected from =$NR^{13}$, $COOC_1$-$C_6$ alkyl, and $CONR^{11}R^{12}$;

each $R^{20}$ is the same and is H or $C_1$-$C_6$ alkyl;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and =$NR^{13}$.

In some embodiments, provided herein is a compound of Formula IV

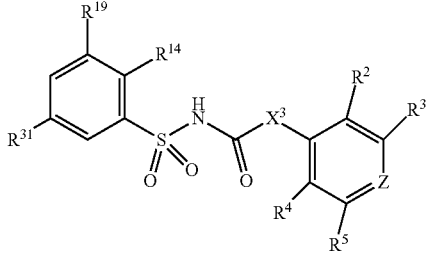

Formula IV or a pharmaceutically acceptable salt thereof, wherein:
$X^3$ is $CH_2$;
Z is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

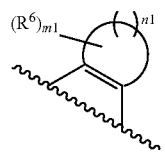

Ring A and ring B is

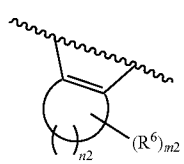

Ring B wherein
ring A is a carbocyclic ring or a heterocyclic ring containing 1 or 2 heteroatoms independently selected from O, N, and S;
n1 is from 2 to 5;
m1 is from 1 to 10;

wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$; oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{31}$ is selected from H, CN, Cl, or F;
$R^{14}$ is selected from H, CN, Cl, or F;
$R^{19}$ is selected from $C_1$-$C_6$ alkyl, $C(R^{20})_2OH$, $C(R^{20})_2NR^{11}R^{12}$; $C_3$-$C_6$ cycloalkyl and $C_3$-$C_6$ heterocycloalkyl;
wherein, when $R^{19}$ is $C_1$-$C_6$ alkyl, $C_3$-$C_6$ cycloalkyl or $C_3$-$C_6$ heterocycloalkyl, $R^{19}$ is optionally substituted with one or more substituents each independently selected from $=NR^{13}$, $COOC_1$-$C_6$ alkyl, and $CONR^{11}R^{12}$;
each $R^{20}$ is the same and is H or $C_1$-$C_6$ alkyl;
each of $R^{11}$, $R^{12}$ and $R^{13}$ at each occurrence is independently selected from hydrogen and $C_1$-$C_6$ alkyl.

In some embodiments, provided herein is a compound of Formula IVa

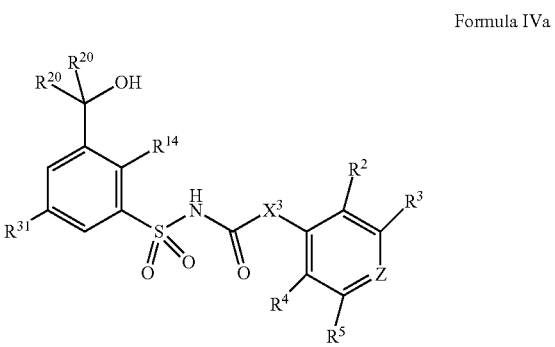

Formula IVa or a pharmaceutically acceptable salt thereof, wherein:
$X^3$ is $CH_2$;
Z is N or $CR^8$;
$R^8$ is selected from H, CN, Cl, F, $CO_2C_1$-$C_6$ alkyl and $CONH_2$;
$R^2$ is hydrogen or $C_1$-$C_6$ alkyl optionally substituted with hydroxy;
$R^3$ is hydrogen or $C_1$-$C_6$ alkyl optionally substituted with hydroxy;
$R^4$ is hydrogen or $C_1$-$C_6$ alkyl optionally substituted with hydroxy and is the same as $R^2$;
$R^5$ is hydrogen or $C_1$-$C_6$ alkyl optionally substituted with hydroxy and is the same as $R^3$;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a five-membered ring A and $R^4$ and $R^5$ taken together with the carbons connecting them form a five-membered ring B, wherein ring A is

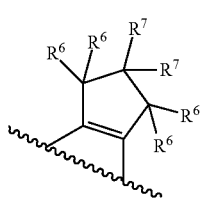

Ring A and ring B is

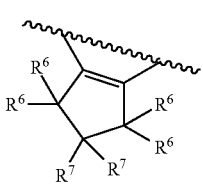

Ring B wherein each $R^6$ in each ring is the same and is H or $C_1$-$C_6$ alkyl, and each $R^7$ each ring is the same and is H or $C_1$-$C_6$ alkyl;
$R^{31}$ is selected from H, CN, Cl, or F;
$R^{14}$ is selected from H, CN, Cl, or F;
each $R^{20}$ is the same and is selected from H and $C_1$-$C_6$ alkyl.

In some embodiments, provided herein is a compound of Formula IVa

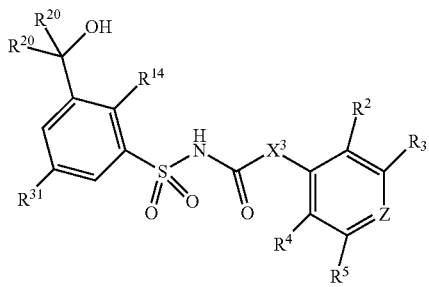

Formula IVa or a pharmaceutically acceptable salt thereof, wherein:
$X^3$ is $CH_2$;
Z is N or $CR^8$;
$R^8$ is selected from H, CN, Cl, F, $CO_2C_1$-$C_6$ alkyl and $CONH_2$;
$R^2$ is hydrogen or $C_1$-$C_6$ alkyl optionally substituted with hydroxy;
$R^3$ is hydrogen or $C_1$-$C_6$ alkyl optionally substituted with hydroxy;
$R^4$ is hydrogen or $C_1$-$C_6$ alkyl optionally substituted with hydroxy and is the same as $R^2$;
$R^5$ is hydrogen or $C_1$-$C_6$ alkyl optionally substituted with hydroxy and is the same as $R^3$;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a five-membered ring A and $R^4$ and $R^5$ taken together with the carbons connecting them form a five-membered ring B, wherein ring A is

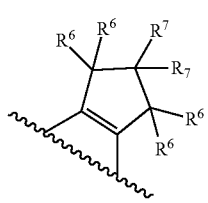

Ring A and ring B is

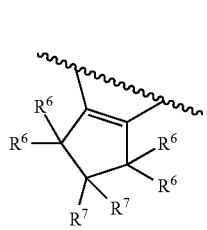

Ring B wherein each $R^6$ in each ring is the same and is H or $C_1$-$C_6$ alkyl, and each $R^7$ each ring is the same and is H or $C_1$-$C_6$ alkyl;
$R^1$ is selected from H, CN, Cl, or F;
$R^{14}$ is selected from H, CN, Cl, or F;
each $R^{20}$ is the same and is selected from H and $C_1$-$C_6$ alkyl.

The Group $X^3$

In some embodiments of one or more formulae herein, $X^3$ is $CH_2$.

In some embodiments, $X^3$ and $R^2$ taken together with the atoms connecting them form a four-to-seven-membered carbocyclic ring optionally substituted with one or more $R^{16}$.

In some embodiments, $X^3$ and $R^4$ taken together with the atoms connecting them form a four-to-seven-membered carbocyclic ring optionally substituted with one or more $R^{16}$.

In some embodiments, $X^3$ and $R^2$ taken together with the atoms connecting them form a four-to-seven-membered ring C of the formula

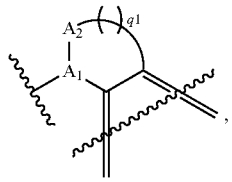

Ring C wherein q1 is 0, 1, 2 or 3; A1 is CH; A2 is $CH_2$; and ring C is optionally substituted with 1 to 8 $R^{16}$.

In some embodiments of ring C, A1 is CH and the CH has (R) stereochemistry.

In some embodiments of ring C, A1 is CH and the CH has (S) stereochemistry.

In some embodiments of ring C, $R^{16}$ is H.

The Group $R^{16}$

In some embodiments of one or more formulae herein, $R^{16}$ is hydrogen.

In some embodiments of one or more formulae herein, $R^{16}$ is $C_1$-$C_6$ alkyl.

In some embodiments of one or more formulae herein, $R^{16}$ is $C_1$-$C_6$ alkoxy.

In some embodiments of one or more formulae herein, $R^{16}$ is $NR^{11}R^{12}$.

In some embodiments of one or more formulae herein, $R^{16}$ is oxo.

In some embodiments of one or more formulae herein, $R^{16}$ is $C_1$=$NR^{13}$.

Unless otherwise indicated, when a disclosed compound is named or depicted by a structure without specifying the stereochemistry and has one or more chiral centers, it is understood to represent all possible stereoisomers of the compound.

It is understood that the combination of variables in the formulae herein is such that the compounds are stable.

In some embodiments, provided herein is a compound selected from the group consisting of the compounds below:

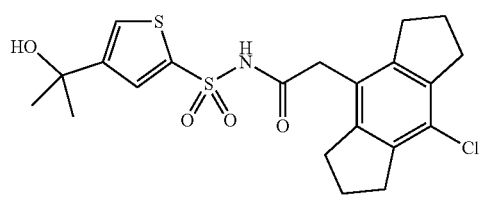

101

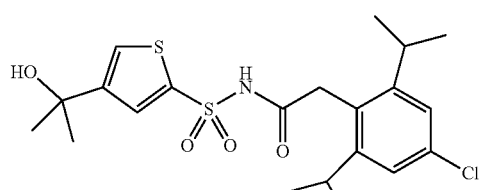

102

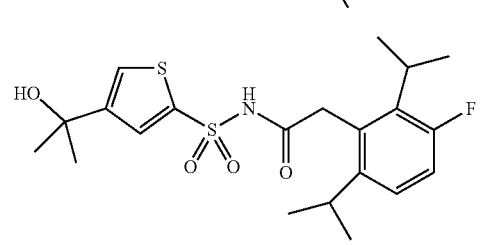

103

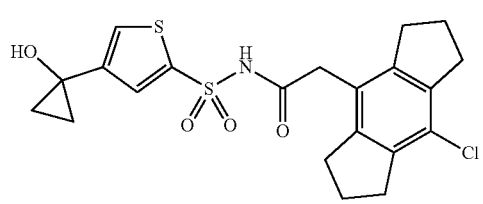

104

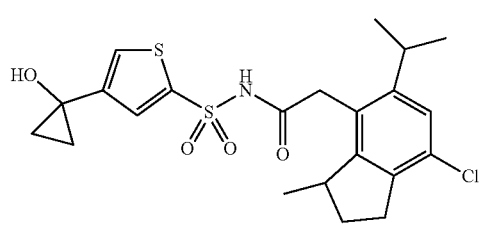

105

-continued

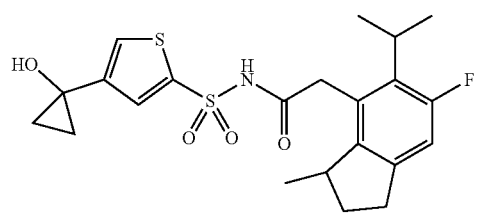

106

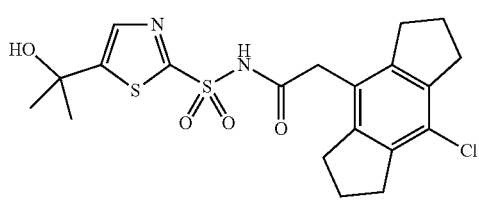

107

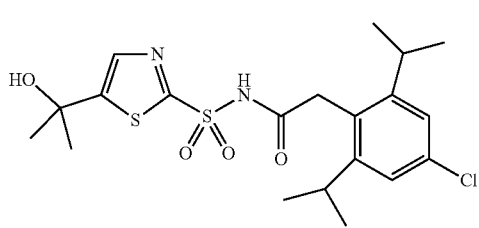

108

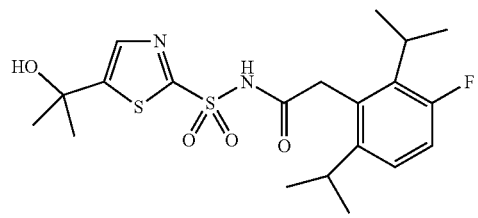

109

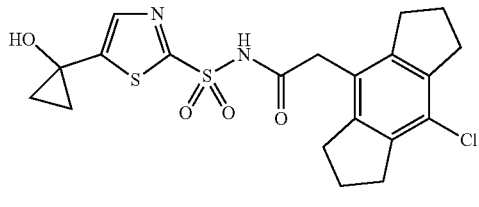

110

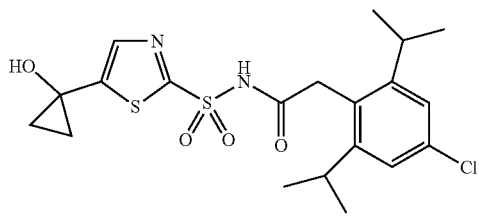

111

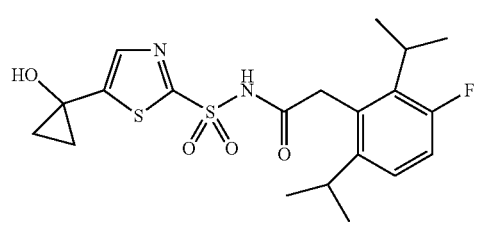

112

133
-continued
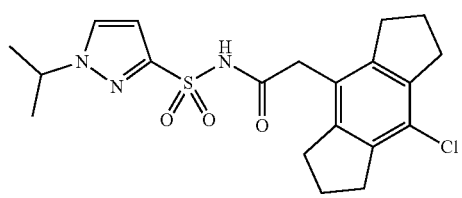
113
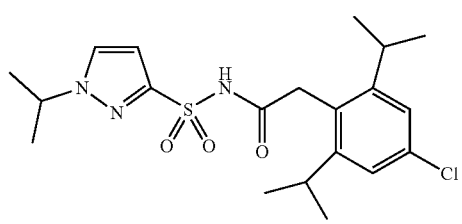
114
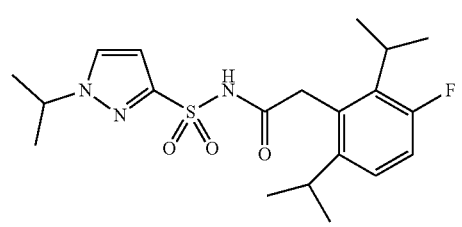
115
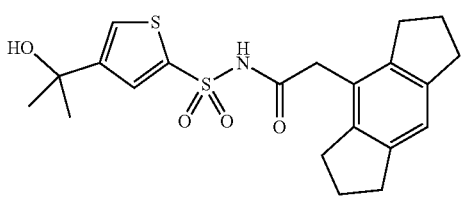
116
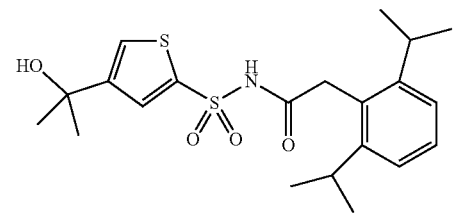
117
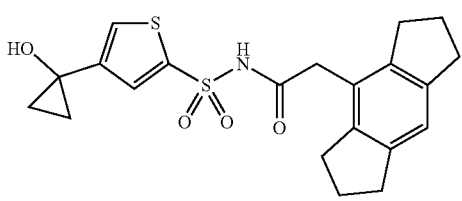
118
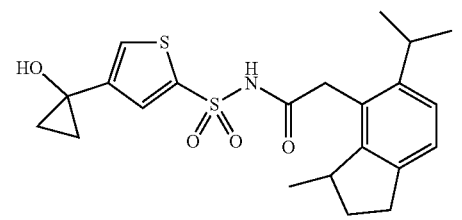
119
134
-continued
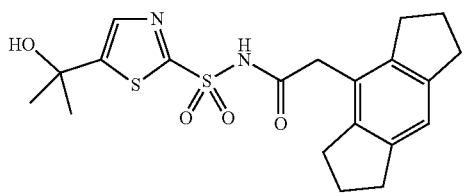
120
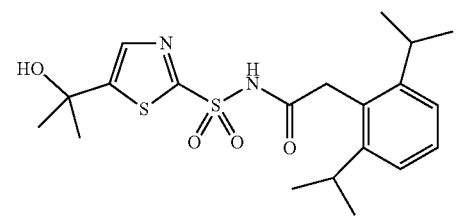
121
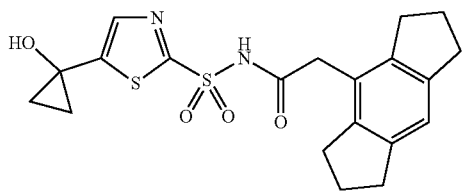
122
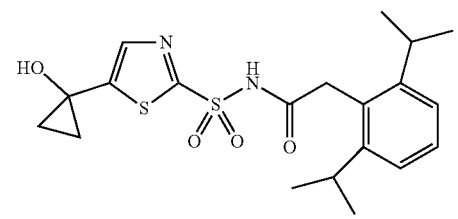
123
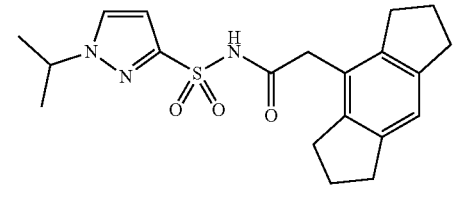
124
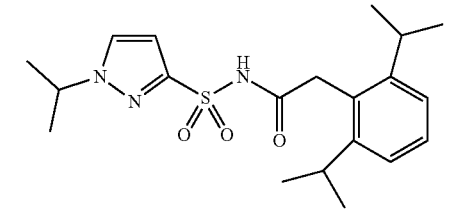
125
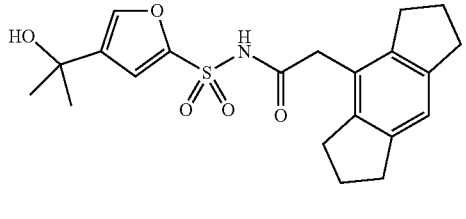
126
and pharmaceutically acceptable salts thereof.

In some embodiments, provided herein is a compound selected from the group consisting of the compounds below:

| Compound | Structure |
|---|---|
| 127 | 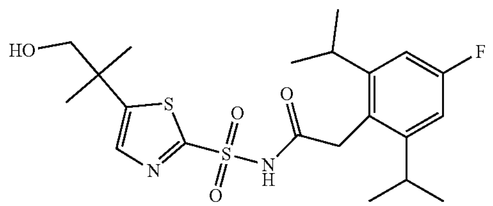 [SMILES: CC(C)c1cc(F)cc(C(C)C)c1CC(=O)NS(=O)(=O)c1ncc(C(C)(C)CO)s1] |
| 128 | 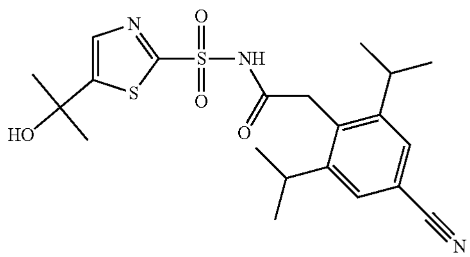 [SMILES: CC(C)c1cc(C#N)cc(C(C)C)c1CC(=O)NS(=O)(=O)c1ncc(C(C)(C)O)s1] |
| 129 | 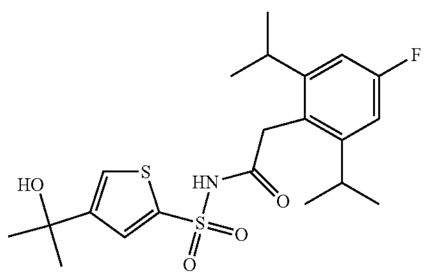 [SMILES: CC(C)c1cc(F)cc(C(C)C)c1CC(=O)NS(=O)(=O)c1cc(C(C)(C)O)cs1] |
| 130 | 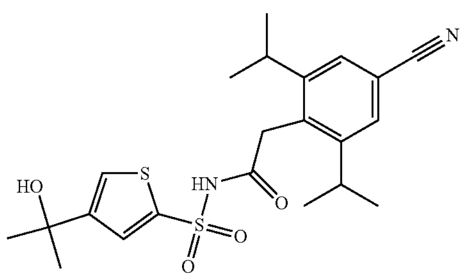 [SMILES: CC(C)c1cc(C#N)cc(C(C)C)c1CC(=O)NS(=O)(=O)c1cc(C(C)(C)O)cs1] |
| 131 | 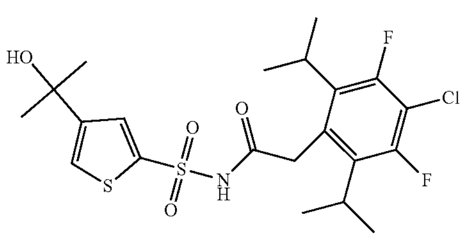 [SMILES: CC(C)c1c(F)c(Cl)c(F)c(C(C)C)c1CC(=O)NS(=O)(=O)c1cc(C(C)(C)O)cs1] |
| 132 | 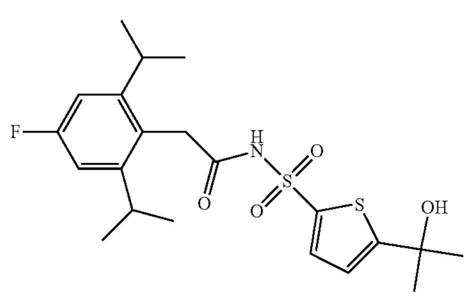 [SMILES: CC(C)c1cc(F)cc(C(C)C)c1CC(=O)NS(=O)(=O)c1ccc(C(C)(C)O)s1] |
| 133 | |
| 134 | |
| 135 | |
| 136 | |
| 137 | |
| 138 | |

| Compound | Structure |
|---|---|
| 139 | 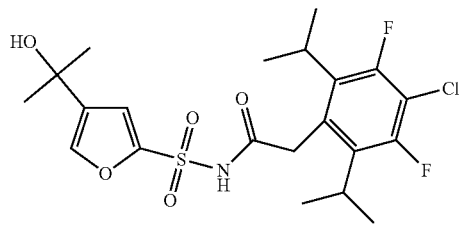 [SMILES: CC(C)c1c(F)c(Cl)c(F)c(C(C)C)c1CC(=O)NS(=O)(=O)c1cc(C(C)(C)O)co1] |
| 140 | 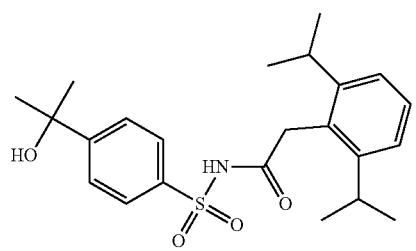 [SMILES: CC(C)c1cccc(C(C)C)c1CC(=O)NS(=O)(=O)c1ccc(C(C)(C)O)cc1] |
| 141 | 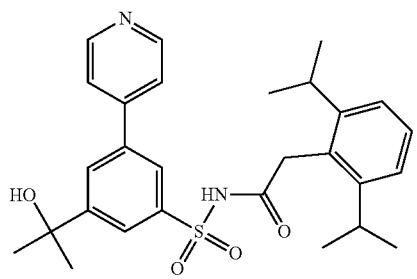 [SMILES: CC(C)c1cccc(C(C)C)c1CC(=O)NS(=O)(=O)c1cc(-c2ccncc2)cc(C(C)(C)O)c1] |
| 142 | 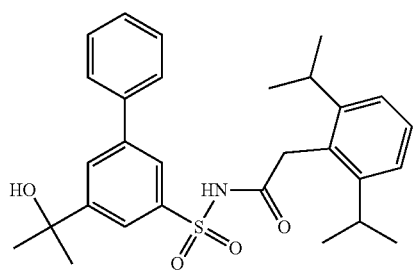 [SMILES: CC(C)c1cccc(C(C)C)c1CC(=O)NS(=O)(=O)c1cc(-c2ccccc2)cc(C(C)(C)O)c1] |
| 143 | 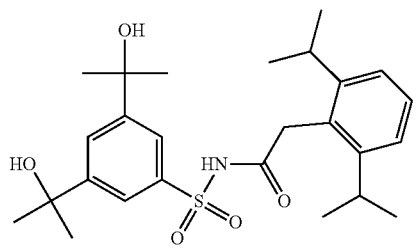 [SMILES: CC(C)c1cccc(C(C)C)c1CC(=O)NS(=O)(=O)c1cc(C(C)(C)O)cc(C(C)(C)O)c1] |
| 144 | 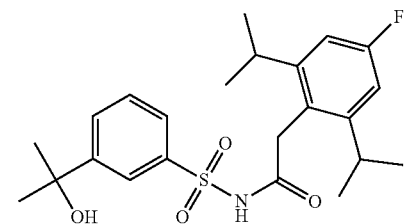 [SMILES: CC(C)c1cc(F)cc(C(C)C)c1CC(=O)NS(=O)(=O)c1cccc(C(C)(C)O)c1] |
| Compound | Structure |
|---|---|
| 145 | 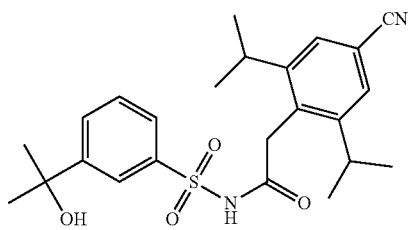 [SMILES: CC(C)c1cc(C#N)cc(C(C)C)c1CC(=O)NS(=O)(=O)c1cccc(C(C)(C)O)c1] |
| 146 | 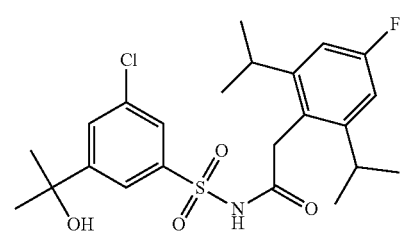 [SMILES: CC(C)c1cc(F)cc(C(C)C)c1CC(=O)NS(=O)(=O)c1cc(Cl)cc(C(C)(C)O)c1] |
| 147 | 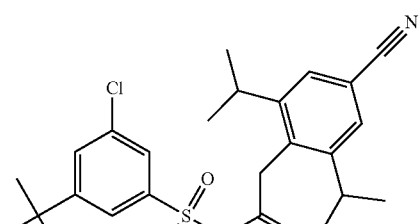 |
| 148 | 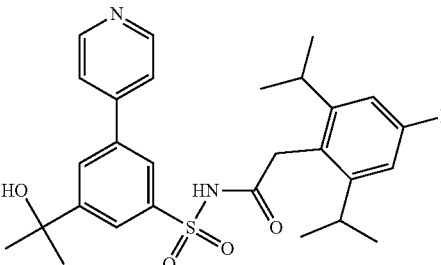 |
| 149 | 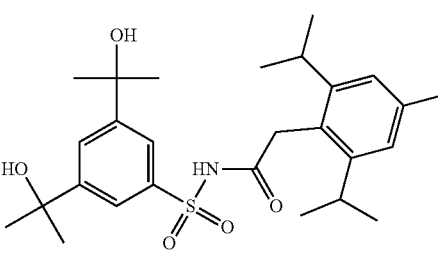 |
| 150 | 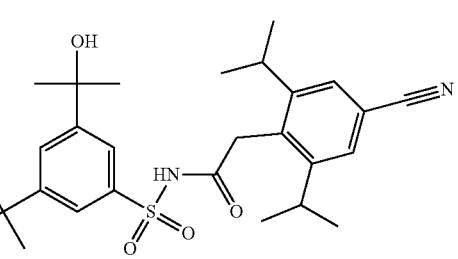 |

-continued
| Compound | Structure |
|---|---|
| 151 | 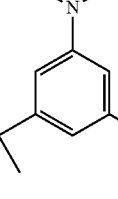 |
| 152 | 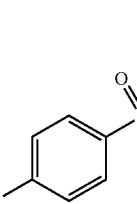 |
| 153 | 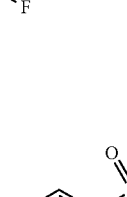 |
| 154 | 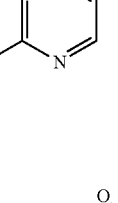 |
| 155 | 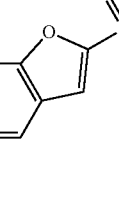 |
| 156 | 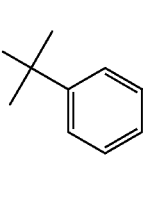 |
-continued
| Compound | Structure |
|---|---|
| 157 | 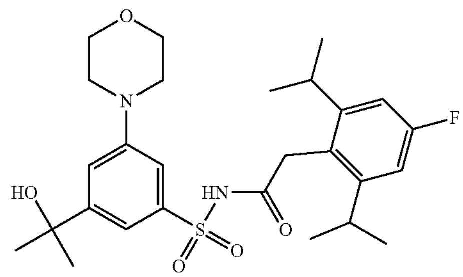 [SMILES: CC(C)c1cc(F)cc(C(C)C)c1CC(=O)NS(=O)(=O)c1cc(N2CCOCC2)cc(C(C)(C)O)c1] |
| 158 | 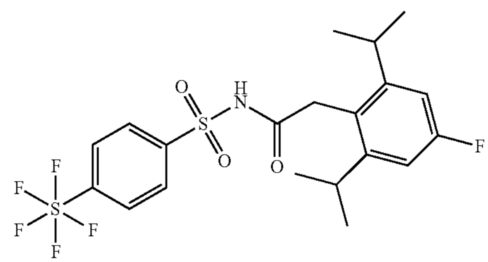 [SMILES: CC(C)c1cc(F)cc(C(C)C)c1CC(=O)NS(=O)(=O)c1ccc(S(F)(F)(F)(F)F)cc1] |
| 159 | 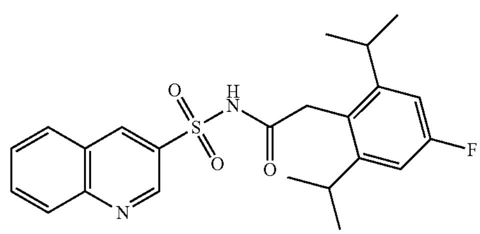 [SMILES: CC(C)c1cc(F)cc(C(C)C)c1CC(=O)NS(=O)(=O)c1cnc2ccccc2c1] |
| 160 | 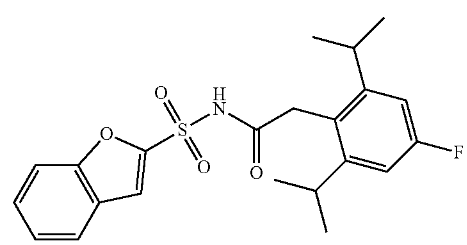 [SMILES: CC(C)c1cc(F)cc(C(C)C)c1CC(=O)NS(=O)(=O)c1cc2ccccc2o1] |
| 161 | 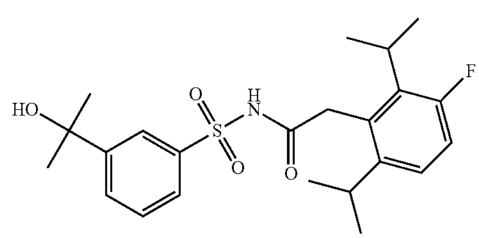 [SMILES: CC(C)c1ccc(F)c(C(C)C)c1CC(=O)NS(=O)(=O)c1cccc(C(C)(C)O)c1] |
| 162 | 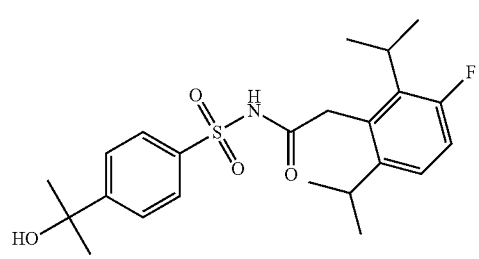 [SMILES: CC(C)c1ccc(F)c(C(C)C)c1CC(=O)NS(=O)(=O)c1ccc(C(C)(C)O)cc1] |

| Compound | Structure |
|---|---|
| 163 | 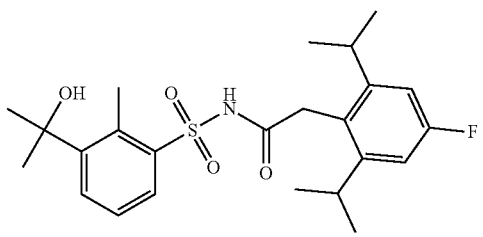 [SMILES: Cc1c(C(C)(C)O)cccc1S(=O)(=O)NC(=O)Cc1c(C(C)C)cc(F)cc1C(C)C] |
| 164 | 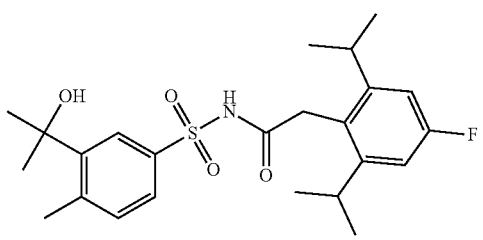 [SMILES: Cc1ccc(S(=O)(=O)NC(=O)Cc2c(C(C)C)cc(F)cc2C(C)C)cc1C(C)(C)O] |
| 165 | 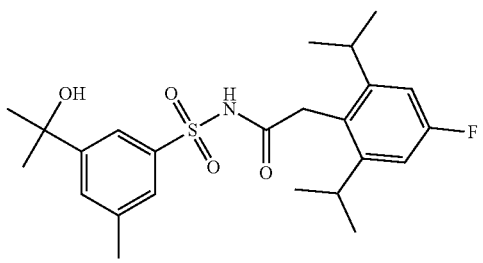 [SMILES: Cc1cc(C(C)(C)O)cc(S(=O)(=O)NC(=O)Cc2c(C(C)C)cc(F)cc2C(C)C)c1] |
| 166 | 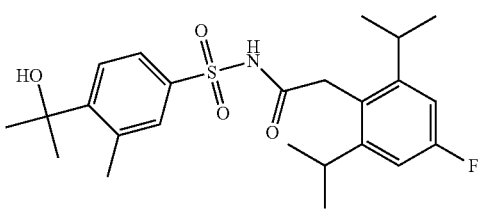 [SMILES: Cc1cc(S(=O)(=O)NC(=O)Cc2c(C(C)C)cc(F)cc2C(C)C)ccc1C(C)(C)O] |
| 167 | 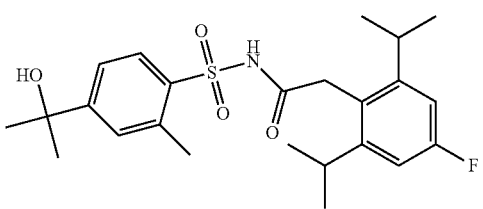 [SMILES: Cc1cc(C(C)(C)O)ccc1S(=O)(=O)NC(=O)Cc1c(C(C)C)cc(F)cc1C(C)C] |
| 168 | 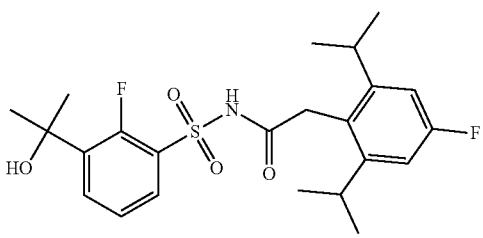 [SMILES: CC(C)c1cc(F)cc(C(C)C)c1CC(=O)NS(=O)(=O)c1cccc(C(C)(C)O)c1F] |
| Compound | Structure |
|---|---|
| 169 | 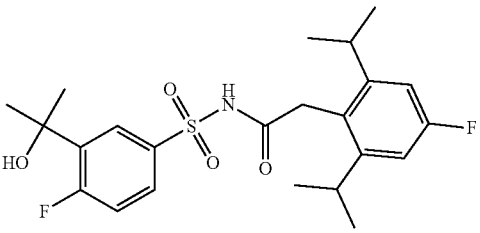 [SMILES: CC(C)c1cc(F)cc(C(C)C)c1CC(=O)NS(=O)(=O)c1ccc(F)c(C(C)(C)O)c1] |
| 170 | 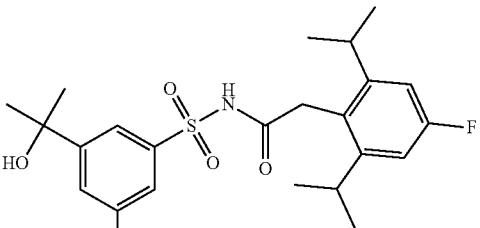 |
| 171 | 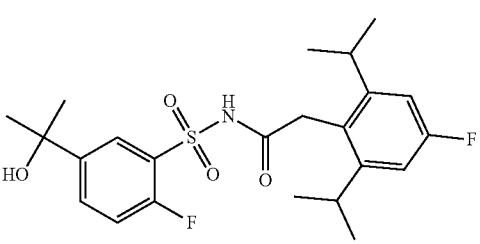 [SMILES: CC(C)c1cc(F)cc(C(C)C)c1CC(=O)NS(=O)(=O)c1cc(C(C)(C)O)ccc1F] |
| 172 | 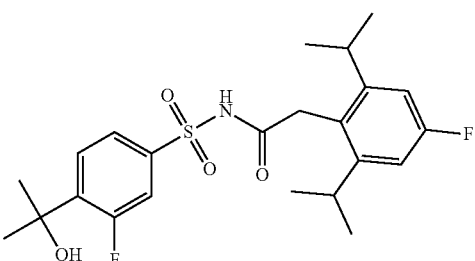 |
| 173 | 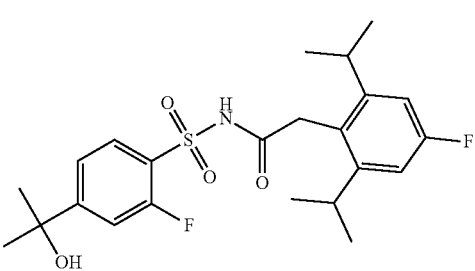 [SMILES: CC(C)c1cc(F)cc(C(C)C)c1CC(=O)NS(=O)(=O)c1ccc(C(C)(C)O)cc1F] |
| 174 | 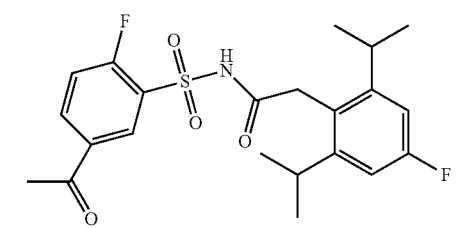 [SMILES: CC(=O)c1ccc(F)c(S(=O)(=O)NC(=O)Cc2c(C(C)C)cc(F)cc2C(C)C)c1] |

| Compound | Structure |
|---|---|
| 175 | 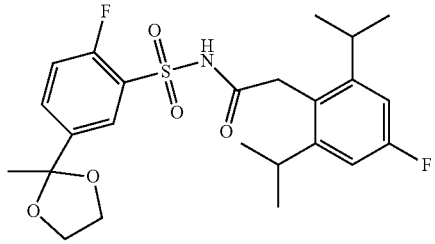 [SMILES: CC(C)c1cc(F)cc(C(C)C)c1CC(=O)NS(=O)(=O)c1cc(C2(C)OCCO2)ccc1F] |
| 176 | 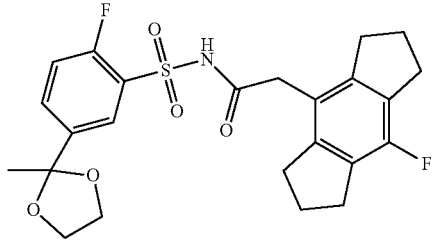 [SMILES: CC1(c2ccc(F)c(S(=O)(=O)NC(=O)Cc3c4c(c(F)c5c3CCC5)CCC4)c2)OCCO1] |
| 177 | 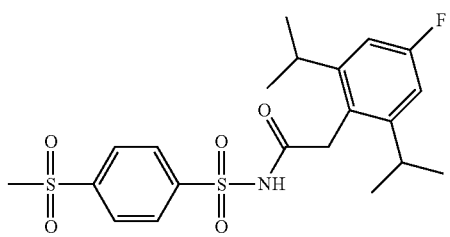 [SMILES: CC(C)c1cc(F)cc(C(C)C)c1CC(=O)NS(=O)(=O)c1ccc(S(C)(=O)=O)cc1] |
| 178 | 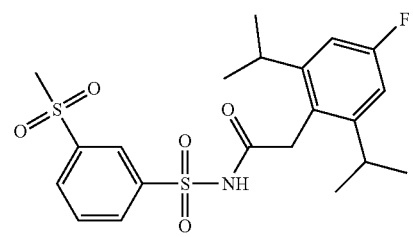 [SMILES: CC(C)c1cc(F)cc(C(C)C)c1CC(=O)NS(=O)(=O)c1cccc(S(C)(=O)=O)c1] |
| 179 | 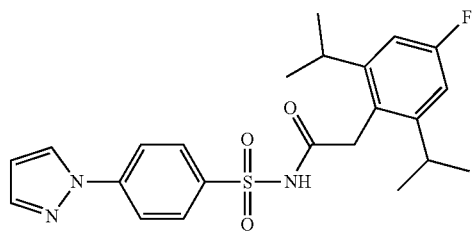 [SMILES: CC(C)c1cc(F)cc(C(C)C)c1CC(=O)NS(=O)(=O)c1ccc(-n2cccn2)cc1] |
| 180 | 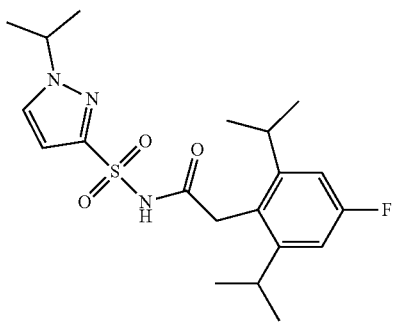 [SMILES: CC(C)c1cc(F)cc(C(C)C)c1CC(=O)NS(=O)(=O)c1ccn(C(C)C)n1] |
| Compound | Structure |
|---|---|
| 181 | 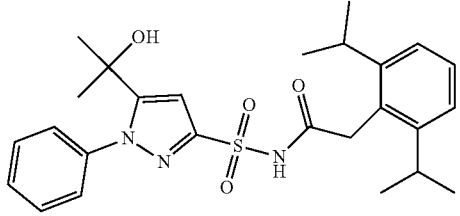 [SMILES: CC(C)c1cccc(C(C)C)c1CC(=O)NS(=O)(=O)c1cc(C(C)(C)O)n(-c2ccccc2)n1] |
| 182 | 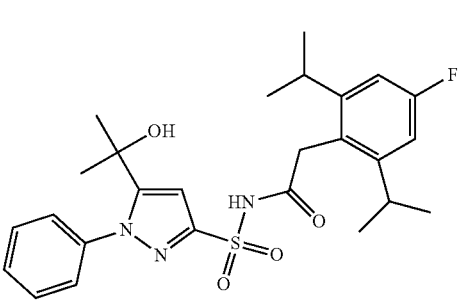 [SMILES: CC(C)c1cc(F)cc(C(C)C)c1CC(=O)NS(=O)(=O)c1cc(C(C)(C)O)n(-c2ccccc2)n1] |
| 183 | 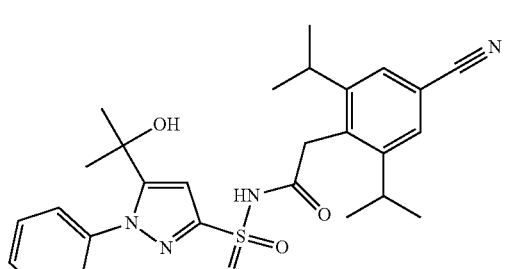 |
| 184 | 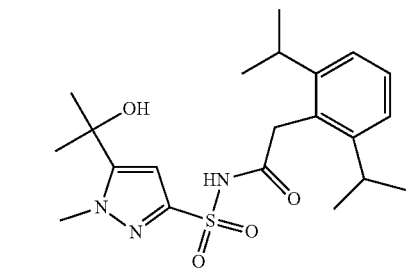 [SMILES: CC(C)c1cccc(C(C)C)c1CC(=O)NS(=O)(=O)c1cc(C(C)(C)O)n(C)n1] |
| 185 | 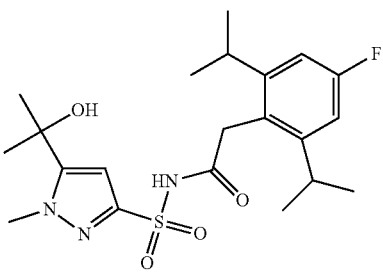 [SMILES: CC(C)c1cc(F)cc(C(C)C)c1CC(=O)NS(=O)(=O)c1cc(C(C)(C)O)n(C)n1] |

| Compound | Structure |
|---|---|
| 186 | 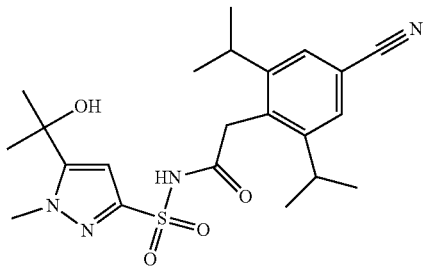 [SMILES: CC(C)c1cc(C#N)cc(C(C)C)c1CC(=O)NS(=O)(=O)c1cc(C(C)(C)O)n(C)n1] |
| 187 | 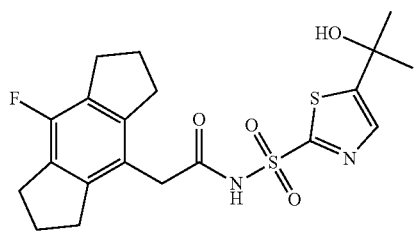 [SMILES: CC(C)(O)c1cnc(S(=O)(=O)NC(=O)Cc2c3c(c(F)c4c2CCC4)CCC3)s1] |
| 188 | 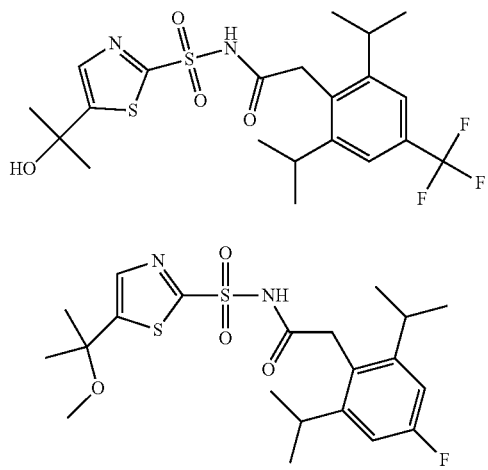 |
| 189 | 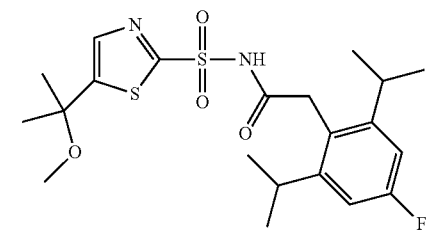 [SMILES: COC(C)(C)c1cnc(S(=O)(=O)NC(=O)Cc2c(C(C)C)cc(F)cc2C(C)C)s1] |
| 190 | 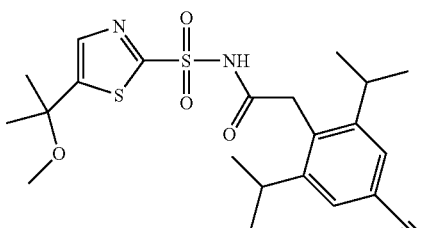 |
| 191 | 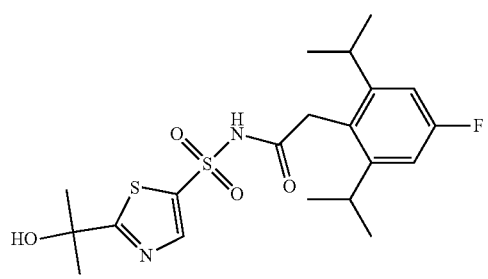 [SMILES: CC(C)c1cc(F)cc(C(C)C)c1CC(=O)NS(=O)(=O)c1cnc(C(C)(C)O)s1] |
| Compound | Structure |
|---|---|
| 192 | 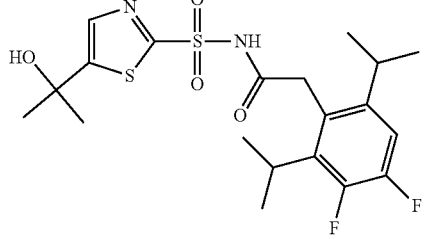 |
| 193 | 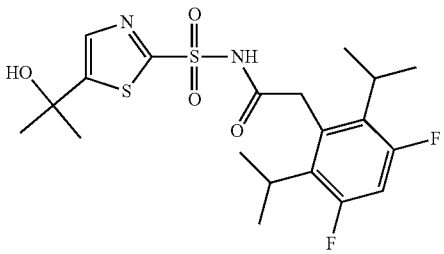 [SMILES: CC(C)c1c(F)cc(F)c(C(C)C)c1CC(=O)NS(=O)(=O)c1ncc(C(C)(C)O)s1] |
| 194 | 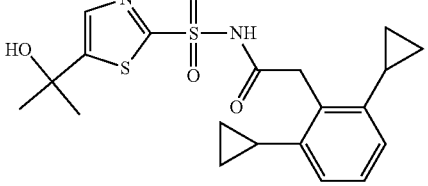 |
| 195 | 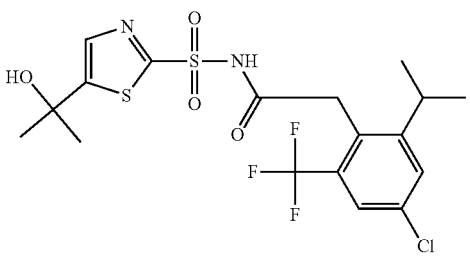 [SMILES: CC(C)c1cc(Cl)cc(C(F)(F)F)c1CC(=O)NS(=O)(=O)c1ncc(C(C)(C)O)s1] |
| 196 | 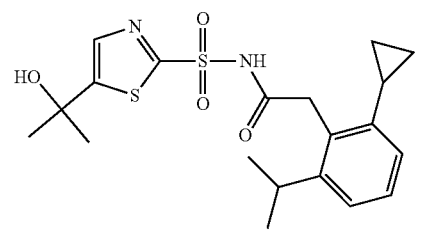 [SMILES: CC(C)c1cccc(C2CC2)c1CC(=O)NS(=O)(=O)c1ncc(C(C)(C)O)s1] |
| 197 | 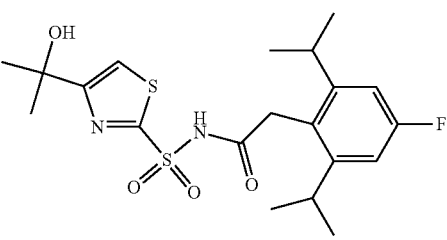 [SMILES: CC(C)c1cc(F)cc(C(C)C)c1CC(=O)NS(=O)(=O)c1nc(C(C)(C)O)cs1] |

| Compound | Structure |
|---|---|
| 198 | 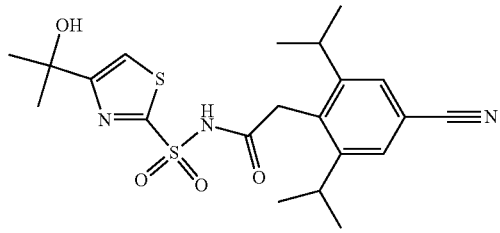 [SMILES: CC(C)c1cc(C#N)cc(C(C)C)c1CC(=O)NS(=O)(=O)c1nc(C(C)(C)O)cs1] |
| 199 | 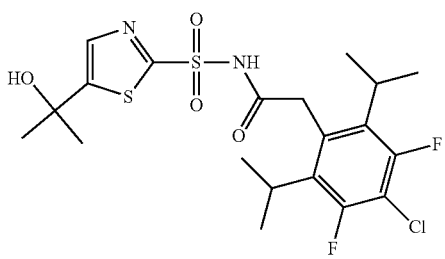 [SMILES: CC(C)c1c(F)c(Cl)c(F)c(C(C)C)c1CC(=O)NS(=O)(=O)c1ncc(C(C)(C)O)s1] |
| 200 | 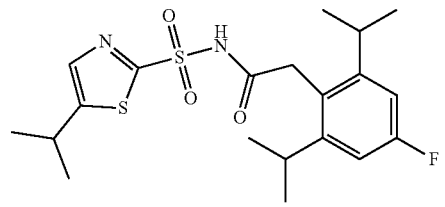 [SMILES: CC(C)c1cnc(S(=O)(=O)NC(=O)Cc2c(C(C)C)cc(F)cc2C(C)C)s1] |
| 201 | 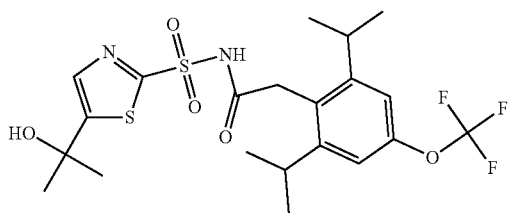 [SMILES: CC(C)c1cc(OC(F)(F)F)cc(C(C)C)c1CC(=O)NS(=O)(=O)c1ncc(C(C)(C)O)s1] |
| 202 | 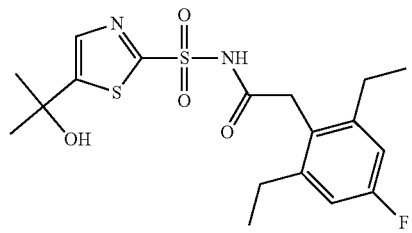 [SMILES: CCc1cc(F)cc(CC)c1CC(=O)NS(=O)(=O)c1ncc(C(C)(C)O)s1] |
| 203 | 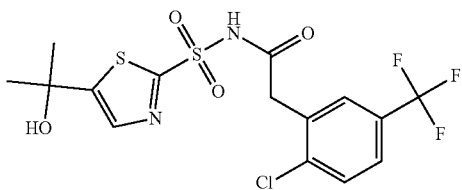 [SMILES: CC(C)(O)c1cnc(S(=O)(=O)NC(=O)Cc2cc(C(F)(F)F)ccc2Cl)s1] |
| Compound | Structure |
|---|---|
| 204 | 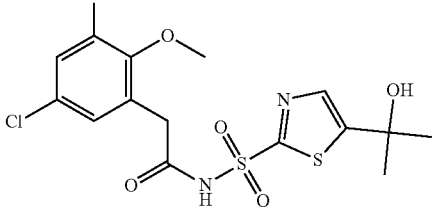 |
| 205 | 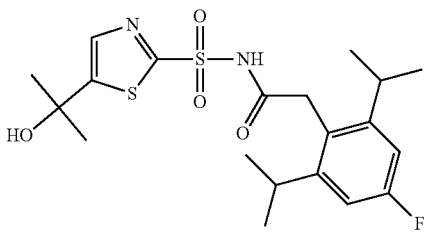 [SMILES: CC(C)c1cc(F)cc(C(C)C)c1CC(=O)NS(=O)(=O)c1ncc(C(C)(C)O)s1] |
| 206 | 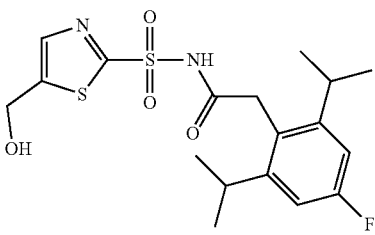 [SMILES: CC(C)c1cc(F)cc(C(C)C)c1CC(=O)NS(=O)(=O)c1ncc(CO)s1] |
| 207 | 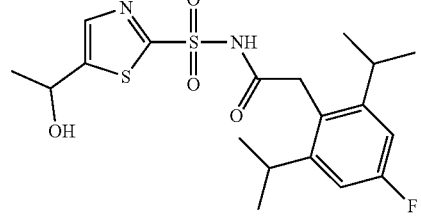 |
| 208 | 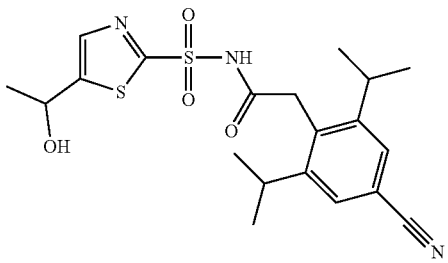 [SMILES: CC(C)c1cc(C#N)cc(C(C)C)c1CC(=O)NS(=O)(=O)c1ncc(C(C)O)s1] |
| 209 | 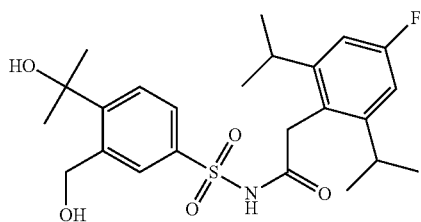 [SMILES: CC(C)c1cc(F)cc(C(C)C)c1CC(=O)NS(=O)(=O)c1ccc(C(C)(C)O)c(CO)c1] |

-continued

| Compound | Structure |
|---|---|
| 210 | |
| 211 | |
| 212 | |
| 213 | |
| 214 | |
| 215 | | and pharmaceutically acceptable salts thereof.

In some embodiments, provided herein is a compound that is not a compound selected from compounds 101 to 126.

In some embodiments, provided herein is a compound that is not a compound selected from compounds 127 to 215.

Pharmaceutical Compositions and Administration

General

In some embodiments, a chemical entity (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP1 or NLRP3 or both NLRP1 and NLRP3 activity (e.g., an increase, e.g., NLRP1/3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CML); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS.

In some embodiments, the indication is non-small lung cancer in patients carrying mutation or overexpression of NLRP3.

In some embodiments, the indication is ALL in patients resistant to glucocorticoids treatment.

In some embodiments, the indication is LCH.

In some embodiments, the indication is multiple myeloma.

In some embodiments, the indication is promyelocytic leukemia.

In some embodiments, the indication is gastric cancer.

In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function.

In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR_014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20

In some embodiments, the methods described herein further include the step of identifying a subject (e.g., a patient) in need of treatment for an indication related to NLRP1 activity, such as an indication related NLRP1 polymorphism.

In some embodiments, the methods described herein further include the step of identifying a subject (e.g., a patient) in need of treatment for an indication related to NLRP1 activity, such as an indication related to NLRP1 where polymorphism is a gain of function In some embodiments, the methods described herein further include the step of identifying a subject (e.g., a patient) in need of treatment for an indication related to NLRP1 activity, such as an indication related NLRP1 polymorphism found in vitiligo Vitiligo-Associated Autoimmune Disease.

In some embodiments, the methods described herein further include the step of identifying a subject (e.g., a patient) in need of treatment for an indication related to NLRP1 activity, such as an indication related where NLRP1 polymorphism is VAR 033239 (L155H)

In some embodiments, the methods described herein further include the step of identifying a subject (e.g., a patient) in need of treatment for an indication related to NLRP1 activity, such as an indication related where NLRP1 polymorphism is a natural variant reported in http://www.uniprot.org/uniprot/Q9C000

In some embodiments, the methods described herein further include the step of identifying a subject (e.g., a patient) in need of treatment for an indication related to NLRP1/3 activity, such as an indication related to point mutation of NLRP1/3 signaling.

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds herein may be prepared, for example, as shown in Scheme 1.

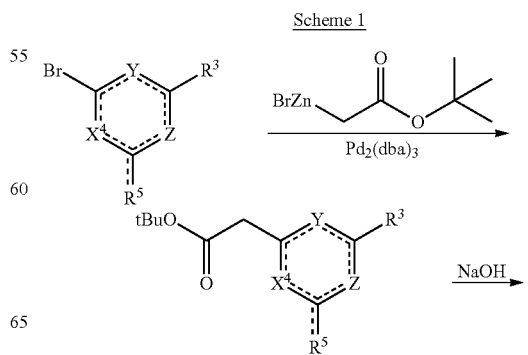

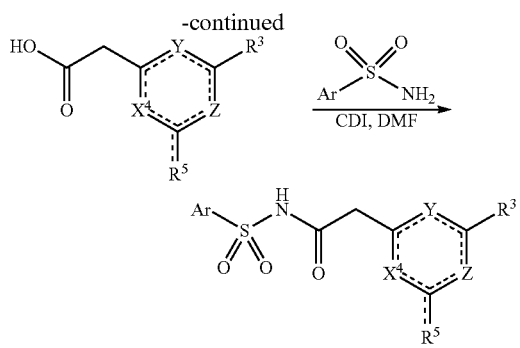

PREPARATIVE EXAMPLES

The following abbreviations have the indicated meanings:
ACN=acetonitrile
AcOH=acetic acid
BINAP=(±)-2,2'-bis(diphenylphosphino)-1,1'-binaphthyl
CDI=carbonyldiimidazole
DBU=1,8-diazabicycloundec-7-ene
DCM=dichloromethane:
Dess-Martin=(1,1,1-triacetoxy)-1,1-dihydro-1,2-benziodoxol-3(1H)-one
DIEA=N,N-diisopropylethylamine
DMAP=4-(dimethylamino)pyridine
DMEDA=N,N'-dimethylethylenediamine
DMF=N,N-dimethylformamide
EDCI=N-(3-dimethylaminopropyl)-N'-ethylcarbodiimide hydrochloride
Et=ethyl
EtOH=ethanol
HATU=O-(7-azabenzotriazol-1-yl)-N,N,N',N'-tetramethyluronium hexafluorophosphate
HBTU=O-benzotriazole-N,N,N',N'-tetramethyluronium-hexafluorophosphate
HOBt=1-hydroxybenzotrizole
LC-MS=liquid chromatography-mass spectrometry
LiHMDS=lithium bis(trimethylsilyl)amid
Me=methyl
MeOH=methanol
NBS=N-bromosuccinimide
NCS=N-chlorosuccinimide
NMR=nuclear magnetic resonance
Pd(dppf)Cl$_2$=dichloro[1,1'-bis(diphenylphosphino)ferrocene]palladium
Pd$_2$(dba)$_3$=tris(dibenzylideneacetone)dipalladium
Ph=phenyl
HPLC=high performance liquid chromatography
Py=pyridine
RT=room temperature
TBAF=tetrabutylammonium fluoride
TBDMSCl=tert-butyldimethylsilyl chloride
TBDPSCl=tert-butyldiphenylsilyl chloride
TEA=triethylamine
TFA=trifluoroacetic acid
THF=tetrahydrofuran
Ti(i-PrO)$_4$=tetraisopropyl titanate
TLC=thin layer chromatography
TsOH=p-toluenesulfonicacidmonohydrate
X-phos=2-(Dicyclohexylphosphino)-2',4',6'-triisopropyl-biphenyl The progress of reactions was often monitored by TLC or LC-MS. The identity of the products was often confirmed by LC-MS. The LC-MS was recorded using one of the following methods.

Method A: Shim-pack XR-ODS, C18, 3×50 mm, 2.5 um column, 1.0 uL injection, 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, 1.5 mL/min flow rate, 90-900 amu scan range, 190-400 nm UV range, 10-95% (1.1 min), 95% (0.6 min) gradient with ACN and water (0.5% NH$_4$HCO$_3$), 2 minute total run time.

Method C: Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 min, 2.2 um column, 1.0 uL injection, 1.5 mL/min flow rate, 90-900 amu scan range, 190-400 nm UV range, 10-95% (2.1 min), 95% (0.6 min) gradient with ACN and water (0.5% NH$_4$HCO$_3$), 3 minute total run time.

The final targets were purified by Prep-HPLC. The Prep-HPLC was carried out using the following method.

Method E: Pre-HPLC: Column, XBridge Shield RP18 OBD (19×250 mm, 10 um); mobile phase, Water (10 mmol/L NH$_4$HCO$_3$) and ACN, UV detection 254/210 nm.

NMR was recorded on BRUKER NMR 300.03 Mz, DUL-C-H, ULTRASHIELD™300, AVANCE II 300 B-ACS™120 or BRUKER NMR 400.13 Mz, BBFO, ULTRASHIELD™400, AVANCE III 400, B-ACS™120.

Scheme of final targets: Schemes A-E illustrate several conditions used for coupling of acid and sulfonamide 2 to afford acyl sulfonamide 3.

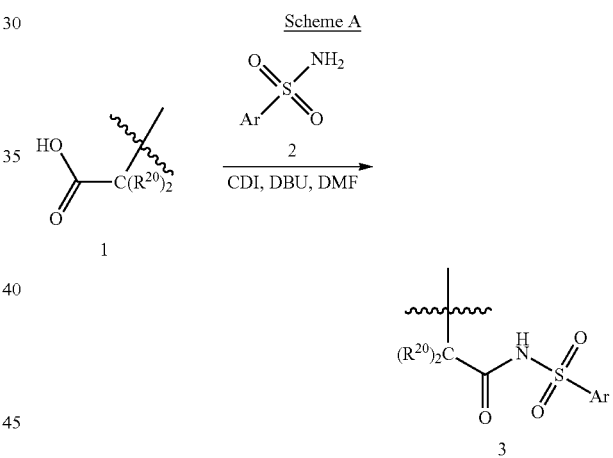

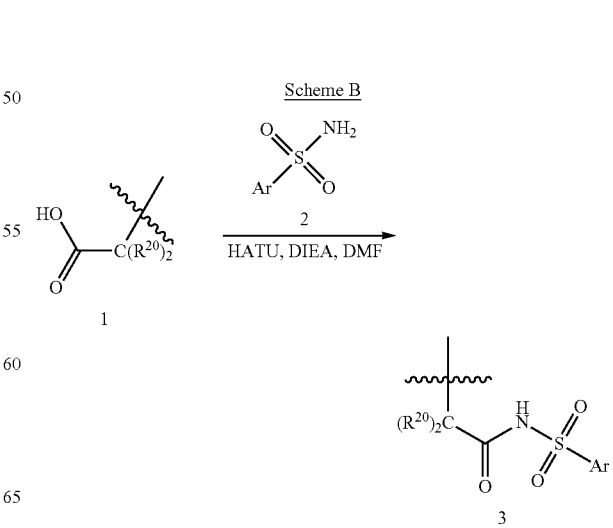

Scheme C

[Structure 1: HO-C(=O)-C(R²⁰)₂- ] + [Structure 2: Ar-S(=O)₂-NH₂]
→ (HATU, DIEA, DMF) →
[Structure 3: (R²⁰)₂C-C(=O)-NH-S(=O)₂-Ar]

Scheme D

[Structure 1: HO-C(=O)-C(R²⁰)₂- ] + [Structure 2: Ar-S(=O)₂-NH₂]
→ (EDCl, HOBt, DMAP, DMF) →
[Structure 3]

Scheme E

[Structure 1] 
→ (1) oxalyl chloride, DMF, DCM
(2) [Structure 2: Ar-S(=O)₂-NH₂], TEA, DCM →
[Structure 3]

Scheme of Sulfonamides Intermediates: Schemes F-Z illustrate the preparation of sulfonamide intermediates. It is understood that the numbering used in the schemes below refers only to the intermediates and that the intermediates are distinct from compounds of formula A, I, and/or II. that may have the same numerical designation. Thus, by way of example, intermediate number "101" in Scheme AE below—that is, the compound

[Structure: 2,6-diisopropyl-3-fluoroaniline]

—is distinct from compound 101 disclosed herein, that is,

101

[Structure of compound 101]

Scheme F

Step 1: [methyl 2-bromothiazole-5-carboxylate] 1 → NaHS, EtOH → [methyl 2-mercaptothiazole-5-carboxylate] 2

Step 2: 2 → NaClO, AcOH → [methyl 2-(chlorosulfonyl)thiazole-5-carboxylate] 3

Step 3: 3 → NH₃/DCM → [methyl 2-sulfamoylthiazole-5-carboxylate] 4

Step 4: 4 → MeMgBr/THF → Intermediate 1 [5-(2-hydroxypropan-2-yl)-thiazole-2-sulfonamide]

Step 5: Intermediate 1 → Et₃SiH, TFA → Intermediate 2 [5-isopropylthiazole-2-sulfonamide]

Intermediate 1

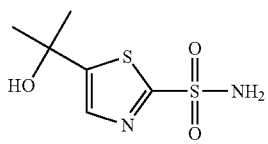

5-(2-Hydroxypropan-2-yl)thiazole-2-sulfonamide

Step 1: Methyl 2-mercaptothiazole-5-carboxylate

Into a 250-mL round-bottom flask, was placed methyl 2-bromothiazole-5-carboxylate (10 g, 45 mmol), EtOH (100 mL), sodium hydrogensulfide (5 g, 89 mmol). The resulting solution was stirred for 2 h at 80° C. and then was cooled to 0° C. with a water/ice bath. The pH value of the solution was adjusted to 3 with hydrogen chloride (1 N). The solids were collected by filtration. This resulted in 6 g (76%) of the title compound as a light yellow solid. MS-ESI: 176.0 (M+1).

Step 2: Methyl 2-(chlorosulfonyl)thiazole-5-carboxylate

Into a 250-mL round-bottom flask, was placed methyl 2-mercaptothiazole-5-carboxylate (6 g, 34 mmol), acetic acid (60 mL). This was followed by the addition of sodium hypochloride (60 mL, 8%-10% wt) in portions at 0° C. The resulting solution was stirred for 1 h at RT and then was diluted with 100 mL of water. The solution was extracted with 3×50 mL of DCM and the organic layers combined and dried over anhydrous Na$_2$SO$_4$, then concentrated under vacuum. This resulted in 5 g (crude, 60%) of the title compound as yellow oil. The crude product was used in the next step.

Step 3: Methyl 2-sulfamoylthiazole-5-carboxylate

Into a 250-mL round-bottom flask, was placed methyl 2-(chlorosulfonyl)thiazole-5-carboxylate (5 g, 21 mmol), DCM (50 mL). This was followed by the addition of a saturated solution of ammonia in DCM (10 mL) in portions at RT. The resulting solution was stirred for 2 h at RT and then was concentrated under vacuum. The residue was applied onto a silica gel column and eluted with ethyl acetate/petroleum ether (1:5 to 1:3). This resulted in 3 g (65%) of the title compound as a white solid. MS-ESI: 223.0 (M+1).

Step 4: 5-(2-Hydroxypropan-2-yl)thiazole-2-sulfonamide

Into a 250-mL round-bottom flask purged with and maintained under nitrogen, was placed a solution of methyl 2-sulfamoylthiazole-5-carboxylate (3 g, 13.5 mmol) in THF (25 mL). This was followed by the addition of MeMgBr/THF (3 M, 18 mL) dropwise with stirring at 0° C. The resulting solution was stirred for 14 h at RT and then was quenched by the addition of 20 mL of NH$_4$Cl (sat.). The resulting solution was extracted with 3×30 mL of DCM and the organic layers combined and dried over anhydrous Na$_2$SO$_4$, then concentrated under vacuum. The residue was applied onto a silica gel column and eluted with ethyl acetate/petroleum ether (1:5 to 1:3). This resulted in 2.3 g (78%) of the title compound as a white solid. MS-ESI: 223.0 (M+1), 221.0 (M−1).

Intermediate 2

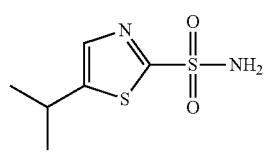

5-Isopropylthiazole-2-sulfonamide

Step 5: 5-Isopropylthiazole-2-sulfonamide

Into a 40-mL sealed tube, was placed 5-(2-hydroxypropan-2-yl)thiazole-2-sulfonamide (500 mg, 2.25 mmol) in TFA (5 mL), Et$_3$SiH (5 mL). The resulting solution was stirred for 4 h at 70° C. and then was concentrated under vacuum. The residue was applied onto a silica gel column and eluted with ethyl acetate/petroleum ether (1:4 to 1:2). This resulted in 380 mg (82%) of the title compound as a yellow solid. MS-ESI: 205.0 (M−1).

Scheme G

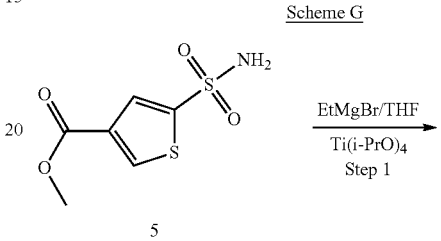

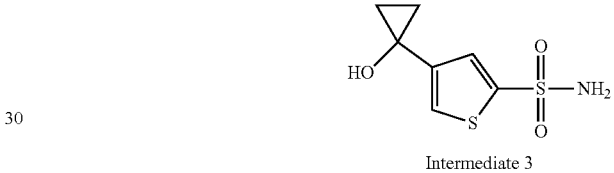

Intermediate 3

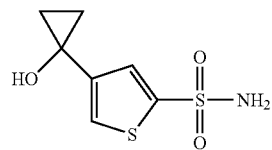

4-(1-Hydroxycyclopropyl)thiophene-2-sulfonamide

Step 1: 4-(1-Hydroxycyclopropyl)thiophene-2-sulfonamide

Into a 500-mL 3-necked round-bottom flask purged with and maintained under nitrogen, was placed methyl 5-sulfamoylthiophene-3-carboxylate (5.525 g, 24.97 mmol), THF (80 mL), Ti(i-PrO)$_4$ (1.5 mL). This was followed by the addition of EtMgBr/THF (3 M, 21 mL) dropwise with stirring at 0° C. The resulting solution was stirred for 2 h at RT and then was quenched by the addition of 30 mL of NH$_4$Cl (sat.). The resulting solution was extracted with 3×40 mL of ethyl acetate and the organic layers combined and concentrated under vacuum. The residue was applied onto a silica gel column and eluted with ethyl acetate/petroleum ether (1:3 to 1:1). This resulted in 662 mg (12%) of the title compound as a light yellow solid. MS-ESI: 218.0 (M−1).

Scheme H

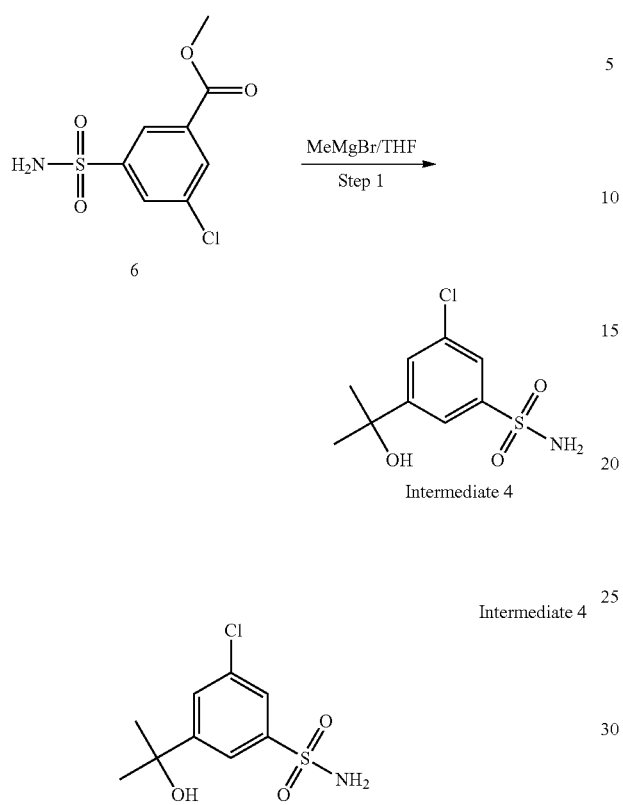

3-Chloro-5-(2-hydroxypropan-2-yl)benzenesulfonamide

Step 1: 3-Chloro-5-(2-hydroxypropan-2-yl)benzenesulfonamide

Into a 100-mL 3-necked round-bottom flask purged with and maintained under nitrogen, was placed a solution of methyl 3-chloro-5-sulfamoylbenzoate (579 mg, 2.32 mmol) in THF (30 mL). This was followed by the addition of MeMgBr/THF (3 M, 3.5 mL) dropwise with stirring at 0° C.

The resulting solution was stirred for 12 h at RT and then was quenched by the addition of 20 mL of NH₄Cl (sat.). The solution was extracted with 3×20 mL of ethyl acetate and the organic layers combined and concentrated under vacuum. The residue was applied onto a silica gel column and eluted with ethyl acetate/petroleum ether (1:3 to 1:1). This resulted in 415 mg (72%) of the title compound as a light yellow solid. MS-ESI: 248.0, 250.0 (M−1).

Scheme I

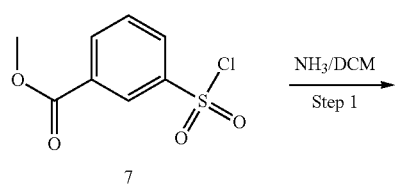

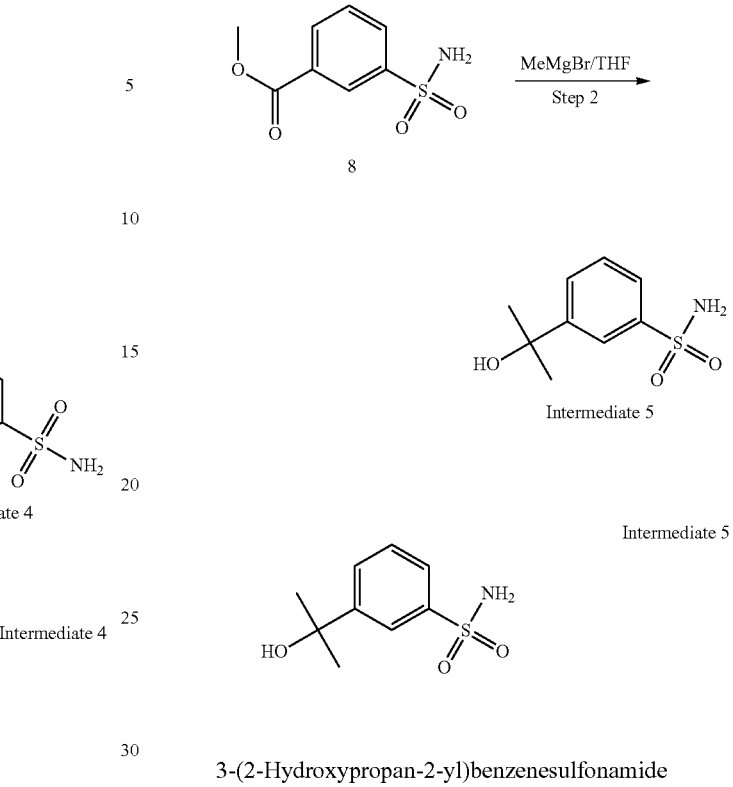

3-(2-Hydroxypropan-2-yl)benzenesulfonamide

Step 1: Methyl 3-sulfamoylbenzoate

Into a 100-mL round-bottom flask, was placed a solution of methyl 3-(chlorosulfonyl)benzoate (2 g, 8.5 mmol) in DCM (35 mL). To the above was added a saturated solution of ammonia in DCM (15 mL). The resulting solution was stirred for 2 h at RT and then was concentrated under vacuum. The residue was applied onto a silica gel column and eluted with ethyl acetate/petroleum ether (1:3 to 1:1). This resulted in 1.753 g (93%) of the title compound as a white solid. MS-ESI: 214.0 (M−1).

Step 2: 3-(2-Hydroxypropan-2-yl)benzenesulfonamide

Into a 250-mL 3-necked round-bottom flask purged with and maintained under nitrogen, was placed a solution of methyl 3-sulfamoylbenzoate (1.753 g, 8.14 mmol) in THF (70 mL). This was followed by the addition of MeMgBr/THF (3 M, 12.2 mL) dropwise with stirring at 0° C. The resulting solution was stirred for 12 h at RT and then was quenched by the addition of 30 mL of NH₄Cl (sat.). The resulting solution was extracted with 5×30 mL of ethyl acetate and the organic layers combined and concentrated under vacuum. The residue was applied onto a silica gel column and eluted with ethyl acetate/petroleum ether (1:3 to 1:1). This resulted in 1.642 g (94%) of the title compound as a white solid. MS-ESI: 214.0 (M−1).

TABLE 1

The Intermediates in the following Table were prepared using the similar procedure for converting compound 7 to compound 8 shown in Scheme I.

| Intermediate # | Structure | IUPAC Name | Mass Spec[M + H]+ |
|---|---|---|---|
| Intermediate 6 | 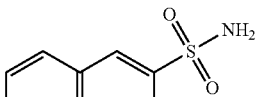 | quinoline-3-sulfonamide | 209.0 (M + 1) |
| Intermediate 7 | 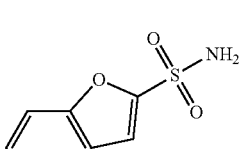 | benzofuran-2-sulfonamide | 196.0 (M − 1) |

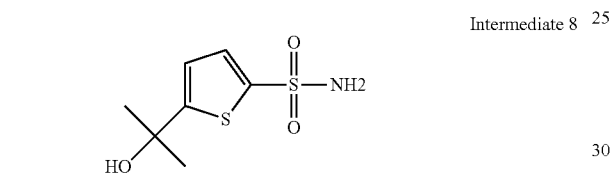

Intermediate 8

5-(2-Hydroxypropan-2-yl)thiophene-2-sulfonamide

Intermediate 8 was prepared using the similar procedures for converting compound 7 to Intermediate 5 shown in Scheme I. MS-ESI: 220.0 (M−1).

Scheme J

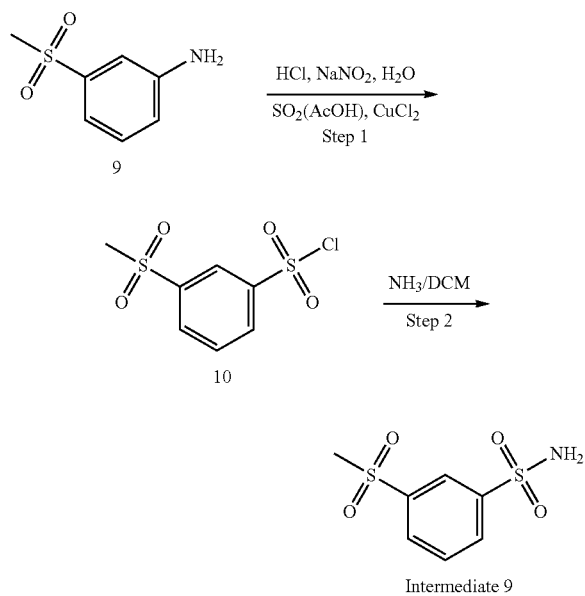

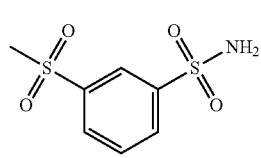

Intermediate 9

3-(Methylsulfonyl)benzenesulfonamide

Step 1: 3-(Methylsulfonyl)benzene-1-sulfonyl chloride

Into a 100-mL round-bottom flask, was placed a solution of 3-(methylsulfonyl)benzenamine (200 mg, 1.17 mmol) in HCl (6 M, 5 mL). This was followed by the addition of a solution of NaNO$_2$ (97 mg, 1.41 mmol) in water (0.5 mL) dropwise with stirring at 0° C. The resulting solution was stirred for 20 min at 0° C. The above mixture was added to a saturated solution of SO$_2$ in AcOH (5 mL) dropwise with stirring at 0° C. Then to the above was added CuCl$_2$ (157 mg, 1.17 mmol). The resulting solution was stirred for 1 h at RT and then was quenched by the addition of 10 mL of water. The resulting solution was extracted with 3×10 mL of DCM and the organic layers combined and dried over anhydrous Na$_2$SO$_4$, then concentrated under vacuum. This resulted in 250 mg (84%) of the title compound as a light yellow solid. The crude product was used in the next step.

Step 2: 3-(Methylsulfonyl)benzenesulfonamide

Into a 50-mL round-bottom flask, was placed 3-(methylsulfonyl)benzene-1-sulfonyl chloride (250 mg, 0.98 mmol), DCM (3 mL). To the above was added a saturated solution of ammonia in DCM (5 mL). The resulting solution was stirred for 1 h at RT and then was diluted with 5 mL of water. The resulting solution was extracted with 3×10 mL of ethyl acetate and the organic layers combined and dried over anhydrous Na$_2$SO$_4$, then concentrated under vacuum. This resulted in 220 mg (crude, 95%) of the title compound as a white solid. MS-ESI: 234.0 (M−1).

TABLE 2

The Intermediates in the following Table were prepared using the similar procedures
for converting compound 9 to Intermediate 9 shown in Scheme J.

| Intermediate # | Structure | IUPAC Name | Mass Spec[M − H]⁻ |
|---|---|---|---|
| Intermediate 10 | 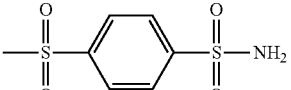 | (methylsulfonyl)benzenesulfonamide | 234.0 |
| Intermediate 11 | 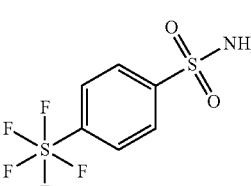 | 4-pentafluorobenzenesulfonamide | 282.0 |
| Intermediate 12 | 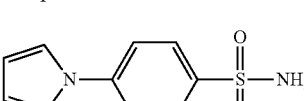 | 4-(1H-pyrazol-1-yl)benzenesulfonamide | 222.0 |

Scheme K

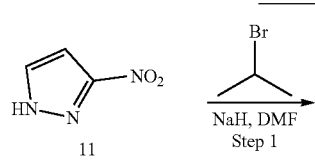

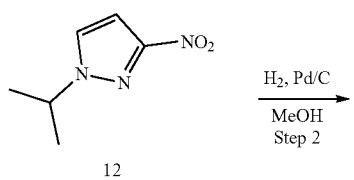

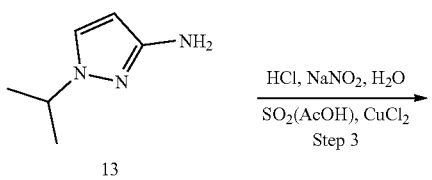

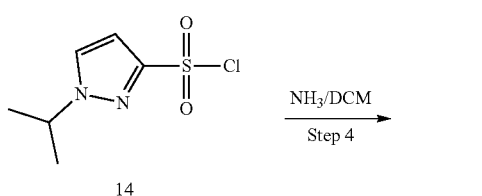

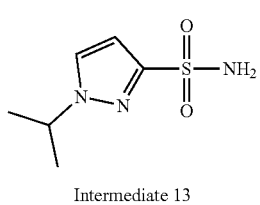

Intermediate 13

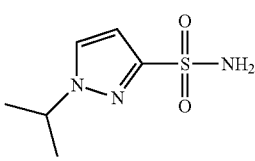

1-Isopropyl-1H-pyrazole-3-sulfonamide

Step 1: 1-Isopropyl-3-nitro-1H-pyrazole

Into a 250-mL round-bottom flask, was placed a solution of 3-nitro-1H-pyrazole (10 g, 88.4 mmol) in DMF (100 mL). This was followed by the addition of NaH (60%, 3.9 g) in portions at 0° C. The resulting solution was stirred for 0.5 h at 0° C. This was followed by the addition of 2-bromopropane (14.1 g, 114.6 mmol) dropwise with stirring at 0° C. in 10 min. The resulting solution was stirred for 16 h at RT and then was quenched by the addition of 100 mL of water. The resulting solution was extracted with 3×100 mL of ethyl acetate and the organic layers combined and dried over anhydrous Na₂SO₄, then concentrated under vacuum. The residue was applied onto a silica gel column and eluted with ethyl acetate/petroleum ether (1:5 to 1:3). This resulted in 11.8 g (86%) of the title compound as yellow oil. MS-ESI: 156.1 (M+1).

Step 2: 3-Amino-1-(propan-2-yl)-1H-pyrazole

Into a 250-mL round-bottom flask, was placed a solution of 1-isopropyl-3-nitro-1H-pyrazole (10.8 g, 69.6 mmol) in MeOH (100 mL). Then Pd/C (10% wt, 1.5 g) was added. The flask was evacuated and flushed three times with hydrogen. The mixture was stirred for 24 h at RT under an atmosphere of hydrogen. The solids were filtered out. The resulting mixture was concentrated under vacuum. This resulted in 7.27 g (83%) of the title compound as yellow oil. MS-ESI: 126.1 (M+1).

Steps 3-4 used similar procedures for converting compound 9 to Intermediate 9 shown in Scheme J to afford Intermediate 13. MS-ESI: 188.0 (M−1).

Scheme L

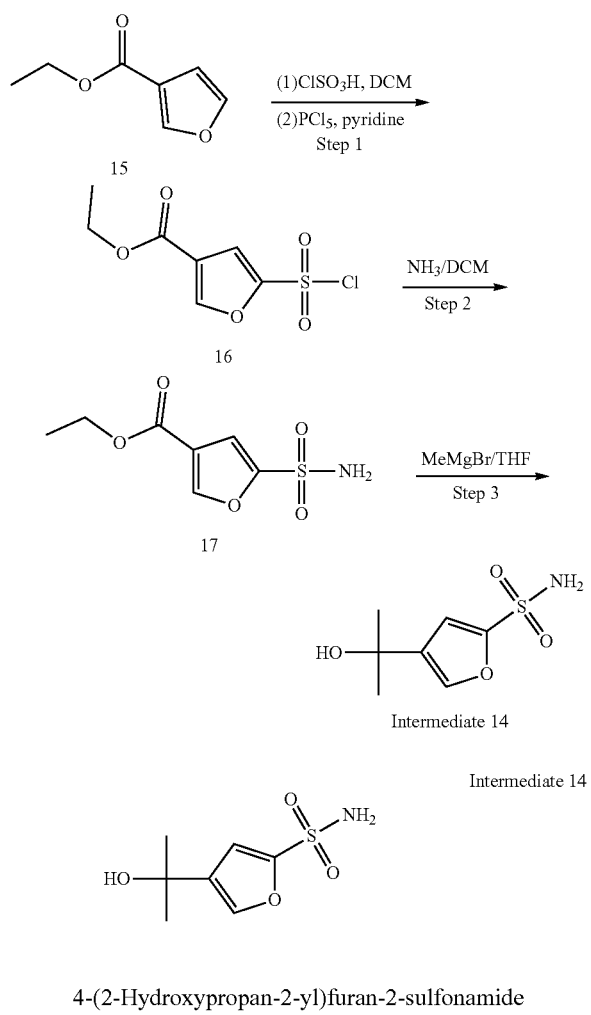

4-(2-Hydroxypropan-2-yl)furan-2-sulfonamide

Step 1: Ethyl 5-(chlorosulfonyl)furan-3-carboxylate

Into a 500-mL 3-necked round-bottom flask, was placed ethyl furan-3-carboxylate (7 g, 50 mmol), DCM (200 mL). This was followed by the addition of chloranesulfonic acid (5.8 g, 49.8 mmol) dropwise with stirring at −10° C. Then the reaction was stirred for 48 h at RT and the system was cooled to −10° C. Then to the above was added pyridine (3.96 g, 50.1 mmol), phosphorus pentachloride (11.46 g, 55.0 mmol). The resulting solution was stirred for 12 h at RT and then was quenched by the addition of 200 mL of water. The resulting solution was extracted with 3×200 mL of DCM and the organic layers combined and dried over anhydrous $Na_2SO_4$, then concentrated under vacuum. This resulted in 7.13 g (60%) of the title compound as light brown oil. The crude product was used in the next step.

Step 2: Ethyl 5-sulfamoylfuran-3-carboxylate

Into a 250-mL round-bottom flask, was placed a solution of ethyl 5-(chlorosulfonyl)furan-3-carboxylate (6.111 g, 25.61 mmol) in DCM (60 mL). To the above was added a saturated solution of ammonia in DCM (40 mL). The resulting solution was stirred for 3 h at RT and then was concentrated under vacuum. The residue was applied onto a silica gel column and eluted with ethyl acetate/petroleum ether (1:4 to 1:2). This resulted in 3.698 g (66%) of the title compound as a light yellow solid. MS-ESI: 218.0 (M−1).

Step 3: 4-(2-Hydroxypropan-2-yl)furan-2-sulfonamide

Into a 250-mL 3-necked round-bottom flask purged with and maintained under nitrogen, was placed a solution of ethyl 5-sulfamoylfuran-3-carboxylate (3.698 g, 16.87 mmol) in THF (100 mL). This was followed by the addition of MeMgBr/THF (3 M, 25 mL) dropwise with stirring at −10° C. The resulting solution was stirred for 10 h at RT and then was quenched by the addition of 50 mL of $NH_4Cl$ (sat.). The resulting solution was extracted with 3×50 mL of ethyl acetate and the organic layers combined and dried over anhydrous $Na_2SO_4$, then concentrated under vacuum. The residue was applied onto a silica gel column and eluted with ethyl acetate/petroleum ether (1:3 to 1:1). This resulted in 2.6 g (75%) of the title compound as a light yellow solid. MS-ESI: 204.0 (M−1).

TABLE 3

The Intermediates in the following Table were prepared using the similar procedures for converting compound 15 to Intermediate 14 shown in Scheme L.

| Intermediate # | Structure | IUPAC Name | Mass Spec[M − H]− |
|---|---|---|---|
| Intermediate 15 | 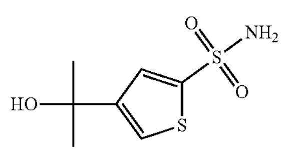 | 4-(2-hydroxypropan-2-yl)thiophene-2-sulfonamide | 220.0 |
| Intermediate 16 | 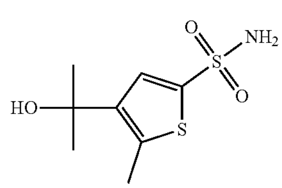 | 4-(2-hydroxypropan-2-yl)-5-methylthiophene-2-sulfonamide | 234.0 |

TABLE 3-continued

The Intermediates in the following Table were prepared using the similar procedures for converting compound 15 to Intermediate 14 shown in Scheme L.

| Intermediate # | Structure | IUPAC Name | Mass Spec[M − H]⁻ |
|---|---|---|---|
| Intermediate 17 | (structure) | 4-(2-hydroxypropan-2-yl)-5-methylfuran-2-sulfonamide | 218.1 |
| Intermediate 18 | (structure) | 4-(2-hydroxypropan-2-yl)-3-methylthiophene-2-sulfonamide | 234.1 |

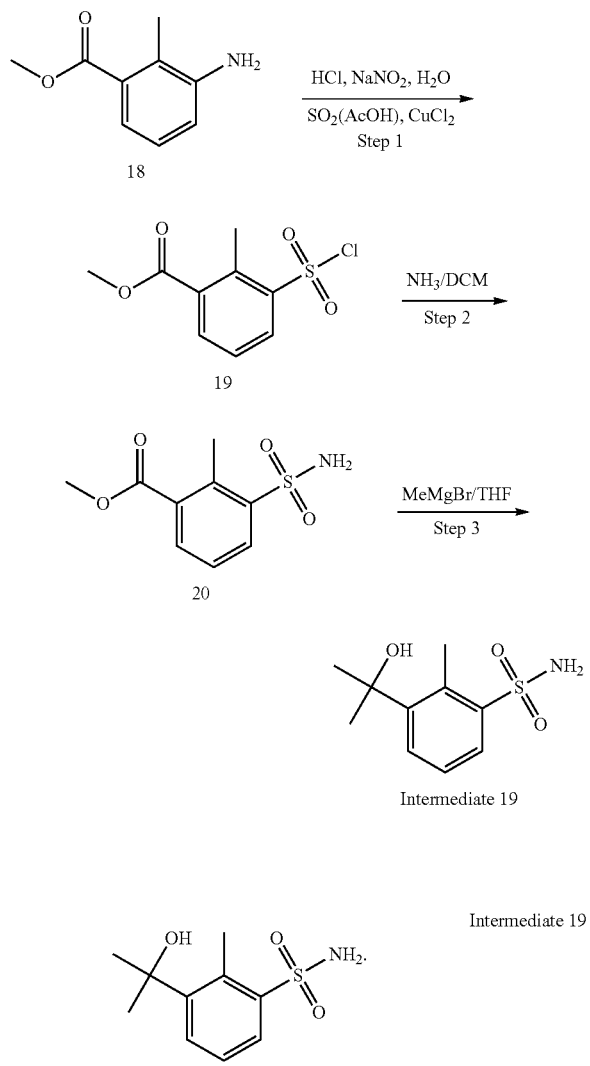

Scheme M

Intermediate 19

3-(2-Hydroxypropan-2-yl)-2-methylbenzenesulfonamide

Step 1: Methyl 3-(chlorosulfonyl)-2-methylbenzoate

Into a 100-mL round-bottom flask, was placed methyl methyl 3-amino-2-methylbenzoate (2 g, 12.1 mmol), HCl (6 M, 10 mL). This was followed by the addition of a solution of NaNO₂ (1 g, 14.5 mmol) in water (5 mL) dropwise with stirring at 0° C. The resulting solution was stirred for 20 min at 0° C. The above mixture was added to a saturated solution of SO₂ in AcOH (15 mL) dropwise with stirring at 0° C. Then to the above was added CuCl₂ (1.63 g, 12.1 mmol). The resulting solution was stirred for 1 h at RT and then was quenched by the addition of 15 mL of water. The resulting solution was extracted with 2×20 mL of DCM and the organic layers combined and dried over anhydrous Na₂SO₄, then concentrated under vacuum. This resulted in 2 g (66%) of the title compound as a light yellow solid. The crude product was used in the next step.

Step 2: Methyl 2-methyl-3-sulfamoylbenzoate

Into a 100-mL round-bottom flask, was placed a solution of methyl 3-(chlorosulfonyl)-2-methylbenzoate (2 g, 8.04 mmol) in DCM (10 mL). To the above was added a saturated solution of ammonia in DCM (15 mL). The resulting solution was stirred for 1 h at RT and then was concentrated under vacuum. The residue was applied onto a silica gel column and eluted with ethyl acetate/petroleum ether (1:3 to 1:1). This resulted in 1.2 g (65%) of the title compound as a white solid. MS-ESI: 228.0 (M−1).

Step 3: 3-(2-Hydroxypropan-2-yl)-2-methylbenzenesulfonamide

Into a 100-mL 3-necked round-bottom flask purged with and maintained under nitrogen, was placed a solution of methyl 2-methyl-3-sulfamoylbenzoate (1.2 g, 5.23 mmol) in THF (20 mL). This was followed by the addition MeMgBr/THF (3 M, 8.7 mL) dropwise with stirring at 0° C. The resulting solution was stirred for 12 h at RT. The reaction was then quenched by the addition of 15 mL of NH₄Cl (sat.). The resulting solution was extracted with 3×20 mL of ethyl acetate and the organic layers combined and dried over anhydrous Na₂SO₄, then concentrated under vacuum. This resulted in 1.1 g (crude, 92%) of the title compound as an off-white solid. MS-ESI: 228.1 (M−1).

TABLE 4

The Intermediates in the following Table were prepared using the similar procedures
for converting compound 18 to Intermediate 19 shown in Scheme M.

| Intermediate # | Structure | IUPAC Name | Mass Spec[M − H]⁻ |
|---|---|---|---|
| Intermediate 20 | 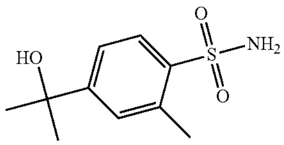 | 4-(2-hydroxypropan-2-yl)-2-methylbenzenesulfonamide | 228.1 |
| Intermediate 21 | 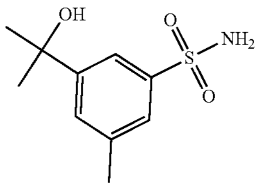 | 3-(2-hydroxypropan-2-yl)-5-methylbenzenesulfonamide | 228.1 |
| Intermediate 22 | 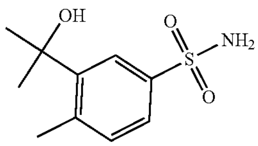 | 3-(2-hydroxypropan-2-yl)-4-methylbenzenesulfonamide | 228.1 |
| Intermediate 23 | 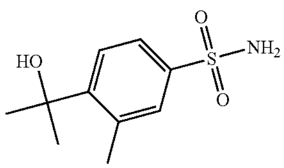 | 4-(2-hydroxypropan-2-yl)-3-methylbenzenesulfonamide | 228.1 |
| Intermediate 24 | 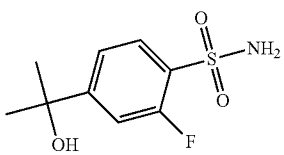 | 2-fluoro-4-(2-hydroxypropan-2-yl)benzenesulfonamide | 232.1 |
| Intermediate 25 | 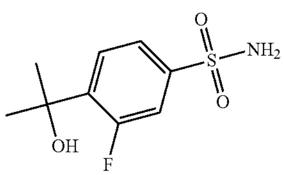 | 3-fluoro-4-(2-hydroxypropan-2-yl)benzenesulfonamide | 232.1 |
| Intermediate 26 | 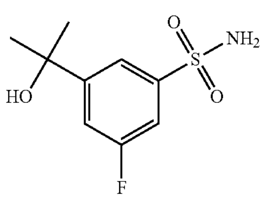 | 3-fluoro-5-(2-hydroxypropan-2-yl)benzenesulfonamide | 232.1 |
| Intermediate 27 | 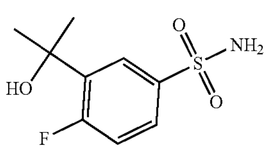 | 4-fluoro-3-(2-hydroxypropan-2-yl)benzenesulfonamide | 232.1 |
| Intermediate 28 | 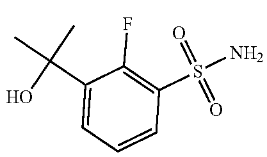 | 2-fluoro-3-(2-hydroxypropan-2-yl)benzenesulfonamide | 232.1 |

TABLE 4-continued

The Intermediates in the following Table were prepared using the similar procedures for converting compound 18 to Intermediate 19 shown in Scheme M.

| Intermediate # | Structure | IUPAC Name | Mass Spec[M − H]⁻ |
|---|---|---|---|
| Intermediate 29 | 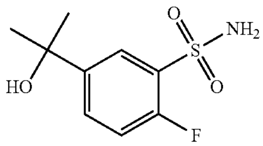 | 2-fluoro-5-(2-hydroxypropan-2-yl)benzenesulfonamide | 232.1 |
| Intermediate 30 | 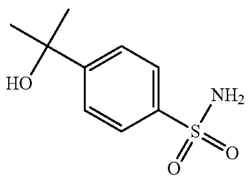 | 4-(2-hydroxypropan-2-yl)benzenesulfonamide | 214.1 |
| Intermediate 31 | 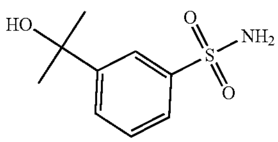 | 3-(2-hydroxypropan-2-yl)benzenesulfonamide | 214.1 |
| Intermediate 32 | 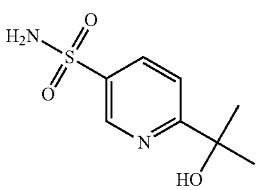 | 6-(2-hydroxypropan-2-yl)pyridine-3-sulfonamide | 217.1 (M + 1) |
| Intermediate 33 | 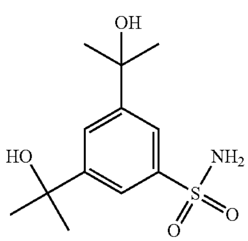 [SMILES: CC(C)(O)c1cc(C(C)(C)O)cc(S(N)(=O)=O)c1] | 3,5-bis(2-hydroxypropan-2-yl)benzenesulfonamide | 272.1 |

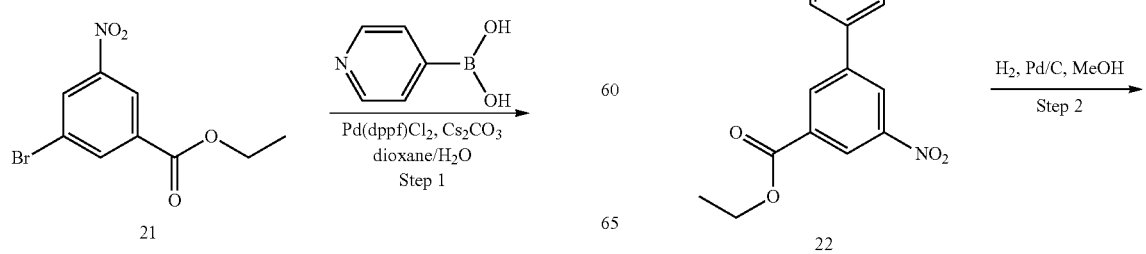

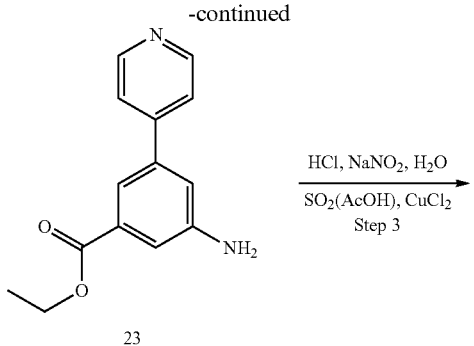

23

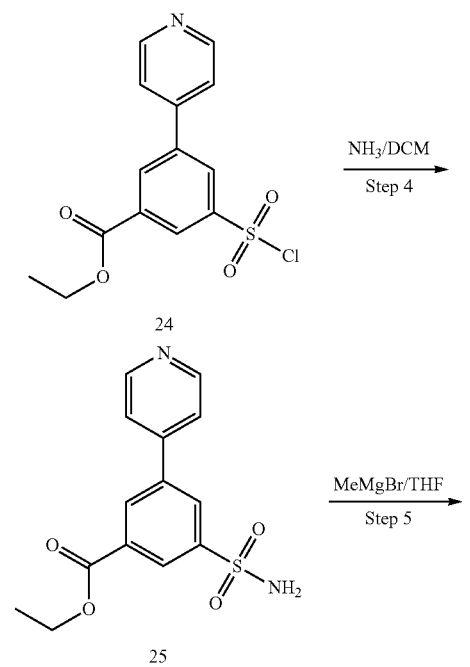

24

25

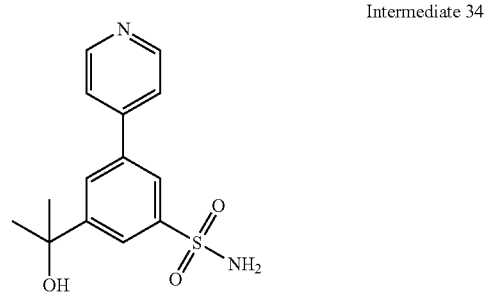 [SMILES: CC(C)(O)c1cc(-c2ccncc2)cc(S(N)(=O)=O)c1]

3-(2-Hydroxypropan-2-yl)-5-(pyridin-4-yl)benzene-sulfonamide

Step 1: Ethyl 3-nitro-5-(pyridin-4-yl)benzoate

Into a 500-mL round-bottom flask purged with and maintained under nitrogen, was placed ethyl 3-bromo-5-nitrobenzoate (5.5 g, 20.1 mmol), dioxane (250 mL), water (50 mL), (pyridin-4-yl)boronic acid (3.0 g, 24.4 mmol), $Cs_2CO_3$ (12.7 g, 38.98 mmol), $Pd(dppf)Cl_2$ (600 mg, 0.82 mmol). The resulting solution was stirred for 12 h at 90° C. and then was concentrated under vacuum. The residue was applied onto a silica gel column and eluted with ethyl acetate/petroleum ether (1:1 to 3:1). This resulted in 4.2 g (77%) of the title compound as a white solid. MS-ESI: 273.1 (M+1).

Step 2: Ethyl 3-amino-5-(pyridin-4-yl)benzoate

Into a 250-mL round-bottom flask, was placed ethyl 3-nitro-5-(pyridin-4-yl)benzoate (4.2 g, 15.4 mmol), MeOH (150 mL). Then Pd/C (10% wt, 500 mg) was added. The flask was evacuated and flushed three times with hydrogen. The resulting solution was stirred for 2 days at RT under an atmosphere of hydrogen. The solids were filtered out. The resulting solution was concentrated under vacuum. This resulted in 3.7 g (99%) of the title compound as a white solid. MS-ESI: 243.1 (M+1).

Steps 3-5 used similar procedures for converting compound 18 to Intermediate 19 shown in Scheme M to afford Intermediate 34. MS-ESI: 293.1 (M+1), 291.1 (M−1).

Intermediate 35

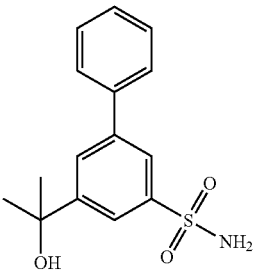

5-(2-Hydroxypropan-2-yl)biphenyl-3-sulfonamide

Intermediate 35 was prepared using the similar procedures for converting compound 21 to Intermediate 34 shown in Scheme N. MS-ESI: 290.1 (M−1).

Scheme O

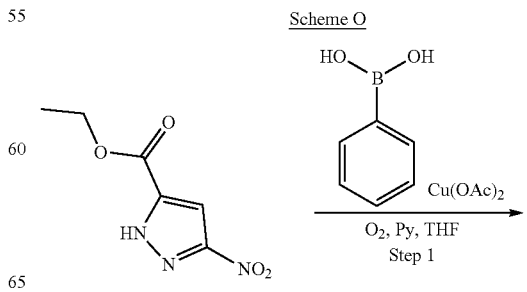

26

-continued

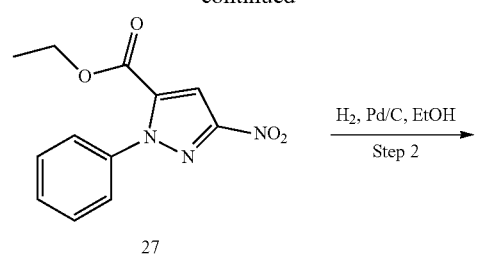

27

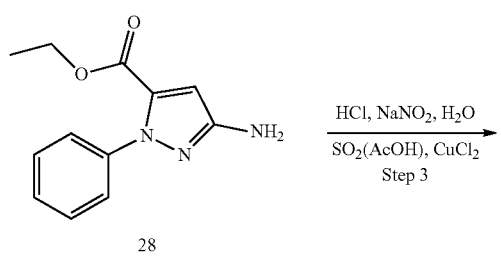

28

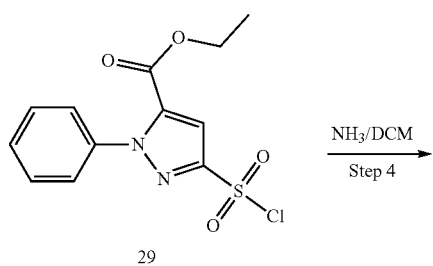

29

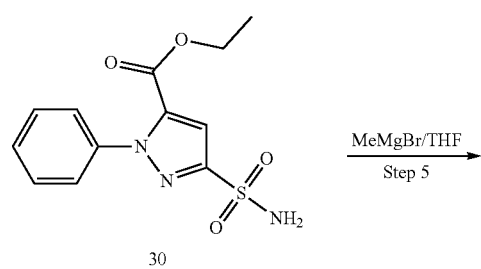

30

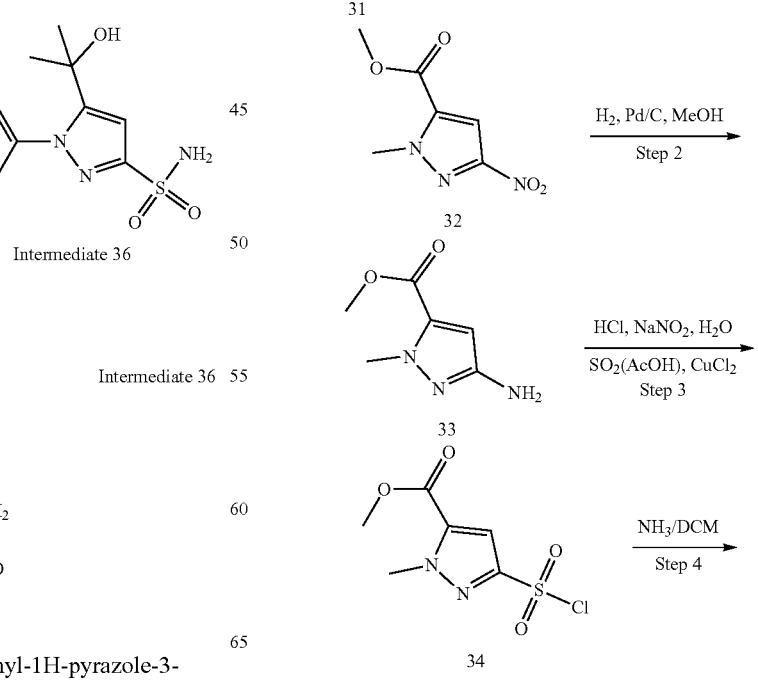

Intermediate 36

Intermediate 36

5-(2-Hydroxypropan-2-yl)-1-phenyl-1H-pyrazole-3-sulfonamide

Step 1: Ethyl 3-nitro-1-phenyl-1H-pyrazole-5-carboxylate

Into a 500-mL round-bottom flask, was placed ethyl 3-nitro-1H-pyrazole-5-carboxylate (5 g, 27.0 mmol), THF (150 mL), phenylboronic acid (6.59 g, 54.1 mmol), Cu(OAc)$_2$ (7.36 g, 40.5 mmol), pyridine (8.54 g, 108 mmol). The resulting solution was stirred for 14 h at 55° C. and then was concentrated under vacuum. The residue was applied onto a silica gel column and eluted with ethyl acetate/petroleum ether (1:7 to 1:4). This resulted in 2 g (28%) of the title compound as an off-white solid. MS-ESI: 262.1 (M+1).

Step 2: Ethyl 3-amino-1-phenyl-1H-pyrazole-5-carboxylate

Into a 100-mL round-bottom flask, was placed ethyl 3-nitro-1-phenyl-1H-pyrazole-5-carboxylate (2 g, 7.66 mmol), EtOH (50 mL). Then Pd/C (10% wt, 200 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:3 to 1:1). This resulted in 1 g (56%) of the title compound as a light yellow solid. MS-ESI: 232.1 (M+1).

Steps 3-5 used similar procedures for converting compound 18 to Intermediate 19 shown in Scheme M to afford Intermediate 36. MS-ESI: 280.1 (M−1).

Scheme P

-continued

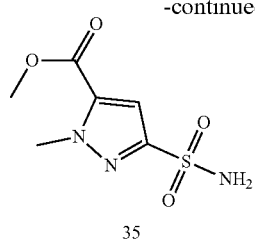

35

MeMgBr/THF
———————→
Step 5

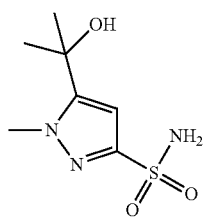

Intermediate 37

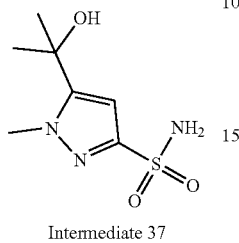

Intermediate 37

5-(2-Hydroxypropan-2-yl)-1-methyl-1H-pyrazole-3-sulfonamide

Step 1: Methyl 1-methyl-3-nitro-1H-pyrazole-5-carboxylate

Into a 250-mL round-bottom flask purged with and maintained under nitrogen, was placed methyl 3-nitro-1H-pyrazole-5-carboxylate (15 g, 87.7 mmol), DMF (50 mL), potassium carbonate (22.4 g, 162 mmol), CH₃I (18.5 g, 130 mmol). The resulting solution was stirred for 15 h at RT and then was quenched by the addition of 50 mL of water. The resulting solution was extracted with 3×40 mL of ethyl acetate and the organic layers combined and dried over anhydrous Na₂SO₄, then concentrated under vacuum. This resulted in 17 g (crude) of the title compound as a yellow solid. MS-ESI: 186.0 (M+1).

Step 2: Methyl 3-amino-1-methyl-1H-pyrazole-5-carboxylate

Into a 500-mL round-bottom flask, was placed methyl 1-methyl-3-nitro-1H-pyrazole-5-carboxylate (17 g, 91.8 mmol), MeOH (100 mL). Then Pd/C (10% wt, 2 g) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:4 to 2:3). This resulted in 11.6 g (81%) of the title compound as a yellow solid. MS-ESI: 156.1 (M+1).

Steps 3-5 used similar procedures for converting compound 18 to Intermediate 19 shown in Scheme M to afford Intermediate 37. MS-ESI: 218.0 (M−1).

Scheme Q

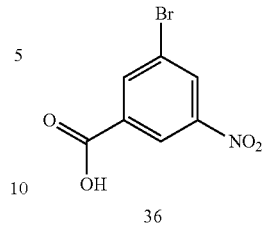

36

EtOH, SOCl₂
———————→
Step 1

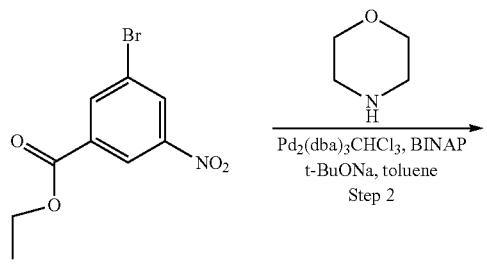

37

Pd₂(dba)₃CHCl₃, BINAP
t-BuONa, toluene
Step 2

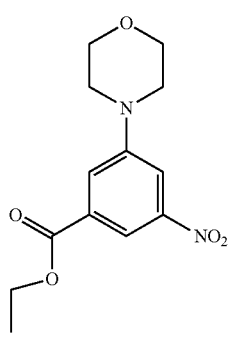

38

H₂, Pd/C, MeOH
———————→
Step 3

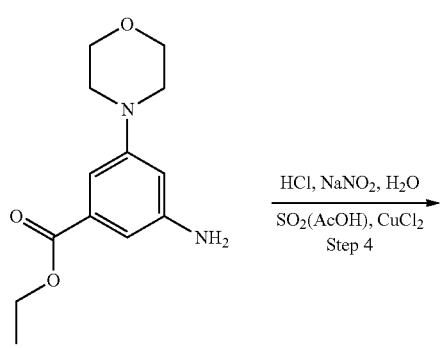

39

HCl, NaNO₂, H₂O
———————————→
SO₂(AcOH), CuCl₂
Step 4

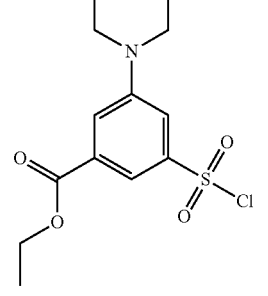

40

NH₃/DCM
———————→
Step 5

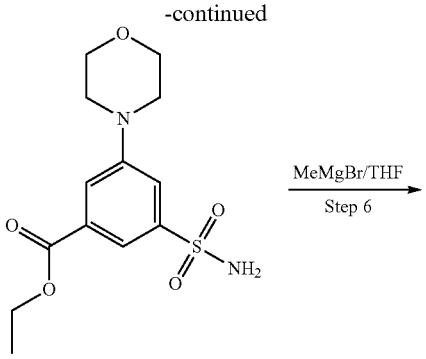

41

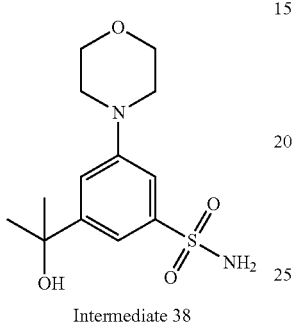

Intermediate 38

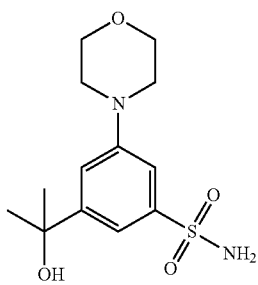

Intermediate 38

3-(2-Hydroxypropan-2-yl)-5-morpholinobenzene-sulfonamide

Step 1: Ethyl 3-bromo-5-nitrobenzoate

Into a 500-mL round-bottom flask, was placed 3-bromo-5-nitrobenzoic acid (25 g, 101.6 mmol), EtOH (200 mL). This was followed by the addition of thionyl chloride (15 mL) dropwise with stirring at 0° C. The resulting solution was stirred for 4 h at 80° C. and then was quenched by the addition of 50 mL water. The resulting solution was extracted with 3×50 mL of DCM and the organic layers combined and concentrated under vacuum. The residue was applied onto a silica gel column and eluted with ethyl acetate/petroleum ether (1:20 to 1:10). This resulted in 27.5 g (99%) of the title compound as a white solid.

Step 2: Ethyl 3-(morpholin-4-yl)-5-nitrobenzoate

Into a 500-mL round-bottom flask purged with and maintained under nitrogen, was placed ethyl 3-bromo-5-nitrobenzoate (10 g, 36.5 mmol), toluene (250 mL), morpholine (4.6 g, 52.8 mmol), t-BuONa (5 g, 52.0 mmol), Pd$_2$(dba)$_3$CHCl$_3$ (1.9 g, 1.93 mmol), BINAP (1.2 g, 1.93 mmol). The resulting solution was stirred for 18 h at 60° C. and then was concentrated under vacuum. The residue was applied onto a silica gel column and eluted with ethyl acetate/petroleum ether (1:30 to 1:10). This resulted in 2.8 g (27%) of the title compound as a yellow solid. MS-ESI: 281.1 (M+1).

Step 3: Ethyl 3-amino-5-(morpholin-4-yl)benzoate

Into a 250-mL round-bottom flask, was placed ethyl 3-(morpholin-4-yl)-5-nitrobenzoate (3.0 g, 10.7 mmol), MeOH (100 mL). Then Pd/C (10% wt, 300 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:5 to 1:3). This resulted in 2.6 g (97%) of the title compound as a yellow solid. MS-ESI: 251.1 (M+1).

Steps 4-6 used similar procedures for converting compound 18 to Intermediate 19 shown in Scheme M to afford Intermediate 38. MS-ESI: 299.1 (M−1).

Scheme R

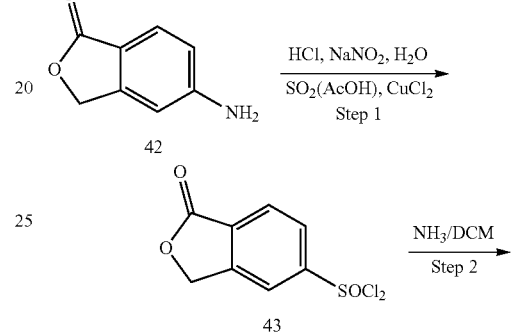

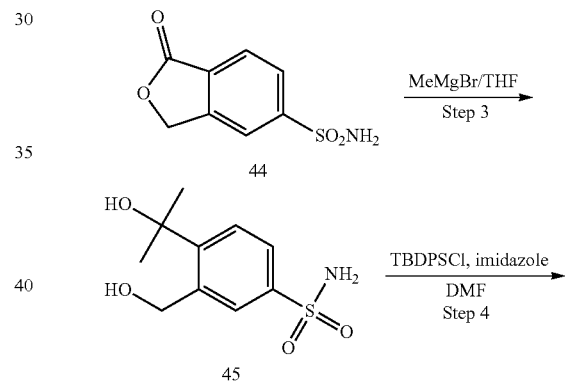

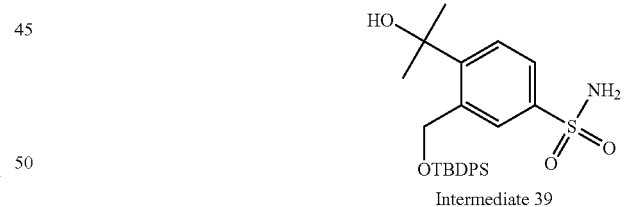

Intermediate 39

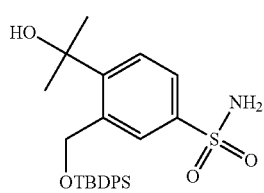

Intermediate 39

3-((Tert-butyldiphenylsilyloxy)methyl)-4-(2-hydroxypropan-2-yl)benzenesulfonamide Steps 1-3 used similar procedures for converting compound 18 to Intermediate 19 shown in Scheme M to afford compound 45. MS-ESI: 212.1 (M−1).

Step 4: 3-((Tert-butyldiphenylsilyloxy)methyl)-4-(2-hydroxypropan-2-yl)benzenesulfonamide Into a 100-mL round-bottom flask, was placed 3-(hydroxymethyl)-4-(2-hydroxypropan-2-yl)benzenesulfonamide (1.9 g, 7.75 mmol), DMF (20 mL), imidazole (1.06 g, 15.57 mmol), TBDPSCl (3.2 g, 11.64 mmol). The resulting solution was stirred overnight at RT and then was diluted with 20 mL of water. The resulting solution was extracted with 2×20 mL of DCM and the organic layers combined and dried over anhydrous Na$_2$SO$_4$, then concentrated under vacuum. The crude product was purified by Flash-Prep-HPLC with the following conditions (IntelFlash-1): Column, C18 silica gel; mobile phase, ACN/H$_2$O (10 mmol/NH$_4$HCO$_3$)=1:4 increasing to ACN/H$_2$O (10 mmol/NH$_4$HCO$_3$)=4:1 within 30 min; Detector, UV 210 nm. This resulted in 1.4 g (37%) of the title compound as an off-white solid. MS-ESI: 482.2 (M−1).

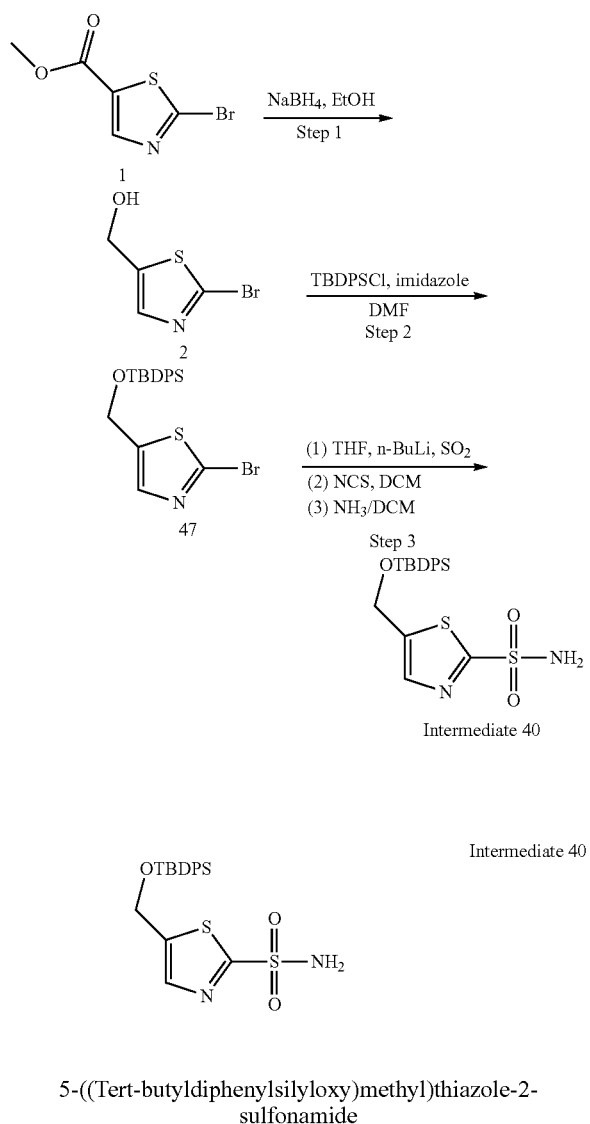

Scheme S 5-((Tert-butyldiphenylsilyloxy)methyl)thiazole-2-sulfonamide

Step 1: (2-Bromothiazol-5-yl)methanol

Into a 250-mL round-bottom flask, was placed a solution of methyl 2-bromothiazole-5-carboxylate (15 g, 67.55 mmol) in EtOH (100 mL). This was followed by the addition of sodium borohydride (5.13 g, 139.3 mmol) in portions at 0° C. The resulting solution was stirred for 12 h at RT and then was quenched by the addition of 100 mL of water. The resulting solution was extracted with 3×50 mL of DCM and the organic layers combined and dried over anhydrous Na$_2$SO$_4$, then concentrated under vacuum. This resulted in 10 g (crude, 76%) of the title compound as a light yellow oil. MS-ESI: 195.9, 193.9 (M+1).

Step 2: 2-Bromo-5-((tert-butyldiphenylsilyloxy)methyl)thiazole

Into a 250-mL round-bottom flask, was placed (2-bromothiazol-5-yl)methanol (8 g, 41.2 mmol), DMF (50 mL), TBDPSCl (12.5 g, 45.5 mmol), imidazole (5.6 g, 82.4 mmol). The resulting solution was stirred for 2 h at RT and then was concentrated under vacuum. The residue was applied onto a silica gel column and eluted with ethyl acetate/petroleum ether (1:100 to 1:80). This resulted in 15 g (84%) of the title compound as a light yellow solid. MS-ESI: 434.0, 432.0 (M+1).

Step 3: 5-((Tert-butyldiphenylsilyloxy)methyl)thiazole-2-sulfonamide

Into a 500-mL 3-necked round-bottom flask purged with and maintained under nitrogen, was placed a solution of 2-bromo-5-((tert-butyldiphenylsilyloxy)methyl)thiazole (15 g, 34.7 mmol) in THF (200 mL). This was followed by the addition of n-BuLi (2.5 M, 16.7 mL) dropwise with stirring at −78° C. The resulting solution was stirred for 30 min at −78° C. To the above SO$_2$ was introduced. The reaction was warmed to RT and stirred for 30 min and then was concentrated under vacuum. The residue diluted in DCM (150 mL) and then NCS (5.7 g, 42.69 mmol) was added. The resulting solution was stirred for 30 min at RT. To the above was added a saturated solution of ammonia in DCM (100 mL). The resulting solution was stirred for 2 h at RT and then was concentrated under vacuum. The residue was applied onto a silica gel column and eluted with ethyl acetate/petroleum ether (1:20 to 1:10). This resulted in 7.5 g (50%) of the title compound as a light yellow solid. MS-ESI: 431.1 (M−1).

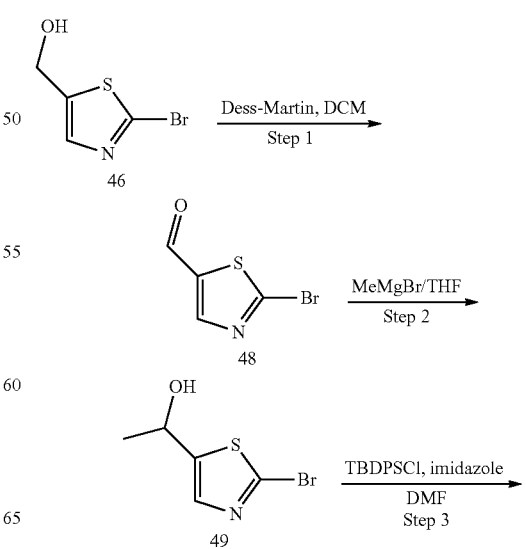

Scheme T

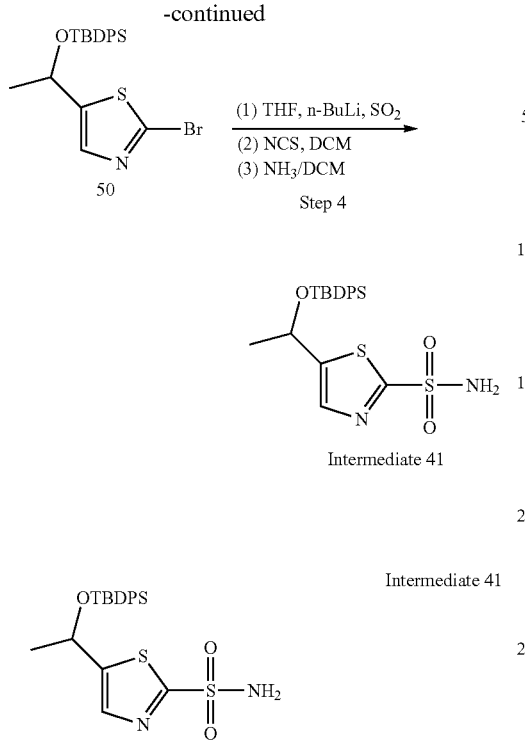

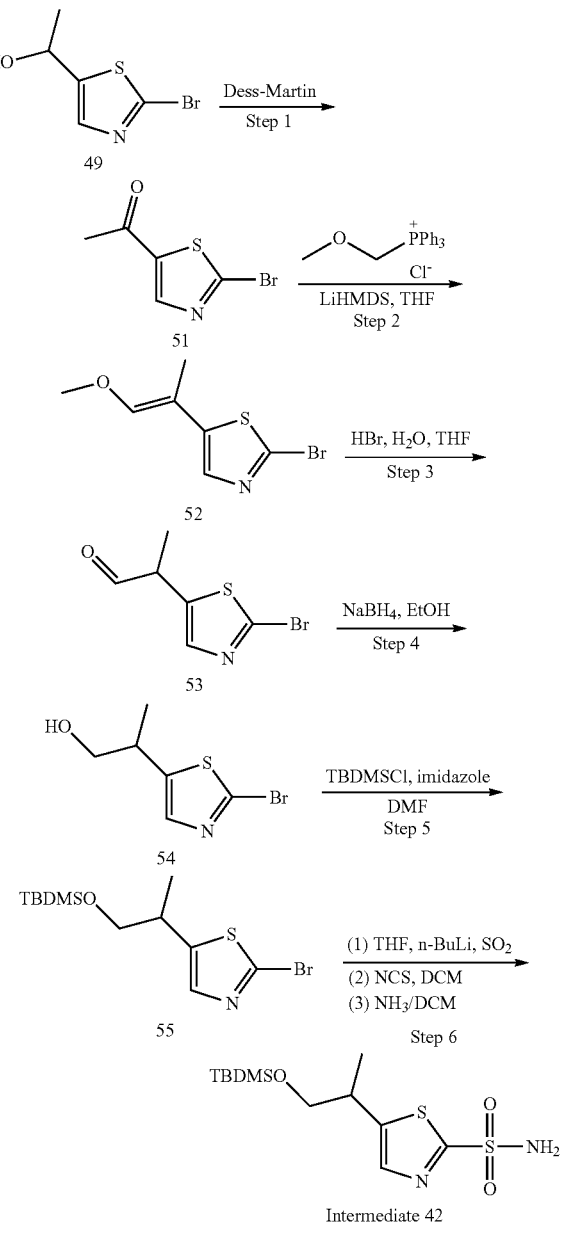

5-(1-(Tert-butyldiphenylsilyloxy)ethyl)thiazole-2-sulfonamide

Step 1: 2-Bromothiazole-5-carbaldehyde

Into a 500-mL round-bottom flask, was placed (2-bromothiazol-5-yl)methanol (20 g, 103 mmol), DCM (200 mL). This was followed by the addition of Dess-Martin reagent (46 g, 103 mmol) in portions at 0° C. The resulting solution was stirred for 2 h at RT and then was concentrated under vacuum. The residue was applied onto a silica gel column and eluted with ethyl acetate/petroleum ether (1:20 to 1:10). This resulted in 18 g (91%) of the title compound as a white solid. MS-ESI: 193.9, 191.9 (M+1).

Step 2: 1-(2-Bromothiazol-5-yl)ethanol

Into a 500-mL 3-necked round-bottom flask purged with and maintained under nitrogen, was placed a solution of 2-bromothiazole-5-carbaldehyde (18 g, 93.7 mmol) in THF (200 mL). This was followed by the addition of MeMgBr/THF (3 M, 33 mL) dropwise with stirring at 0° C. The resulting solution was stirred for 0.5 h at 0° C. The reaction was then quenched by the addition of 200 mL of NH₄Cl (sat.). The resulting solution was extracted with 2×200 mL of DCM and the organic layers combined and concentrated under vacuum. The residue was applied onto a silica gel column and eluted with ethyl acetate/petroleum ether (1:20 to 1:15). This resulted in 15 g (77%) of the title compound as colorless oil. MS-ESI: 209.9, 207.9 (M+1).

Steps 3-4 used similar procedures for converting compound 46 to Intermediate 40 shown in Scheme S to afford Intermediate 41. MS-ESI: 445.1 (M−1).

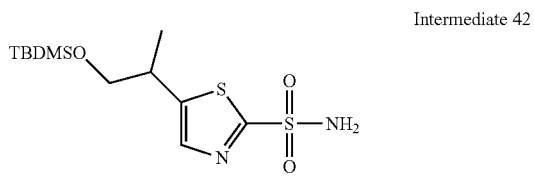 [SMILES: CC(CO[Si](C)(C)C(C)(C)C)c1cnc(S(N)(=O)=O)s1]

5-(1-(Tert-butyldimethylsilyloxy)propan-2-yl)thiazole-2-sulfonamide

Step 1: 1-(2-Bromothiazol-5-yl)ethanone

Into a 250-mL round-bottom flask, was placed 1-(2-bromothiazol-5-yl)ethanol (5.792 g, 27.84 mmol), DCM (150 mL), and Dess-Martin reagent (17.72 g, 41.78 mmol). The resulting solution was stirred for 2 h at RT and then was concentrated under vacuum. The residue was applied onto a silica gel column and eluted with ethyl acetate/petroleum ether (1:10 to 1:5). This resulted in 5.29 g (92%) of the title compound as an off-white solid. MS-ESI: 207.9, 205.9 (M+1).

Step 2: 2-Bromo-5-(1-methoxyprop-1-en-2-yl)thiazole

Into a 250-mL 3-necked round-bottom flask purged with and maintained under nitrogen, was placed (methoxymethyl)triphenylphosphanium chloride (13.16 g, 38.39 mmol), THF (100 mL). This was followed by the addition of LiHMDS (1 M, 38.52 mL) dropwise with stirring at 0° C. The resulting solution was stirred for 0.5 h at 0° C. To this was added a solution of 1-(2-bromothiazol-5-yl)ethanone (5.29 g, 25.67 mmol) in THF (30 mL) dropwise with stirring at 0° C. The resulting solution was stirred for 1 h at RT and then was quenched by the addition of 100 mL of NH$_4$Cl (sat.). The resulting solution was extracted with 3×80 mL of DCM and the organic layers combined and dried over anhydrous Na$_2$SO$_4$, then concentrated under vacuum. The residue was applied onto a silica gel column and eluted with ethyl acetate/petroleum ether (1:5 to 1:3). This resulted in 4.38 g (73%) of the title compound as light yellow oil. MS-ESI: 235.9, 234.0 (M+1).

Step 3: 2-(2-Bromothiazol-5-yl)propanal

Into a 250-mL round-bottom flask, was placed 2-bromo-5-(1-methoxyprop-1-en-2-yl)thiazole (4.38 g, 18.7 mmol), THF (30 mL), water (50 mL), HBr (47% wt, 50 mL). The resulting solution was stirred for 4 h at 70° C. and then was diluted with 30 mL of water. The resulting solution was extracted with 3×50 mL of DCM and the organic layers combined and dried over anhydrous Na$_2$SO$_4$, then concentrated under vacuum. This resulted in 3.79 g (crude, 92%) of the title compound as light yellow oil. MS-ESI: 221.9, 219.9 (M+1).

Step 4: 2-(2-Bromothiazol-5-yl)propan-1-ol

Into a 250-mL round-bottom flask, was placed 2-(2-bromothiazol-5-yl)propanal (4 g, 18.2 mmol), EtOH (60 mL). This was followed by the addition of NaBH$_4$ (1.38 g, 36.5 mmol) in portions at 0° C. The resulting solution was stirred overnight at RT and then was quenched by the addition of 50 mL of water. The resulting solution was extracted with 3×50 mL of DCM and the organic layers combined and dried over anhydrous Na$_2$SO$_4$, then concentrated under vacuum. This resulted in 3.79 g (94%) of the title compound as light yellow oil. MS-ESI: 223.9, 222.0 (M+1).

Step 5: 2-Bromo-5-(1-(tert-butyldimethylsilyloxy)propan-2-yl)thiazole

Into a 100-mL round-bottom flask, was placed 2-(2-bromothiazol-5-yl)propan-1-ol (3.79 g, 17.1 mmol), DMF (25 mL), imidazole (2.33 g, 34.2 mmol), TBDMSCl (3.87 g, 25.7 mmol). The resulting solution was stirred overnight at RT and then was diluted with 30 mL of water. The resulting solution was extracted with 3×30 mL of DCM and the organic layers combined and dried over anhydrous Na$_2$SO$_4$, then concentrated under vacuum. The residue was applied onto a silica gel column and eluted with ethyl acetate/petroleum ether (1:15 to 1:10). This resulted in 3.12 g (54%) of the title compound as a white solid. MS-ESI: 338.0, 336.0 (M+1).

Step 6 used similar procedure for converting compound 47 to Intermediate 40 shown in Scheme S to afford Intermediate 42. MS-ESI: 335.1 (M−1).

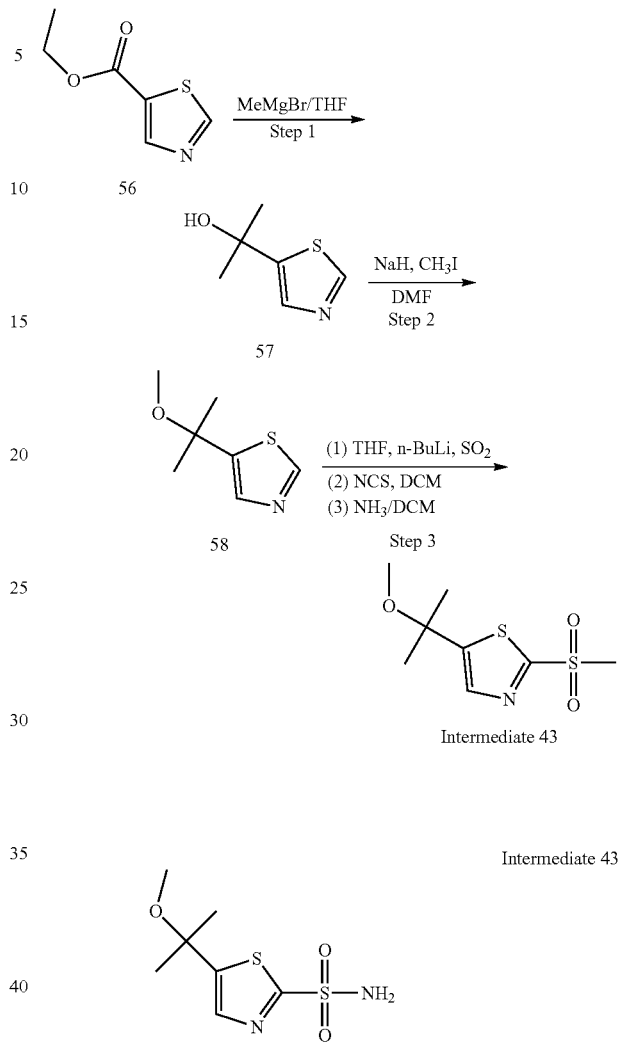

Scheme V 5-(2-Methoxypropan-2-yl)thiazole-2-sulfonamide

Step 1: 2-(Thiazol-5-yl)propan-2-ol

Into a 250-mL 3-necked round-bottom flask purged with and maintained under nitrogen, was placed a solution of ethyl ethyl thiazole-5-carboxylate (3.75 g, 23.9 mmol) in THF (50 mL). This was followed by the addition of MeMgBr/THF (3 M, 40 mL) dropwise with stirring at 0° C. The resulting solution was stirred for 2 h at RT and then was quenched by the addition of 50 mL of NH$_4$Cl (sat.). The resulting solution was extracted with 3×80 mL of DCM and the organic layers combined and dried over anhydrous Na$_2$SO$_4$, then concentrated under vacuum. The residue was applied onto a silica gel column and eluted with ethyl acetate/petroleum ether (1:3 to 1:1). This resulted in 2.1 g (61%) of the title compound as yellow oil. MS-ESI: 144.0 (M+1).

Step 2: 5-(2-Methoxypropan-2-yl)thiazole

Into a 100-mL round-bottom flask, was placed a solution of 2-(thiazol-5-yl)propan-2-ol (2.06 g, 14.4 mmol) in DMF (20 mL). This was followed by the addition of NaH (60%, 1.15 g, 28.8 mmol) in portions at 0° C. To this was added CH₃I (3.07 g, 21.6 mmol) dropwise with stirring at 0° C. The resulting solution was stirred for 1 h at RT and then was quenched by the addition of 20 mL of water. The resulting solution was extracted with 3×30 mL of ethyl acetate and the organic layers combined and dried over anhydrous $Na_2SO_4$, then concentrated under vacuum. The residue was applied onto a silica gel column and eluted with ethyl acetate/petroleum ether (1:5 to 1:3). This resulted in 1.42 g (63%) of the title compound as yellow oil. MS-ESI: 158.1 (M+1).

Step 3 used similar procedure for converting compound 47 to Intermediate 40 shown in Scheme S to afford Intermediate 43. MS-ESI: 235.0 (M−1).

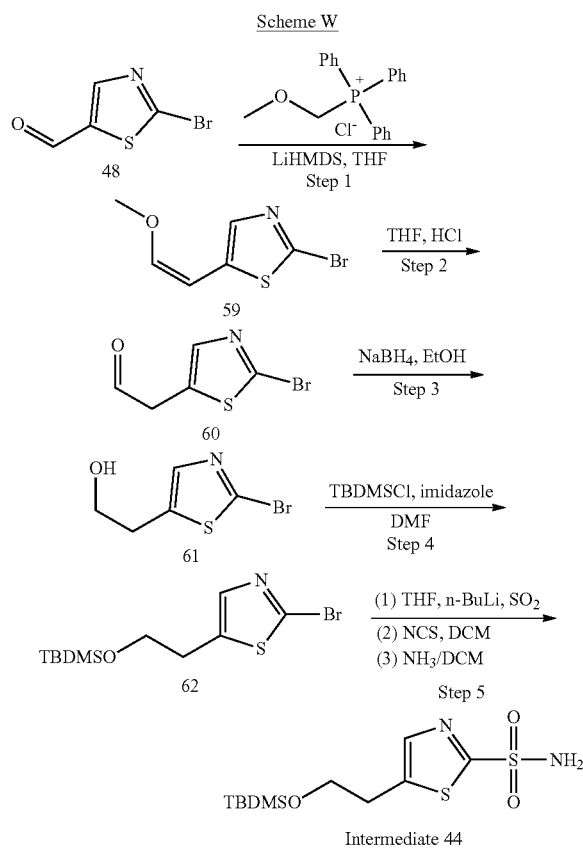

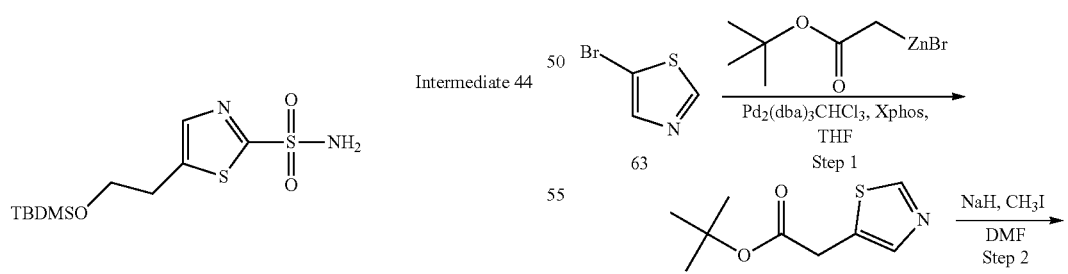

5-(2-(Tert-butyldimethylsilyloxy)ethyl)thiazole-2-sulfonamide

Step 1: 2-Bromo-5-(2-methoxyvinyl)thiazole

Into a 100-mL 3-necked round-bottom flask purged with and maintained under nitrogen, was placed (methoxymethyl)triphenylphosphanium chloride (3.2 g, 9.33 mmol), THF (15 mL). This was followed by the addition of LiHMDS (1 M, 9.4 mL) dropwise with stirring at 0° C. To this was added a solution of 2-bromo-1,3-thiazole-5-carbaldehyde (1.5 g, 7.81 mmol) in THF (10 mL) dropwise with stirring at 0° C. The resulting solution was stirred for 0.5 h at 0° C. and then was quenched by the addition of 50 mL of NH₄Cl (sat.). The resulting solution was extracted with 3×50 mL of DCM and the organic layers combined and concentrated under vacuum. The residue was applied onto a silica gel column and eluted with ethyl acetate/petroleum ether (1:100 to 1:80). This resulted in 1.3 g (76%) of the title compound as brown oil. The crude product was used in the next step.

Step 2: 2-(2-Bromo-1,3-thiazol-5-yl)acetaldehyde

Into a 50-mL round-bottom flask purged with and maintained under nitrogen, was placed 2-bromo-5-(2-methoxyvinyl)thiazole (1.3 g, 5.91 mmol), THF (10 mL). This was followed by the addition of aqueous hydrogen chloride (4 M, 5 mL) dropwise with stirring at 0° C. The resulting solution was stirred for 4 h at 60° C. The resulting solution was extracted with 3×30 mL of DCM and the organic layers combined and dried over anhydrous $Na_2SO_4$, then concentrated under vacuum. This resulted in 1.1 g (90%) of the title compound as light yellow oil. MS-ESI: 205.9, 207.9 (M+1).

Step 3: 2-(2-Bromo-1,3-thiazol-5-yl)ethan-1-ol

Into a 50-mL round-bottom flask, was placed 2-(2-bromo-1,3-thiazol-5-yl)acetaldehyde (1.1 g, 5.34 mmol), EtOH (10 mL), sodium borohydride (200 mg, 5.43 mmol). The resulting solution was stirred for 2 h at RT and then was quenched by the addition of 20 mL of water. The resulting solution was extracted with 3×30 mL of DCM and the organic layers combined and dried over anhydrous $Na_2SO_4$, then concentrated under vacuum. This resulted in 1.0 g (90%) of the title compound as light yellow oil. MS-ESI: 207.9, 209.9 (M+1).

Step 4: 2-Bromo-5-(2-(tert-butyldimethylsilyloxy)ethyl)thiazole

Into a 50-mL round-bottom flask, was placed 2-(2-bromo-1,3-thiazol-5-yl)ethan-1-ol (1.0 g, 4.81 mmol), DMF (10 mL), imidazole (650 mg, 9.56 mmol), TBDMSCl (1.1 g, 7.30 mmol). The resulting solution was stirred for 2 h at RT and then was diluted with 20 mL of water. The resulting solution was extracted with 2×20 mL of DCM and the organic layers combined and concentrated under vacuum. This resulted in 1.2 g (77%) of the title compound as light yellow oil. MS-ESI: 324.0, 322.0 (M+1).

Step 5 used similar procedure for converting compound 47 to Intermediate 40 shown in Scheme S to afford Intermediate 44. MS-ESI: 321.1 (M−1).

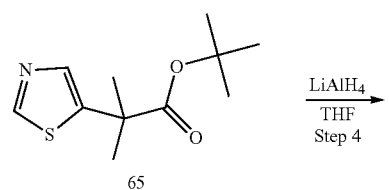

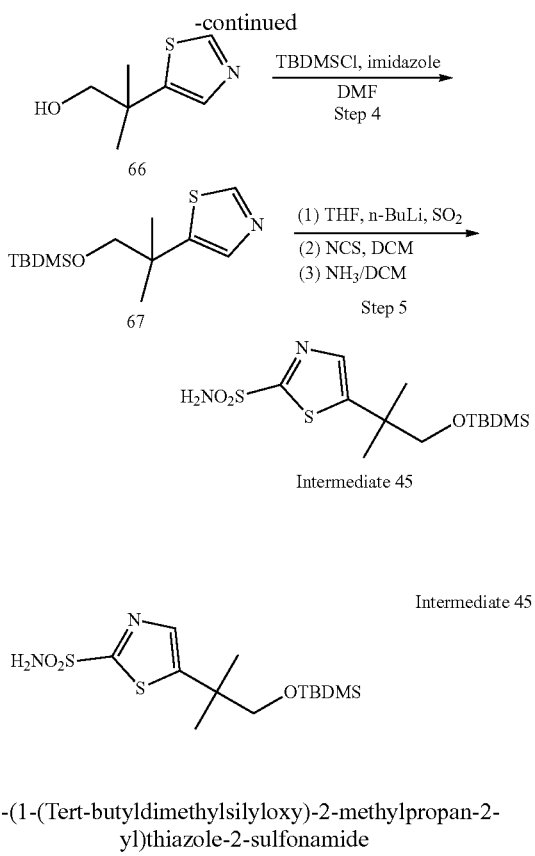

5-(1-(Tert-butyldimethylsilyloxy)-2-methylpropan-2-yl)thiazole-2-sulfonamide

Step 1: Tert-butyl 2-(thiazol-5-yl)acetate

Into a 100-mL 3-necked round-bottom flask purged with and maintained under nitrogen, was placed 5-bromothiazole (3 g, 18.29 mmol), THF (30 mL), X-phos (1.74 g, 3.66 mmol), Pd$_2$(dba)$_3$CHCl$_3$ (950 mg, 0.91 mmol). The resulting solution was stirred for 0.5 h at RT. To the above was added tert-butyl 2-(bromozincio)acetate (7.13 g, 27.37 mmol). The resulting solution was stirred for 4 h at 70° C. and then was concentrated under vacuum. The residue was applied onto a silica gel column and eluted with ethyl acetate/petroleum ether (1:10 to 1:3). This resulted in 2.4 g (66%) of the title compound as brown oil. MS-ESI: 200.1 (M+1).

Step 2: Tert-butyl 2-methyl-2-(thiazol-5-yl)propanoate

Into a 100-mL round-bottom flask purged with and maintained under nitrogen, was placed tert-butyl 2-(thiazol-5-yl) acetate (1 g, 5.02 mmol), DMF (20 mL). This was followed by the addition of NaH (60%, 600 mg, 25.00 mmol) in portions at 0° C. The solution was stirred for 0.5 h at 0° C. This was followed by the addition of CH$_3$I (2.13 g, 15.06 mmol) dropwise with stirring at 0° C. The resulting solution was stirred for 2 h at RT and then was quenched by the addition of 40 mL of NH$_4$Cl (sat.). The resulting solution was extracted with 3×50 mL of DCM and the organic layers combined and concentrated under vacuum. The residue was applied onto a silica gel column and eluted with ethyl acetate/petroleum ether (1:10 to 1:3). This resulted in 0.7 g (61%) of the title compound as light yellow oil. MS-ESI: 228.1 (M+1).

Step 3: 2-Methyl-2-(thiazol-5-yl)propan-1-ol

Into a 100-mL round-bottom flask, was placed tert-butyl 2-methyl-2-(thiazol-5-yl)propanoate (700 mg, 3.08 mmol), THF (20 mL). This was followed by the addition of LiAlH$_4$ (200 mg, 5.27 mmol) in portions at 0° C. and was stirred for 2 h at 0° C. and then was quenched by the addition of 1 mL of water. The solids were filtered out. The resulting mixture was concentrated under vacuum. This resulted in 400 mg (83%) of the title compound as brown oil. MS-ESI: 158.1 (M+1).

Steps 4-5 used similar procedures for converting compound 54 to Intermediate 42 shown in Scheme U to afford Intermediate 45. MS-ESI: 349.1 (M−1).

Scheme Y

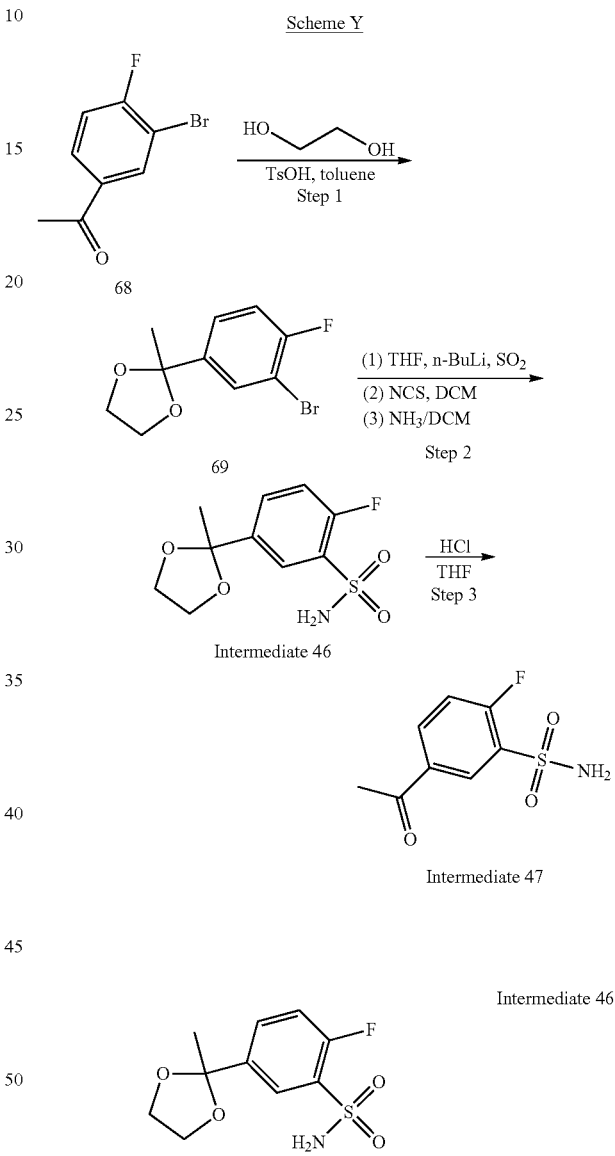

2-Fluoro-5-(2-methyl-1,3-dioxolan-2-yl)benzenesulfonamide

Step 1: 2-(3-Bromo-4-fluorophenyl)-2-methyl-1,3-dioxolane

Into a 250-mL round-bottom flask, was placed a solution of 1-(3-bromo-4-fluorophenyl)ethan-1-one (5 g, 23.0 mmol) in toluene (50 mL), ethane-1,2-diol (4 mL), TsOH (200 mg, 1.16 mmol). The resulting solution was stirred for 6 h at 120° C. The reaction was then quenched by the addition of 100 mL of water. The resulting solution was extracted with 3×100 mL of ethyl acetate and the organic layers combined and dried over anhydrous Na₂SO₄, then concentrated under vacuum. The residue was applied onto a silica gel column and eluted with ethyl acetate/petroleum ether (1:5 to 1:4). This resulted in 5.5 g (91%) of the title compound as yellow oil.

Step 2 used similar procedure for converting compound 47 to Intermediate 40 shown in Scheme S to afford Intermediate 46. MS-ESI: 260.0 (M−1).

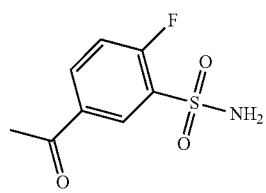

Intermediate 47

5-Acetyl-2-fluorobenzenesulfonamide

Step 3: 5-Acetyl-2-fluorobenzenesulfonamide

Into a 50-mL round-bottom flask, was placed 2-fluoro-5-(2-methyl-1,3-dioxolan-2-yl)benzene-1-sulfonamide (300 mg, 1.15 mmol), THF (5 mL), hydrogen chloride (1 N, 5 mL). The resulting solution was stirred for 12 h at RT. The pH value of the solution was adjusted to 7-8 with NaOH (2 N). The resulting solution was extracted with 3×30 mL of ethyl acetate and the organic layers combined and concentrated under vacuum. This resulted in 240 mg (crude, 96%) of the title compound as a light yellow solid. MS-ESI: 216.0 (M−1).

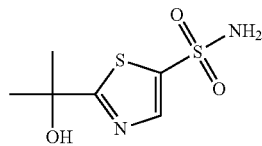

Intermediate 48

2-(2-Hydroxypropan-2-yl)thiazole-5-sulfonamide

Compound 73 was prepared using similar procedures for converting compound 68 to Intermediate 47 shown in Scheme Y.

Step 4: 2-(2-Hydroxypropan-2-yl)thiazole-5-sulfonamide

Into a 100-mL 3-necked round-bottom flask purged with and maintained under nitrogen, was placed 2-acetylthiazole-5-sulfonamide (1 g, 4.85 mmol), THF (20 mL). This was followed by the addition of MeMgBr (3 M, 7 mL) dropwise with stirring at 0° C. The resulting solution was stirred for 14 h at RT and then was quenched by the addition of 20 mL of NH₄Cl (sat.). The resulting solution was extracted with 2×30 mL of DCM and the organic layers combined and concentrated under vacuum. The residue was applied onto a silica gel column and eluted with ethyl acetate/petroleum ether (1:5 to 1:3). This resulted in 580 mg (54%) of the title compound as a light yellow solid. MS-ESI: 221.0 (M−1).

Schemes for phenylacetic acids Intermediates: Schemes AA-AQ illustrate the phenylacetic acid intermediates preparation.

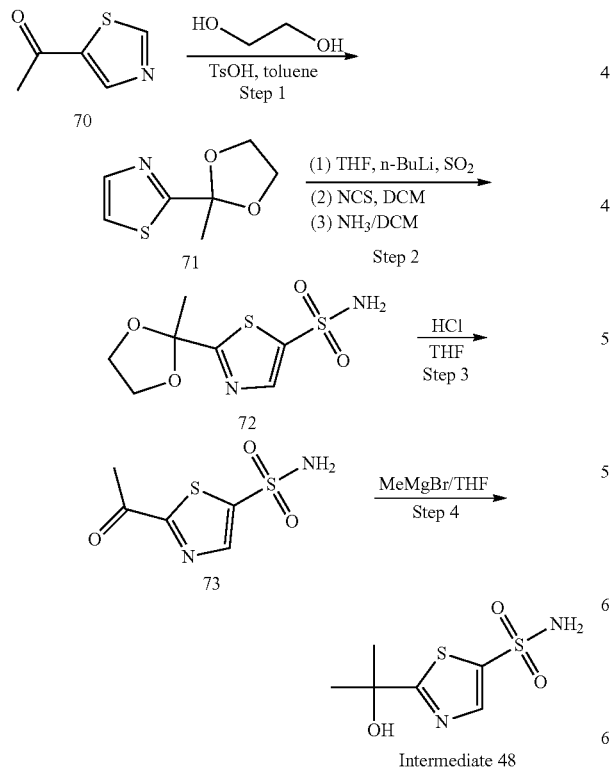

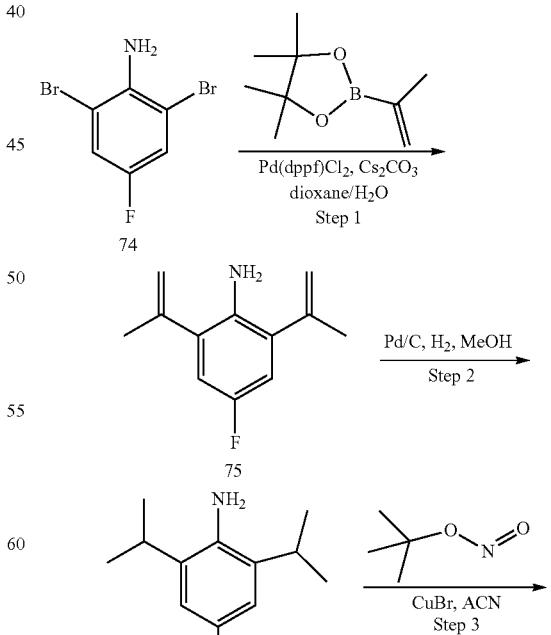

-continued

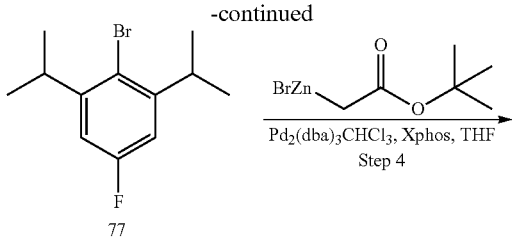

77

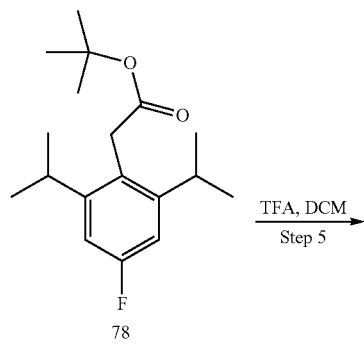

78

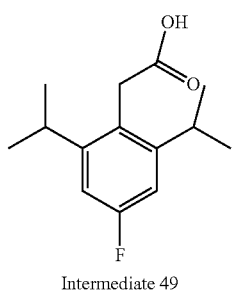

Intermediate 49

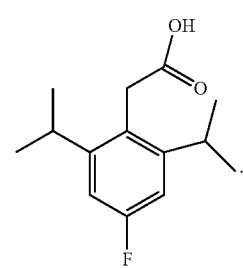

Intermediate 49

2-(4-Fluoro-2,6-diisopropylphenyl)acetic acid

Step 1: 4-Fluoro-2,6-bis(prop-1-en-2-yl)aniline

Into a 500-mL round-bottom flask purged with and maintained under nitrogen, was placed 2,6-dibromo-4-fluoroaniline (15 g, 55.8 mmol), dioxane (150 mL), water (15 mL), $Cs_2CO_3$ (55 g, 169 mmol), 4,4,5,5-tetramethyl-2-(prop-1-en-2-yl)-1,3,2-dioxaborolane (25 g, 149 mmol), Pd(dppf)Cl$_2$ (4 g, 5.47 mmol). The resulting solution was stirred for 15 h at 100° C. and then was concentrated under vacuum. The residue was applied onto a silica gel column and eluted with ethyl acetate/petroleum ether (1:10 to 1:8). This resulted in 9.2 g (86%) of the title compound as brown oil. MS-ESI: 192.1 (M+1).

Step 2: 4-Fluoro-2,6-bis(propan-2-yl)aniline

Into a 500-mL round-bottom flask, was placed 4-fluoro-2,6-bis(prop-1-en-2-yl)aniline (9.2 g, 48.1 mmol), MeOH (200 mL). Then Pd/C (10% wt, 900 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:10 to 1:8). This resulted in 7.2 g (77%) of the title compound as brown oil. MS-ESI: 196.1 (M+1).

Step 3: 2-Bromo-5-fluoro-1,3-bis(propan-2-yl)benzene

Into a 500-mL round-bottom flask purged with and maintained under nitrogen, was placed 4-fluoro-2,6-bis(propan-2-yl)aniline (7 g, 35.9 mmol), ACN (300 mL), CuBr (7.71 g, 53.9 mmol). This was followed by the addition of tert-butyl nitrite (5.55 g, 53.8 mmol) dropwise with stirring at 0° C. The resulting solution was stirred for 3 h at 60° C. and then was concentrated under vacuum. The residue was applied onto a silica gel column with petroleum ether. This resulted in 3.0 g (32%) of the title compound as yellow oil. $^1$H NMR (400 MHz, DMSO-$d_6$): δ 7.09 (d, J=9.8 Hz, 2H), 3.40 (hept, J=6.9 Hz, 2H), 1.20 (d, J=6.8 Hz, 12H).

Step 4: Tert-butyl 2-[4-fluoro-2,6-bis(propan-2-yl)phenyl]acetate

Into a 250-mL 3-necked round-bottom flask purged with and maintained under nitrogen, was placed 2-bromo-5-fluoro-1,3-bis(propan-2-yl)benzene (3.0 g, 11.6 mmol), THF (150 mL), X-phos (553 mg, 1.16 mmol), Pd$_2$(dba)$_3$CHCl$_3$ (600 mg, 0.58 mmol). The resulting solution was stirred for 0.5 h at RT. Then to the above tert-butyl 2-(bromozincio)acetate (6.0 g, 23.04 mmol) was added. The resulting solution was stirred for 5 h at 70° C. and then was quenched by the addition of 100 mL of NH$_4$Cl (sat.). The resulting solution was extracted with 3×100 mL of ethyl acetate and the organic layers combined and concentrated under vacuum. The residue was applied onto a silica gel column and eluted with ethyl acetate/petroleum ether (1:100 to 3:97).

This resulted in 3.14 g (92%) of the title compound as yellow oil. $^1$H NMR (400 MHz, DMSO-$d_6$) δ 6.93 (d, J=10.4 Hz, 2H), 3.67 (s, 2H), 3.19-3.07 (m, 2H), 1.39 (s, 9H), 1.15 (d, J=6.7 Hz, 12H).

Step 5: 2-(4-Fluoro-2,6-diisopropylphenyl)acetic acid

Into a 50-mL round-bottom flask, was placed tert-butyl 2-[4-fluoro-2,6-bis(propan-2-yl)phenyl]acetate (1.56 g, 5.30 mmol), DCM (10 mL), TFA (10 mL). The resulting solution was stirred for 3 h at RT and then was concentrated under vacuum. This resulted in 1.36 g (crude, 108%) of the title compound as a light yellow solid. MS-ESI: 237.1 (M−1).

Scheme AB

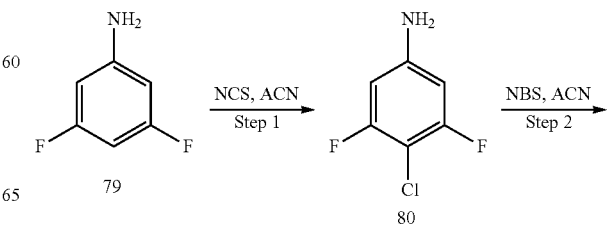

79            80

-continued

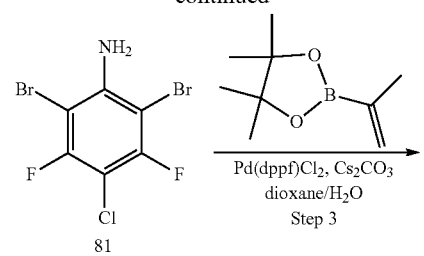
81

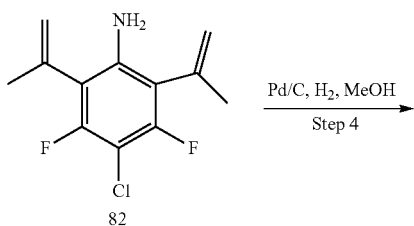
82

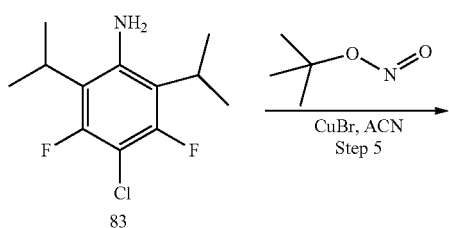
83

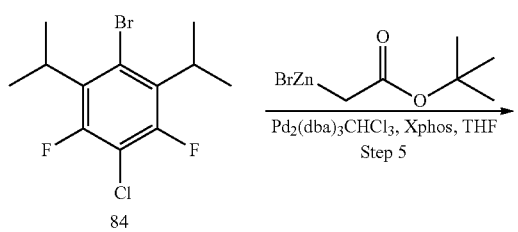
84

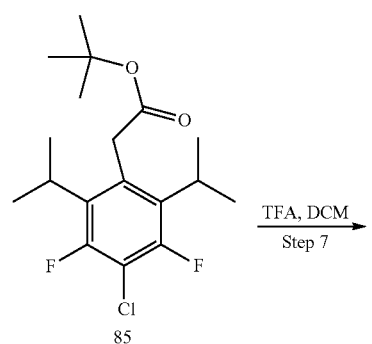
85

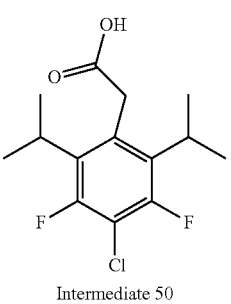
Intermediate 50

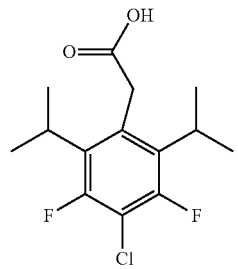
Intermediate 50

2-(4-Chloro-3,5-difluoro-2,6-diisopropylphenyl)acetic acid

Step 1: 4-Chloro-3,5-difluorobenzenamine

Into a 500-mL round-bottom flask, was placed 3,5-difluorobenzenamine (10.3 g, 79.8 mmol), ACN (100 mL), NCS (10.8 g, 80.9 mmol). The resulting solution was stirred for 5 h at 80° C. and then was concentrated under vacuum. The residue was applied onto a silica gel column and eluted with ethyl acetate/petroleum ether (1:3 to 1:1). This resulted in 7.1 g (54%) of the title compound as a gray solid. 164.0, 166.0 (M+1).

Step 2: 2,6-Dibromo-4-chloro-3,5-difluorobenzenamine

Into a 250-mL round-bottom flask, was placed 4-chloro-3,5-difluorobenzenamine (4.0 g, 24.5 mmol), ACN (100 mL), NBS (13.0 g, 73.0 mmol). The resulting solution was stirred for 1 h at RT and then was concentrated under vacuum. The residue was applied onto a silica gel column and eluted with ethyl acetate/petroleum ether (1:6 to 1:4). This resulted in 7.4 g (94%) of the title compound as a yellow solid. MS-ESI: 319.8, 321.8, 323.8 (M+1).

Steps 3-7 used similar procedures for converting compound 74 to Intermediate 49 shown in Scheme AA to afford Intermediate 50. MS-ESI: 289.1, 291.1 (M−1).

Compound 84: $^1$H NMR (400 MHz, CDCl$_3$-d) δ 3.67 (hept, J=7.2 Hz, 2H), 1.33 (d, J=7.2 Hz, 12H).

Scheme AC

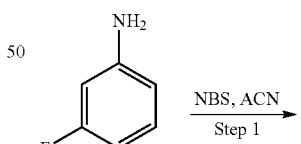
86

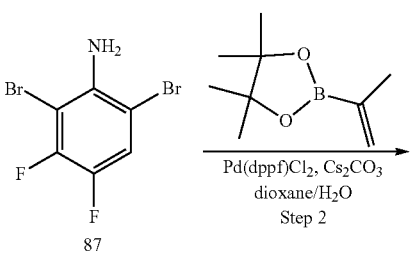
87

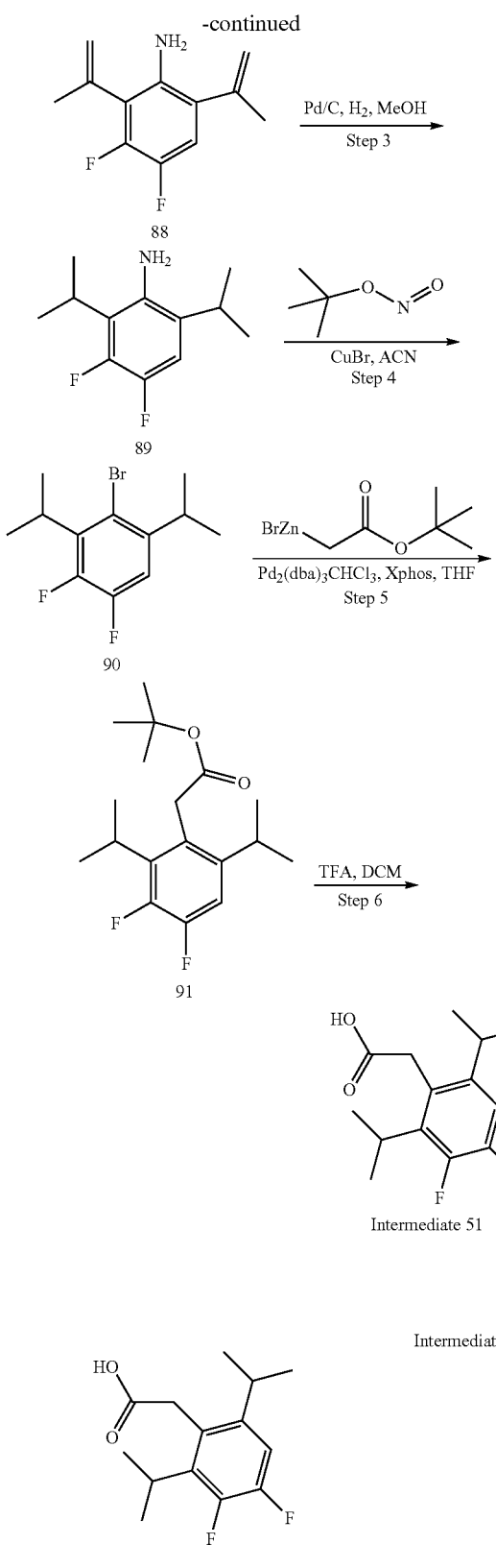
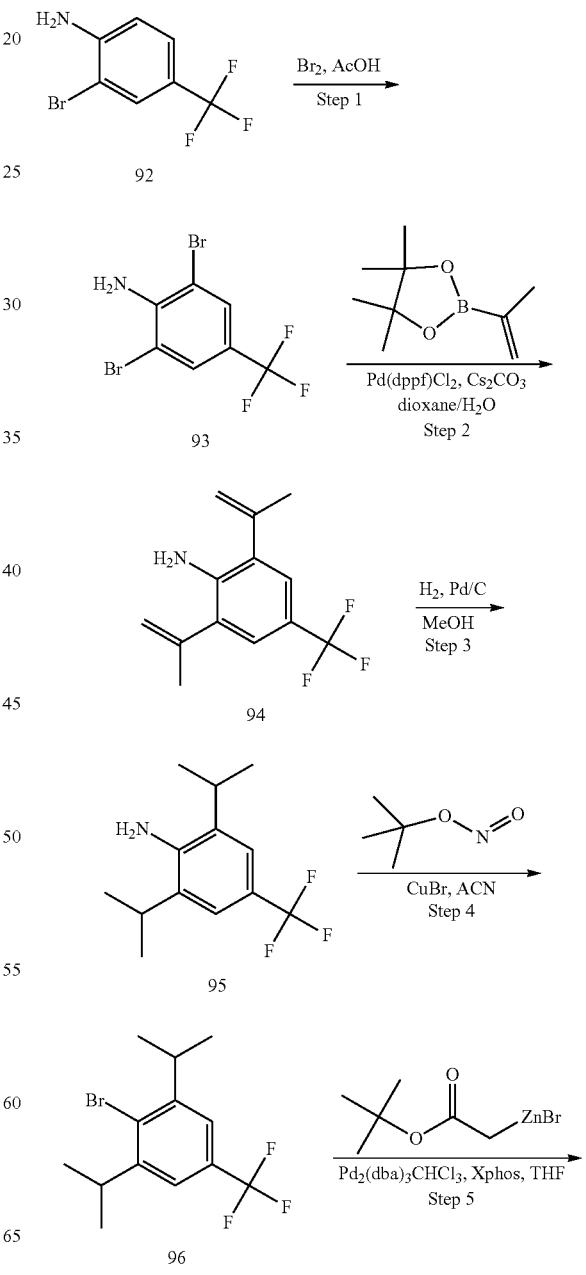

(16.2 g, 91.0 mmol). The resulting solution was stirred for 16 h at 85° C. and then was concentrated under vacuum. The residue was applied onto a silica gel column and eluted with ethyl acetate/petroleum ether (1:6 to 1:4). This resulted in 5.49 g (49%) of the title compound as a yellow solid. MS-ESI: 287.9, 285.9, 289.9 (M+1).

Steps 2-6 used similar procedures for converting compound 74 to Intermediate 49 shown in Scheme AA to afford Intermediate 51. MS-ESI: 255.1 (M−1).

Compound 90: $^1$H NMR (300 MHz, MeOD-$d_4$) δ 7.10 (dd, J=11.7, 8.4 Hz, 1H), 3.79-3.70 (m, 1H), 3.48-3.29 (m, 1H), 1.32 (dd, J=6.8, 1.8 Hz, 6H), 1.18 (d, J=6.8 Hz, 6H).

Compound 91: $^1$H NMR (300 MHz, DMSO-$d_6$) δ 7.13 (dd, J=12.3, 8.3 Hz, 1H), 3.65 (s, 2H), 3.21-3.00 (m, 2H), 1.35 (s, 9H), 1.28-1.05 (m, 12H).

Scheme AD 2-(3,4-Difluoro-2,6-diisopropylphenyl)acetic acid

Step 1: 2,6-Dibromo-3,4-difluorobenzenamine

Into a 250-mL round-bottom flask, was placed 3,4-difluorobenzenamine (5 g, 38.7 mmol), ACN (100 mL), NBS

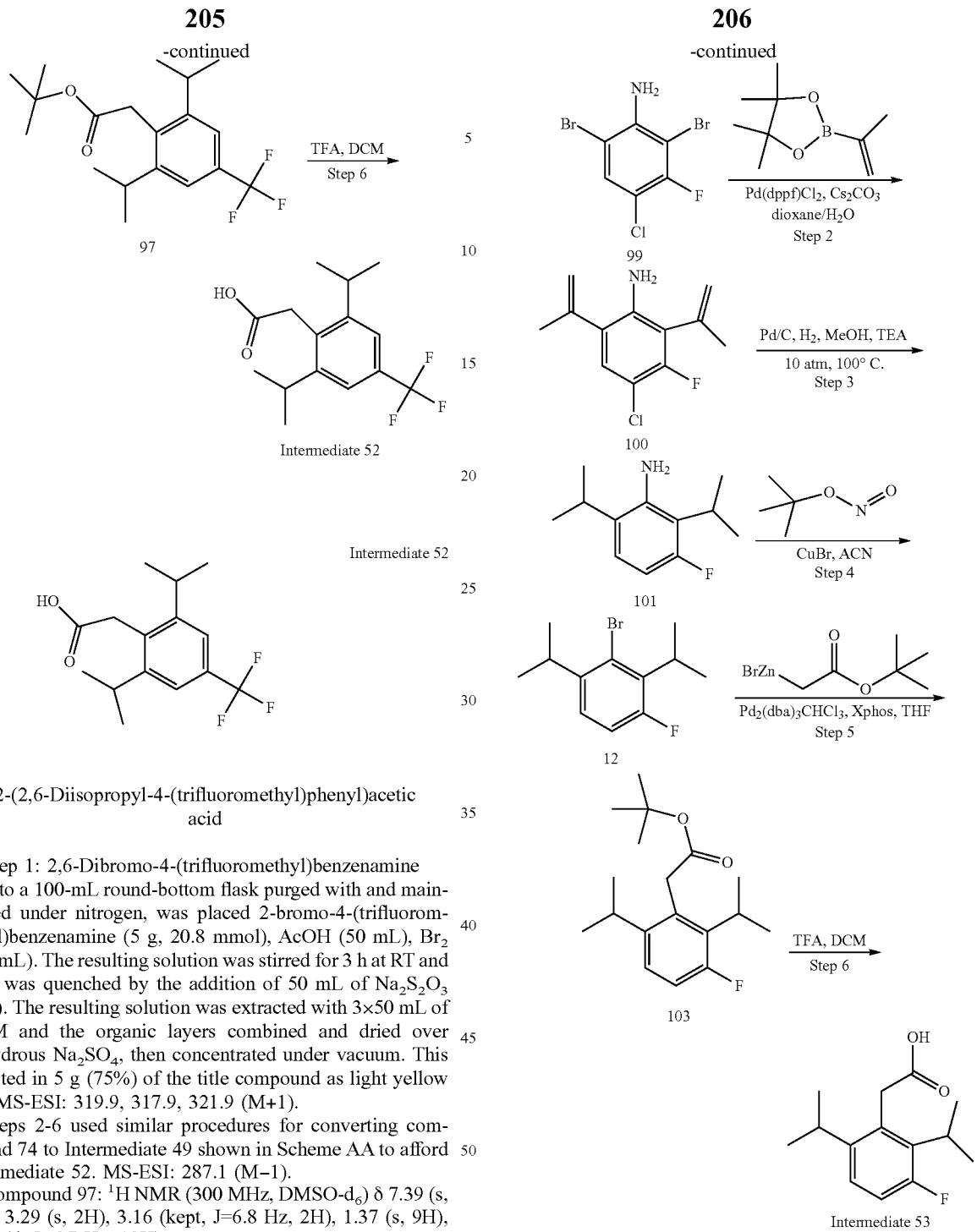

2-(2,6-Diisopropyl-4-(trifluoromethyl)phenyl)acetic acid

Step 1: 2,6-Dibromo-4-(trifluoromethyl)benzenamine

Into a 100-mL round-bottom flask purged with and maintained under nitrogen, was placed 2-bromo-4-(trifluoromethyl)benzenamine (5 g, 20.8 mmol), AcOH (50 mL), Br$_2$ (1.3 mL). The resulting solution was stirred for 3 h at RT and then was quenched by the addition of 50 mL of Na$_2$S$_2$O$_3$ (sat.). The resulting solution was extracted with 3×50 mL of DCM and the organic layers combined and dried over anhydrous Na$_2$SO$_4$, then concentrated under vacuum. This resulted in 5 g (75%) of the title compound as light yellow oil. MS-ESI: 319.9, 317.9, 321.9 (M+1).

Steps 2-6 used similar procedures for converting compound 74 to Intermediate 49 shown in Scheme AA to afford Intermediate 52. MS-ESI: 287.1 (M−1).

Compound 97: $^1$H NMR (300 MHz, DMSO-d$_6$) δ 7.39 (s, 2H), 3.29 (s, 2H), 3.16 (kept, J=6.8 Hz, 2H), 1.37 (s, 9H), 1.16 (d, J=6.7 Hz, 12H).

Scheme AE

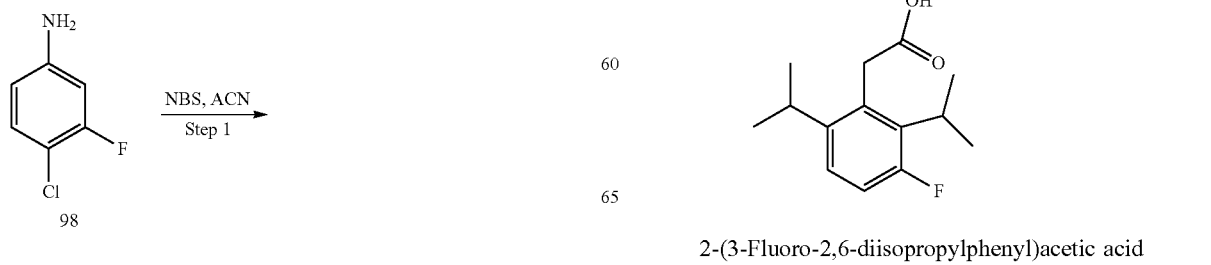

2-(3-Fluoro-2,6-diisopropylphenyl)acetic acid

Step 1: 2,6-Dibromo-4-chloro-3-fluoroaniline

Into a 500-mL round-bottom flask, was placed 4-chloro-3-fluoroaniline (5.08 g, 34.9 mmol), ACN (200 mL), NBS (18.69 g, 105.0 mmol). The resulting solution was stirred for 12 h at RT and then was concentrated under vacuum. The residue was applied onto a silica gel column and eluted with ethyl acetate/petroleum ether (1:200 to 1:100). This resulted in 9.7 g (92%) of the title compound as a light yellow solid. MS-ESI: 303.8, 305.8, 301.8 (M+1).

Step 2: 4-Chloro-3-fluoro-2,6-bis(prop-1-en-2-yl)aniline

Into a 500-mL round-bottom flask purged with and maintained under nitrogen, was placed 2,6-dibromo-4-chloro-3-fluoroaniline (9.03 g, 29.8 mmol), dioxane (200 mL), water (20 mL), 4,4,5,5-tetramethyl-2-(prop-1-en-2-yl)-1,3,2-dioxaborolane (15.12 g, 89.98 mmol), $Cs_2CO_3$ (29.34 g, 90.05 mmol), Pd(dppf)$Cl_2$ (2.20 g, 3.01 mmol). The resulting solution was stirred for 12 h at 90° C. and then was concentrated under vacuum. The residue was applied onto a silica gel column and eluted with ethyl acetate/petroleum ether (1:30 to 1:20). This resulted in 4.3 g (64%) of the title compound as yellow oil. MS-ESI: 226.1, 228.1 (M+1).

Step 3: 3-Fluoro-2,6-bis(propan-2-yl)aniline

Into a 250-mL pressure tank reactor (10 atm) purged with and maintained under nitrogen, was placed 4-chloro-3-fluoro-2,6-bis(prop-1-en-2-yl)aniline (4.3 g, 19.1 mmol), MeOH (100 mL), TEA (2.0 g, 19.8 mmol). Then Pd/C (10% wt, 0.5 g) was added. The flask was evacuated and flushed three times with hydrogen. The resulting solution was stirred for 7 days at 100° C. under an atmosphere of hydrogen. The solids were filtered out. The resulting mixture was concentrated under vacuum. The residue was applied onto a silica gel column and eluted with ethyl acetate/petroleum ether (1:5 to 1:3). This resulted in 3.6 g (97%) of the title compound as light yellow oil. MS-ESI: 196.1 (M+1).

Steps 4-6 used similar procedures for converting compound 76 to Intermediate 49 shown in Scheme AA to afford Intermediate 53. MS-ESI: 237.1 (M−1).

Compound 102: $^1$H NMR (400 MHz, DMSO-$d_6$) δ 7.28 (dd, J=8.7, 5.9 Hz, 1H), 7.18 (dd, J=11.3, 8.7 Hz, 1H), 3.64 (hept, J=6.9 Hz, 1H), 3.36 (hept, J=6.9 Hz, 1H), 1.30 (dd, J=6.9, 1.9 Hz, 6H), 1.19 (d, J=6.8 Hz, 6H).

Compound 103: $^1$H NMR (400 MHz, DMSO-$d_6$) δ 7.16 (dd, J=8.6, 5.6 Hz, 1H), 7.00 (dd, J=11.9, 8.7 Hz, 1H), 3.72 (s, 2H), 3.23-3.00 (m, 2H), 1.40 (s, 9H), 1.28 (d, J=6.9 Hz, 6H), 1.15 (d, J=6.8 Hz, 6H).

Scheme AF

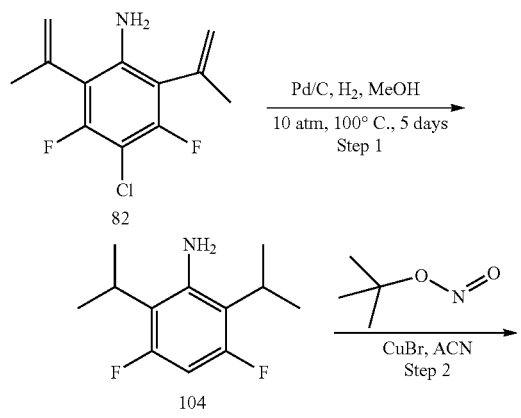

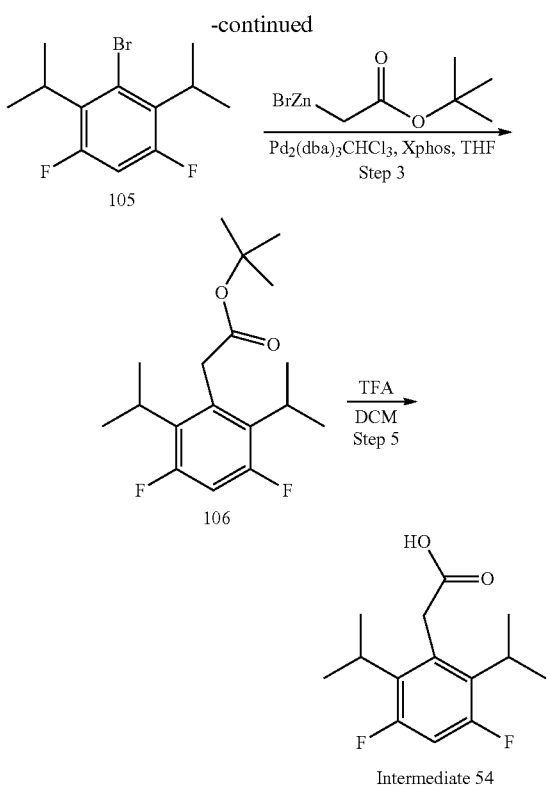

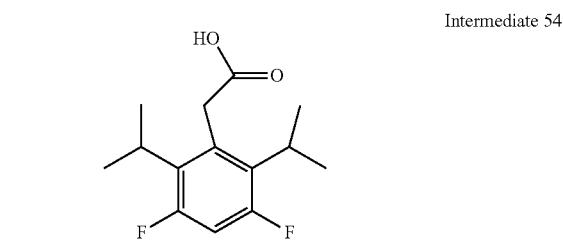 [SMILES: CC(C)c1c(F)cc(F)c(C(C)C)c1CC(=O)O]

2-(3,5-Difluoro-2,6-diisopropylphenyl)acetic acid

Step 1: 3,5-Difluoro-2,6-bis(propan-2-yl)aniline

Into a 100-mL pressure tank reactor (10 atm), was placed 4-chloro-3,5-difluoro-2,6-bis(prop-1-en-2-yl)aniline (1.6 g, 6.57 mmol), MeOH (60 mL), TEA (0.2 mL). Then Pd/C (10% wt, 800 mg) was added. The flask was evacuated and flushed three times with hydrogen. The resulting solution was stirred for 5 days at 100° C. under an atmosphere of hydrogen. The solids were filtered out.

The resulting mixture was concentrated under vacuum. The residue was applied onto a silica gel column and eluted with ethyl acetate/petroleum ether (1:5 to 1:3). This resulted in 1.2 g (86%) of the title compound as light yellow oil. MS-ESI: 214.1 (M+1).

Steps 2-4 used similar procedures for converting compound 76 to Intermediate 49 shown in Scheme AA to afford Intermediate 54. MS-ESI: 255.1 (M−1).

Compound 105: $^1$H NMR (300 MHz, $CDCl_3$-d) δ 6.71 (t, J=11.4 Hz, 1H), 3.64 (hept, J=7.0 Hz, 2H), 1.29 (d, J=7.0 Hz, 12H).

Compound 106: ¹H NMR (300 MHz, CDCl₃-d) δ 6.64 (t, J=11.8 Hz, 1H), 3.67 (s, 2H), 3.16 (hept, J=7.0 Hz, 2H), 1.43 (s, 9H), 1.30 (d, J=7.0 Hz, 12H).

Scheme AG

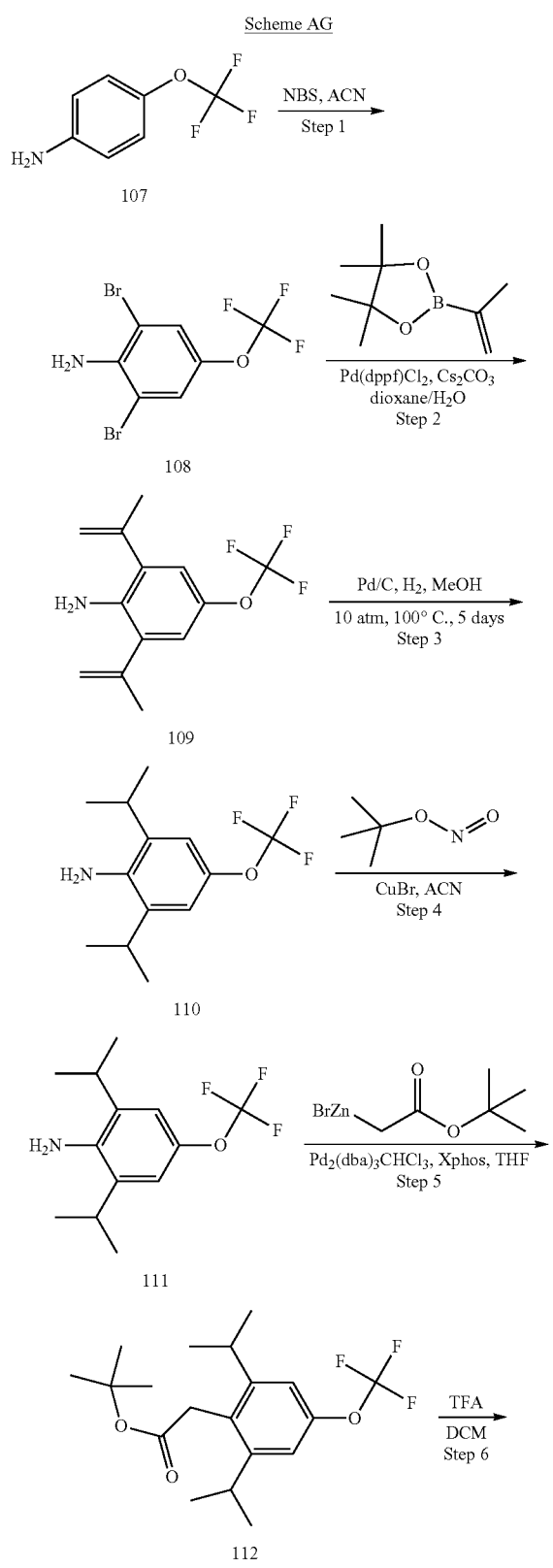

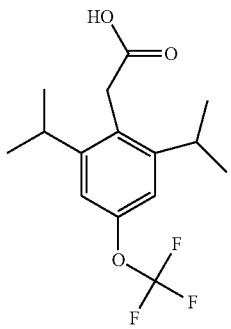

Intermediate 55

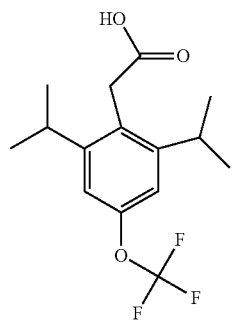

Intermediate 55

2-(2,6-Diisopropyl-4-(trifluoromethoxy)phenyl)acetic acid

Step 1: 2,6-Dibromo-4-(trifluoromethoxy)aniline

Into a 500-mL round-bottom flask, was placed 4-(trifluoromethoxy)aniline (7.15 g, 40.4 mmol), ACN (300 mL), NBS (18 g, 101 mmol). The resulting solution was stirred for 12 h at RT and then was concentrated under vacuum. The residue was applied onto a silica gel column and eluted with ethyl acetate/petroleum ether (1:15 to 1:10). This resulted in 12 g (89%) of the title compound as a white solid. MS-ESI: 335.9, 333.9, 337.9 (M+1).

Step 2: 2,6-Bis(prop-1-en-2-yl)-4-(trifluoromethoxy)aniline

Into a 500-mL 3-necked round-bottom flask purged with and maintained under nitrogen, was placed 2,6-dibromo-4-(trifluoromethoxy)aniline (2.67 g, 7.97 mmol), dioxane (40 mL), water (4 mL), Cs₂CO₃ (8 g, 24.8 mol), 4,4,5,5-tetramethyl-2-(prop-1-en-2-yl)-1,3,2-dioxaborolane (3.06 g, 18.2 mmol), Pd(dppf)Cl₂ (656 mg, 0.80 mmol). The resulting solution was stirred overnight at 90° C. and then concentrated under vacuum. The residue was applied onto a silica gel column and eluted with ethyl acetate/petroleum ether (1:15 to 1:10). This resulted in 1.15 g (56%) of the title compound as light yellow oil. MS-ESI: 258.1 (M+1).

Steps 3-6 used similar procedures for converting compound 82 to Intermediate 54 shown in Scheme AF to afford Intermediate 55. MS-ESI: 303.1 (M−1).

Compound 111: ¹H NMR (300 MHz, MeOD-d₄) δ 7.10-7.03 (s, 2H), 3.55 (hept, J=6.8 Hz, 2H), 1.25 (d, J=6.8 Hz, 12H).

Scheme AH

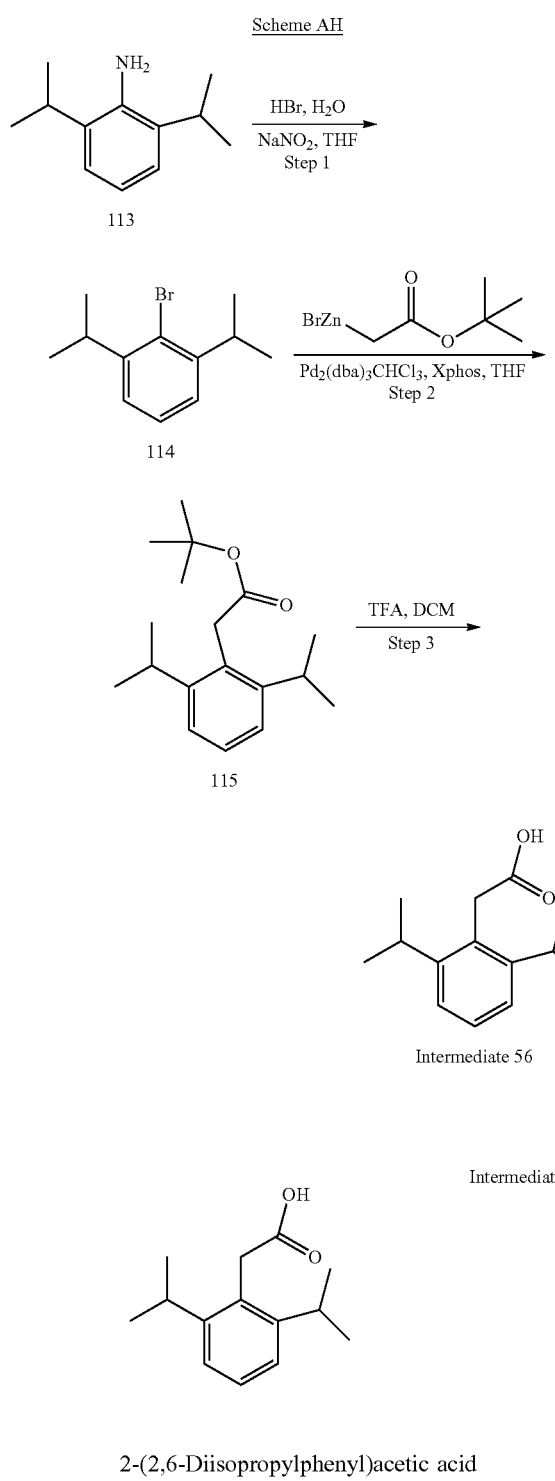

2-(2,6-Diisopropylphenyl)acetic acid

Step 1: 2-Bromo-1,3-bis(propan-2-yl)benzene

Into a 500-mL round-bottom flask, was placed 2,6-diisopropylbenzenamine (10 g, 56.4 mmol). This was followed by the addition of HBr (47% wt, 51 mL) dropwise with stirring at RT during 5 min. The white suspension was cooled down to −56° C. and 23.6 g (0.34 mol) of NaNO$_2$ (6.65 g, 96.4 mmol) was added in portions during 10 min and stirred continued at the same temperature for 1 h. Then 70 mL of ice-cold THF was slowly added during 10 min and the temperature let slowly rising to −15° C. during 2 h until no more gas evolved. The temperature was decreased again to −56° C. and 24 mL of water was added followed by the addition of sodium carbonate decahydrate (33.38 g, 11.67 mmol) giving a brown suspension. The temperature was let raising to RT during 3 h. The mixture was stirred for 16 h at RT. The resulting solution was extracted with 3×50 mL of DCM and the organic layers combined and concentrated under vacuum. The residue was applied onto a silica gel column and eluted with ethyl acetate/petroleum ether (1:15 to 1:10). This resulted in 11 g (81%) of the title compound as yellow oil.

Steps 2-3 used similar procedures for converting compound 77 to Intermediate 49 shown in Scheme AA to afford Intermediate 56. MS-ESI: 219.1 (M−1).

Compound 115: $^1$H NMR (400 MHz, DMSO-d$_6$) δ 7.21-7.09 (m, 3H), 3.69 (s, 2H), 3.12 (kept, J=6.8 Hz, 2H), 1.39 (s, 9H), 1.18 (d, J=6.8 Hz, 12H).

Scheme AI

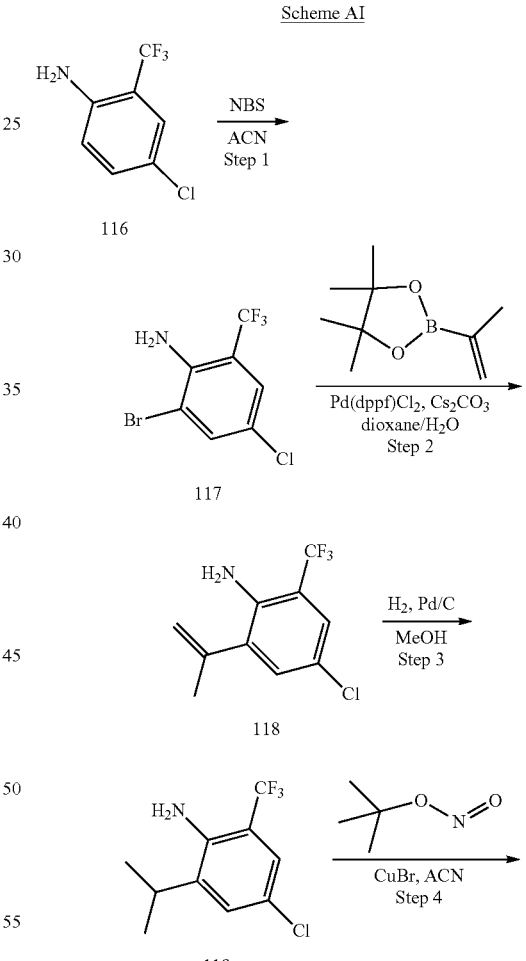

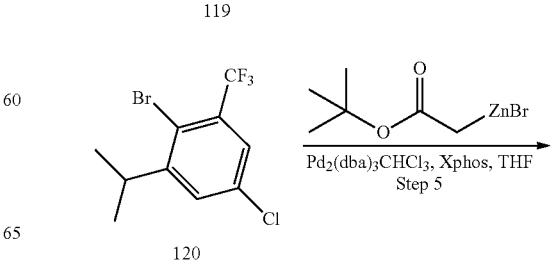

213

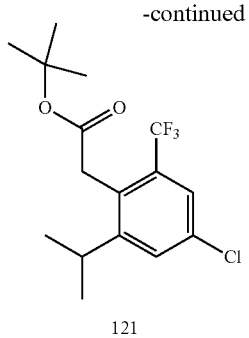

121

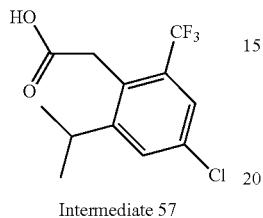

Intermediate 57

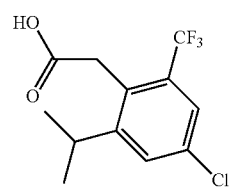

2-(4-Chloro-2-isopropyl-6-(trifluoromethyl)phenyl) acetic acid

Step 1: 2-Bromo-4-chloro-6-(trifluoromethyl)aniline

Into a 250-mL round-bottom flask, was placed 4-chloro-2-(trifluoromethyl)aniline (5 g, 25.6 mmol), ACN (150 mL), NBS (9.2 g, 51.7 mmol). The resulting solution was stirred overnight at RT and then was concentrated under vacuum. The residue was applied onto a silica gel column and eluted with ethyl acetate/petroleum ether (1:15 to 1:10). This resulted in 6 g (86%) of the title compound as a white solid. MS-ESI: 275.9, 273.9 (M+1).

Steps 2-6 used similar procedures for converting compound 74 to Intermediate 49 shown in Scheme AA to afford Intermediate 57. MS-ESI: 279.0 (M−1).

Compound 121: $^1$H NMR (300 MHz, DMSO-d$_6$) δ 7.70 (s, 1H), 7.58 (s, 1H), 3.77 (s, 2H), 3.11-2.97 (m, 1H), 1.35 (s, 9H), 1.17 (d, J=6.8 Hz, 6H).

Scheme AJ

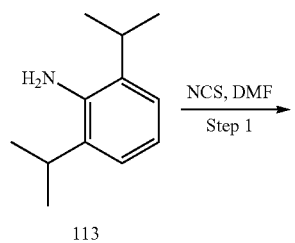

113

214

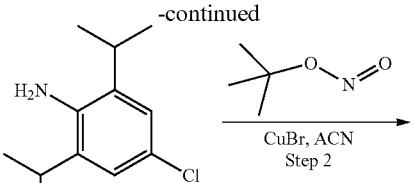

122

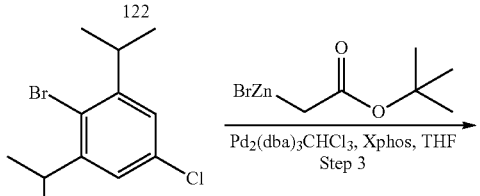

123

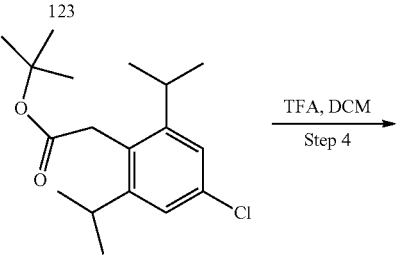

124

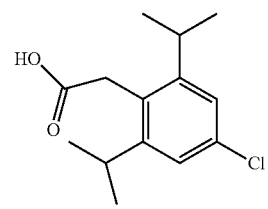

Intermediate 58

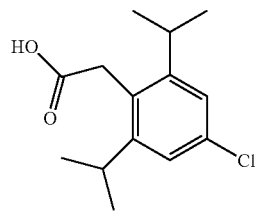

Intermediate 58

2-(4-Chloro-2,6-diisopropylphenyl)acetic acid

Step 1: 4-Chloro-2,6-bis(propan-2-yl)aniline

Into a 100-mL round-bottom flask, was placed 2,6-bis(propan-2-yl)aniline (5 g, 28.2 mmol), DMF (20 mL), NCS (4.9 g, 36.7 mmol). The resulting solution was stirred for 15 h at RT and then was diluted with 20 mL of water. The resulting solution was extracted with 3×20 mL of DCM and the organic layers combined and concentrated under vacuum. The residue was applied onto a silica gel column and eluted with ethyl acetate/petroleum ether (1:10 to 1:5). This resulted in 3.7 g (62%) of the title compound as brown oil. MS-ESI: 212.1, 214.1 (M+1).

Steps 2-4 used similar procedures for converting compound 76 to Intermediate 49 shown in Scheme AA to afford Intermediate 58. MS-ESI: 253.1, 255.1 (M−1).

Step 1: 4-Amino-3,5-bis(propan-2-yl)benzonitrile

Into a 100-mL round-bottom flask purged with and maintained under nitrogen, was placed 4-bromo-2,6-bis(propan-2-yl)aniline (5.1 g, 19.9 mmol), DME (30 mL), CuCN (2.16 g, 23.9 mmol), CuI (380 mg, 2.00 mmol), KI (664 mg, 3.98 mmol), DMEDA (2.0 mL). The resulting solution was stirred for 24 h at 100° C. and then was diluted with 20 mL of water. The solution was extracted with 3×30 mL of ethyl acetate and the organic layers combined and concentrated under vacuum. The residue was applied onto a silica gel column and eluted with ethyl acetate/petroleum ether (1:30 to 1:20). This resulted in 1.2 g (30%) of the title compound as a yellow solid. MS-ESI: 203.1 (M+1).

Steps 2-4 used similar procedures for converting compound 76 to Intermediate 49 shown in Scheme AA to afford Intermediate 59. MS-ESI: 244.1 (M−1). $^1$H NMR (400 MHz, DMSO-d$_6$) δ 12.54 (s, 1H), 7.56 (s, 2H), 3.79 (s, 2H), 3.12 (hept, J=6.8 Hz, 2H), 1.15 (d, J=6.7 Hz, 12H).

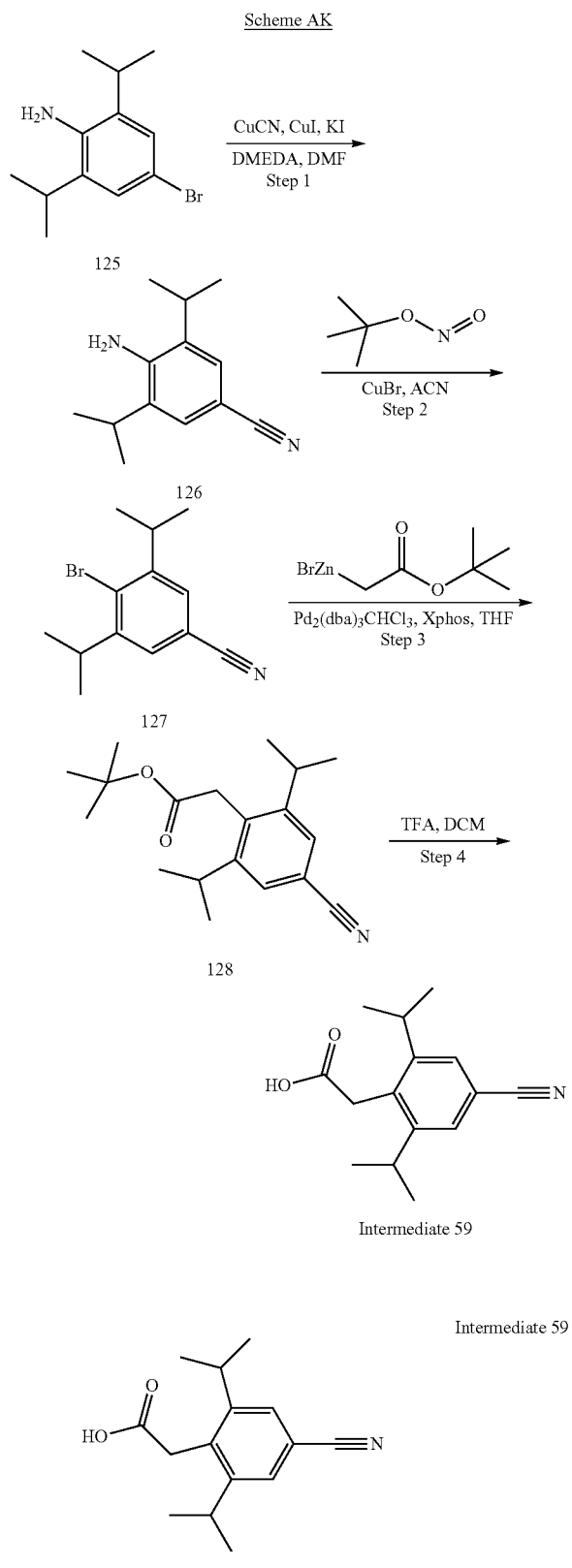

Scheme AK

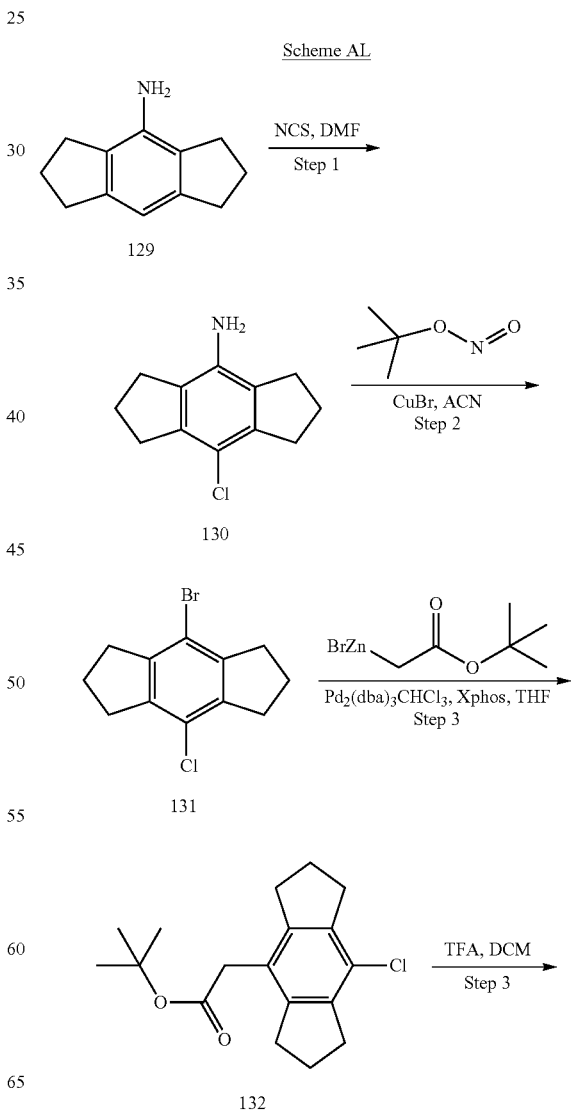

Scheme AL 2-(4-Cyano-2,6-diisopropylphenyl)acetic acid

217
-continued

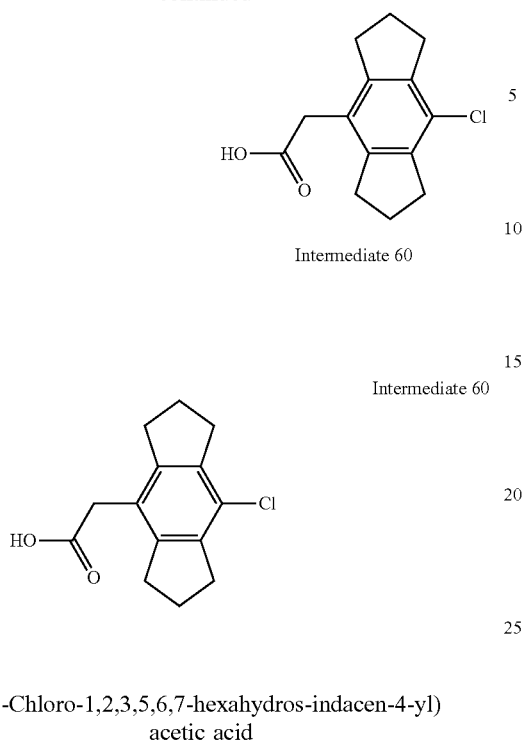

Intermediate 60

Intermediate 60

2-(8-Chloro-1,2,3,5,6,7-hexahydros-indacen-4-yl) acetic acid

Step 1: 8-Chloro-1,2,3,5,6,7-hexahydros-indacen-4-amine

Into a 100-mL round-bottom flask, was placed 1,2,3,5,6,7-hexahydros-indacen-4-amine (1.73 g, 9.99 mmol), DMF (10 mL), NCS (1.47 g, 11.0 mmol). The resulting solution was stirred for 12 h at RT and then was diluted with 50 mL of DCM. The resulting mixture was washed with 3×10 mL of water. The resulting mixture was concentrated under vacuum. The residue was applied onto a silica gel column and eluted with ethyl acetate/petroleum ether (1:5 to 1:10). This resulted in 1.88 g (91%) of the title compound as a yellow solid. MS-ESI: 208.1, 210.1 (M+1).

Steps 2-4 used similar procedures for converting compound 76 to Intermediate 49 shown in Scheme AA to afford Intermediate 60. MS-ESI: 249.1, 251.1 (M−1).

Scheme AM

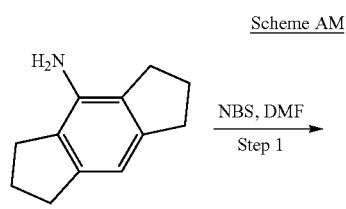

218
-continued

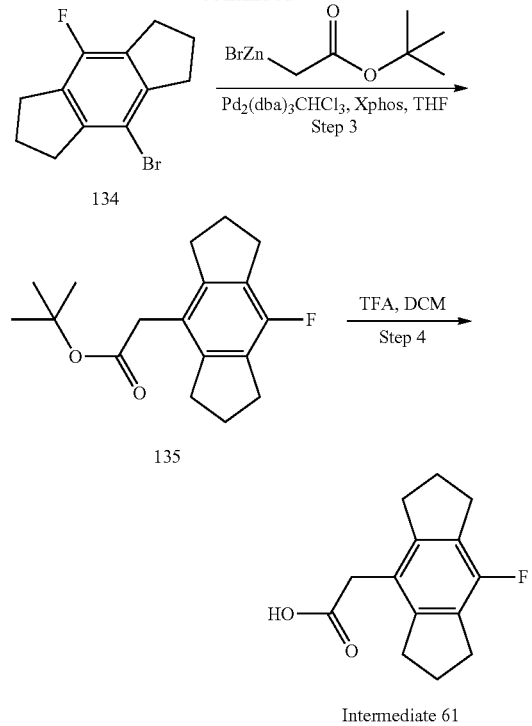

Intermediate 61

Intermediate 61

2-(8-Fluoro-1,2,3,5,6,7-hexahydros-indacen-4-yl) acetic acid

Step 1: 8-Bromo-1,2,3,5,6,7-hexahydro-s-indacen-4-amine

Into a 100-mL round-bottom flask, was placed 1,2,3,5,6,7-hexahydro-s-indacen-4-amine (2.6 g, 15.0 mmol), DMF (30 mL), NBS (2.9 g, 16.3 mmol). The resulting solution was stirred for 12 h at RT and then was diluted with 80 mL of ethyl acetate. The resulting mixture was washed with 3×20 mL of water. The resulting mixture was concentrated under vacuum. The residue was applied onto a silica gel column and eluted with ethyl acetate/petroleum ether (1:30 to 1:20). This resulted in 3.0 g (79%) of the title compound as a brown solid. MS-ESI: 252.0, 254.0 (M+1).

Step 2: 4-Bromo-8-fluoro-1,2,3,5,6,7-hexahydros-indacene

Into a 100-mL round-bottom flask, was placed 8-bromo-1,2,3,5,6,7-hexahydro-s-indacen-4-amine (1.5 g, 5.95 mmol), DCM (40 mL), HF/Py (70%, 4 mL), 3-methylbutyl nitrite (1.05 g, 8.96 mmol). The resulting solution was stirred for 2 h at RT and then was diluted with 50 mL of DCM. The resulting mixture was washed with 3×10 mL of water. The resulting mixture was concentrated under vacuum. The residue was applied onto a silica gel column and eluted with petroleum ether. This resulted in 1.2 g (79%) of the title compound as an off-white solid. ¹H NMR (400 MHz, DMSO-d₆) δ 3.00-2.80 (m, 8H), 2.15-2.00 (m, 4H).

Steps 3-4 used similar procedures for converting compound 77 to Intermediate 49 shown in Scheme AA to afford Intermediate 61. ¹H NMR (400 MHz, DMSO-d₆) δ 12.23 (s, 1H), 3.44 (s, 2H), 2.80 (dt, J=15.0, 7.5 Hz, 8H), 2.04-2.02 (m, 4H).

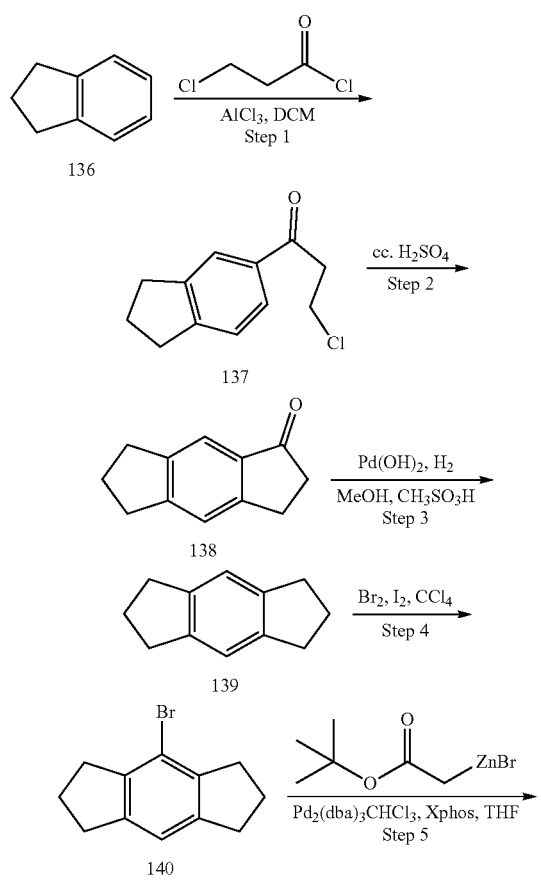

Scheme AN

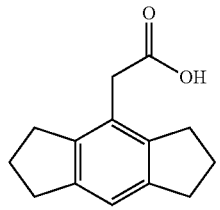

Intermediate 62

2-(1,2,3,5,6,7-Hexahydros-indacen-4-yl)acetic acid

Step 1: 3-Chloro-1-(2,3-dihydro-1H-inden-5-yl)propan-1-one

Into a 1000-mL round-bottom flask, was placed a solution of AlCl₃ (37 g, 278 mmol) in DCM (400 mL). This was followed by the addition of a solution of 2,3-dihydro-1H-indene (30 g, 254 mmol) and 3-chloropropanoyl chloride (32.1 g, 253 mmol) in DCM (100 mL) dropwise with stirring at −10° C. in 30 min. The resulting solution was stirred for 16 h at RT. Then the reaction mixture was added dropwise to cold HCl (3 N, 400 mL) over 45 min at −10° C. The resulting solution was extracted with 3×200 mL of DCM and the organic layers combined and dried over anhydrous Na₂SO₄, then concentrated under vacuum. This resulted in 53.5 g (crude) of the title compound as a yellow solid.

Step 2: 1,2,3,5,6,7-Hexahydros-indacen-1-one

Into a 1000-mL round-bottom flask, was placed a solution of 3-chloro-1-(2,3-dihydro-1H-inden-5-yl)propan-1-one (53.5 g, 253 mmol) in cc. H₂SO₄ (300 mL). The resulting solution was stirred for 16 h at 55° C. and then was quenched by the addition of 1500 mL of water/ice. The solids were collected by filtration and then was dried over infrared lamp for 24 h. This resulted in 37.4 g (85%) of the title compound as a yellow solid.

Step 3: 1,2,3,5,6,7-Hexahydros-indacene

Into a 1000-mL round-bottom flask, was placed a solution of 1,2,3,5,6,7-hexahydros-indacen-1-one (37.2 g, 216.00 mmol), MeOH (300 mL), CH₃SO₃H (42 g). Then Pd(OH)₂/C (20% wt, 8 g) was added. The flask was evacuated and flushed three times with hydrogen. The resulting solution was stirred for 16 h at RT under an atmosphere of hydrogen. The solids were filtered out. The resulting mixture was concentrated under vacuum. The residue was applied onto a silica gel column and eluted with ethyl acetate/petroleum ether (1:150 to 1:100). This resulted in 27.1 g (79%) of the title compound as a white solid.

Step 4: 4-Bromo-1,2,3,5,6,7-hexahydros-indacene

Into a 500-mL 3-necked round-bottom flask purged with and maintained under nitrogen, was placed a solution of 1,2,3,5,6,7-hexahydros-indacene (15 g, 94.8 mmol) in CCl₄ (200 mL). Then I₂ (1.2 g, 4.72 mmol) was added. This was followed by the addition of a solution of Br₂ (16 g, 100 mmol) in CCl₄ (50 mL) dropwise with stirring at 0° C. in 10 min. The resulting solution was stirred for 2 h at 0° C. The reaction was then quenched by the addition of 150 mL of NH₄Cl (sat.). The resulting solution was extracted with 3×150 mL of DCM and the organic layers combined and dried over anhydrous Na₂SO₄, then concentrated under vacuum. This resulted in 23.3 g (crude) of the title compound as yellow oil. ¹H NMR (300 MHz, DMSO-d₆) δ 7.02 (s, 1H), 2.95-2.75 (m, 8H), 2.03-2.01 (m, 4H)

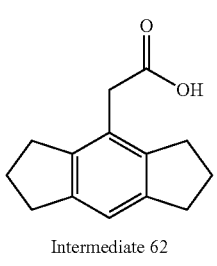

Intermediate 62

Step 5: Tert-butyl 2-(1,2,3,5,6,7-hexahydros-indacen-4-yl)acetate

Into a 100-mL round-bottom flask purged with and maintained under nitrogen, was placed a solution of 4-bromo-1,2,3,5,6,7-hexahydros-indacene (1 g, 4.2 mmol) in THF (20 mL). Then X-phos (200 mg, 0.42 mmol) and Pd$_2$(dba)$_3$·CHCl$_3$ (220 mg, 0.21 mmol) were added. The resulting solution was stirred for 10 min at RT. This was followed by the addition of tert-butyl 2-(bromozincio)acetate (2.2 g, 8.45 mmol). The resulting solution was stirred for 4 h at 80° C. and then was quenched by the addition of 50 mL of NH$_4$Cl (sat.). The resulting solution was extracted with 3×100 mL of DCM and the organic layers combined and dried over anhydrous Na$_2$SO$_4$, then concentrated under vacuum. This resulted in 1.4 g (crude) of the title compound as brown oil. $^1$H NMR (400 MHz, DMSO-d$_6$) δ 6.96 (s, 1H), 3.47 (s, 2H), 2.79 (dt, J=17.6, 7.5 Hz, 8H), 2.01-1.99 (m, 4H), 1.39 (s, 9H).

Step 6: 2-(1,2,3,5,6,7-hexahydros-indacen-4-yl)acetic acid

Into a 40-mL sealed tube, was placed a solution of tert-butyl 2-(1,2,3,5,6,7-hexahydros-indacen-4-yl)acetate (1.4 g, 5.14 mmol) in 6 M sodium hydroxide/MeOH (4/6 mL). The resulting solution was stirred for 16 h at 100° C. The reaction was then quenched by the addition of 20 mL of water. The resulting solution was extracted with 2×30 mL of DCM and the aqueous layers combined. The pH value of the solution was adjusted to 2 with hydrogen chloride (1 N). The resulting solution was extracted with 3×50 mL of ethyl acetate and the organic layers combined and dried over anhydrous Na$_2$SO$_4$, then concentrated under vacuum. This resulted in 180 mg (16%) of the title compound as a yellow solid. MS-ESI: 215.1 (M−1).

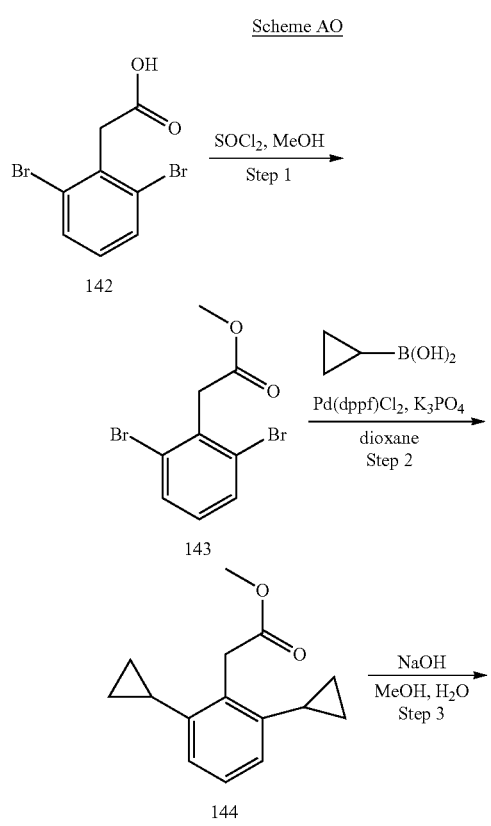

Scheme AO

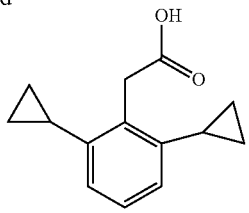

Intermediate 63

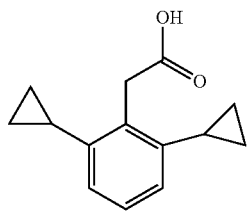

Intermediate 63

2-(2,6-Dicyclopropylphenyl)acetic acid

Step 1: Methyl 2-(2,6-dibromophenyl)acetate

Into a 250-mL round-bottom flask, was placed 2-(2,6-dibromophenyl)acetic acid (5 g, 17.0 mmol), methanol (50 mL). This was followed by the addition of sulfuroyl dichloride (4.1 g, 34.5 mmol) dropwise with stirring at 0° C. The resulting solution was stirred for 3 h at 60° C. and then was concentrated under vacuum. The residue was applied onto a silica gel column and eluted with ethyl acetate/petroleum ether (1:15 to 1:10). This resulted in 4.5 g (86%) of the title compound as light yellow oil. MS-ESI: 308.9, 306.9, 310.9 (M+1).

Step 2: Methyl 2-(2,6-dicyclopropylphenyl)acetate

Into a 50-mL round-bottom flask purged with and maintained under nitrogen, was placed methyl 2-(2,6-dibromophenyl)acetate (600 mg, 1.95 mmol), dioxane (20 mL), cyclopropylboronic acid (688 mg, 8.01 mmol), K$_3$PO$_4$ (2.1 g, 9.89 mmol), Pd(dppf)Cl$_2$ (146 mg, 0.20 mmol). The resulting solution was stirred for 4 h at 100° C. and then was concentrated under vacuum. The residue was applied onto a silica gel column and eluted with ethyl acetate/petroleum ether (1:30 to 1:20). This resulted in 440 mg (98%) of the title compound as yellow oil. MS-ESI: 231.1 (M+1).

Step 3: 2-(2,6-Dicyclopropylphenyl)acetic acid

Into a 50-mL round-bottom flask, was placed methyl 2-(2,6-dicyclopropylphenyl)acetate (440 mg, 1.91 mmol). Then to the above was added a solution of sodium hydroxide (228 mg, 5.70 mmol) in MeOH (15 mL) and water (4 mL). The resulting solution was stirred for 2 days at 50° C. The resulting solution was extracted with 20 mL of ethyl acetate and the aqueous layers combined. The pH value of the solution was adjusted to 4 with hydrogen chloride (6 N). The resulting solution was extracted with 3×20 mL of ethyl acetate and the organic layers combined dried over anhydrous Na$_2$SO$_4$, then concentrated under vacuum. This resulted in 260 mg (63%) of the title compound as a yellow solid. MS-ESI: 215.1 (M−1).

Scheme AP
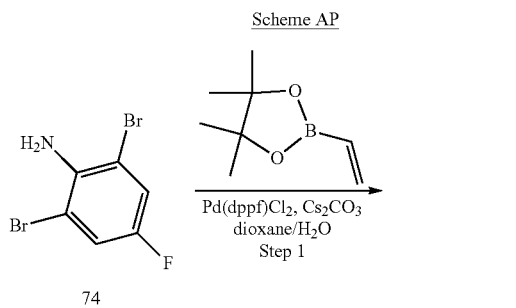
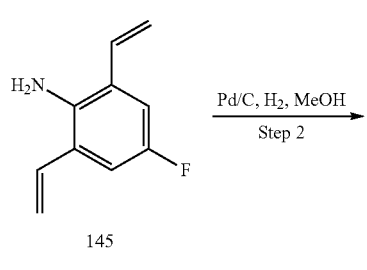
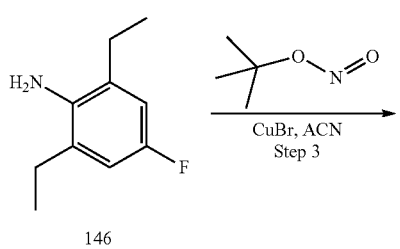
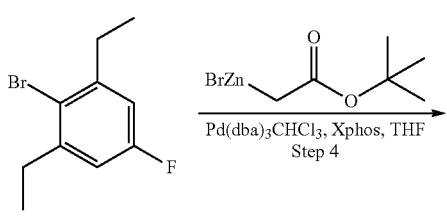
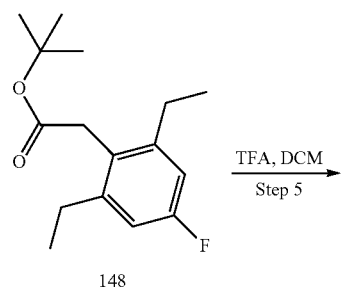
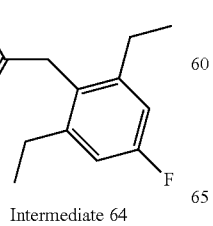
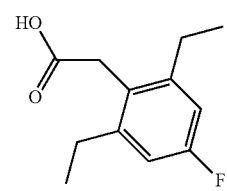
2-(2,6-Diethyl-4-fluorophenyl)acetic acid
Intermediate 64 was prepared using the similar procedures for converting compound 74 to Intermediate 49 shown in Scheme AA. MS-ESI: 209.1 (M−1).
Scheme AQ
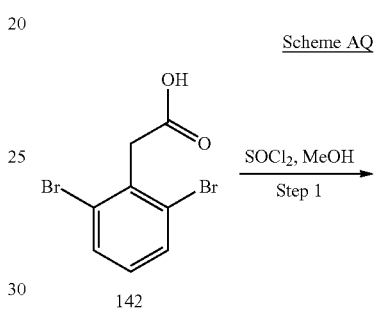
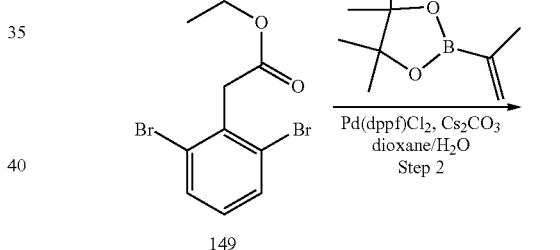
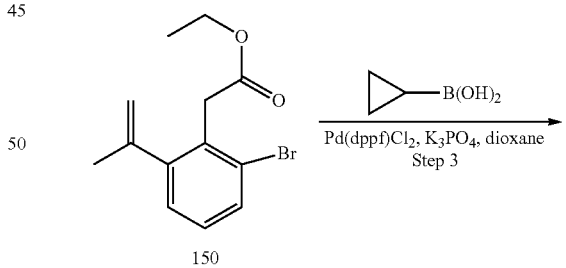
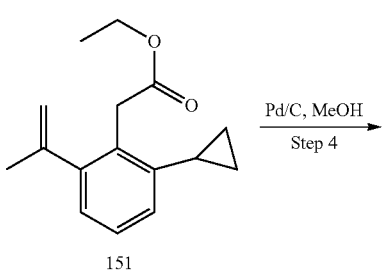

-continued

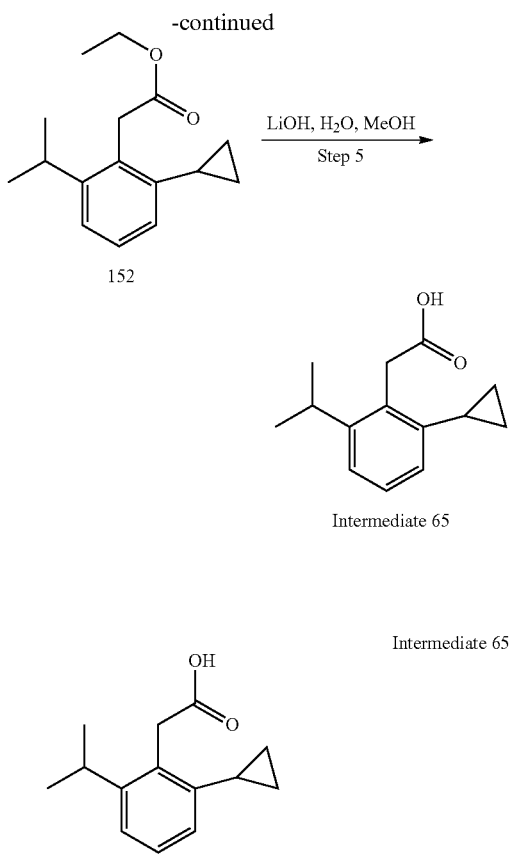

152

Intermediate 65

Intermediate 65

2-(2-Cyclopropyl-6-i sopropylphenyl)acetic acid

Step 1: Ethyl 2-(2,6-dibromophenyl)acetate

Into a 250-mL round-bottom flask, was placed 2-(2,6-dibromophenyl)acetic acid (3.1 g, 10.55 mmol), EtOH (80 mL). This was followed by the addition of sulfuroyl dichloride (4 g, 33.61 mmol) dropwise with stirring at 0° C. The resulting solution was stirred overnight at 60° C. and then was concentrated under vacuum. The residue was applied onto a silica gel column and eluted with ethyl acetate/petroleum ether (1:3 to 1:1). This resulted in 3.4 g (crude) of the title compound as colorless oil. MS-ESI: 322.9, 320.9, 324.9 (M+1).

Step 2: Ethyl 2-(2-bromo-6-(prop-1-en-2-yl)phenyl)acetate

Into a 250-mL round-bottom flask purged with and maintained under nitrogen, was placed ethyl 2-(2,6-dibromophenyl)acetate (3.4 g, 10.6 mmol), dioxane (90 mL), water (20 mL), Cs$_2$CO$_3$ (3.6 g, 11.1 mmol), 4,4,5,5-tetramethyl-2-(prop-1-en-2-yl)-1,3,2-dioxaborolane (2.06 g, 12.3 mmol), Pd(dppf)Cl$_2$ (320 mg, 0.44 mmol). The resulting solution was stirred for 7.5 h at 50° C. and then quenched by the addition of 30 mL of water. The resulting solution was extracted with 3×50 mL of ethyl acetate and the organic layers combined and dried over anhydrous Na$_2$SO$_4$, and then concentrated under vacuum. The residue was applied onto a silica gel column and eluted with ethyl acetate/petroleum ether (1:5 to 1:3). This resulted in 920 mg (31%) of the title compound as light yellow oil. MS-ESI: 283.0, 285.0 (M+1).

Step 3: Ethyl 2-(2-cyclopropyl-6-(prop-1-en-2-yl)phenyl)acetate

Into a 100-mL round-bottom flask purged with and maintained under nitrogen, was placed ethyl 2-(2-bromo-6-(prop-1-en-2-yl)phenyl)acetate (300 mg, 1.06 mmol), dioxane (10 mL), cyclopropylboronic acid (180 mg, 2.10 mmol), K$_3$PO$_4$ (429 mg, 2.02 mmol), Pd(dppf)Cl$_2$ (43 mg, 0.06 mmol). The resulting solution was stirred for 5 h at 110° C. and then was quenched by the addition of 30 mL of water. The resulting solution was extracted with 3×50 mL of ethyl acetate and the organic layers combined and dried over anhydrous Na$_2$SO$_4$, and then concentrated under vacuum. The residue was applied onto a silica gel column and eluted with ethyl acetate/petroleum ether (1:3 to 1:1). This resulted in 228 mg (88%) of the title compound as light yellow oil. MS-ESI: 245.1 (M+1).

Step 4: Ethyl 2-(2-cyclopropyl-6-isopropylphenyl)acetate

Into a 250-mL round-bottom, was placed ethyl 2-(2-cyclopropyl-6-(prop-1-en-2-yl)phenyl)acetate (228 mg, 0.93 mmol), MeOH (10 mL). Then Pd/C (10% wt, 50 mg) was added. The flask was evacuated and flushed three times with hydrogen. The resulting solution was stirred for 3.5 h at RT under an atmosphere of hydrogen. The solids were filtered out. The resulting mixture was concentrated under vacuum. This resulted in 162 mg (70%) of the title compound as colorless oil. MS-ESI: 247.1 (M+1).

Step 5: 2-(2-Cyclopropyl-6-isopropylphenyl)acetic acid

Into a 100-mL round-bottom flask, was placed ethyl 2-(2-cyclopropyl-6-isopropylphenyl)acetate (162 mg, 0.66 mmol), MeOH (10 mL), water (2 mL), LiOH (200 mg, 8.35 mmol). The resulting solution was stirred for 5 h at RT and then was concentrated under vacuum. The resulting solution was diluted with 10 mL of 1 N hydrogen chloride. The resulting solution was extracted with 3×10 mL of DCM and the organic layers combined and dried over anhydrous Na$_2$SO$_4$, and then concentrated under vacuum. This resulted in 140 mg (98%) of the title compound as a light yellow solid. MS-ESI: 217.1 (M−1).

Example 1

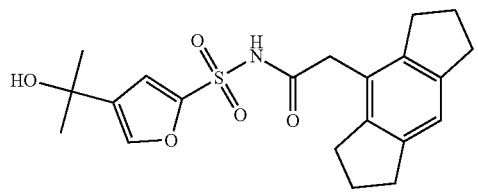

126

2-(1,2,3,5,6,7-Hexahydros-indacen-4-yl)-N-(4-(2-hydroxypropan-2-yl)furan-2-ylsulfonyl)acetamide
(Scheme A)

Into a 50-mL round-bottom flask purged with and maintained under nitrogen, was placed 2-(1,2,3,5,6,7-hexahydros-indacen-4-yl)acetic acid (125 mg, 0.58 mmol), DMF (5 mL), CDI (113 mg, 0.70 mmol). The resulting solution was stirred for 1 h at RT and then to the above was added 4-(2-hydroxypropan-2-yl)furan-2-sulfonamide (119 mg, 0.58 mmol), DBU (0.11 mL). The resulting solution was stirred for 3 h at RT and then was diluted with 10 mL of water. The resulting solution was extracted with 3×10 mL of ethyl acetate and the organic layers combined and concentrated under vacuum. The crude product was purified by Prep-HPLC using method E eluted with a gradient of 30~40% ACN. This resulted in 59.9 mg (26%) of the title compound as a white solid. MS-ESI: 402.0 (M−1). ¹H NMR (400 MHz, MeOD-d₄) δ 7.44 (s, 1H), 6.86 (s, 1H), 6.84 (s, 1H), 3.48 (s, 2H), 2.89-2.65 (m, 8H), 2.10-1.90 (m, 4H), 1.45 (s, 6H).

Example 2

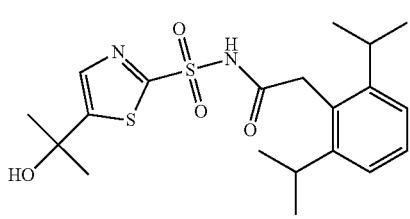

121

2-(2,6-Diisopropylphenyl)-N-(5-(2-hydroxypropan-2-yl)thiazol-2-ylsulfonyl)acetamide(Scheme B)

Into a 50-mL round-bottom flask, was placed 2-(2,6-diisopropylphenyl)acetic acid (60 mg, 0.27 mmol), DMF (5 mL), HBTU (124 mg, 0.33 mmol), DIEA (105 mg, 0.81 mmol), 5-(2-hydroxypropan-2-yl)thiazole-2-sulfonamide (67 mg, 0.30 mmol). The resulting solution was stirred overnight at RT and then was concentrated under vacuum. The crude product was purified by Prep-HPLC using method E eluted with a gradient of 21~43% ACN. This resulted in 44.3 mg (38%) of the title compound as a white solid. MS-ESI: 423.2 (M−1). ¹H NMR (300 MHz, MeOD-d₄) δ 7.60 (s, 1H), 7.18-7.00 (m, 3H), 3.76 (s, 2H), 3.14 (hept, J=6.6 Hz, 2H), 1.59 (s, 6H), 1.14 (d, J=6.6 Hz, 12H).

Example 3

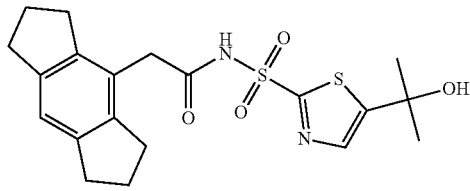

120

2-(1,2,3,5,6,7-Hexahydros-indacen-4-yl)-N-(5-(2-hydroxypropan-2-yl)thiazol-2-ylsulfonyl)acetamide (Scheme C)

Into a 50-mL round-bottom flask purged with and maintained under nitrogen, was placed 2-(1,2,3,5,6,7-hexahydros-indacen-4-yl)acetic acid (500 mg, 2.31 mmol), DCM (20 mL), DIEA (900 mg, 6.96 mmol), HATU (1.06 g, 2.79 mmol). The resulting solution was stirred for 0.5 h at RT and then to the above was added 5-(2-hydroxypropan-2-yl) thiazole-2-sulfonamide (570 mg, 2.56 mmol). The resulting solution was stirred for 2 h at RT and then was quenched by the addition of 15 mL of water. The resulting solution was extracted with 2×30 mL of DCM and the organic layers combined and dried over anhydrous Na₂SO₄, and then concentrated under vacuum. The crude product was purified by Prep-HPLC using method E eluted with a gradient of 25~50% ACN. This resulted in 293.2 mg (30%) of the title compound as a yellow solid. MS-ESI: 421.1 (M+1). ¹H NMR (300 MHz, MeOD-d₄) δ 7.61 (s, 1H), 6.84 (s, 1H), 3.50 (s, 2H), 2.86-2.66 (m, 8H), 2.10-1.90 (m, 4H), 1.57 (s, 6H).

Example 4

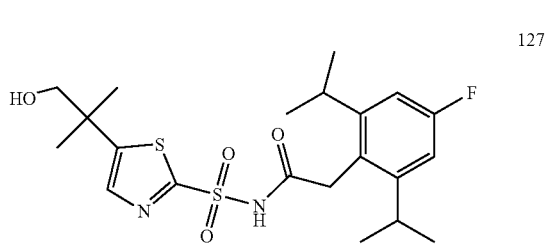 [SMILES: CC(C)c1cc(F)cc(C(C)C)c1CC(=O)NS(=O)(=O)c1ncc(C(C)(C)CO)s1]

127

2-(4-Fluoro-2,6-diisopropylphenyl)-N-(5-(1-hydroxy-2-methylpropan-2-yl)thiazol-2-ylsulfonyl) acetamide Scheme D)

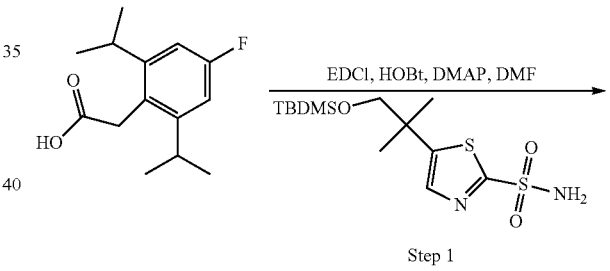

(Scheme D)

Step 1

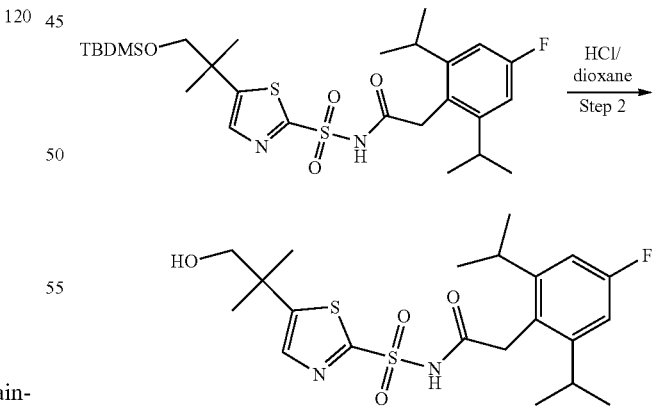

Step 1: N-(5-(1-(tert-butyldimethylsilyloxy)-2-methylpropan-2-yl)thiazol-2-ylsulfonyl)-2-(4-fluoro-2,6-diisopropylphenyl)acetamide Into a 50-mL round-bottom flask, was placed 2-(4-fluoro-2,6-diisopropylphenyl)acetic acid (100 mg, 0.42 mmol), DMF (5 mL), EDCI (121 mg, 0.63 mmol), HOBt (85 mg, 0.63 mmol), DMAP (5 mg, 0.04 mmol). The resulting solution was stirred for 20 min at RT and then to the above was added 5-(1-(tert-butyldimethylsilyloxy)-2-methylpropan-2-yl)thiazole-2-sulfonamide (147 mg, 0.42 mmol). The resulting solution was stirred for 3 h at RT and then was diluted with 10 mL of water. The resulting solution was extracted with 2×10 mL of DCM and the organic layers combined and dried over anhydrous $Na_2SO_4$, and then concentrated under vacuum. This resulted in 150 mg (crude, 63%) of the title compound as brown oil. MS-ESI: 569.2 (M−1).

Step 2: 2-(4-Fluoro-2,6-diisopropylphenyl)-N-(5-(1-hydroxy-2-methylpropan-2-yl)thiazol-2-ylsulfonyl)acetamide Into a 50-mL round-bottom flask, was placed N-(5-(1-(tert-butyldimethylsilyloxy)-2-methylpropan-2-yl)thiazol-2-ylsulfonyl)-2-(4-fluoro-2,6-diisopropylphenyl)acetamide (150 mg, 0.26 mmol), HCl/dioxane (4 M, 5 mL). The resulting solution was stirred for 3 h at RT and then was concentrated under vacuum. The crude product was purified by Prep-HPLC using method E eluted with a gradient of 15~60% ACN. This resulted in 117.3 mg (78%) of the title compound as a white solid. MS-ESI: 455.1 (M−1). $^1$H NMR (300 MHz, MeOD-$d_4$) δ 7.64 (s, 1H), 6.74 (d, J=10.2 Hz, 2H), 3.73 (s, 2H), 3.45 (s, 2H), 3.10-2.90 (m, 2H), 1.33 (s, 6H), 1.09 (d, J=6.9 Hz, 12H).

Example 5

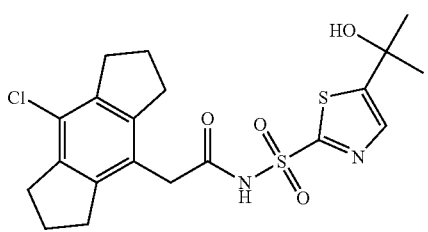

2-(8-Chloro-1,2,3,5,6,7-hexahydros-indacen-4-yl)-N-(5-(2-hydroxypropan-2-yl)thiazol-2-ylsulfonyl)acetamide (Scheme E)

Into a 50-mL round-bottom flask, was placed 2-(8-chloro-1,2,3,5,6,7-hexahydros-indacen-4-yl)acetic acid (60 mg, 0.27 mmol), DCM (3 mL), DMF (0.05 mL). This was followed by the addition of oxalic dichloride (0.5 mL) dropwise with stirring at RT. The resulting solution was stirred for 30 min at RT and then was concentrated under vacuum. The above mixture diluted in DCM (1 mL) was added to a solution of 5-(2-hydroxypropan-2-yl)thiazole-2-sulfonamide (60 mg, 0.27 mmol) and TEA (0.2 mL) in DCM (3 mL) dropwise with stirring at RT. The resulting solution was stirred for 2 h at RT and then was concentrated under vacuum. The crude product was purified by Prep-HPLC using method E eluted with a gradient of 30~50% ACN. This resulted in 26.7 mg (37%) of the title compound as a white solid. MS-ESI: 455.1 (M+1). $^1$H NMR (300 MHz, MeOD-$d_4$) δ 7.66 (s, 1H), 3.51 (s, 2H), 2.95-2.78 (m, 8H), 2.15-1.95 (m, 4H), 1.61 (s, 6H).

TABLE 5

Example in the following table was prepared using similar conditions as described in Example 3 and Scheme C from appropriate starting materials.

| Example # | Final Target Number | IUPAC Name | Mass Spec [M + H]+ |
|---|---|---|---|
| 6 | 128 | 2-(4-cyano-2,6-diisopropylphenyl)-N-(5-(2-hydroxypropan-2-yl)thiazol-2-ylsulfonyl)acetamide | 450.1 |

TABLE 6

Examples in the following table were prepared using similar conditions as described in Example 5 and Scheme E from appropriate starting materials.

| Example # | Final Target Number | IUPAC Name | Mass Spec [M − H]− |
|---|---|---|---|
| 7 | 116 | 2-(1,2,3,5,6,7-hexahydro-sindacen-4-yl)-N-(4-(2-hydroxypropan-2-yl)thiophen-2-ylsulfonyl)acetamide | 418.1 |
| 8 | 117 | 2-(2,6-diisopropylphenyl)-N-(4-(2-hydroxypropan-2-yl)thiophen-2-ylsulfonyl)acetamide | 422.1 |
| 9 | 129 | 2-(4-fluoro-2,6-diisopropylphenyl)-N-(4-(2-hydroxypropan-2-yl)thiophen-2-ylsulfonyl)acetamide | 440.1 |
| 10 | 130 | 2-(4-cyano-2,6-diisopropylphenyl)-N-(4-(2-hydroxypropan-2-yl)thiophen-2-ylsulfonyl)acetamide | 447.2 |
| 11 | 103 | 2-(3-fluoro-2,6-diisopropylphenyl)-N-(4-(2-hydroxypropan-2-yl)thiophen-2-ylsulfonyl)acetamide | 440.0 |
| 12 | 131 | 2-(4-chloro-3,5-difluoro-2,6-diisopropylphenyl)-N-(4-(2-hydroxypropan-2-yl)thiophen-2-ylsulfonyl)acetamide | 492.1 |
| 13 | 132 | 2-(4-fluoro-2,6-diisopropylphenyl)-N-(5-(2-hydroxypropan-2-yl)thiophen-2-ylsulfonyl)acetamide | 440.1 |
| 14 | 133 | 2-(2,6-diisopropylphenyl)-N-(4-(1-hydroxycyclopropyl)thiophen-2-ylsulfonyl)acetamide | 420.2 |
| 15 | 134 | 2-(4-fluoro-2,6-diisopropylphenyl)-N-(4-(1-hydroxycyclopropyl)thiophen-2-ylsulfonyl)acetamide | 438.1 |
| 16 | 135 | 2-(4-cyano-2,6-diisopropylphenyl)-N-(4-(1-hydroxycyclopropyl)thiophen-2-ylsulfonyl)acetamide | 445.2 |
| 17 | 136 | 2-(4-fluoro-2,6-diisopropylphenyl)-N-(4-(2-hydroxypropan-2-yl)-5-methylthiophen-2-ylsulfonyl)acetamide | 454.1 |
| 18 | 137 | 2-(4-fluoro-2,6-diisopropylphenyl)-N-(4-(2-hydroxypropan-2-yl)-5-methylfuran-2-ylsulfonyl)acetamide | 438.2 |
| 19 | 138 | 2-(4-fluoro-2,6-diisopropylphenyl)-N-(4-(2-hydroxypropan-2-yl)-3-methylthiophen-2-ylsulfonyl)acetamide | 454.1 |

TABLE 6-continued

Examples in the following table were prepared using similar conditions as described in Example 5 and Scheme E from appropriate starting materials.

| Example # | Final Target Number | IUPAC Name | Mass Spec [M − H]− |
|---|---|---|---|
| 20 | 139 | 2-(4-chloro-3,5-difluoro-2,6-diisopropylphenyl)-N-(4-(2-hydroxypropan-2-yl)furan-2-ylsulfonyl)acetamide | 476.1 |

TABLE 7

Examples in the following table were prepared using similar conditions as described in Example 5 and Scheme E from appropriate starting materials.

| Example # | Final Target Number | IUPAC Name | Mass Spec [M − H]− |
|---|---|---|---|
| 21 | 140 | 2-(2,6-diisopropylphenyl)-N-(4-(2-hydroxypropan-2-yl)phenylsulfonyl)acetamide | 418.3 (M + 1) |
| 22 | 141 | 2-(2,6-diisopropylphenyl)-N-(3-(2-hydroxypropan-2-yl)-5-(pyridin-4-yl)phenylsulfonyl)acetamide | 493.2 |
| 23 | 142 | 2-(2,6-diisopropylphenyl)-N-(5-(2-hydroxypropan-2-yl)biphenyl-3-ylsulfonyl)acetamide | 492.2 |
| 24 | 143 | N-(3,5-bis(2-hydroxypropan-2-yl)phenylsulfonyl)-2-(2,6-diisopropylphenyl)acetamide | 440.1 (M − 2OH) |
| 25 | 144 | 2-(4-fluoro-2,6-diisopropylphenyl)-N-(3-(2-hydroxypropan-2-yl)phenylsulfonyl)acetamide | 434.0 |
| 26 | 145 | 2-(4-cyano-2,6-diisopropylphenyl)-N-(3-(2-hydroxypropan-2-yl)phenylsulfonyl)acetamide | 441.2 |
| 27 | 146 | N-(3-chloro-5-(2-hydroxypropan-2-yl)phenylsulfonyl)-2-(4-fluoro-2,6-diisopropylphenyl)acetamide | 468.1 |
| 28 | 147 | N-(3-chloro-5-(2-hydroxypropan-2-yl)phenylsulfonyl)-2-(4-cyano-2,6-diisopropylphenyl)acetamide | 475.2 |
| 29 | 148 | 2-(4-fluoro-2,6-diisopropylphenyl)-N-(3-(2-hydroxypropan-2-yl)-5-(pyridin-4-yl)phenylsulfonyl)acetamide | 511.2 |
| 30 | 149 | N-(3,5-bis(2-hydroxypropan-2-yl)phenylsulfonyl)-2-(4-fluoro-2,6-diisopropylphenyl)acetamide | 492.2 |
| 31 | 150 | N-(3,5-bis(2-hydroxypropan-2-yl)phenylsulfonyl)-2-(4-cyano-2,6-diisopropylphenyl)acetamide | 499.2 |
| 32 | 151 | 2-(4-fluoro-2,6-diisopropylphenyl)-N-(5-(2-hydroxypropan-2-yl)biphenyl-3-ylsulfonyl)acetamide | 510.2 |
| 33 | 152 | 2-(4-cyano-2,6-diisopropylphenyl)-N-(5-(2-hydroxypropan-2-yl)biphenyl-3-ylsulfonyl)acetamide | 517.31 |
| 34 | 153 | 2-(4-fluoro-2,6-diisopropylphenyl)-N-(4-(2-hydroxypropan-2-yl)phenylsulfonyl)acetamide | 434.2 |
| 35 | 154 | 2-(4-cyano-2,6-diisopropylphenyl)-N-(4-(2-hydroxypropan-2-yl)phenylsulfonyl)acetamide | 441.2 |
| 36 | 155 | 2-(4-fluoro-2,6-diisopropylphenyl)-N-(6-(2-hydroxypropan-2-yl)pyridin-3-ylsulfonyl)acetamide | 435.1 |
| 37 | 156 | 2-(4-cyano-2,6-diisopropylphenyl)-N-(6-(2-hydroxypropan-2-yl)pyridin-3-ylsulfonyl)acetamide | 442.2 |
| 38 | 157 | 2-(4-fluoro-2,6-diisopropylphenyl)-N-(3-(2-hydroxypropan-2-yl)-5-morpholinophenylsulfonyl)acetamide | 521.3 (M + 1) |
| 39 | 158 | N-(4-pentafluorophenylsulfonyl)-2-(4-fluoro-2,6-diisopropylphenyl)acetamide | 502.1 |
| 40 | 159 | 2-(4-fluoro-2,6-diisopropylphenyl)-N-(quinolin-3-ylsulfonyl)acetamide2-(4-fluoro-2,6-diisopropylphenyl)-N-(quinolin-3-ylsulfonyl)acetamide | 427.1 |
| 41 | 160 | N-(benzofuran-2-ylsulfonyl)-2-(4-fluoro-2,6-diisopropylphenyl)acetamide | 416.1 |
| 42 | 161 | 2-(3-fluoro-2,6-diisopropylphenyl)-N-(3-(2-hydroxypropan-2-yl)phenylsulfonyl)acetamide | 434.2 |
| 43 | 162 | 2-(3-fluoro-2,6-diisopropylphenyl)-N-(4-(2-hydroxypropan-2-yl)phenylsulfonyl)acetamide | 434.2 |
| 44 | 163 | 2-(4-fluoro-2,6-diisopropylphenyl)-N-(3-(2-hydroxypropan-2-yl)-2-methylphenylsulfonyl)acetamide | 448.2 |
| 45 | 164 | 2-(4-fluoro-2,6-diisopropylphenyl)-N-(3-(2-hydroxypropan-2-yl)-4-methylphenylsulfonyl)acetamide | 448.2 |
| 46 | 165 | 2-(4-fluoro-2,6-diisopropylphenyl)-N-(3-(2-hydroxypropan-2-yl)-5-methylphenylsulfonyl)acetamide | 448.2 |
| 47 | 166 | 2-(4-fluoro-2,6-diisopropylphenyl)-N-(4-(2-hydroxypropan-2-yl)-3-methylphenylsulfonyl)acetamide | 450.2 (M + 1) |
| 48 | 167 | 2-(4-fluoro-2,6-diisopropylphenyl)-N-(4-(2-hydroxypropan-2-yl)-2-methylphenylsulfonyl)acetamide | 448.2 |
| 49 | 168 | 2-(4-fluoro-2,6-diisopropylphenyl)-N-(1-fluoro-3-(2-hydroxypropan-2-yl)phenylsulfonyl)acetamide | 452.3 |
| 50 | 169 | 2-(4-fluoro-2,6-diisopropylphenyl)-N-(2-fluoro-3-(2-hydroxypropan-2-yl)phenylsulfonyl)acetamide | 452.3 |
| 51 | 170 | 2-(4-fluoro-2,6-diisopropylphenyl)-N-(3-fluoro-5-(2-hydroxypropan-2-yl)phenylsulfonyl)acetamide | 452.3 |
| 52 | 171 | 2-(4-fluoro-2,6-diisopropylphenyl)-N-(2-fluoro-5-(2-hydroxypropan-2-yl)phenylsulfonyl)acetamide | 452.3 |
| 53 | 172 | 2-(4-fluoro-2,6-diisopropylphenyl)-N-(3-fluoro-4-(2-hydroxypropan-2-yl)phenylsulfonyl)acetamide | 452.2 |
| 54 | 173 | 2-(4-fluoro-2,6-diisopropylphenyl)-N-(2-fluoro-4-(2-hydroxypropan-2-yl)phenylsulfonyl)acetamide | 452.2 |
| 55 | 174 | N-(5-acetyl-2-fluorophenylsulfonyl)-2-fluoro-2,6-diisopropylphenyl)acetamide | 438.2 (M + 1) |
| 56 | 175 | 2-(4-fluoro-2,6-diisopropylphenyl)-N-(2-fluoro-5-(2-methyl-1,3-dioxolan-2-yl)phenylsulfonyl)acetamide | 482.3 (M + 1) |
| 57 | 176 | 2-(8-fluoro-1,2,3,5,6,7-hexahydros-indacen-4-yl)-N-(2-fluoro-5-(2-methyl-1,3-dioxolan-2-yl)phenylsulfonyl)acetamide | 478.4 (M + 1) |

TABLE 7-continued

Examples in the following table were prepared using similar conditions as described in Example 5 and Scheme E from appropriate starting materials.

| Example # | Final Target Number | IUPAC Name | Mass Spec [M − H]⁻ |
|---|---|---|---|
| 58 | 177 | 2-(4-fluoro-2,6-diisopropylphenyl)-N-(4-(methylsulfonyl)phenylsulfonyl)acetamide | 454.1 |
| 59 | 178 | 2-(4-fluoro-2,6-diisopropylphenyl)-N-(3-(methylsulfonyl)phenylsulfonyl)acetamide | 454.1 |
| 60 | 179 | N-(4-(1H-pyrazol-1-yl)phenylsulfonyl)-2-(4-fluoro-2,6-diisopropylphenyl)acetamide | 444.2 (M + 1) |

TABLE 8

Examples in the following table were prepared using similar conditions as described in Example 5 and Scheme E from appropriate starting materials.

| Example # | Final Target Number | IUPAC Name | Mass Spec [M − H]⁻ |
|---|---|---|---|
| 61 | 114 | 2-(4-chloro-2,6-diisopropylphenyl)-N-(1-isopropyl-1H-pyrazol-3-ylsulfonyl)acetamide | 424.0 |
| 62 | 180 | 2-(4-fluoro-2,6-diisopropylphenyl)-N-(1-isopropyl-1H-pyrazol-3-ylsulfonyl)acetamide | 408.2 |
| 63 | 181 | 2-(2,6-diisopropylphenyl)-N-(5-(2-hydroxypropan-2-yl)-1-phenyl-1H-pyrazol-3-ylsulfonyl)acetamide | 482.2 |
| 64 | 182 | 2-(4-fluoro-2,6-diisopropylphenyl)-N-(5-(2-hydroxypropan-2-yl)-1-phenyl-1H-pyrazol-3-ylsulfonyl)acetamide | 502.2 (M + 1) |
| 65 | 183 | 2-(4-cyano-2,6-diisopropylphenyl)-N-(5-(2-hydroxypropan-2-yl)-1-phenyl-1H-pyrazol-3-ylsulfonyl)acetamide | 507.2 |
| 66 | 184 | 2-(2,6-diisopropylphenyl)-N-(5-(2-hydroxypropan-2-yl)-1-methyl-1H-pyrazol-3-ylsulfonyl)acetamide | 422.2 (M + 1) |
| 67 | 185 | 2-(4-fluoro-2,6-diisopropylphenyl)-N-(5-(2-hydroxypropan-2-yl)-1-methyl-1H-pyrazol-3-ylsulfonyl)acetamide | 438.2 |
| 68 | 186 | 2-(4-cyano-2,6-diisopropylphenyl)-N-(5-(2-hydroxypropan-2-yl)-1-methyl-1H-pyrazol-3-ylsulfonyl)acetamide | 445.2 |

TABLE 9

Examples in the following table were prepared using similar conditions as described in Example 5 and Scheme E from appropriate starting materials.

| Example # | Final Target Number | IUPAC Name | Mass Spec [M − H]⁻ |
|---|---|---|---|
| 69 | 187 | 2-(8-fluoro-1,2,3,5,6,7-hexahydros-indacen-4-yl)-N-(5-(2-hydroxypropan-2-yl)thiazol-2-ylsulfonyl)acetamide | 439.1 (M + 1) |
| 70 | 108 | 2-(4-chloro-2,6-diisopropylphenyl)-N-(5-(2-hydroxypropan-2-yl)thiazol-2-ylsulfonyl)acetamide | 459.1 (M + 1) |
| 71 | 109 | 2-(3-fluoro-2,6-diisopropylphenyl)-N-(5-(2-hydroxypropan-2-yl)thiazol-2-ylsulfonyl)acetamide | 443.1 (M + 1) |
| 72 | 188 | 2-(2,6-diisopropyl-4-(trifluoromethyl)phenyl)-N-(5-(2-hydroxypropan-2-yl)thiazol-2-ylsulfonyl)acetamide | 491.1 |
| 73 | 189 | 2-(4-fluoro-2,6-diisopropylphenyl)-N-(5-(2-methoxypropan-2-yl)thiazol-2-ylsulfonyl)acetamide | 457.0 (M + 1) |
| 74 | 190 | 2-(4-cyano-2,6-diisopropylphenyl)-N-(5-(2-methoxypropan-2-yl)thiazol-2-ylsulfonyl)acetamide | 464.1 (M + 1) |
| 75 | 191 | 2-(4-fluoro-2,6-diisopropylphenyl)-N-(2-(2-hydroxypropan-2-yl)thiazol-5-ylsulfonyl)acetamide | 441.1 |
| 76 | 192 | 2-(3,4-difluoro-2,6-diisopropylphenyl)-N-(5-(2-hydroxypropan-2-yl)thiazol-2-ylsulfonyl)acetamide | 461.0 (M + 1) |
| 77 | 193 | 2-(3,5-difluoro-2,6-diisopropylphenyl)-N-(5-(2-hydroxypropan-2-yl)thiazol-2-ylsulfonyl)acetamide | 459.1 |
| 78 | 194 | 2-(2,6-dicyclopropylphenyl)-N-(5-(2-hydroxypropan-2-yl)thiazol-2-ylsulfonyl)acetamide | 420.9 (M + 1) |
| 79 | 195 | 2-(4-chloro-2-isopropyl-6-(trifluoromethyl)phenyl)-N-(5-(2-hydroxypropan-2-yl)thiazol-2-ylsulfonyl)acetamide | 483.1 |
| 80 | 196 | 2-(2-cyclopropyl-6-isopropylphenyl)-N-(5-(2-hydroxypropan-2-yl)thiazol-2-ylsulfonyl)acetamide | 421.1 |
| 81 | 197 | 2-(4-fluoro-2,6-diisopropylphenyl)-N-(4-(2-hydroxypropan-2-yl)thiazol-2-ylsulfonyl)acetamide | 441.1 |
| 82 | 198 | 2-(4-cyano-2,6-diisopropylphenyl)-N-(4-(2-hydroxypropan-2-yl)thiazol-2-ylsulfonyl)acetamide | 448.1 |
| 83 | 199 | 2-(4-chloro-3,5-difluoro-2,6-diisopropylphenyl)-N-(5-(2-hydroxypropan-2-yl)thiazol-2-ylsulfonyl)acetamide | 493.1 |
| 84 | 200 | 2-(4-fluoro-2,6-diisopropylphenyl)-N-(5-isopropylthiazol-2-ylsulfonyl)acetamide | 427.3 (M + 1) |
| 85 | 201 | 2-(2,6-diisopropyl-4-(trifluoromethoxy)phenyl)-N-(5-(2-hydroxypropan-2-yl)thiazol-2-ylsulfonyl)acetamide | 507.1 |
| 86 | 202 | 2-(2,6-diethyl-4-fluorophenyl)-N-(5-(2-hydroxypropan-2-yl)thiazol-2-ylsulfonyl)acetamide | 415.1 (M + 1) |
| 87 | 203 | 2-(2-chloro-5-(trifluoromethyl)phenyl)-N-(5-(2-hydroxypropan-2-yl)thiazol-2-ylsulfonyl)acetamide | 442.9 (M + 1) |
| 88 | 204 | 2-(3,5-dichloro-2-methoxyphenyl)-N-(5-(2-hydroxypropan-2-yl)thiazol-2-ylsulfonyl)acetamide | 438.9 (M + 1) |

Example 89

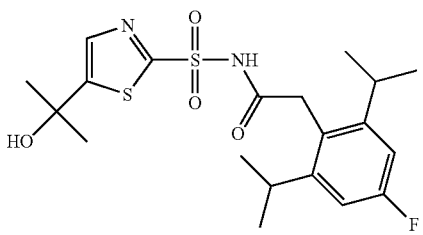

2-(4-Fluoro-2,6-diisopropylphenyl)-N-(5-(2-hydroxypropan-2-yl)thiazol-2-ylsulfonyl)acetamide
(Scheme E)

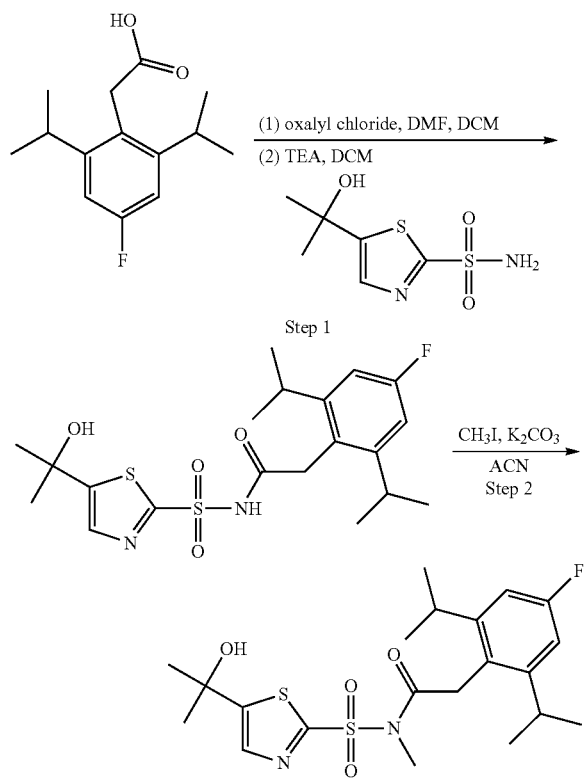

Step 1: 2-(4-Fluoro-2,6-diisopropylphenyl)-N-(5-(2-hydroxypropan-2-yl)thiazol-2-ylsulfonyl)acetamide Into a 50-mL round-bottom flask was placed 2-(4-fluoro-2,6-diisopropylphenyl)acetic acid (80 mg, 0.34 mmol), DCM (4 mL), DMF (0.05 mL). This was followed by the addition of oxalyl chloride (0.5 mL) dropwise with stirring at RT. The solution was stirred for 30 min at RT and then was concentrated under vacuum. The above mixture diluted in DCM (1 mL) was added to a solution of 5-(2-hydroxypropan-2-yl)thiazole-2-sulfonamide (80 mg, 0.36 mmol) and TEA (0.2 mL) in DCM (3 mL) dropwise with stirring at RT. The resulting solution was stirred for 2 h at RT and then was concentrated under vacuum. The crude product was purified by Prep-HPLC using method E eluted with a gradient of 1968% ACN. This resulted in 82.5 mg (56%) of Example 89 as a white solid. MS-ESI: 443.2 (M+1). $^1$H NMR (300 MHz, MeOD-d$_4$) δ 7.79 (s, 1H), 6.77 (d, J=10.2 Hz, 2H), 3.80 (s, 2H), 3.00-2.80 (m, 2H), 1.58 (s, 6H), 1.08 (d, J=6.6 Hz, 12H).

Step 2: 2-(4-Fluoro-2,6-diisopropylphenyl)-N-(5-(2-hydroxypropan-2-yl)thiazol-2-ylsulfonyl)-N-methyl acetamide Into a 50-mL round-bottom flask purged with and maintained under nitrogen, was placed 2-(4-fluoro-2,6-diisopropylphenyl)-N-(5-(2-hydroxypropan-2-yl)thiazol-2-ylsulfonyl)acetamide (80 mg, 0.18 mmol), ACN (5 mL), potassium carbonate (50 mg, 0.36 mmol), CH$_3$I (50 mg, 0.35 mmol). The resulting solution was stirred for 4 h at 80° C. and then was concentrated under vacuum. The crude product was purified by Prep-HPLC using method E eluted with a gradient of 55~80% ACN. This resulted in 22.9 mg (28%) of Example 90 as a yellow solid. MS-ESI: 457.0 (M+1). $^1$H NMR (300 MHz, MeOD-d$_4$) δ 7.89 (s, 1H), 6.80 (d, J=10.2 Hz, 2H) 4.30 (s, 2H), 3.37 (s, 3H), 2.90-2.70 (m, 2H), 1.63 (s, 6H), 1.09 (d, J=6.6 Hz, 12H).

Example 91

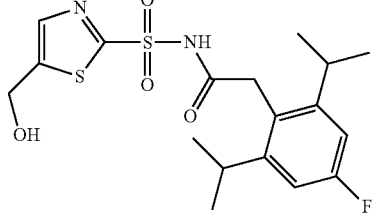

2-(4-Fluoro-2,6-diisopropylphenyl)-N-(5-(hydroxymethyl)thiazol-2-ylsulfonyl)acetamide

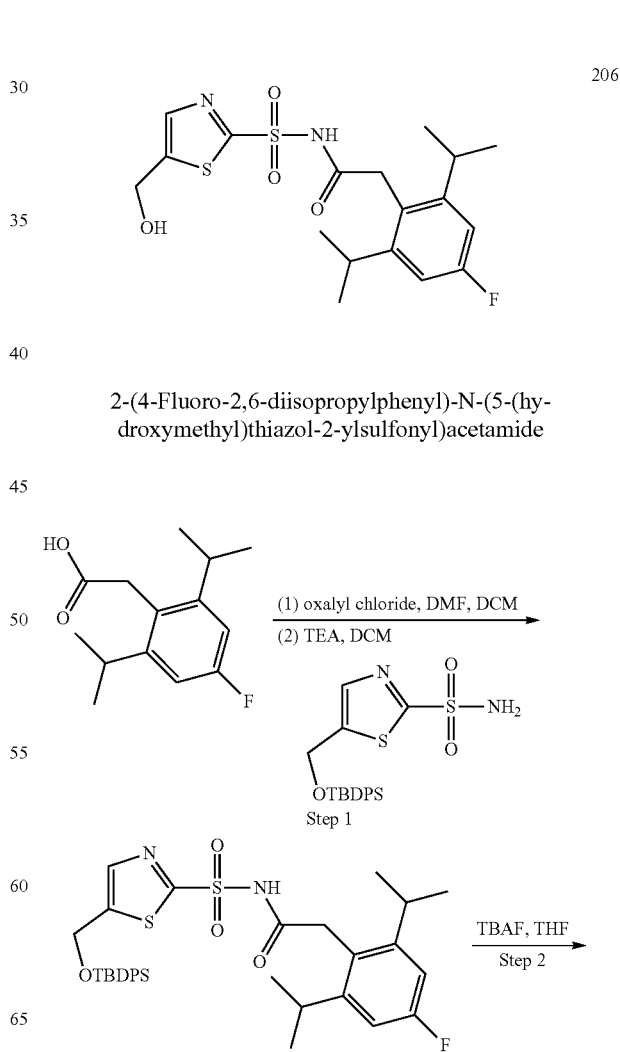

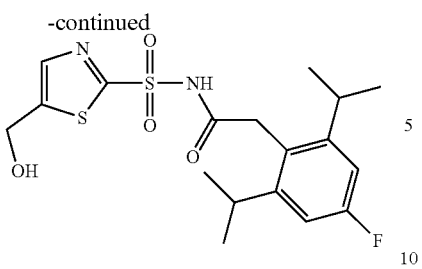

Step 1: N-(5-((tert-butyldiphenylsilyloxy)methyl)thiazol-2-ylsulfonyl)-2-(4-fluoro-2,6-diisopropylphenyl)acetamide Into a 50-mL round-bottom flask, was placed 2-(4-fluoro-2,6-diisopropylphenyl)acetic acid (93 mg, 0.39 mmol), DCM (5 mL), DMF (0.05 mL). This was followed by the addition of oxalyl chloride (0.5 mL) dropwise with stirring at RT. The solution was stirred for 30 min at RT and then was concentrated under vacuum. The above mixture diluted in DCM (1 mL) was added to a solution of 5-((tert-butyldiphenylsilyloxy)methyl)thiazole-2-sulfonamide (169 mg, 0.39 mmol) and TEA (0.2 mL) in DCM (3 mL) dropwise with stirring at RT. The resulting solution was stirred for 2 h at RT and diluted with 5 mL of water. The resulting solution was extracted with 3×5 mL of ethyl acetate and the organic layers combined and dried over anhydrous $Na_2SO_4$, and then concentrated under vacuum. This resulted in 200 mg (78%) of the title compound as a yellow solid. MS-ESI: 651.2 (M−1).

Step 2: 2-(4-Fluoro-2,6-diisopropylphenyl)-N-(5-(hydroxymethyl)thiazol-2-ylsulfonyl)acetamide Into a 50-mL round-bottom flask, was placed N-(5-((tert-butyldiphenylsilyloxy)methyl)thiazol-2-ylsulfonyl)-2-(4-fluoro-2,6-diisopropylphenyl)acetamide (200 mg, 0.31 mmol), THF (5 mL), TBAF (160 mg, 0.61 mmol). The resulting solution was stirred for 5 h at RT and then was concentrated under vacuum. The residue was applied onto a silica gel column and eluted with DCM/MeOH (50:1 to 20:1). The crude product was purified by Prep-HPLC using method E eluted with a gradient of 20~55% ACN. This resulted in 33.0 mg (26%) of the title compound as a white solid. MS-ESI: 413.1 (M−1). $^1$H NMR (300 MHz, MeOD-$d_4$) δ 7.69 (s, 1H), 6.75 (d, J=13.6 Hz, 2H), 4.78 (s, 2H), 3.74 (s, 2H), 3.20-3.00 (m, 2H), 1.12 (d, J=7.2 Hz, 12H)

TABLE 10

Examples in the following table were prepared using similar conditions as described in Example 91 and Scheme E from appropriate starting materials.

| Example # | Final Target Number | IUPAC Name | Mass Spec [M − H]⁻ |
|---|---|---|---|
| 92 | 207 | 2-(4-fluoro-2,6-diisopropylphenyl)-N-(5-(1-hydroxyethyl)thiazol-2-ylsulfonyl)acetamide | 429.1 (M + 1) |
| 93 | 208 | 2-(4-cyano-2,6-diisopropylphenyl)-N-(5-(1-hydroxyethyl)thiazol-2-ylsulfonyl)acetamide | 436.1 (M + 1) |
| 94 | 209 | 2-(4-fluoro-2,6-diisopropylphenyl)-N-(3-(hydroxymethyl)-4-(2-hydroxypropan-2-yl)phenylsulfonyl)acetamide | 464.2 |
| 95 | 210 | 2-(4-cyano-2,6-diisopropylphenyl)-N-(3-(hydroxymethyl)-4-(2-hydroxypropan-2-yl)phenylsulfonyl)acetamide | 471.2 |

Example 96

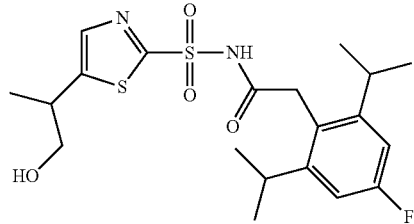

2-(4-Fluoro-2,6-diisopropylphenyl)-N-(5-(1-hydroxypropan-2-yl)thiazol-2-ylsulfonyl)acetamide

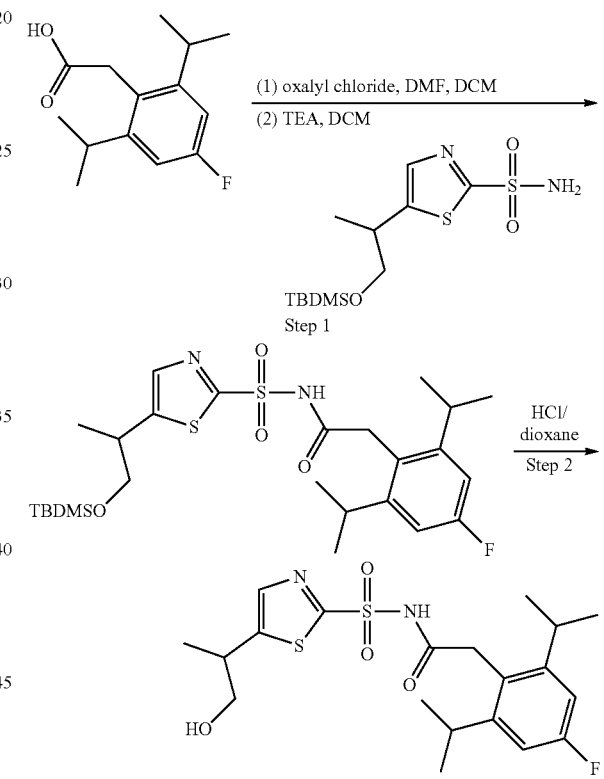

Step 1: N-(5-(1-(tert-butyldimethylsilyloxy)propan-2-yl)thiazol-2-ylsulfonyl)-2-(4-fluoro-2,6-diisopropyl phenyl)acetamide Into a 50-mL round-bottom flask, was placed 2-(4-fluoro-2,6-diisopropylphenyl)acetic acid (57 mg, 0.24 mmol), DCM (2 mL), and DMF (0.05 mL). This was followed by the addition of oxalic dichloride (0.5 mL) dropwise with stirring at RT. The resulting solution was stirred for 30 min at RT and then was concentrated under vacuum. The mixture diluted in DCM (1 mL) was added to a solution of 5-(1-(tert-butyldimethylsilyloxy)propan-2-yl)thiazole-2-sulfonamide (80 mg, 0.24 mmol) and TEA (0.2 mL) in DCM (2 mL) dropwise with stirring at RT. The resulting solution was stirred for 1 h at RT and then was diluted with 5 mL of water. The resulting solution was extracted with 3×5 mL of ethyl acetate and the organic layers combined and dried over anhydrous $Na_2SO_4$, and then concentrated under vacuum. This resulted in 120 mg (90%) of the title compound as a white solid. MS-ESI: 555.2 (M−1).

Step 2: 2-(4-Fluoro-2,6-diisopropylphenyl)-N-(5-(1-hydroxypropan-2-yl)thiazol-2-ylsulfonyl)acetamide Into a 50-mL round-bottom flask, was placed N-(5-(1-(tert-butyldimethylsilyloxy)propan-2-yl)thiazol-2-ylsulfonyl)-2-(4-fluoro-2,6-diisopropylphenyl)acetamide (120 mg, 0.22 mmol), HCl/dioxane (4 M, 3 mL). The resulting solution was stirred for 2 h at RT and then was concentrated under vacuum. The crude product was purified by Prep-HPLC using method E eluted with a gradient of 25~50% ACN. This resulted in 29.4 mg (31%) of the title compound as a white solid. MS-ESI: 443.2 (M+1). $^1$H NMR (400 MHz, MeOD-$d_4$) δ 7.80 (s, 1H), 6.80 (d, J=10.0 Hz, 2H), 3.82 (s, 2H), 3.62-3.72 (m, 1H), 3.62-3.53 (m, 1H), 3.30-3.20 (m, 1H), 3.00-2.80 (m, 2H), 1.34 (d, J=7.2 Hz, 3H), 1.10 (d, J=7.2 Hz, 12H).

TABLE 11

Example in the following table was prepared using similar conditions as described in Example 96 and Scheme E from appropriate starting materials.

| Example # | Final Target Number | IUPAC Name | Mass Spec [M − H]⁻ |
|---|---|---|---|
| 97 | 212 | 2-(4-fluoro-2,6-diisopropylphenyl)-N-(5-(2-hydroxyethyl)thiazol-2-ylsulfonyl)acetamide | 427.1 |

The following compounds were prepared using procedures analogous to those described herein for other compounds using functional group transformations that are known to the skilled artisan:

The following protocols are suitable for testing the activity of the compounds dislcosed herein.

Bioassay 1:

IL-1β Production in PMA-Differentiated THP-1 Cells Stimulated with Gramicidin.

Cell culture-THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 µg/ml), and maintained in log phase prior to experimental setup. Prior to the experiment THP-1 were treated with PMA (Phorbol 12-myristate 13-acetate) (10 µg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×106 cells/ml, and 100 ul was plated in a 96 well plate. Cells were incubated with compounds for 1 hours and then stimulated with Gramicidin (5 µM) (Enzo) for 2 hours. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 µM). A vehicle only control was run concurrently with each experiment. Final DMSO concentration was 1%. Compounds exhibit a dose-related inhibition of IL-1β production in PMA-differentiated THP-1 cells.

| Final Target Number | Structure | IUPAC Name | Mass Spec |
|---|---|---|---|
| 213 | 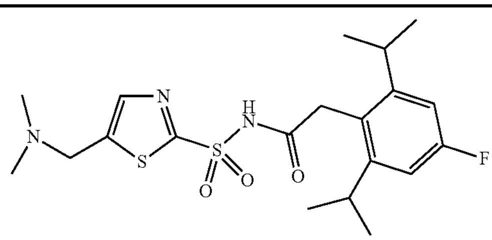 | 2-(4-fluoro-2,6-diisopropylphenyl)-N-(5-(dimethylaminomethyl)thiazol-2-ylsulfonyl)acetamide | 442.2 |
| 214 | 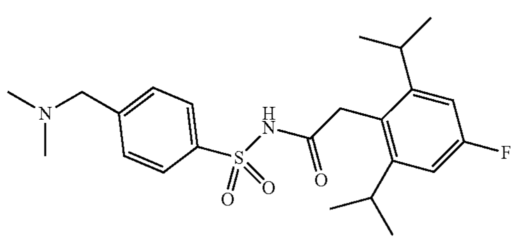 [SMILES: CC(C)c1cc(F)cc(C(C)C)c1CC(=O)NS(=O)(=O)c1ccc(CN(C)C)cc1] | 2-(4-fluoro-2,6-diisopropylphenyl)-N-(4-dimethylaminomethyl)phenylsulfonyl)acetamide | 435.2 |
| 215 | 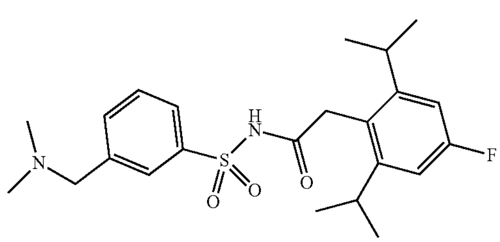 [SMILES: CC(C)c1cc(F)cc(C(C)C)c1CC(=O)NS(=O)(=O)c1cccc(CN(C)C)c1] | 2-(4-fluoro-2,6-diisopropylphenyl)-N-(3-dimethylaminomethyl)phenylsulfonyl)acetamide | 435.2 |

Bioassay 2:

IL-1β Production in PMA-Differentiated THP-1 Cells Stimulated with Gramicidin.

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were dissolved in dimethyl sulfoxide (DMSO) and added to the culture medium to achieve desired concentration (e.g. 100, 33, 11, 3.7, 1.2, 0.41, 0.14, 0.046, 0.015, 0.0051, 0.0017 μM). Cells were incubated with compounds for 1 hour and then stimulated with gramicidin (5 μM) (Enzo) for 2 hours. Cell free supernatant was collected and the production of IL-1β was evaluated by HTRF (cisbio). A vehicle only control was run concurrently with each experiment. Final DMSO concentration was 0.38%.

Compounds exhibited a concentration-dependent inhibition of IL-1β production in PMA-differentiated THP-1 cells.

Compounds tested with protocols 1 and 2 provided $IC_{50}$ values that are within the variability of the assay.

Tables 12 and 13 show the biological activity of compounds in hTHP-1 assay containing 2% bovine serum: <1 μM="++++"; ≥1 and <5 μM="+++"; ≥5 and <15 μM="++"; ≥15 and <60 μM="+".

TABLE 12

Average $IC_{50}$ of compounds in hTHP-1 assay

| Example # | Average $IC_{50}$ |
|---|---|
| 1 | ++ |
| 2 | +++ |
| 3 | + |
| 4 | ++ |
| 5 | + |
| 6 | +++ |
| 7 | ++ |
| 8 | ++++ |
| 9 | ++++ |
| 10 | ++++ |
| 11 | ++++ |
| 12 | ++++ |
| 13 | +++ |
| 14 | +++ |
| 15 | +++ |
| 16 | ++++ |
| 17 | +++ |
| 18 | +++ |
| 19 | +++ |
| 20 | ++++ |
| 21 | +++ |
| 22 | + |
| 23 | +++ |
| 24 | + |
| 25 | +++ |
| 26 | +++ |
| 27 | +++ |
| 28 | +++ |
| 29 | + |
| 30 | ++ |

TABLE 12-continued

Average $IC_{50}$ of compounds in hTHP-1 assay

| Example # | Average $IC_{50}$ |
|---|---|
| 31 | ++ |
| 32 | ++ |
| 33 | ++ |
| 34 | +++ |
| 35 | +++ |
| 36 | +++ |
| 37 | ++ |
| 38 | ++ |
| 39 | + |
| 40 | + |
| 41 | ++ |
| 42 | ++ |
| 43 | +++ |
| 44 | ++ |
| 45 | +++ |
| 46 | +++ |
| 47 | +++ |
| 48 | ++++ |
| 49 | ++ |
| 50 | +++ |
| 51 | ++ |
| 52 | +++ |
| 53 | ++++ |
| 54 | ++++ |
| 55 | +++ |
| 56 | ++++ |
| 57 | + |
| 58 | +++ |
| 59 | + |
| 61 | ++ |
| 62 | ++ |
| 63 | ++ |
| 64 | +++ |
| 65 | ++ |
| 66 | + |
| 67 | +++ |
| 68 | ++ |
| 69 | + |
| 70 | ++++ |
| 71 | +++ |
| 72 | +++ |
| 73 | +++ |
| 74 | ++ |
| 75 | ++++ |
| 76 | ++++ |
| 77 | +++ |
| 78 | ++ |
| 79 | + |
| 80 | ++ |
| 81 | + |
| 82 | + |
| 83 | ++++ |
| 84 | ++ |
| 85 | +++ |
| 86 | ++ |
| 87 | + |
| 88 | + |
| 89 | +++ |
| 91 | + |
| 92 | +++ |
| 93 | +++ |
| 94 | +++ |
| 95 | +++ |
| 96 | ++ |
| 97 | ++ |

TABLE 13

| Average IC$_{50}$ of compounds in hTHP-1 assay | |
| --- | --- |
| Final Target Number | Average IC$_{50}$ |
| 213 | ++ |
| 214 | ++++ |
| 215 | ++ |

A number of embodiments of the invention have been described. Nevertheless, it will be understood that various modifications may be made without departing from the spirit and scope of the invention. Accordingly, other embodiments are within the scope of the following claims.

We claim:

1. A compound of Formula A

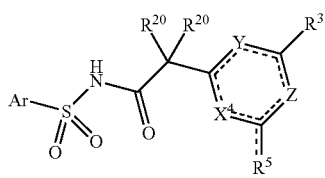

Formula A or a pharmaceutically acceptable salt thereof, wherein:
the substituents on the compound of Formula A are the following:
Ar is a heteroaryl group

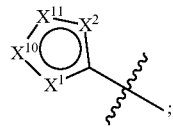

$X^1$ is O, S, N, $CR^{41}$ or $NR^{41}$;
$X^{10}$ is O, S, N, $CR^{10}$ or $NR^{10}$;
$X^{11}$ is O, S, N, $CR^1$ or $NR^1$;
$X^2$ is O, S, N, $CR^{42}$ or $NR^{42}$;
$X^4$ is $CR^4$;
each $R^{20}$ is the same or different and is independently selected from hydrogen and $C_1$-$C_6$ alkyl;
Y is $CR^2$;
Z is N or $CR^8$;
$R^8$ is selected from H, CN, halo, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ alkoxy, $C_1$-$C_6$ haloalkoxy, and $C_1$-$C_6$ haloalkyl;
$R^2$ is $C_1$-$C_6$ haloalkyl, $C_3$-$C_7$ cycloalkyl or $C_1$-$C_6$ alkyl substituted with hydroxy;
$R^3$ is hydrogen, $C_1$-$C_6$ alkoxy, $C_1$-$C_6$ haloalkyl, CN, $C_1$-$C_6$ haloalkoxy, $C_3$-$C_7$ cycloalkyl or $C_1$-$C_6$ alkyl optionally substituted with hydroxy;
$R^4$ is $C_1$-$C_6$ haloalkyl, $C_3$-$C_7$ cycloalkyl or $C_1$-$C_6$ alkyl substituted with hydroxy;
$R^5$ is hydrogen, $C_1$-$C_6$ alkoxy, halo, $C_1$-$C_6$ haloalkyl, CN, $C_1$-$C_6$ haloalkoxy, $C_3$-$C_7$ cycloalkyl or $C_1$-$C_6$ alkyl optionally substituted with hydroxy;
provided that at least one of $R^2$, $R^3$, $R^4$ and $R^5$ is not hydrogen;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

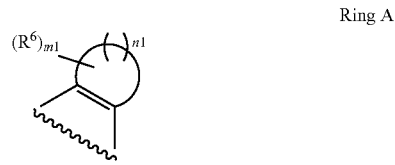

Ring A and ring B is

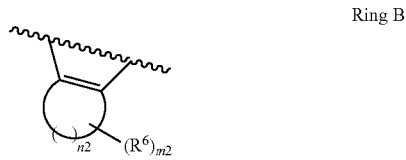

Ring B wherein
ring A is a carbocyclic ring or a heterocyclic ring wherein 1 or 2 members are heteroatoms independently selected from O, N, and S;
n1 is from 2 to 5;
m1 is from 1 to 10;
wherein ring B is a carbocyclic ring or a heterocyclic ring wherein 1 or 2 members are heteroatoms independently selected from O, N, and S;
n2 is from 2 to 5;
m2 is from 1 to 10;
wherein each $R^6$ in each ring is the same or different and is selected from H, F, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring wherein 1 or 2 members are heteroatoms independently selected from O, N, and S;
each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkyl, $C_1$-$C_6$ alkoxy, $NR^{11}R^{12}$, $=NR^{13}$, $COOC_1$-$C_6$ alkyl, $C_6$-$C_{10}$ aryl, and $CONR^{11}R^{12}$;
and each of $R^1$, $R^{41}$, $R^{42}$ when bonded to nitrogen is independently selected from H, $C_1$-$C_6$ alkyl, $C_1$-$C_6$ haloalkyl, $CO_2C_1$-$C_6$alkyl, $CO_2C_3$-$C_8$cycloalkyl, $C_6$-$C_{10}$ aryl, $CONR^{11}R^{12}$, $C_3$-$C_7$ cycloalkyl, $S(O_2)C_1$-$C_6$ alkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkyl, $C_1$-$C_6$ alkoxy, $NR^{11}R^{12}$, $=NR^{13}$, $COOC_1$-$C_6$ alkyl, $C_6$-$C_{10}$ aryl, and $CONR^{11}R^{12}$;

or $R^1$ and $R^{10}$ taken together with the atoms connecting them form a 3-to-8-membered carbocyclic or heterocyclic ring wherein 1 or 2 members are heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

or the substituents on the compound of Formula A are the following:

Ar is a heteroaryl group

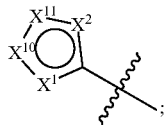

$X^1$ is O, S, N, $CR^{41}$ or $NR^{41}$;
$X^{10}$ is O, S, N, $CR^{10}$ or $NR^{10}$;
$X^{11}$ is O, S, N, $CR^{10}$ or $NR^{10}$;
$X^2$ is O, S, N, $CR^{42}$ or $NR^{42}$;
$X^4$ is $CR^4$;

each $R^{20}$ is the same or different and is independently selected from hydrogen and $C_1$-$C_6$ alkyl;

Y is $CR^2$;
Z is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;

$R^2$ is $C_1$-$C_6$ haloalkyl, $C_3$-$C_7$ cycloalkyl or $C_1$-$C_6$ alkyl optionally substituted with hydroxy;

$R^3$ is hydrogen, $C_1$-$C_6$ alkoxy, $C_1$-$C_6$ haloalkyl, $C_3$-$C_7$ cycloalkyl or $C_1$-$C_6$ alkyl optionally substituted with hydroxy;

$R^4$ is $C_1$-$C_6$ haloalkyl, $C_3$-$C_7$ cycloalkyl or $C_1$-$C_6$ alkyl substituted with hydroxy;

$R^5$ is hydrogen, $C_1$-$C_6$ alkoxy, halo, $C_1$-$C_6$ haloalkyl, $C_3$-$C_7$ cycloalkyl or $C_1$-$C_6$ alkyl optionally substituted with hydroxy;

provided that at least one of $R^2$, $R^3$, $R^4$ and $R^5$ is not hydrogen, and that $R^2$ and $R^4$ are not both hydroxymethyl;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

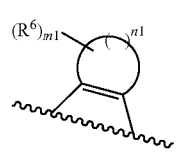

Ring A and ring B is

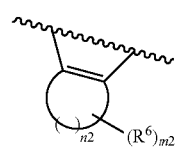

Ring B wherein
ring A is a carbocyclic ring or a heterocyclic ring wherein 1 or 2 members are heteroatoms independently selected from O, N, and S;
n1 is from 2 to 5;
m1 is from 1 to 10;
wherein ring B is a carbocyclic ring or a heterocyclic ring wherein 1 or 2 members are heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, and $=NR^{13}$;
or two $R^6$ taken together with the atom or atoms connecting them form a 3-to-8-membered carbocyclic or saturated heterocyclic ring wherein 1 or 2 members are heteroatoms independently selected from O, N, and S;
each of $R^1$, $R^{10}$, $R^{41}$ and $R^{42}$ when bonded to carbon is independently selected from H, $C_1$-$C_6$ alkyl, $C_1$-$C_6$ haloalkyl, CN, halo, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, $C_6$-$C_{10}$ aryl, and $CONR^{11}R^{12}$;
and each of $R^1$, $R^{10}$, $R^{41}$ and $R^{42}$ when bonded to nitrogen is independently selected from H, $C_1$-$C_6$ alkyl, $C_1$-$C_6$ haloalkyl, $CO_2C_1$-$C_6$ alkyl, $CO_2C_3$-$C_8$ cycloalkyl, $C_6$-$C_{10}$ aryl, $CONR^{11}R^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, $C_6$-$C_{10}$ aryl, and $CONR^{11}R^{12}$;
or $R^1$ and $R^{10}$ taken together with the atoms connecting them form a 3-to-8-membered carbocyclic or heterocyclic ring wherein 1 or 2 members are heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$, is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl.

2. The compound of claim 1, wherein the moiety

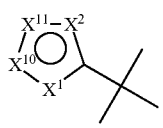

is selected from the group consisting of:

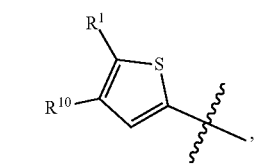
(LHS1)

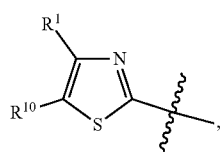
(LHS2)

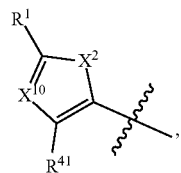
(LHS7)

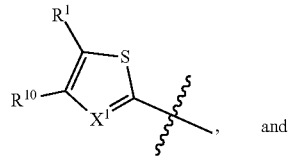
(LHS8)

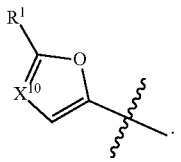
(LHS11)

and

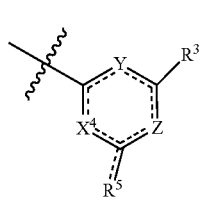

3. The compound of claim 1, wherein the moiety is selected from the group consisting of:

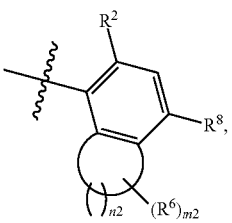
(RHS1)

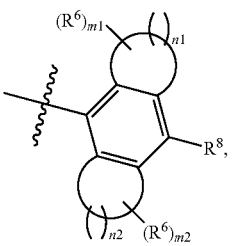
(RHS2)

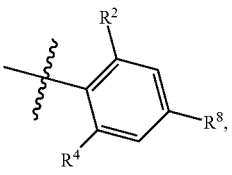
(RHS3)

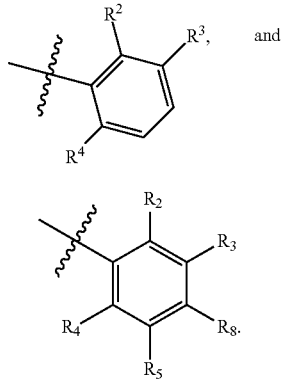
(RHS5) and (RHS12)

4. A compound selected from the group consisting of:

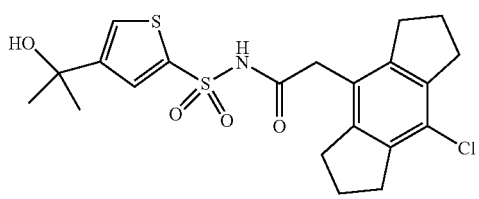
101

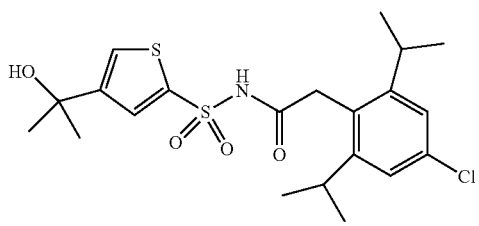
102

104 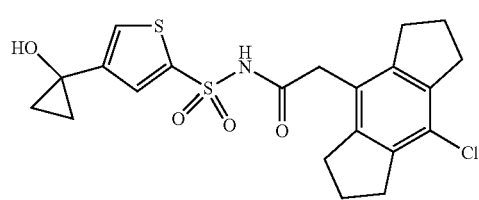
105 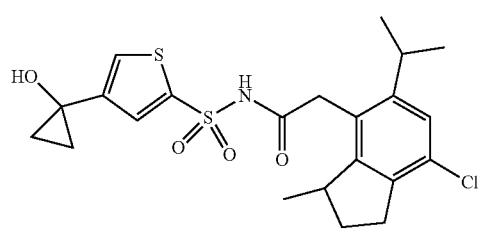
107 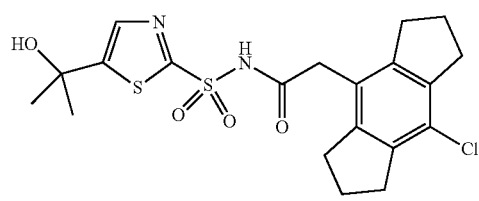
108 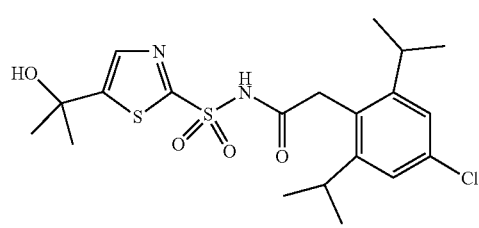
110 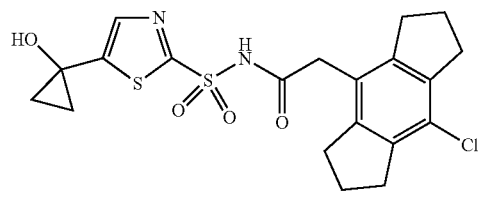
111 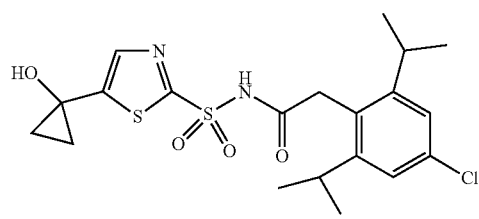
113 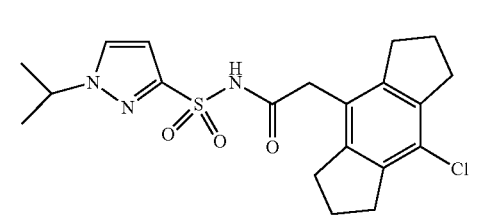
114 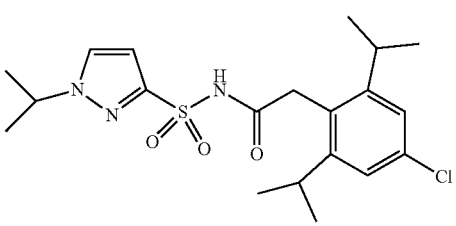
116 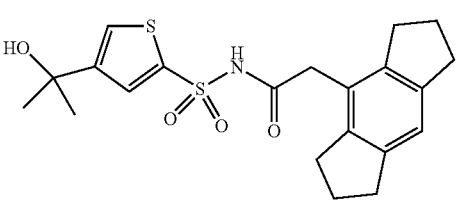
117 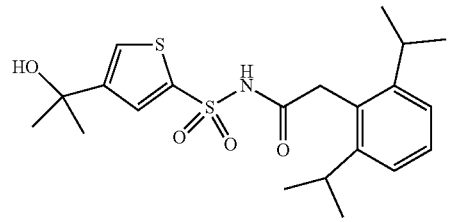
118 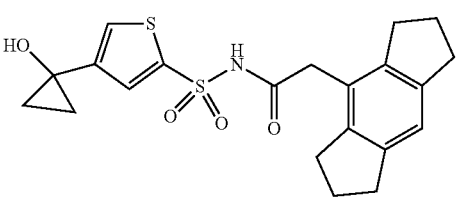
119 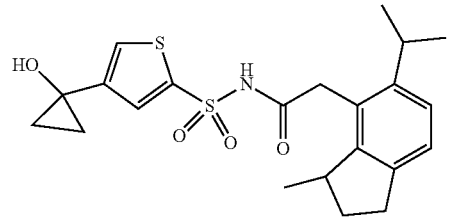
120 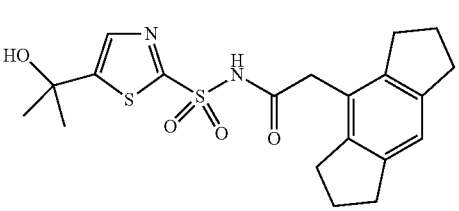
121 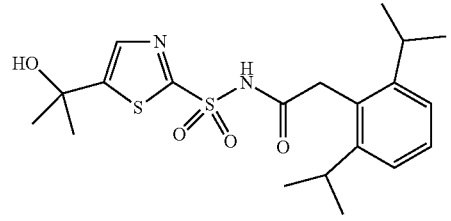

251
-continued
122
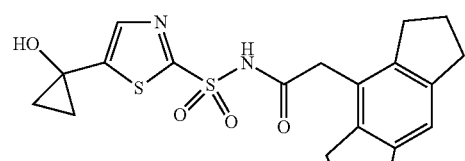
123
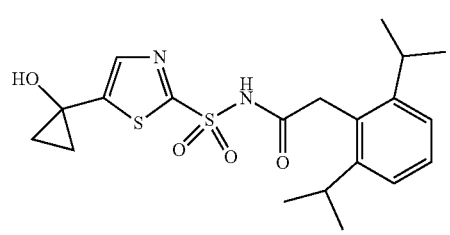
124
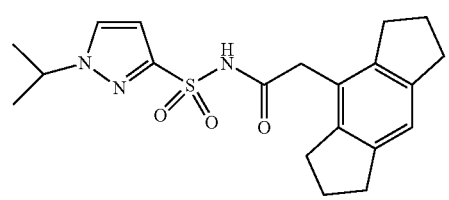
125
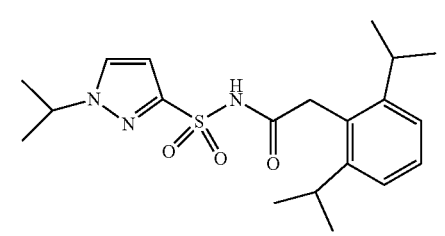
126
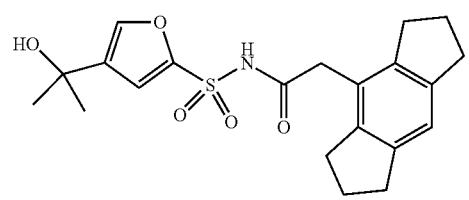
127
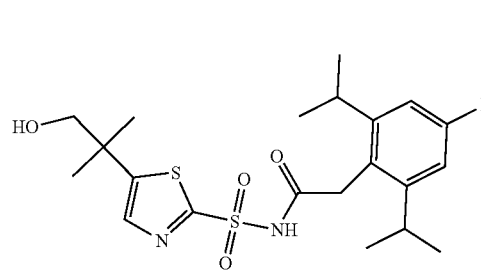
128
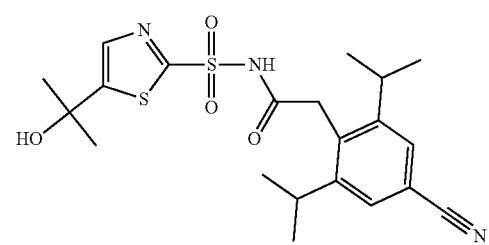
252
-continued
129
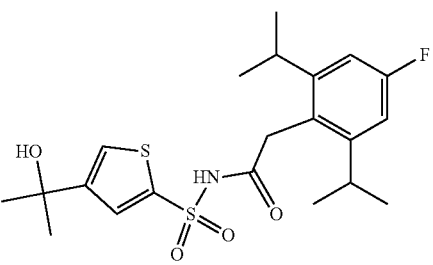
130
132
133
134
135

136 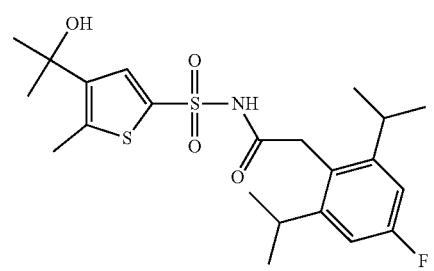
137 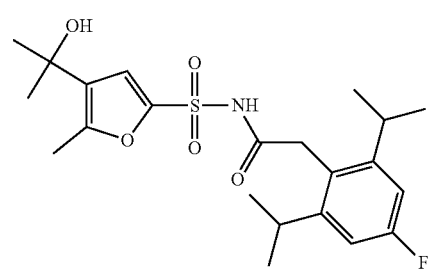
138 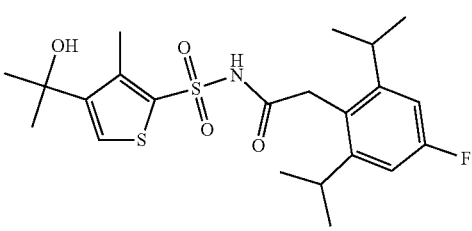
140 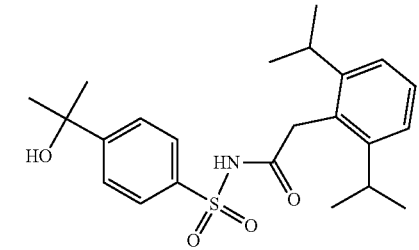
141 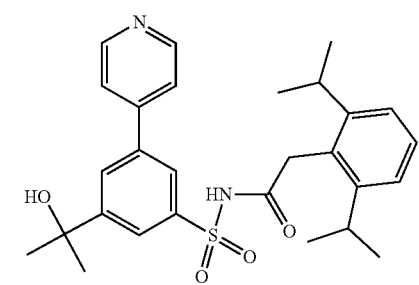
142 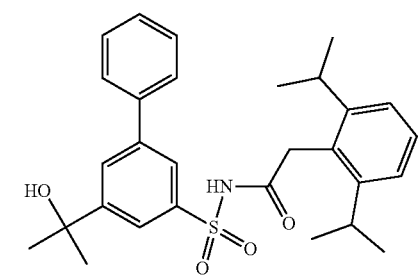
143 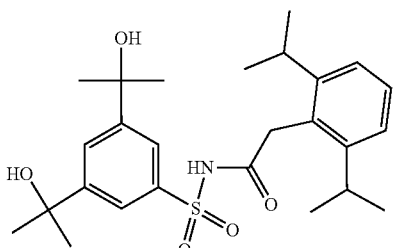
144 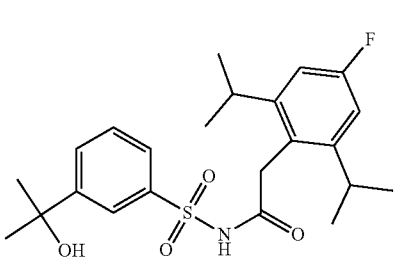
145 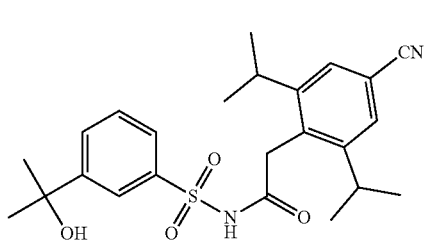
146 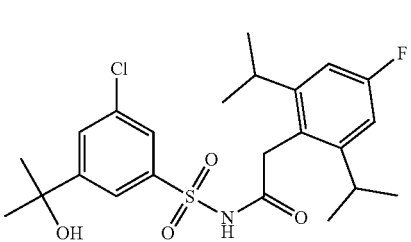
147 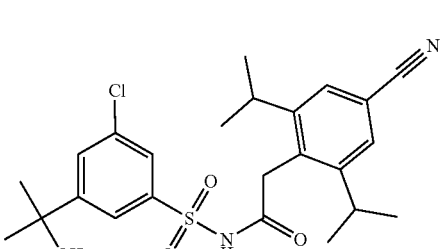
148 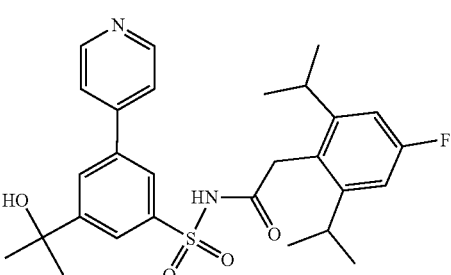

149
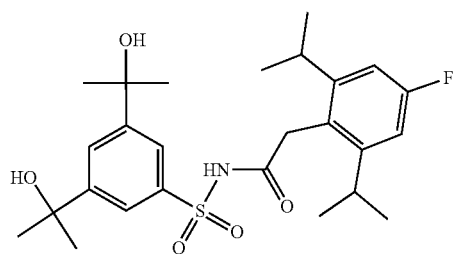
150
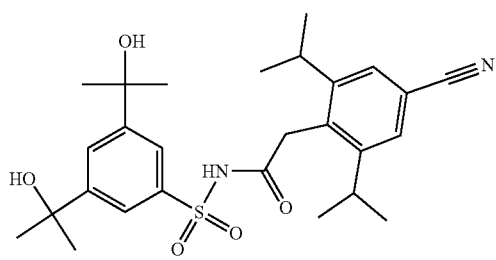
151
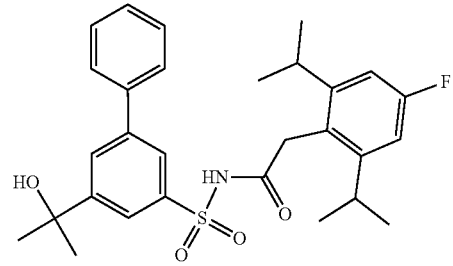
152
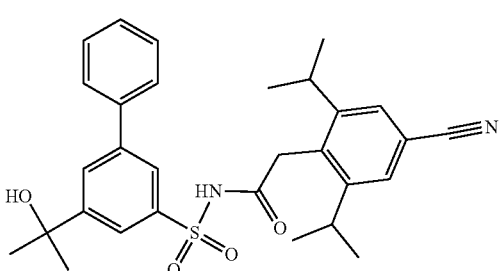
153
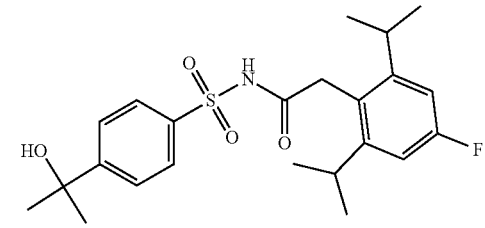
154
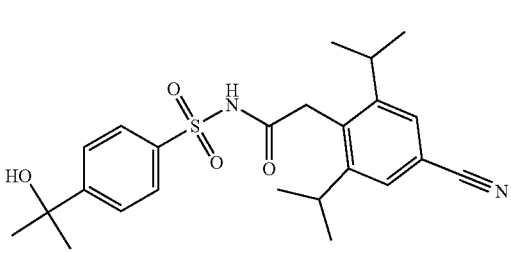
155
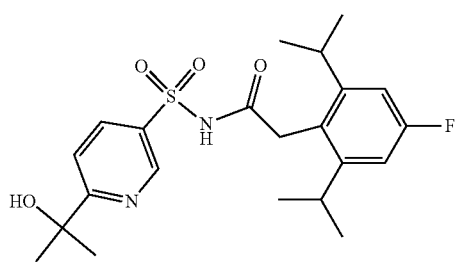
156
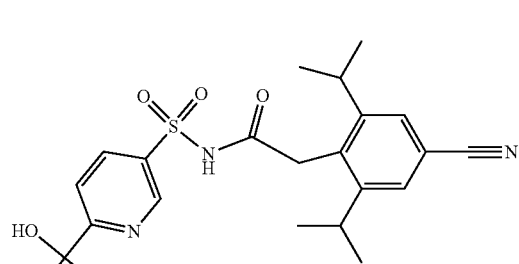
157
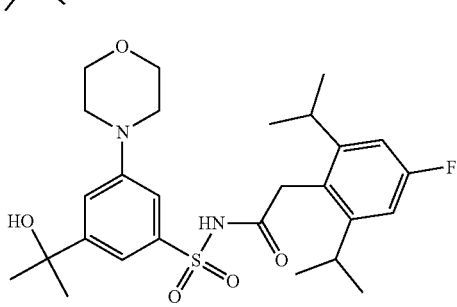
158
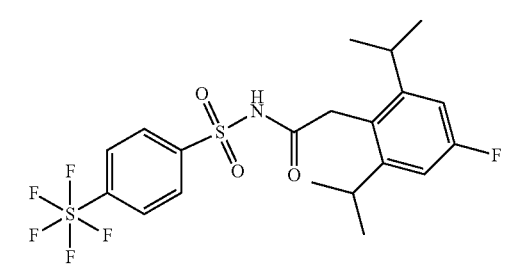
159
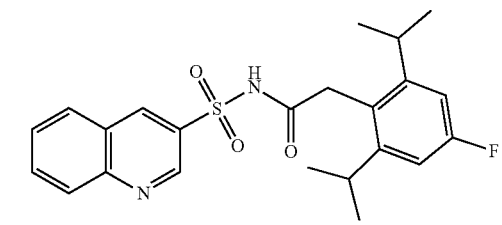
160
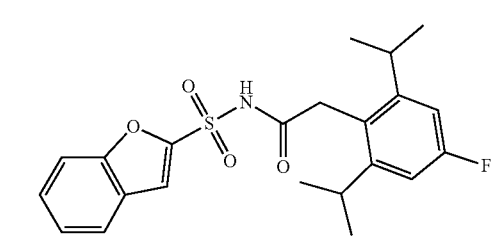

163
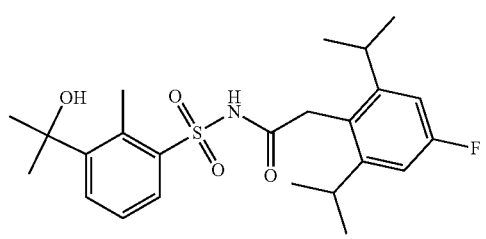
164
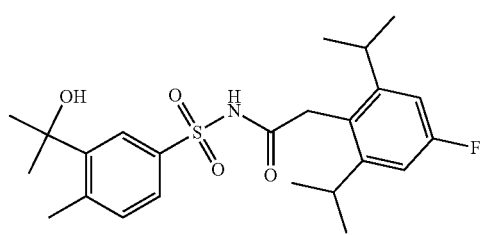
165
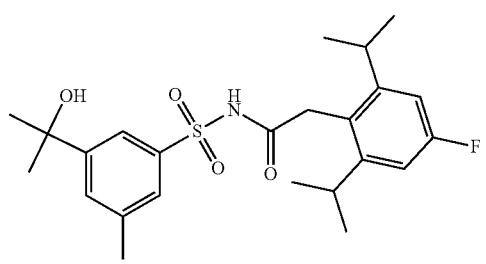
166
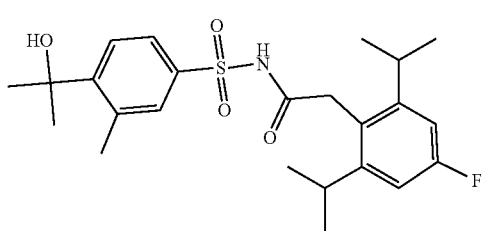
167
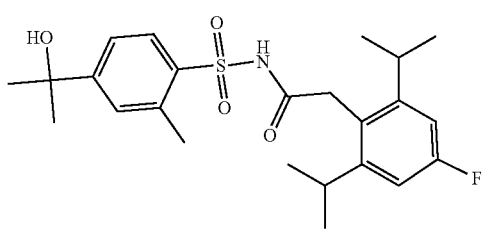
168
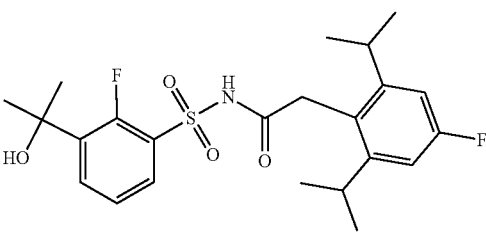
169
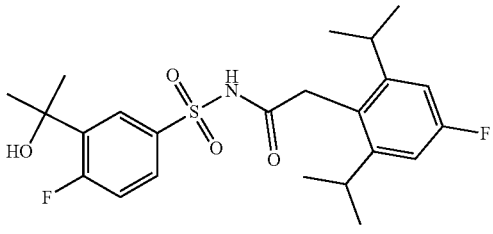
170
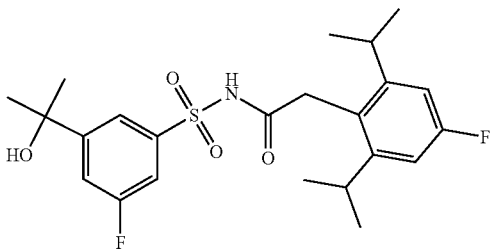
171
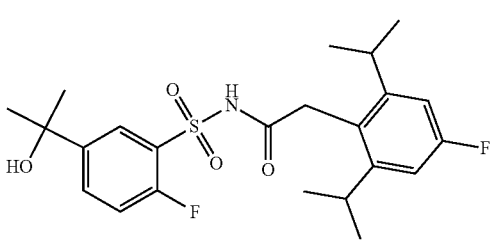
172
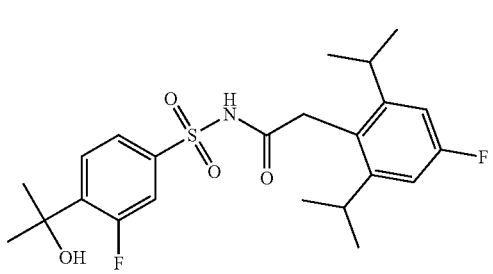
173
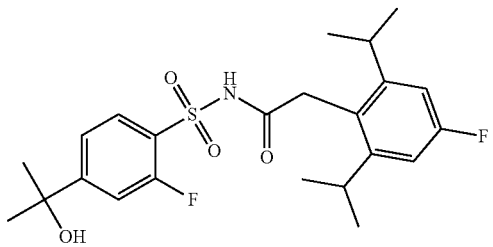
174
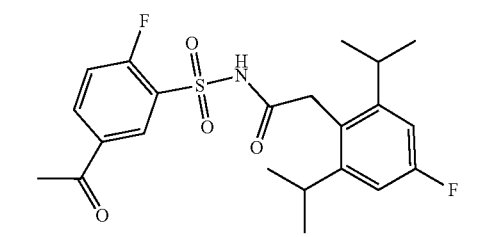

175 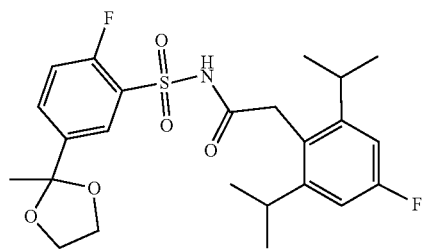
176 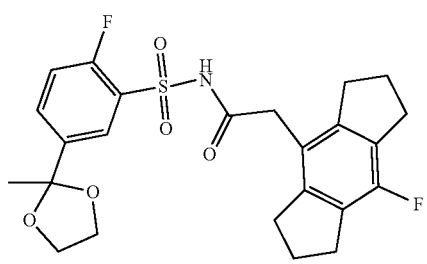
177 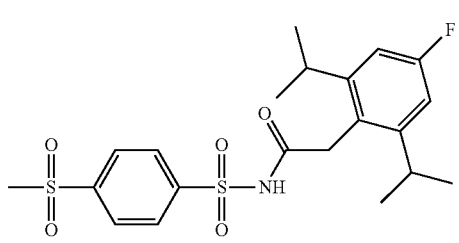
178 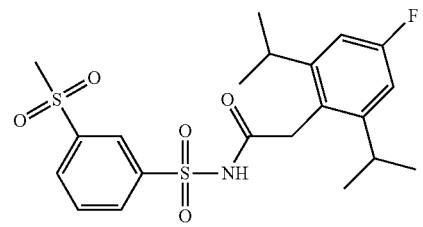
179 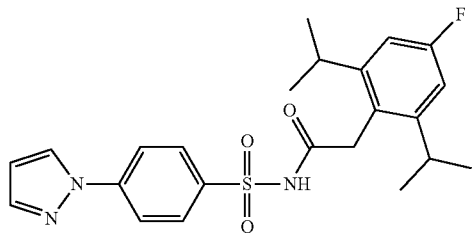
180 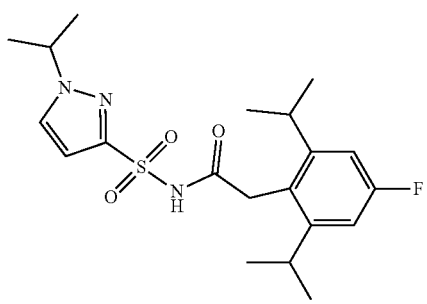
181 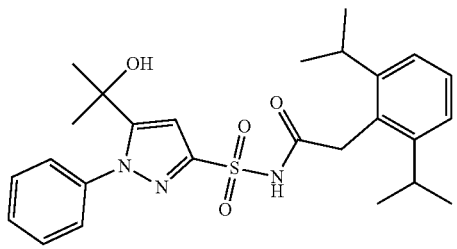
182 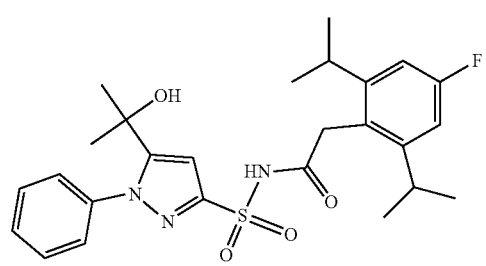
183 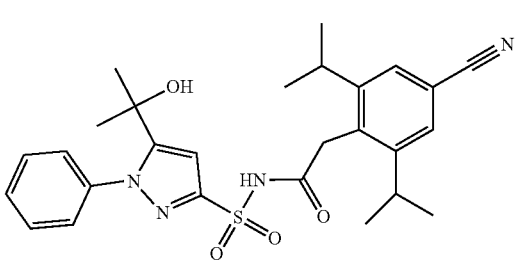
184 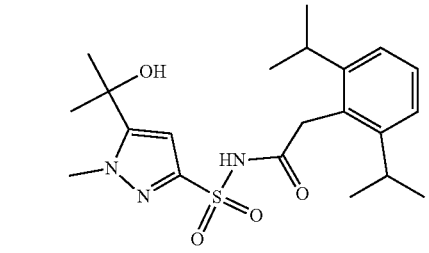
185 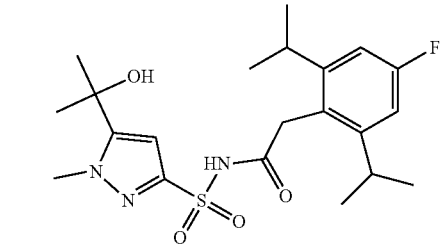
186 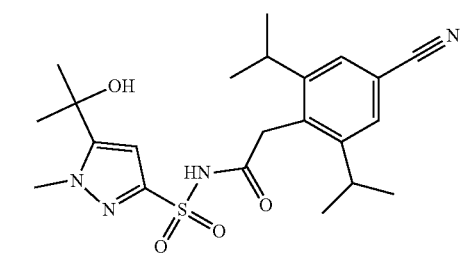

187 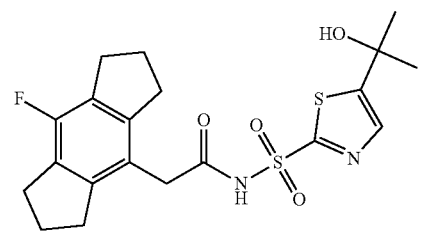
188 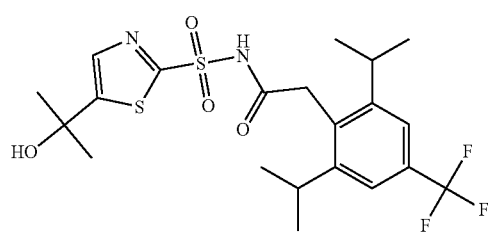
189 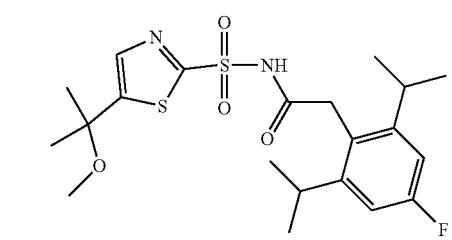
190 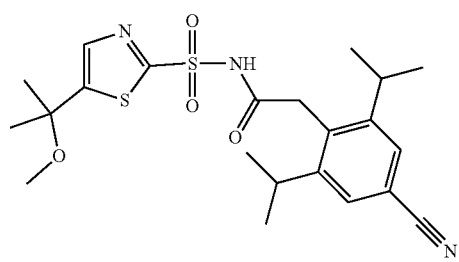
200 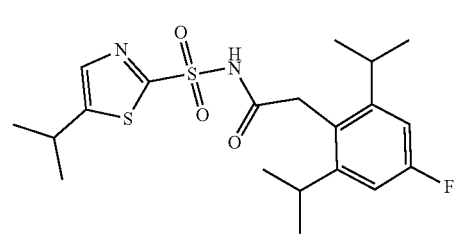
201 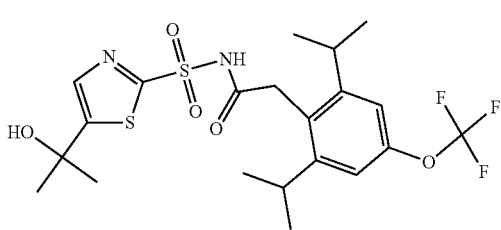
202 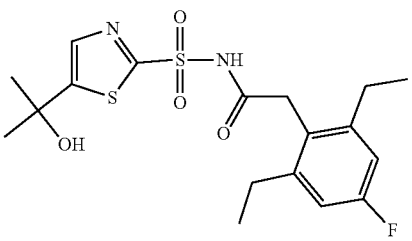
203 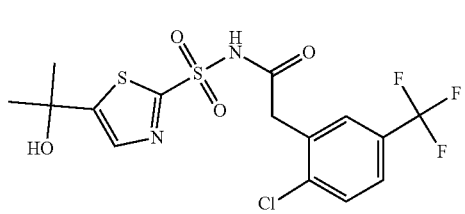
204 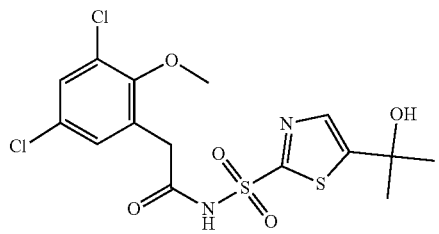
205 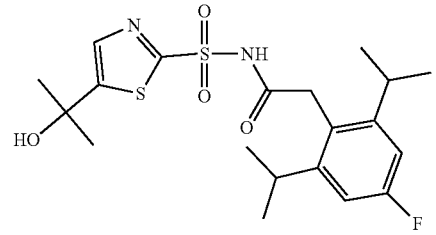
206 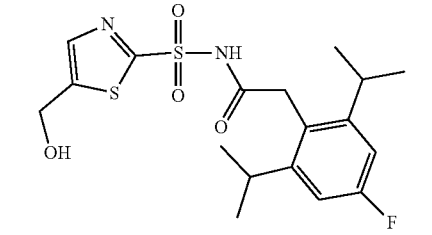
207 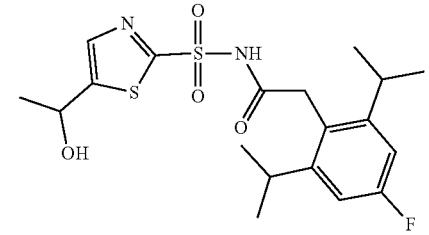

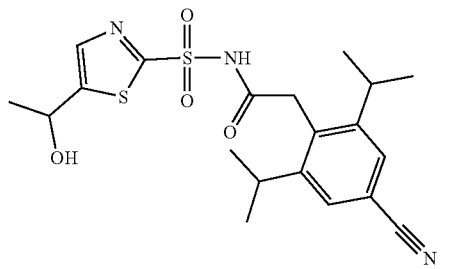
208
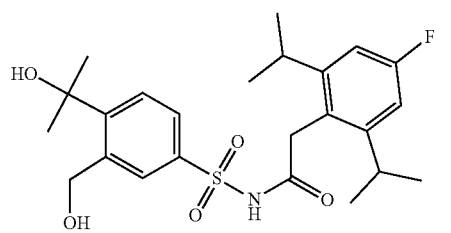
209
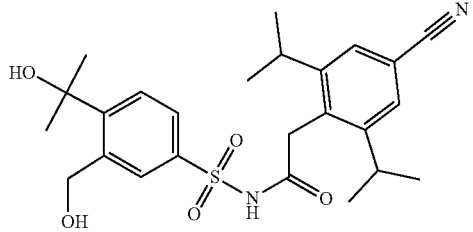
210
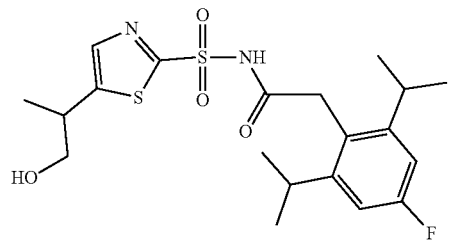
211
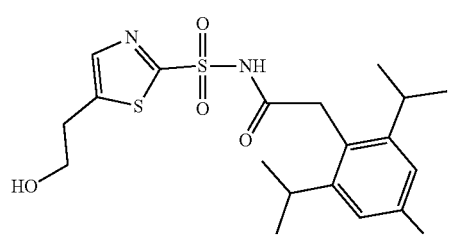
212
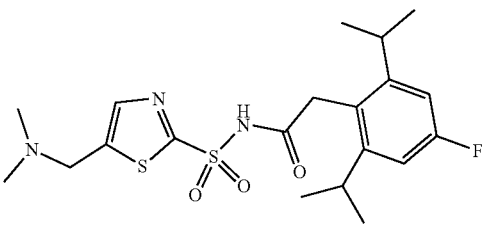
213
214
215
or pharmaceutically acceptable salts thereof.
5. A pharmaceutical composition comprising a compound or salt as claimed in claim 1, and one or more pharmaceutically acceptable excipients.
6. A pharmaceutical composition comprising a compound or salt as claimed in claim 4, and one or more pharmaceutically acceptable excipients.
* * * * *